(12) United States Patent
Di Francesco et al.

(10) Patent No.: US 10,421,765 B2
(45) Date of Patent: Sep. 24, 2019

(54) TETRAHYDROPYRIDO[4,3-D]PYRIMIDINE INHIBITORS OF ATR KINASE

(71) Applicants: Board of Regents, The University of Texas System, Austin, TX (US); ChemPartner Corporation, South San Francisco, CA (US)

(72) Inventors: Maria Emilia Di Francesco, Houston, TX (US); Philip Jones, Houston, TX (US); Christopher Lawrence Carroll, Houston, TX (US); Jason Bryant Cross, Pearland, TX (US); Michael Garrett Johnson, San Francisco, CA (US); Sarah Lively, San Carlos, CA (US)

(73) Assignees: Board of Regents, The University of Texas System, Austin, TX (US); ChemPartner Corporation, South San Francisco, CA (US)

(*) Notice: Subject to any disclaimer, the term of this patent is extended or adjusted under 35 U.S.C. 154(b) by 0 days.

(21) Appl. No.: 15/990,283

(22) Filed: May 25, 2018

(65) Prior Publication Data
US 2018/0370990 A1 Dec. 27, 2018

Related U.S. Application Data

(60) Provisional application No. 62/511,890, filed on May 26, 2017.

(51) Int. Cl.
C07D 519/00 (2006.01)
A61P 35/00 (2006.01)

(52) U.S. Cl.
CPC ............ *C07D 519/00* (2013.01); *A61P 35/00* (2018.01)

(58) Field of Classification Search
CPC .............................. C07D 519/00; A61P 35/00
USPC ....................................................... 514/264.1
See application file for complete search history.

(56) References Cited

U.S. PATENT DOCUMENTS

| | | | |
|---|---|---|---|
| 2012/0035407 A1 | 2/2012 | Charrier | |
| 2014/0315902 A1 | 10/2014 | Sun | |
| 2016/0287604 A1 | 10/2016 | Wortmann | |

FOREIGN PATENT DOCUMENTS

| | | |
|---|---|---|
| WO | 2007080382 | 7/2007 |
| WO | 2008023159 | 2/2008 |
| WO | 2009007748 | 1/2009 |
| WO | 2009007750 | 1/2009 |
| WO | 2009007751 | 1/2009 |
| WO | 2009110510 | 9/2009 |
| WO | 2010073034 | 7/2010 |
| WO | 2010073034 A1 | 7/2010 |
| WO | 2010120996 | 10/2010 |
| WO | 2011062253 | 5/2011 |
| WO | 2011103715 | 9/2011 |
| WO | 2011106276 | 9/2011 |
| WO | 2011107585 | 9/2011 |
| WO | 2011154737 | 12/2011 |
| WO | 2011154737 A1 | 12/2011 |
| WO | 2012004299 | 1/2012 |
| WO | 2014089379 | 6/2014 |
| WO | 2014089379 A9 | 6/2014 |
| WO | 2015085132 | 6/2015 |
| WO | 2015085132 A1 | 6/2015 |
| WO | 2015187451 | 12/2015 |
| WO | 2015187451 A9 | 12/2015 |
| WO | 2016020320 | 2/2016 |
| WO | 2016020320 A1 | 2/2016 |
| WO | 2016061097 | 4/2016 |
| WO | 2016061097 A1 | 4/2016 |
| WO | 2018218197 | 11/2018 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Barsanti, P. et al., "Structure-Based Drug Design of Novel Potent and Selective Tetrahydropyrazolo[1,5-a] pyrazines as ATR Inhibitors", ACS Med. Chem. Lett., 6(1):37-41, (2015).
Barsanti, P.A. et al., "Structure-Based Drug Design of Novel Potent and Selective Azabenzimidazoles (ABI) as ATR Inhibitors", ACS Med. Chem. Lett., 6:42-6, (2015).
Bass, T. et al., "ETAA1 acts at stalled replication forks to maintain genome integrity", Nat Cell Biol, 18(11):1185-95, (25 page document), (2016).
Charrier, J.D. et al., "Discovery of Potent and Selective Inhibitors of Ataxia Telangiectasia Mutated and Rad3 Related (ATR) Protein Kinase as Potential Anticancer Agents", J. Med. Chem., 54(7):2320-30, (Apr. 14, 2011).

(Continued)

*Primary Examiner* — Kristin A Vajda
(74) *Attorney, Agent, or Firm* — Dennis A. Bennett; Cynthia Hathaway; John Desper

(57) ABSTRACT

The present invention relates to tetrahydropyrido[4,3-d] pyrimidine based compounds and methods which may be useful as inhibitors of ATR kinase for the treatment or prevention of cancer.

39 Claims, No Drawings

(56) References Cited

OTHER PUBLICATIONS

Choi, M. et al., "ATM Mutations in Cancer: Therapeutic Implications", Mol Cancer Ther, 15(8):1781-91, (2016).
Foote, K.M. et al., "Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity", J. Med. Chem., 56(5):2125-38, (2013).
Karnitz, L. et al., "Molecular Pathways: Targeting ATR in Cancer Therapy", Clin Cancer Res, 21(21):4780-5, (2015).
Kwok, M. et al., "ATR Inhibition Induces Synthetic Lathality and Overcomes Chemoresistance in TP53- or ATM-Defective Chronic Lymphocytic Leukemia Cells", Blood, 127(5):582-96, (2015).
Menezes, D. et al., "A Synthetic Lethal Screen Reveals Enhanced Sensitivity to ATR Inhibitor Treatment in Mantle Cell Lymphoma with ATM Loss-of-Function", Mol. Cancer Res., 13(1):120-9, (2015).
Mohni, K. et al., "ATR Pathway Inhibition Is Synthetically Lethal in Cancer Cells with ERCC1 Deficiency", Cancer Res., 74:2835-45, (2014).
Toledo, L. et al., "A cell-based screen identifies ATR inhibitors with synthetic lethal properties for cancer-associated mutations", Nat Struct Mol Biol, 18(6):721-7, (21 page document), (2011).
Barsanti, P.A. et al., "Structure-Based Drug Design of Novel Potent and Selective Tetrahydropyrazolo [1,5-a] pyrazines as ATR Inhibitors", ACS Med. Chem Lett., 6:37-41, (2015).
Charrier, J. et al., "Discovery of Potent and Selective Inhibitors of Ataxia Telangiectasia Mutated and Rad3 Related (ATR) Protein Kinase as Potential Anticancer Agents", J. Med. Chem., 54:2320-30, (2011).
Coburn, C. et al., "Discovery of a pharmacologically active antagonist of the two-pore-domain potassium channel K2P9.1 (TASK-3)", Chem. Med. Chem., 7(1):123-33, (2012).
Foote, K. et al., "Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity", J. Med. Chem., 56(5):2125-38, (2013).
International Application No. PCT/US2018/034729; International Search Report and Written Opinion of the International Searching Authority, dated Nov. 9, 2018; 9 pages.
International Application No. PCT/US2018/042128 International Search Report and Written Opinion of the International Searching Authority, dated Oct. 30, 2018; 10 pages.
Pubchem 53541968, 6-[4-(Morpholin-4-yl)-5H,6H,7H,8H-pyrido[4,3-d]pyrimidin-6-yl]pyridine-3-carbonitrile, Created on Dec. 3, 2011 (Mar. 12, 2011) pp. 1-11.
Pubchem 79023842, 4-Phenyl-5,6,7,8-tetrahydropyrido[4,3-d]pyrimidine, deposited on Oct. 19, 2014 (Oct. 19, 2014) pp. 1-10.

* cited by examiner

TETRAHYDROPYRIDO[4,3-D]PYRIMIDINE INHIBITORS OF ATR KINASE

This application claims the benefit of priority of U.S. Provisional Application No. 62/511,890, filed May 26, 2017, the disclosure of which is hereby incorporated by reference as if written herein in its entirety.

Disclosed herein are new tetrahydropyrido[4,3-d]pyrimidine compounds and compositions and their application as pharmaceuticals for the treatment of disease. Methods of inhibition of ATR kinase activity in a human or animal subject are also provided for the treatment diseases such as cancer.

Ataxia-telangiectasia and Rad3-related kinase (ATR) is a member of the phosphatidylinositol 3-kinase-related protein kinase (PIKK) family, which also includes ataxia telangiectasia mutated (ATM) kinase, DNA-dependent protein kinase (DNA-PK), suppressor of morphogenesis in genitalia-1 (SMG-1), mammalian target of rapamycin (mTOR) and transformation/transcription associated protein (TRAPP). ATR and ATM are key regulators of the cellular DNA damage response (DDR) pathways, and are involved in maintaining the genome integrity in response to DNA-damage. Several distinct types of DNA lesions can occur as a consequence of diverse damaging events, including errors in normal replication processing, exposure to ionizing radiations (IR) and genotoxic agents, and different mechanisms of DNA repair have evolved to resolve specific kinds of DNA damage.

ATM is activated mainly by double-stranded DNA breaks (DSB), which may arise from collapsing of stalled replication forks or from exposure to IR. ATM has a key role in the activation of the G1/S checkpoint, which prevents cells with DNA damage to enter the S-phase, and allows DNA repair prior to the start of DNA replication. The effect is mediated primarily through the phosphorylation of two of the main downstream targets of ATM, CHK2 kinase and the tumor suppressor p53.

In turn, ATR is activated mainly in response to single stranded DNA breaks (SSB), that are found at stalled replication forks or are derived from DNA end-resection following processing of DNA DSBs. Replication protein A (RPA) binds to the DNA single strands, the ATR-interacting protein (ATRIP) binds then to the RPA-coated DNA strands and recruits ATR to the SSB damage site. Recruitment of additional protein components to the complex results in activation of ATR kinase, followed by phosphorylation and activation of its downstream effectors, including CHK1 kinase. Activation of ATR results in slow replication origin firing, stabilization of the stalled replication forks which prevents their collapse into DSBs, and restart of fork replication once the damage is repaired. The ATR/CHK1 pathway is a major regulator of the G2/M checkpoint, which prevents the premature entry of cells into mitosis in the presence of incomplete DNA replication and/or DNA damage (reviewed in M. J. O'Connor, Molecular Cell, 2015, 60, November 19, p. 547-560; A. M. Weber et al., Pharmacology and Therapeutics 2015, 149, 124-138).

Because of the critical role of ATR in DDR, pharmacological inhibition of ATR may be an effective cancer treatment in a number of specific settings. Indeed, several cancers (e.g. oncogene-driven tumors) are characterized by higher levels of replication stress compared to normal cells, and blockade of ATR can increase their genomic instability and induce substantial cell death (O. Gilad et al., Cancer Res. 70, 9693-9702, 2010). Moreover, most cancers are characterized by loss or deregulation of one or more DDR pathways, resulting in increased genomic instability and greater dependency on remaining DDR pathways for survival. For example, a cancer cell that has a defective G1 checkpoint as a consequence of mutations in p53, will rely more on the G2/M checkpoints to allow DNA repair and cell survival. Inhibition of ATR, a key regulator of the G2/M checkpoints, can result in complete loss of DNA damage checkpoints, ultimately leading to accumulation of DNA damage and mitotic catastrophe. Normal cells, with a functioning G1 checkpoint, would be less affected by pharmacological inhibition of ATR. Similarly, in cancer cells harboring ATM-deficiency, ATR inhibition results in a synthetic lethality dependency, leading to increased sensitivity and preferential killing. Therefore, ATR inhibition could be used for treatment of tumors with deficient ATM and/or p53 function (P. M. Reaper, M. R. Griffiths et al., Nature Chem. Bio. 7, 428-430, 2011)

Additional potential synthetic lethality interactions between ATR and other components of the DDR pathway have been reported, and might be exploited by treatment with ATR inhibitors, including treatment of cancers characterized by loss/deficiency of XRCC 1, ERCC1, MRE11 and other components if the MRN complex (reviewed in A. M. Weber et al., Pharmacology and Therapeutics 2015, 149, 124-138). Recently, a synthetic lethality dependency has been reported for ATR inhibition in tumors deficient for ARID1A, a member of the SWI/SNF chromatin-remodeling complex frequently mutated in human cancer (C. T. Williamson et al., Nature Communications, 2016, 7, 13837).

ATR inhibition can be exploited for treatment of cancer also in combination with DNA-damaging therapeutic agents, such as radiotherapy and chemotherapy. Widely used chemotherapeutics include antimetabolites (e.g. gemcitabine), DNA crosslinking agents such as platinum salts, alkylating agents (e.g. temozolomide) and inhibitors of topoisomerase (e.g. camptothecin, topotecan, irinotecan). Administration of these agents and/or ionizing radiation results in a variety of DNA lesions that ultimately bring the cancer cells towards mitotic catastrophe and cell death. In cancer cells treated with such agents, inhibition of ATR signaling can prevent DNA damage repair, thus further reducing the often already compromised abilities of cancer cells to respond to the induced replication stress, and hence potentiating the effectiveness of the above treatments.

An additional opportunity to leverage ATR inhibition in combination therapy is together with other DDR agents, for example in combination with inhibitors of Poly ADP ribose polymerase (PARP). PARP inhibitors prevent the repair of single strand DNA breaks, resulting into formation of DNA double strand breaks. In the context of cancers that are deficient in the homologous recombination (HR) DNA repair pathway, such as BRCA 1/2 mutant cancers, PARP inhibition has proven clinically efficacious. Recent reports highlight that targeting critical cell-cycle checkpoints at the same time—for example by combining a PARP inhibitor with an ATR inhibitor—results in increased sensitivity to PARP inhibition and in significant efficacy in several preclinical cancer models, including PARP inhibitor resistant patient derived models. These findings highlight the potential clinical applications of ATR inhibition in combination with other DDR inhibitors, and the field is likely to expand to several other combination opportunities beyond PARP inhibitors (H. Kim et al., Clinical Cancer Research, April 2017, DOI: 10.1158/1078-0432.CCR-16-2273; A. Y. K. Lau et al., AACR National Meeting 2017, Abstract 2494/25, ATR inhibitor AZD6738 as monotherapy and in combination with olaparib or chemotherapy: defining pre-clinical dose-schedules and efficacy modelling).

Thus, disclosed herein are methods for treating cancers using ATR inhibitors, in particular cancers characterized by elevated levels of replication stress, defective in cell cycle checkpoints, or harboring defects in cellular DNA damage repair pathways, such as deficiency in the ATM/p53 pathway or additional synthetic lethality dependencies with other DDR components. Also disclosed herein are methods using ATR inhibitors to treat cancers that are mutated/defective in ARID1A, or are mutated/defective in cellular pathways that are in a synthetic lethal dependency with the ATR pathway. Disclosed herein are also methods for treatment of cancer using ATR inhibitors in combination with radiation, with DNA damaging chemotherapeutic agents, and with other DDR inhibitors, including PARP inhibitors.

Furthermore, inhibition of ATR offers an opportunity for treatment of certain cancers associated with the regulation of telomere length. Telomeres are nucleoprotein complexes comprising both hexanucleotide DNA repeat sequences and telomere-associated proteins, which act to stabilize the ends of chromosomes. In normal somatic cells, shortening of the telomeres over time leads to senescence or apoptosis, and this action can act as an upper limit on cellular life span. In most advanced cancers, the enzyme telomerase is activated, whose role is to add a repeat sequence to the 3' end of the DNA, thus reversing the telomere shortening process and increasing the cellular lifespan. Thus, activation of telomerase has been invoked in cancer cell immortalization. A second, telomerase-independent mechanism for maintaining telomeres, termed Alternate Lengthening of Telomers (ALT), has been implicated in approximately 5% of all human cancers, and it is prevalent in specific kinds of cancer, including osteosarcoma and glioblastoma. ALT is enriched in mesenchymal-originating tumors, and is usually associated with decreased survival rates. Studies revealed that ATR kinase is functionally required for ALT, and that ALT cells are more sensitive to ATR inhibition (R. L. Flynn, K. E. Cox, Science 2015, 347 (6219), 273-277).

There is a need for therapies having efficacy towards ALT-positive cancers. The ALT pathway is poorly understood, and cancers that feature ALT are resistant to the action of telomerase inhibitors. Thus, described herein are methods for treating cancers, particular ALT-positive types of cancers, using ATR inhibitors.

Disclosed herein are novel compounds and pharmaceutical compositions, certain of which have been found to inhibit ATR kinase, together with methods of synthesizing and using the compounds, including methods for the treatment of ATR kinase-mediated diseases in a patient by administering the compounds.

The disclosure provides the following embodiments.

Provided herein is Embodiment 1: a compound of structural Formula (I):

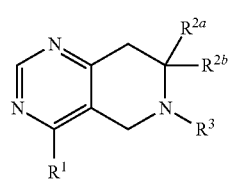

(I)

or a salt thereof, wherein:

$R^1$ is selected from aryl, heteroaryl, $C_{3-10}$cycloalkyl, $C_{6-11}$bridged cycloalkyl, $C_{6-11}$spirocycloalkyl, $C_{3-10}$heterocycloalkyl, $C_{6-11}$bridged heterocycloalkyl, and $C_{6-11}$spiroheterocycloalkyl, and is optionally substituted with one or more $R^4$ groups;

$R^{2a}$ is selected from H, $C_{1-3}$alkyl, and $C_{1-3}$haloalkyl;

$R^{2b}$ is selected from H, $C_{1-3}$alkyl, and $C_{1-3}$haloalkyl;

$R^3$ is $C_{5-10}$aryl or $C_{5-10}$heteroaryl, and is optionally substituted with one or more $R^5$ groups;

each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, $=N-R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;

each $R^5$ is independently selected from amino, halo, cyano, hydroxy, oxo, alkyl, haloalkyl, $C_{3-10}$cycloalkyl, $C_{3-10}$heterocycloalkyl, alkoxy, haloalkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$;

each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, $R^7$ and $R^8$, together with the atom to which they are both attached, can optionally form a 3-7 membered saturated or unsaturated ring optionally containing 1 or 2 heteroatoms, and $R^1$, together with $R^6$, $R^7$, or $R^8$, can optionally form a ring;

each $R^9$, $R^{10}$, and $R^{11}$ is independently selected from hydrogen, alkyl, haloalkyl, $C_{3-7}$cycloalkyl, and $C_{3-7}$heterocycloalkyl, $R^{10}$ and $R^{11}$, together with the atom to which they are both attached, can optionally form a 3-7 membered saturated or unsaturated ring optionally containing 1 or 2 heteroatoms, and $R^3$, together with $R^9$, $R^{10}$, or $R^{11}$, can optionally form a ring; and each $R^{12}$ is independently selected from halo, hydroxy, $C_{1-3}$alkyl, $C_{1-3}$haloalkyl, and alkoxy.

Certain compounds disclosed herein may possess useful ATR kinase inhibiting activity, and may be used in the treatment or prophylaxis of a disease or condition in which ATR kinase plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting ATR kinase. Other embodiments provide methods for treating an ATR kinase-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of ATR kinase.

In certain embodiments, $R^1$ is selected from aryl, heteroaryl, $C_{3-10}$cycloalkyl, and $C_{3-10}$heterocycloalkyl, and is optionally substituted with one or more $R^4$ groups.

In certain embodiments, $R^1$ is selected from $C_{3-10}$cycloalkyl, $C_{3-10}$heterocycloalkyl, $C_{6-11}$bridged heterocycloalkyl, and $C_{6-11}$spiroheterocycloalkyl, and is optionally substituted with one, two, or three $R^4$ groups.

In certain embodiments, $R^1$ is selected from $C_{3-10}$heterocycloalkyl, $C_{6-11}$bridged heterocycloalkyl, and $C_{6-11}$spiroheterocycloalkyl, and is optionally substituted with one, two, or three $R^4$ groups.

In certain embodiments, $R^1$ is $C_{3-10}$heterocycloalkyl, and is optionally substituted with one, two, or three $R^4$ groups.

In certain embodiments, $R^1$ is selected from azetidinyl, pyrrolidinyl, piperidinyl, piperazinyl, azepanyl, and diazepanyl, and is optionally substituted with one or more $R^4$ groups.

In certain embodiments, $R^1$ is selected from azetidinyl, pyrrolidinyl, piperidinyl, piperazinyl, azepanyl, and diazepanyl, and is optionally substituted with one, two, or three $R^4$ groups.

In certain embodiments, $R^1$ is selected from $C_{6-11}$bridged cycloalkyl and $C_{6-11}$bridged heterocycloalkyl, and is optionally substituted with one or more $R^4$ groups.

In certain embodiments, $R^1$ is $C_{6-11}$bridged cycloalkyl, which is optionally substituted with one or more $R^4$ groups.

In certain embodiments, $R^1$ is $C_{6-11}$bridged heterocycloalkyl, which is optionally substituted with one or more $R^4$ groups.

In certain embodiments, $R^1$ is selected from:

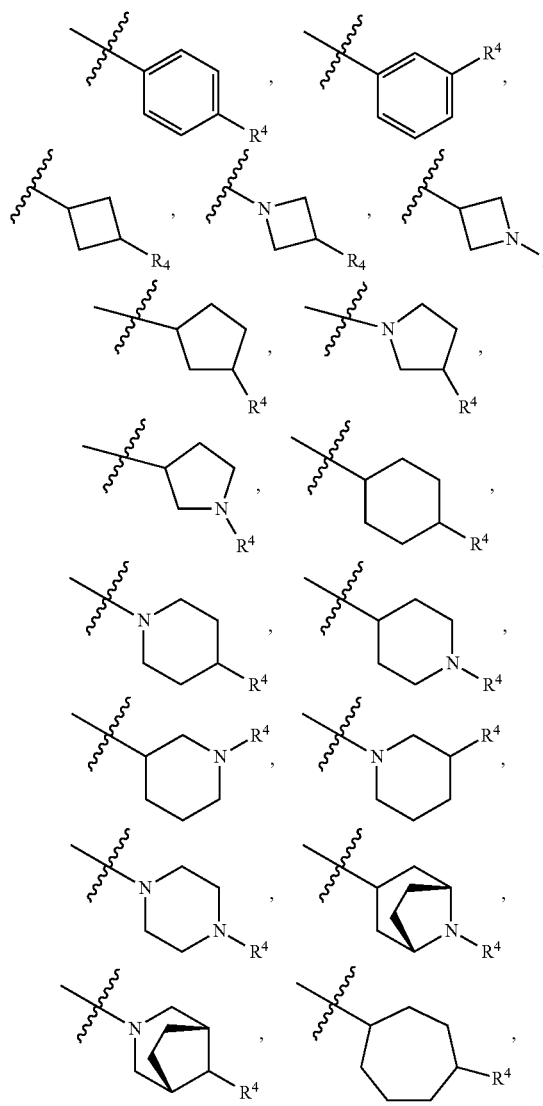

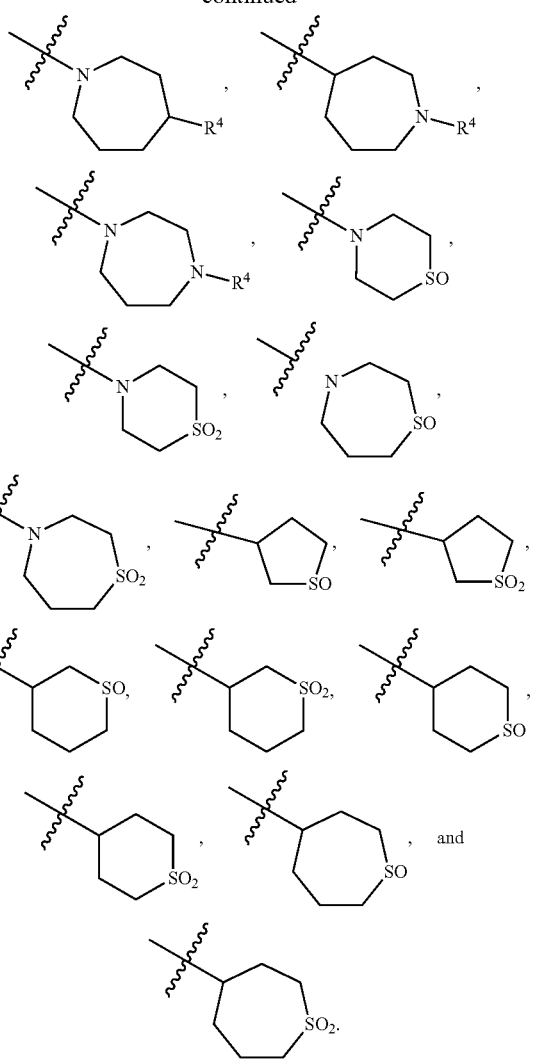

In certain embodiments, $R^1$ is selected from cyclohexyl, piperidinyl, and piperazinyl, and is optionally substituted with one or more $R^4$ groups.

In certain embodiments, R is selected from:

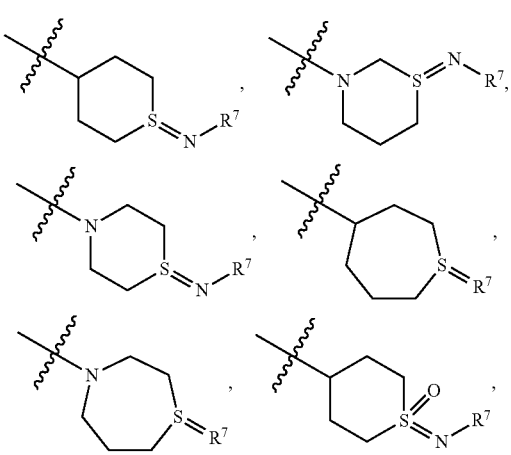

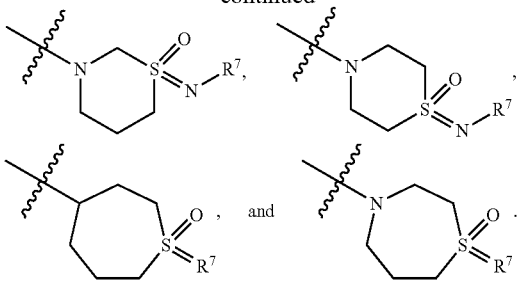

In certain embodiments, R¹ is selected from aryl and heteroaryl, either of which is optionally substituted with one, two, or three R⁴ groups.

In certain embodiments, R¹ is selected from phenyl, azetidinyl, pyridinyl, pyrazinyl, piperidinyl, and pyridazinyl, and is optionally substituted with one, two, or three R⁴ groups.

In certain embodiments, R¹ is selected from phenyl, pyridinyl, pyrazinyl, piperidinyl, and pyridazinyl, and is optionally substituted with one, two, or three R⁴ groups.

In certain embodiments, R¹ is selected from $C_{6-11}$spirocycloalkyl and $C_{6-11}$spiroheterocycloalkyl, and is optionally substituted with one or more R⁴ groups.

In certain embodiments, R¹ is selected from 7-azabicyclo[2.2.1]heptanyl, 8-aza-bicyclo[3.2.1]octanyl, 2-azabicyclo[2.2.2]octanyl, 3-azabicyclo[3.3.1]nonanyl, 9-aza-bicyclo[3.3.1]nonanyl, and 3-azabicyclo[3.2.2]nonanyl, and is optionally substituted with one, two, or three R⁴ groups.

In certain embodiments, R¹ is selected from 2-azaspiro[3.3]heptanyl, 2,6-diazaspiro[3.3]heptanyl, 2-azaspiro[3.3]heptanyl, and 2,7-diazaspiro[4.4]nonanyl, and is optionally substituted with one, two, or three R⁴ groups.

In certain embodiments, R³ is selected from thienyl, pyrrolyl, imidazolyl, pyrazolyl, oxazolyl, isoxazolyl, thiazolyl, isothiazolyl, quinolinyl, isoquinolinyl, indolyl, pyridinyl, pyrimidinyl, pyridazinyl, pyrazinyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two R⁵ groups.

In certain embodiments, R³ is selected from phenyl, pyridinyl, pyrazinyl, piperidinyl, and pyridazinyl, and is optionally substituted with one, two, or three R⁵ groups.

In certain embodiments, R³ is selected from indolyl, pyrrolopyridinyl, pyrazolopyridinyl, pyrazolopyrimidinyl and pyrrolopyrimidinyl, and is optionally substituted with one or more R⁵ groups.

In certain embodiments, R³ is selected from quinolinyl, isoquinolinyl, indolyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two R⁵ groups.

In certain embodiments, R³ is selected from purinyl, pyrrolopyridinyl, pyrazolopyridinyl, pyrazolopyrimidinyl and pyrrolopyrimidinyl, and is optionally substituted with one or two R⁵ groups.

In certain embodiments, R³ is pyrrolopyridinyl, and is optionally substituted with one or more R⁵ groups.

In certain embodiments, R³ is selected from 1H-pyrrolo[2,3-b]pyridin-4-yl and 6-chloro-1H-pyrrolo[2,3-b]pyridin-4-yl, and is optionally substituted with one R⁵ group.

In certain embodiments, R³ is selected from 1H-pyrrolo[2,3-b]pyridin-4-yl and 6-chloro-1H-pyrrolo[2,3-b]pyridin-4-yl.

In certain embodiments,

R³ is selected from:

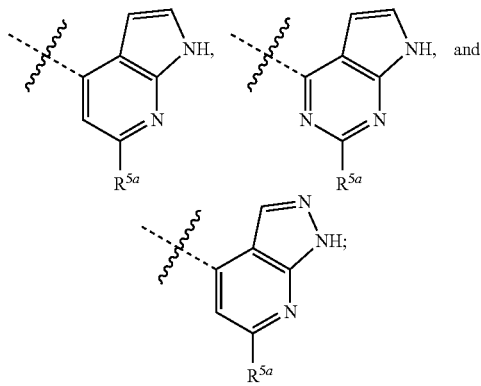

and

R⁵ᵃ is selected from H, amino, halo, and alkoxy.

In certain embodiments, R³ is

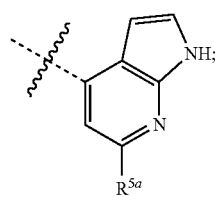

and

R⁵ᵃ is selected from H, amino, halo, cyano, hydroxy, alkyl, haloalkyl, and alkoxy.

In certain embodiments, R³ is selected from:

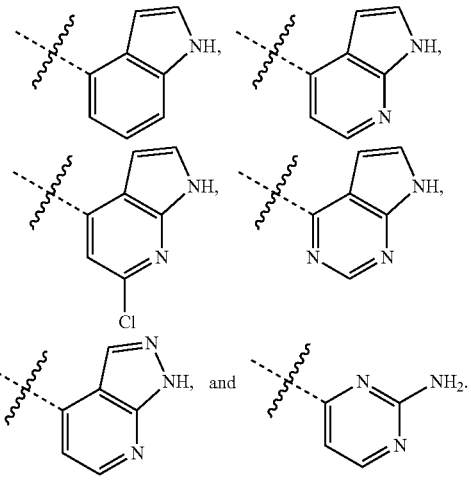

In certain embodiments, each R⁴ is independently selected from amino, halo, cyano, hydroxy, oxo, alkyl, haloakyl, hydroxyalkyl, NR⁶C(O)NR⁷R⁸, NR⁶C(O)R⁷, =N—R⁷, NR⁶C(O)OR⁷, OC(O)NR⁷R⁸, OC(O)R⁷, S(O)R⁷, S(O)₂R⁷, S(O)₂OR⁷, S(O)NR⁷R⁸, S(O)₂NR⁷R⁸, S(O)(NR⁷)R⁸, NR⁶S(O)R⁷, NR⁶S(O)₂R⁷, C(O)OR⁷, C(O)R⁷, C(O)NR⁷R⁸, and OR⁷.

In certain embodiments, each R⁴ is independently selected from amino, halo, cyano, alkyl, haloakyl, hydroxyalkyl, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, and $NR^6S(O)_2R^7$.

In certain embodiments, each $R^4$ is independently selected from amino, halo, cyano, alkyl, haloakyl, hydroxyalkyl, $S(O)_2R^7$, $S(O)_2NR^7R^8$, $S(O)(NR^7)R^8$, and $NR^6S(O)_2R^7$.

In certain embodiments, each $R^4$ is independently selected from alkyl, hydroxy, oxo, $S(O)R^6$, $S(O)_2R^6$, $C(O)NH_2$, =N—$R^7$, $C(O)NHR^7$, $C(O)NR^7R^8$, and $C(O)OR^7$.

In certain embodiments, each $R^4$ is $S(O)_2R^7$.

In certain embodiments, each $R^4$ is $S(O)_2CH_3$.

In certain embodiments, each $R^5$ is independently selected from amino, halo, cyano, hydroxy, oxo, alkyl, haloalkyl, $C_{3-10}$cycloalkyl, $C_{3-10}$heterocycloalkyl, alkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$.

In certain embodiments, each $R^5$ is independently selected from amino, halo, cyano, hydroxy, oxo, and alkyl.

In certain embodiments, each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, and $R^7$ and $R^8$, together with the atom to which they are both attached, can optionally form a 3-7 membered saturated or unsaturated ring optionally containing 1 or 2 heteroatoms.

In certain embodiments, each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, and $R^1$, together with $R^6$, $R^7$, or $R^8$, can optionally form a ring.

In certain embodiments, each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or two $R^{12}$ groups.

In certain embodiments, each $R^9$, $R^{10}$, and $R^{11}$ is independently selected from hydrogen, alkyl, haloalkyl, $C_{3-7}$cycloalkyl, and $C_{3-7}$heterocycloalkyl, and $R^{10}$ and $R^{11}$, together with the atom to which they are both attached, can optionally form a 3-7 membered saturated or unsaturated ring optionally containing 1 or 2 heteroatoms.

In certain embodiments, each $R^9$, $R^{10}$, and $R^{11}$ is independently selected from hydrogen, alkyl, haloalkyl, $C_{3-7}$cycloalkyl, and $C_{3-7}$heterocycloalkyl, and $R^3$, together with $R^9$, $R^{10}$, or $R^{11}$, can optionally form a ring.

In certain embodiments, each $R^9$, $R^{10}$, and $R^{11}$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups.

In certain embodiments, each $R^9$, $R^{10}$, and $R^{11}$ is independently selected from hydrogen, alkyl, haloalkyl, $C_{3-7}$cycloalkyl, and $C_{3-7}$heterocycloalkyl.

The disclosure provides the further embodiments.

Embodiment 2: The compound of Embodiment 1, wherein each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, and $R^7$ and $R^8$, together with the atom to which they are both attached, can optionally form a 3-7 membered saturated or unsaturated ring optionally containing 1 or 2 heteroatoms.

Embodiment 3: The compound of Embodiment 1, wherein each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, and $R^1$, together with $R^6$, $R^7$, or $R^8$, can optionally form a ring.

Embodiment 4: The compound of Embodiment 1, wherein each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or two $R^{12}$ groups.

Embodiment 5: The compound of any of Embodiments 1-4, wherein each $R^9$, $R^{10}$, and $R^{11}$ is independently selected from hydrogen, alkyl, haloalkyl, $C_{3-7}$cycloalkyl, and $C_{3-7}$heterocycloalkyl, and $R^{10}$ and $R^{11}$, together with the atom to which they are both attached, can optionally form a 3-7 membered saturated or unsaturated ring optionally containing 1 or 2 heteroatoms.

Embodiment 6: The compound of any of Embodiments 1-4, wherein each $R^9$, $R^{10}$, and $R^{11}$ is independently selected from hydrogen, alkyl, haloalkyl, $C_{3-7}$cycloalkyl, and $C_{3-7}$heterocycloalkyl, and $R^3$, together with $R^9$, $R^{10}$, or $R^{11}$, can optionally form a ring.

Embodiment 7: The compound of any of Embodiments 1-4, wherein each $R^9$, $R^{10}$, and $R^{11}$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups.

Embodiment 8: The compound of any of Embodiments 1-4, wherein each $R^9$, $R^{10}$, and $R^{11}$ is independently selected from hydrogen, alkyl, haloalkyl, $C_{3-7}$cycloalkyl, and $C_{3-7}$heterocycloalkyl.

Embodiment 9: The compound of Embodiment 1, wherein:
each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, and $R^7$ and $R^8$, together with the atom to which they are both attached, can optionally form a 3-7 membered saturated or unsaturated ring optionally containing 1 or 2 heteroatoms; and
each $R^9$, $R^{10}$, and $R^{11}$ is independently selected from hydrogen, alkyl, haloalkyl, $C_{3-7}$cycloalkyl, and $C_{3-7}$heterocycloalkyl, and $R^{10}$ and $R^{11}$, together with the atom to which they are both attached, can optionally form a 3-7 membered saturated or unsaturated ring optionally containing 1 or 2 heteroatoms.

Embodiment 10: The compound of Embodiment 1, wherein
each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups; and
each $R^9$, $R^{10}$, and $R^{11}$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups.

Embodiment 11: The compound of any of Embodiments 1-10, wherein $R^3$ is selected from thienyl, pyrrolyl, imidazolyl, pyrazolyl, oxazolyl, isoxazolyl, thiazolyl, isothiazolyl, quinolinyl, isoquinolinyl, indolyl, pyridinyl, pyrimidinyl, pyridazinyl, pyrazinyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 12: The compound of Embodiment 11, wherein $R^3$ is selected from phenyl, pyridinyl, pyrazinyl, piperidinyl, and pyridazinyl, and is optionally substituted with one, two, or three $R^5$ groups.

Embodiment 13: The compound of Embodiment 11, wherein $R^3$ is selected from indolyl, pyrrolopyridinyl, pyrazolopyridinyl, pyrazolopyrimidinyl and pyrrolopyrimidinyl, and is optionally substituted with one or more $R^5$ groups.

Embodiment 14: The compound of Embodiment 11, wherein $R^3$ is selected from quinolinyl, isoquinolinyl, indolyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 15: The compound of Embodiment 11, wherein $R^3$ is selected from purinyl, pyrrolopyridinyl, pyrazolopyridinyl, pyrazolopyrimidinyl and pyrrolopyrimidinyl, and is optionally substituted with one or two $R^5$ groups.

Embodiment 16: The compound of Embodiment 11, wherein $R^3$ is pyrrolopyridinyl, and is optionally substituted with one or more $R^5$ groups.

Embodiment 17: The compound of Embodiment 11, wherein $R^3$ is selected from 1H-pyrrolo[2,3-b]pyridin-4-yl and 6-chloro-1H-pyrrolo[2,3-b]pyridin-4-yl, and is optionally substituted with one $R^5$ group.

Embodiment 18: The compound of Embodiment 11, wherein $R^3$ is selected from 1H-pyrrolo[2,3-b]pyridin-4-yl and 6-chloro-1H-pyrrolo[2,3-b]pyridin-4-yl.

Embodiment 19: The compound of Embodiment 11, wherein:
$R^3$ is selected from:

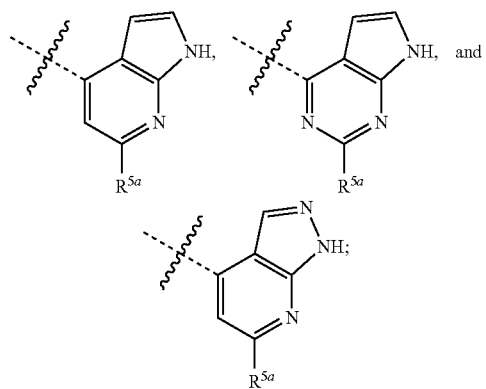

and
$R^{5a}$ is selected from H, amino, halo, and alkoxy.

Embodiment 20: The compound of Embodiment 11, wherein:
$R^3$ is

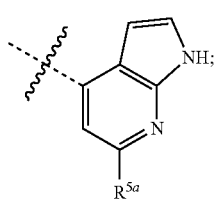

and
$R^{5a}$ is selected from H, amino, halo, cyano, hydroxy, alkyl, haloalkyl, and alkoxy.

Embodiment 21: The compound of Embodiment 11, wherein $R^3$ is selected from:

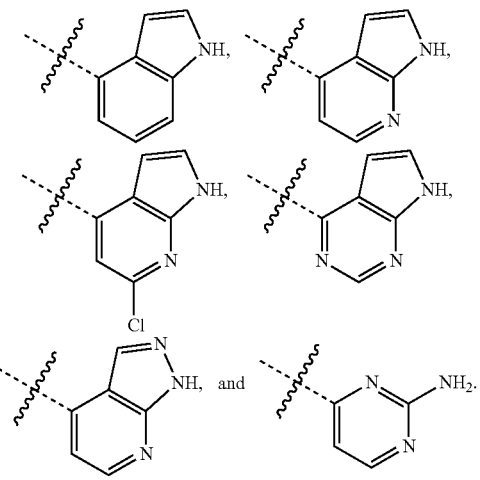

The compound of any of Embodiments 1-21, wherein $R^1$ is selected from $C_{3-10}$cycloalkyl, $C_{3-10}$heterocycloalkyl, $C_{6-11}$bridged heterocycloalkyl, and $C_{6-11}$ spiroheterocycloalkyl, and is optionally substituted with one, two, or three $R^4$ groups.

Embodiment 23: The compound of Embodiment 22, wherein $R^1$ is selected from $C_{3-10}$heterocycloalkyl, $C_{6-11}$bridged heterocycloalkyl, and $C_{6-11}$spiroheterocycloalkyl, and is optionally substituted with one, two, or three $R^4$ groups.

Embodiment 24: The compound of Embodiment 22, wherein $R^1$ is $C_{3-10}$hetero-cycloalkyl, and is optionally substituted with one, two, or three $R^4$ groups.

Embodiment 25: The compound of Embodiment 22, wherein $R^1$ is selected from azetidinyl, pyrrolidinyl, piperidinyl, piperazinyl, azepanyl, and diazepanyl, and is optionally substituted with one, two, or three $R^4$ groups.

Embodiment 26: The compound of Embodiment 22, wherein $R^1$ is selected from $C_{6-11}$bridged cycloalkyl and $C_{6-11}$bridged heterocycloalkyl, and is optionally substituted with one or more $R^4$ groups.

Embodiment 27: The compound of Embodiment 22, wherein $R^1$ is $C_{6-11}$bridged cycloalkyl, which is optionally substituted with one or more $R^4$ groups.

Embodiment 28: The compound of Embodiment 22, wherein $R^1$ is $C_{6-11}$bridged heterocycloalkyl, which is optionally substituted with one or more $R^4$ groups.

Embodiment 29: The compound of Embodiment 22, wherein $R^1$ is selected from:

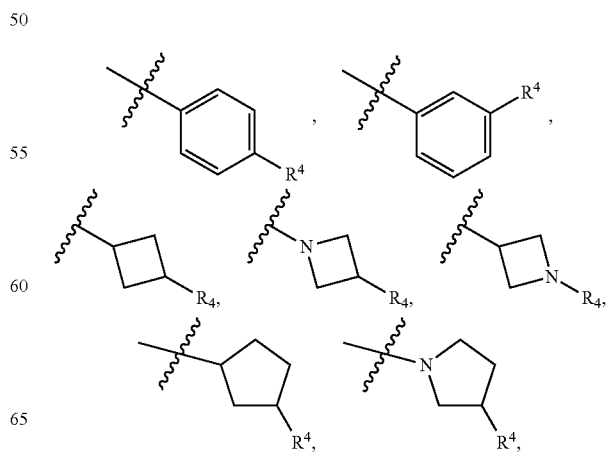

-continued

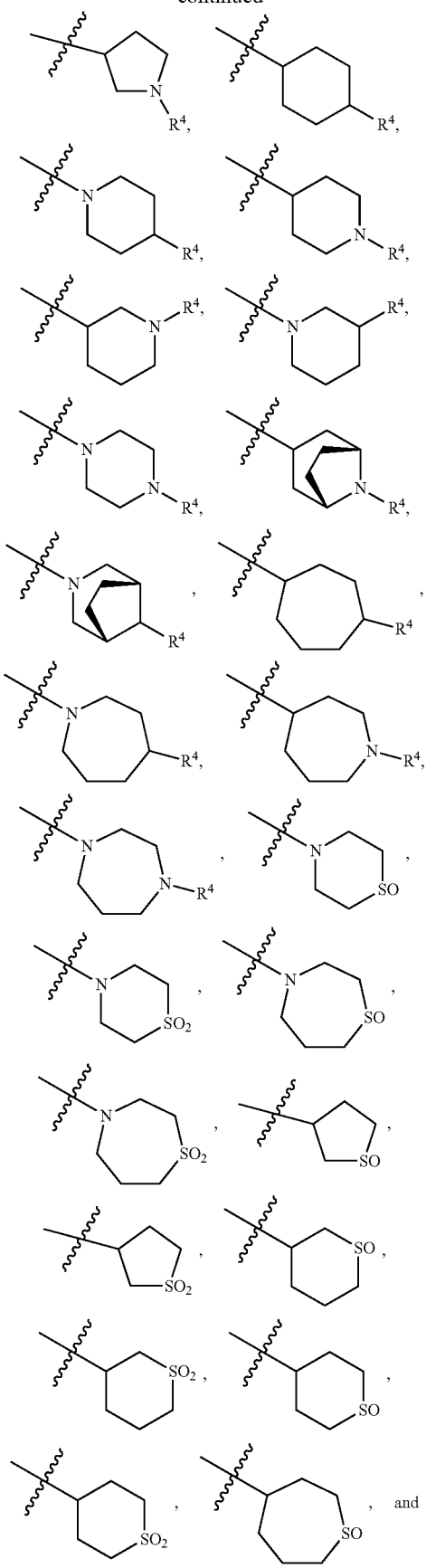

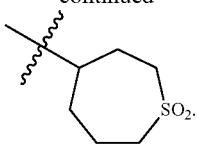

Embodiment 30: The compound of Embodiment 22, wherein $R^1$ is selected from cyclohexyl, piperidinyl, and piperazinyl, and is optionally substituted with one or more $R^4$ groups.

Embodiment 31: The compound of Embodiment 22, wherein $R^1$ is selected from:

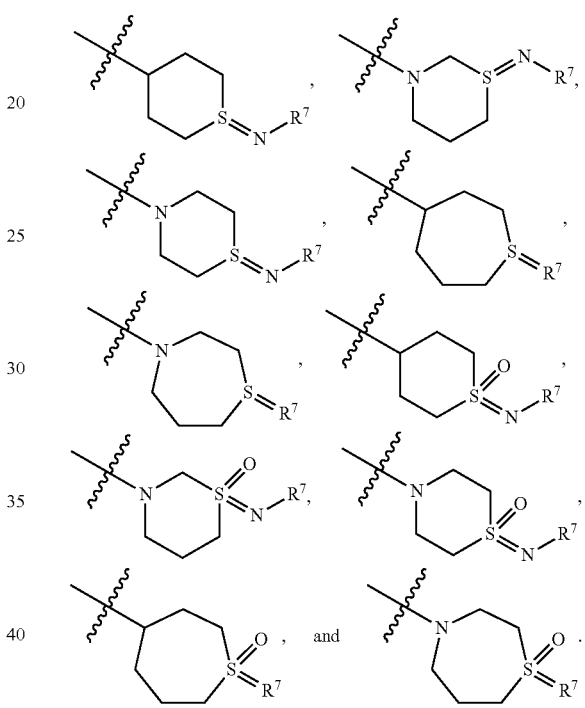

Embodiment 32: The compound of Embodiment 22, wherein $R^1$ is selected from $C_{6-11}$spirocycloalkyl and $C_{6-15}$spiroheterocycloalkyl, and is optionally substituted with one or more $R^4$ groups.

Embodiment 33: The compound of Embodiment 22, wherein $R^1$ is selected from 2-azaspiro[3.3]heptanyl, 2,6-diazaspiro[3.3]heptanyl, 2-azaspiro[3.3]heptanyl, and 2,7-diazaspiro[4.4]nonanyl, and is optionally substituted with one, two, or three $R^4$ groups.

Embodiment 34: The compound of Embodiment 22, wherein $R^1$ is selected from 7-azabicyclo[2.2.1]heptanyl, 8-azabicyclo[3.2.1]octanyl, 2-azabicyclo[2.2.2]octanyl, 3-aza-bicyclo[3.3.1]nonanyl, 9-azabicyclo[3.3.1]nonanyl, and 3-azabicyclo[3.2.2]nonanyl, and is optionally substituted with one, two, or three $R^4$ groups.

Embodiment 35: The compound of any of Embodiments 1-21, wherein $R^1$ is selected from aryl and heteroaryl, either of which is optionally substituted with one, two, or three $R^4$ groups.

Embodiment 36: The compound of Embodiment 35, wherein $R^1$ is selected from phenyl, pyridinyl, pyrazinyl, piperidinyl, and pyridazinyl, and is optionally substituted with one, two, or three $R^4$ groups.

Embodiment 37: The compound of Embodiment 35, wherein $R^1$ is selected from phenyl, pyridinyl, pyrazinyl, piperidinyl, and pyridazinyl, and is optionally substituted with one, two, or three $R^4$ groups.

Embodiment 38: The compound of any of Embodiments 1-37, wherein each $R^4$ is independently selected from amino, halo, cyano, hydroxy, oxo, alkyl, haloakyl, hydroxyalkyl, $NR^6C(O)NR^7R^8$, $NR^6C(O)R^7$, $=N—R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$.

Embodiment 39: The compound of Embodiment 38, wherein each $R^4$ is independently selected from amino, halo, cyano, alkyl, haloakyl, hydroxyalkyl, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, and $NR^6S(O)_2R^7$.

Embodiment 40: The compound of Embodiment 38, wherein each $R^4$ is independently selected from amino, halo, cyano, alkyl, haloakyl, hydroxyalkyl, $S(O)_2R^7$, $S(O)_2NR^7R^8$, $S(O)(NR^7)R^8$, and $NR^6S(O)_2R^7$.

Embodiment 41: The compound of Embodiment 38, wherein each $R^4$ is independently selected from alkyl, hydroxy, oxo, $S(O)R^6$, $S(O)_2R^6$, $C(O)NH_2$, $=N—R^7$, $C(O)NHR^7$, $C(O)NR^7R^8$, and $C(O)OR^7$.

Embodiment 42: The compound of Embodiment 38, wherein each $R^4$ is $S(O)_2R^7$.

Embodiment 43: The compound of Embodiment 38, wherein each $R^4$ is $S(O)_2CH_3$.

Embodiment 44: The compound of any of Embodiments 1-43, wherein each $R^5$ is independently selected from amino, halo, cyano, hydroxy, oxo, alkyl, haloalkyl, $C_{3-10}$cycloalkyl, $C_{3-10}$heterocycloalkyl, alkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2R^{10}$, $S(O)NR^{10}R^{11}$, $S(O)_2NR^{10}R^{11}$, $S(O)(NR^{10})R^{11}$, and $C(O)OR^{10}$.

Embodiment 45: The compound of Embodiment 44, wherein each $R^5$ is independently selected from amino, halo, cyano, hydroxy, oxo, and alkyl.

Also provided herein is Embodiment 46: a compound of Formula (II):

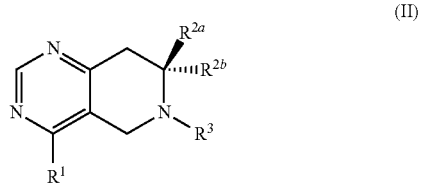

or a salt thereof, wherein:

$R^1$ is selected from aryl, heteroaryl, $C_{3-10}$cycloalkyl, $C_{6-11}$bridged cycloalkyl, $C_{6-11}$spirocycloalkyl, $C_{3-10}$heterocycloalkyl, $C_{6-11}$bridged heterocycloalkyl, and $C_{6-11}$ spiroheterocycloalkyl, and is optionally substituted with one or more $R^4$ groups;

$R^{2a}$ is selected from H, $C_{1-3}$alkyl, and $C_{1-3}$haloalkyl;

$R^{2b}$ is selected from H, $C_{1-3}$alkyl, and $C_{1-3}$haloalkyl;

$R^3$ is $C_{5-10}$aryl or $C_{5-10}$heteroaryl, and is optionally substituted with one or more $R^5$ groups;

each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, $=N—R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;

each $R^5$ is independently selected from amino, halo, cyano, hydroxy, oxo, alkyl, haloalkyl, $C_{3-10}$cycloalkyl, $C_{3-10}$heterocycloalkyl, alkoxy, haloalkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$;

each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, $R^7$ and $R^8$, together with the atom to which they are both attached, can optionally form a 3-7 membered saturated or unsaturated ring optionally containing 1 or 2 heteroatoms, and $R^1$, together with $R^6$, $R^7$, or $R^8$, can optionally form a ring;

each $R^9$, $R^{10}$, and $R^{11}$ is independently selected from hydrogen, alkyl, haloalkyl, $C_{3-7}$cycloalkyl, and $C_{3-7}$heterocycloalkyl, $R^{10}$ and $R^{11}$, together with the atom to which they are both attached, can optionally form a 3-7 membered saturated or unsaturated ring optionally containing 1 or 2 heteroatoms, and $R^3$, together with $R^9$, $R^{10}$, or $R^{11}$, can optionally form a ring; and each $R^{12}$ is independently selected from halo, hydroxy, $C_{1-3}$alkyl, $C_{1-3}$haloalkyl, and alkoxy.

In certain embodiments, $R^{2a}$ and $R^{2b}$ are both H.
In certain embodiments, exactly one of $R^{2a}$ and $R^{2b}$ is H.
In certain embodiments, $R^{2b}$ is H.
In certain embodiments, $R^{2a}$ is $C_{1-3}$alkyl.
In certain embodiments, $R^{2a}$ is selected from methyl and ethyl.
In certain embodiments, $R^{2a}$ is selected from methyl, fluoromethyl, difluoromethyl, and trifluoromethyl.
In certain embodiments, $R^{2a}$ is methyl.

The disclosure provides the further embodiments:

Embodiment 47: The compound of Embodiment 46, wherein exactly one of $R^{2a}$ and $R^{2b}$ is H.

Embodiment 48: The compound of Embodiment 47, wherein $R^{2b}$ is H.

Embodiment 49: The compound of Embodiment 48, wherein $R^{2a}$ is $C_{1-3}$alkyl.

Embodiment 50: The compound of any of Embodiments 46-49, wherein $R^3$ is selected from thienyl, pyrrolyl, imidazolyl, pyrazolyl, oxazolyl, isoxazolyl, thiazolyl, isothiazolyl, quinolinyl, isoquinolinyl, indolyl, pyridinyl, pyrimidinyl, pyridazinyl, pyrazinyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 51: The compound of Embodiment 50, wherein $R^3$ is selected from quinolinyl, isoquinolinyl, indolyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 52: The compound of Embodiment 51, wherein $R^3$ is selected from purinyl, pyrrolopyridinyl, pyrazolopyridinyl, pyrazolopyrimidinyl and pyrrolopyrimidinyl, and is optionally substituted with one or two $R^5$ groups.

Embodiment 53: The compound of any of Embodiments 46-52, wherein each $R^5$ is independently selected from amino, halo, cyano, hydroxy, oxo, and alkyl.

Embodiment 54: The compound of any of Embodiments 46-53, wherein $R^1$ is selected from $C_{3-10}$heterocycloalkyl, $C_{6-11}$ bridged heterocycloalkyl, and $C_{6-11}$ spiroheterocycloalkyl, and is optionally substituted with one, two, or three $R^4$ groups.

Embodiment 55: The compound of Embodiment 54, wherein $R^1$ is $C_{3-10}$heterocycloalkyl, and is optionally substituted with one, two, or three $R^4$ groups.

Embodiment 56: The compound of Embodiment 55, wherein $R^1$ is selected from azetidinyl, pyrrolidinyl, piperidinyl, piperazinyl, azepanyl, and diazepanyl, and is optionally substituted with one, two, or three $R^4$ groups.

Embodiment 57: The compound of any of Embodiments 46-53, wherein $R^1$ is selected from phenyl, pyridinyl, pyrazinyl, piperidinyl, and pyridazinyl, and is optionally substituted with one, two, or three $R^4$ groups.

Also provided herein is Embodiment 58: a compound of structural Formula (III):

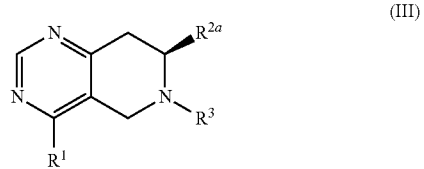

(III)

or a salt thereof, wherein:

$R^1$ is selected from aryl, heteroaryl, $C_{3-10}$cycloalkyl, $C_{6-11}$bridged cycloalkyl, $C_{6-11}$spirocycloalkyl, $C_{3-10}$heterocycloalkyl, $C_{6-11}$bridged heterocycloalkyl, and $C_{6-11}$spiroheterocycloalkyl, and is optionally substituted with one or more $R^4$ groups;

$R^{2a}$ is selected from $C_{1-3}$alkyl, and $C_{1-3}$haloalkyl;

$R^3$ is $C_{5-10}$aryl or $C_{5-10}$heteroaryl, and is optionally substituted with one or more $R^5$ groups;

each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, =N—$R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;

each $R^5$ is independently selected from amino, halo, cyano, hydroxy, oxo, alkyl, haloalkyl, $C_{3-10}$cycloalkyl, $C_{3-10}$heterocycloalkyl, alkoxy, haloalkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$;

each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, $R^7$ and $R^8$, together with the atom to which they are both attached, can optionally form a 3-7 membered saturated or unsaturated ring optionally containing 1 or 2 heteroatoms, and $R^1$, together with $R^6$, $R^7$, or $R^8$, can optionally form a ring;

each $R^9$, $R^{10}$, and $R^{11}$ is independently selected from hydrogen, alkyl, haloalkyl, $C_{3-7}$cycloalkyl, and $C_{3-7}$heterocycloalkyl, $R^{10}$ and $R^{11}$, together with the atom to which they are both attached, can optionally form a 3-7 membered saturated or unsaturated ring optionally containing 1 or 2 heteroatoms, and $R^3$, together with $R^9$, $R^{10}$, or $R^{11}$, can optionally form a ring; and each $R^{12}$ is independently selected from halo, hydroxy, $C_{1-3}$alkyl, $C_{1-3}$haloalkyl, and alkoxy.

The disclosure provides the further embodiments:

Embodiment 59: The compound of Embodiment 58, wherein $R^{2a}$ is $C_{1-3}$alkyl.

Embodiment 60: The compound of any of Embodiments 58-59, wherein $R^3$ is selected from thienyl, pyrrolyl, imidazolyl, pyrazolyl, oxazolyl, isoxazolyl, thiazolyl, isothiazolyl, quinolinyl, isoquinolinyl, indolyl, pyridinyl, pyrimidinyl, pyridazinyl, pyrazinyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 61: The compound of Embodiment 60, wherein $R^3$ is selected from quinolinyl, isoquinolinyl, indolyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

Embodiment 62: The compound of Embodiment 61, wherein $R^3$ is selected from purinyl, pyrrolopyridinyl, pyrazolopyridinyl, pyrazolopyrimidinyl and pyrrolopyrimidinyl, and is optionally substituted with one or two $R^5$ groups.

Embodiment 63: The compound of Embodiment 60, wherein $R^3$ is selected from 1H-pyrrolo[2,3-b]pyridin-4-yl and 6-chloro-1H-pyrrolo[2,3-b]pyridin-4-yl.

Embodiment 64: The compound of any of Embodiments 58-63, wherein each $R^5$ is independently selected from amino, halo, cyano, hydroxy, oxo, and alkyl.

Embodiment 65: The compound of any of Embodiments 58-64, wherein $R^1$ is selected from $C_{3-10}$heterocycloalkyl, $C_{6-11}$ bridged heterocycloalkyl and $C_{6-11}$ spiroheterocycloalkyl, and is optionally substituted with one, two, or three $R^4$ groups.

Embodiment 66: The compound of Embodiment 65, wherein $R^1$ is $C_{3-10}$heterocycloalkyl, and is optionally substituted with one, two, or three $R^4$ groups.

Embodiment 67: The compound of Embodiment 66, wherein $R^1$ is selected from azetidinyl, pyrrolidinyl, piperidinyl, piperazinyl, azepanyl, and diazepanyl, and is optionally substituted with one, two, or three $R^4$ groups.

Embodiment 68: The compound of Embodiment 66, wherein $R^1$ is selected from azetidinyl, pyrrolidinyl, piperidinyl, piperazinyl, azepanyl, and diazepanyl, and is optionally substituted with one, two, or three $R^4$ groups.

Embodiment 69: The compound of any of Embodiments 58-64, wherein $R^1$ is selected from aryl and heteroaryl, either of which is optionally substituted with one, two, or three $R^4$ groups.

Embodiment 70: The compound of Embodiment 69, wherein $R^1$ is selected from phenyl, pyridinyl, pyrazinyl, piperidinyl, and pyridazinyl, and is optionally substituted with one, two, or three $R^4$ groups.

Embodiment 71: The compound of any of Embodiments 58-70, wherein each $R^4$ is independently selected from alkyl, hydroxy, oxo, $S(O)R^6$, $S(O)_2R^6$, $C(O)NH_2$, =N—$R^7$, $C(O)NHR^7$, $C(O)NR^7R^8$, and $C(O)OR^7$.

Also provided herein is Embodiment 72: a compound of structural Formula (IV):

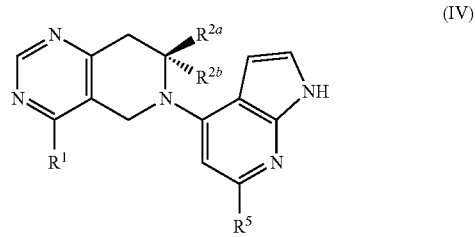

(IV)

or a salt thereof, wherein:

R¹ is selected from aryl, heteroaryl, $C_{3-10}$cycloalkyl, $C_{6-11}$spirocycloalkyl, $C_{6-11}$bridged cycloalkyl, $C_{3-10}$heterocycloalkyl, $C_{6-11}$bridged heterocycloalkyl, and $C_{6-11}$spiroheterocycloalkyl, and is optionally substituted with one or more R⁴ groups;

$R^{2a}$ is selected from H, $C_{1-3}$alkyl, and $C_{1-3}$haloalkyl;

$R^{2b}$ is selected from H, $C_{1-3}$alkyl, and $C_{1-3}$haloalkyl;

each R⁴ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, =N—R⁷, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;

R⁵ is selected from amino, halo, cyano, hydroxy, oxo, alkyl, haloalkyl, $C_{3-10}$cycloalkyl, $C_{3-10}$heterocycloalkyl, alkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2R^{10}$, $S(O)NR^{10}R^{11}$, $S(O)_2NR^{10}R^{11}$, $S(O)(NR^{11})R^{11}$, and $C(O)OR^{10}$;

each R⁶, R⁷, and R⁸ is independently selected from hydrogen, alkyl, haloalkyl, $C_{3-7}$cycloalkyl, and $C_{3-7}$heterocycloalkyl, any of which, excluding hydrogen, is optionally substituted with one or more R¹² groups, R⁷ and R⁸, together with the atom to which they are both attached, can optionally form a 3-7 membered saturated or unsaturated ring optionally containing 1 or 2 heteroatoms, and R¹, together with R⁶, R⁷, or R⁸, can optionally form a ring;

each R⁹, R¹⁰, and R¹¹ is independently selected from hydrogen, alkyl, haloalkyl, $C_{3-7}$cycloalkyl, and $C_{3-7}$heterocycloalkyl, R¹⁰ and R¹¹, together with the atom to which they are both attached, can optionally form a 3-7 membered saturated or unsaturated ring optionally containing 1 or 2 heteroatoms, and R³, together with R⁹, R¹⁰, or R¹¹, can optionally form a ring; and each R¹² is independently selected from halo, hydroxy, $C_{1-3}$alkyl, $C_{1-3}$haloalkyl, and alkoxy.

In certain embodiments, $R^{2a}$ and $R^{2b}$ are both H.

In certain embodiments, exactly one of $R^{2a}$ and $R^{2b}$ is H.

In certain embodiments, $R^{2b}$ is H.

In certain embodiments, R⁵ is selected from H, amino, halo, cyano, alkyl, and cycloalkyl.

The disclosure provides the further embodiments:

Embodiment 73: The compound of Embodiment 72, wherein $R^{2b}$ is H.

Embodiment 74: The compound of any of Embodiments 72-73, wherein:

each R⁶, R⁷, and R⁸ is independently selected from hydrogen, alkyl, haloalkyl, $C_{3-7}$cycloalkyl, and $C_{3-7}$heterocycloalkyl, any of which, excluding hydrogen, is optionally substituted with one or more R¹² groups; and each R⁹, R¹⁰, and R¹¹ is independently selected from hydrogen, alkyl, haloalkyl, $C_{3-7}$cycloalkyl, and $C_{3-7}$heterocycloalkyl.

Embodiment 75: The compound of any of Embodiments 72-74, wherein R¹ is selected from aryl, heteroaryl, $C_{3-10}$cycloalkyl, $C_{6-11}$spirocycloalkyl, $C_{6-11}$bridged cycloalkyl, $C_{3-10}$heterocycloalkyl, $C_{6-11}$bridged heterocycloalkyl, and $C_{6-11}$spiroheterocycloalkyl, and is optionally substituted with one, two, or three R⁴ groups.

Embodiment 76: The compound of Embodiment 75, wherein R¹ is selected from phenyl, azetidinyl, pyridinyl, pyrazinyl, piperidinyl, and pyridazinyl, and is optionally substituted with one, two, or three R⁴ groups.

Embodiment 77: The compound of Embodiment 75, wherein R¹ is selected from $C_{3-10}$heterocycloalkyl, $C_{6-11}$bridged heterocycloalkyl, and $C_{6-11}$spiroheterocycloalkyl, and is optionally substituted with one, two, or three R⁴ groups.

Embodiment 78: The compound of Embodiment 77, wherein R¹ is $C_{3-10}$heterocycloalkyl, and is optionally substituted with one, two, or three R⁴ groups.

Embodiment 79: The compound of Embodiment 78, wherein R¹ is selected from azetidinyl, pyrrolidinyl, piperidinyl, piperazinyl, azepanyl, and diazepanyl, and is optionally substituted with one, two, or three R⁴ groups.

Embodiment 80: The compound of Embodiment 79, wherein R¹ is azetidinyl.

Embodiment 81: The compound of Embodiment 79, wherein R¹ is piperidinyl.

Embodiment 82: The compound of any of Embodiments 72-81, wherein each R⁴ is independently selected from hydroxy, =N—R⁷, $S(O)_2R^7$, $C(O)NR^7R^8$, and $NHS(O)_2R^7$.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein, e.g., chosen from:

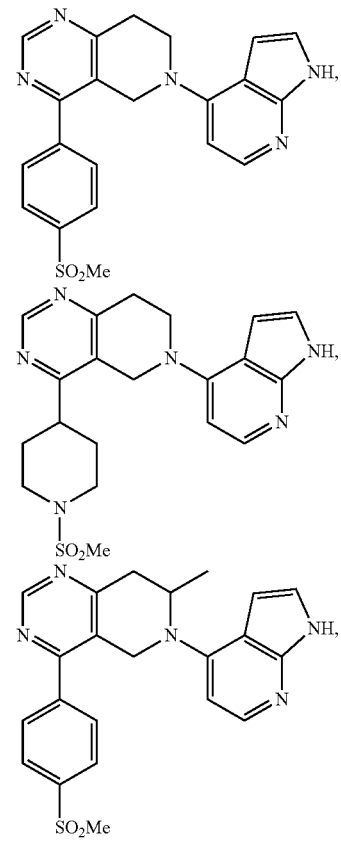

-continued
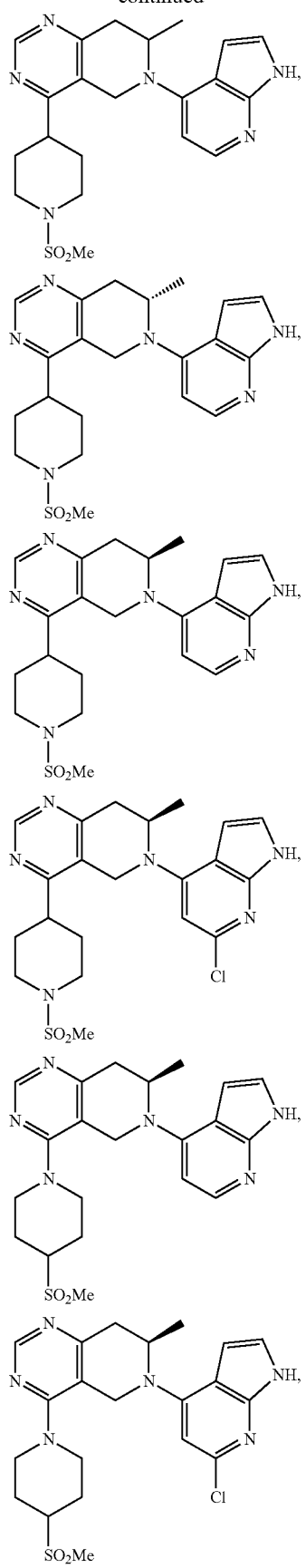
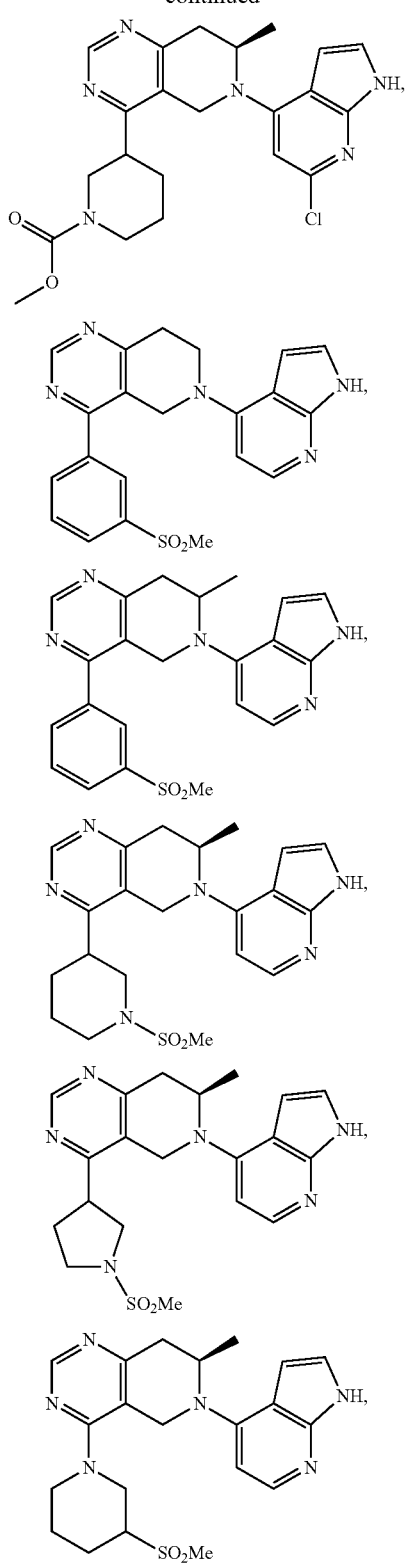

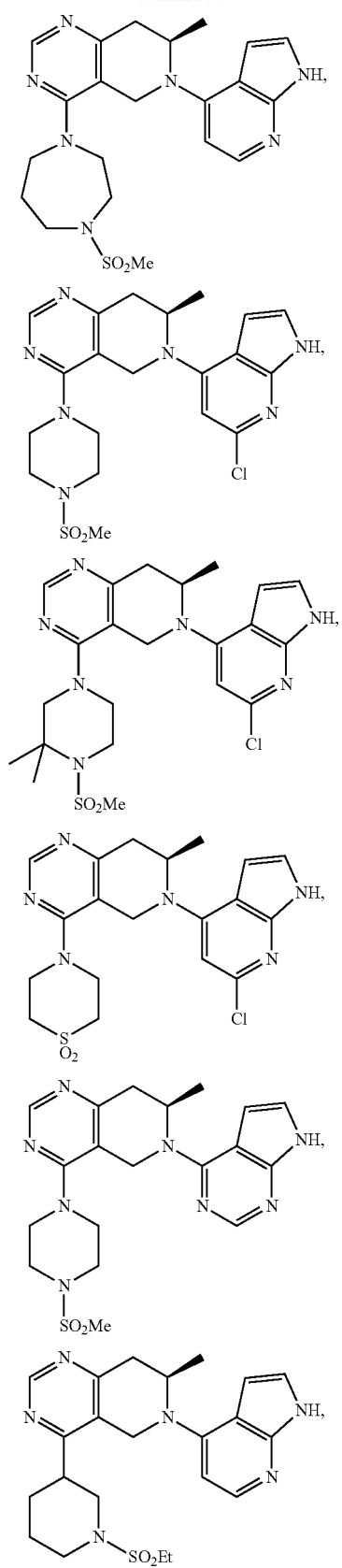
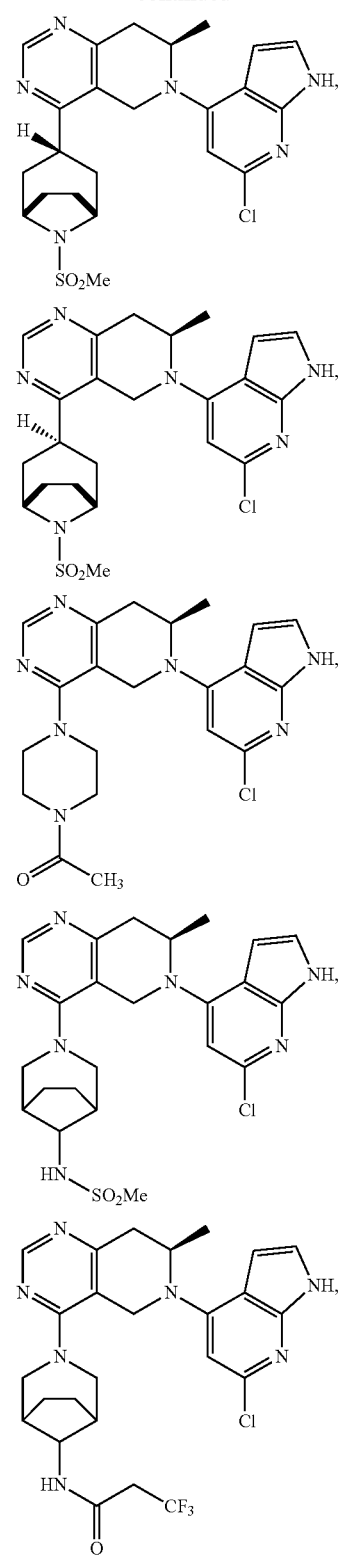

-continued
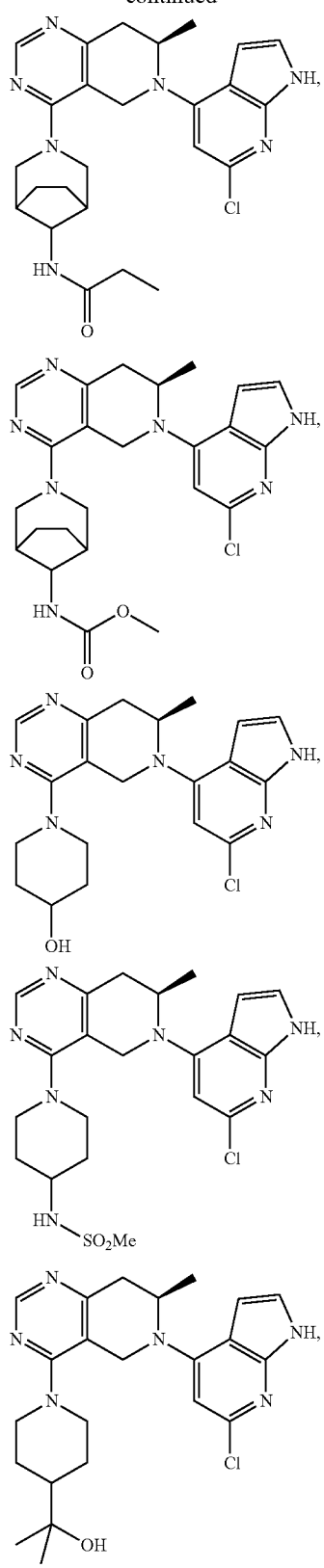
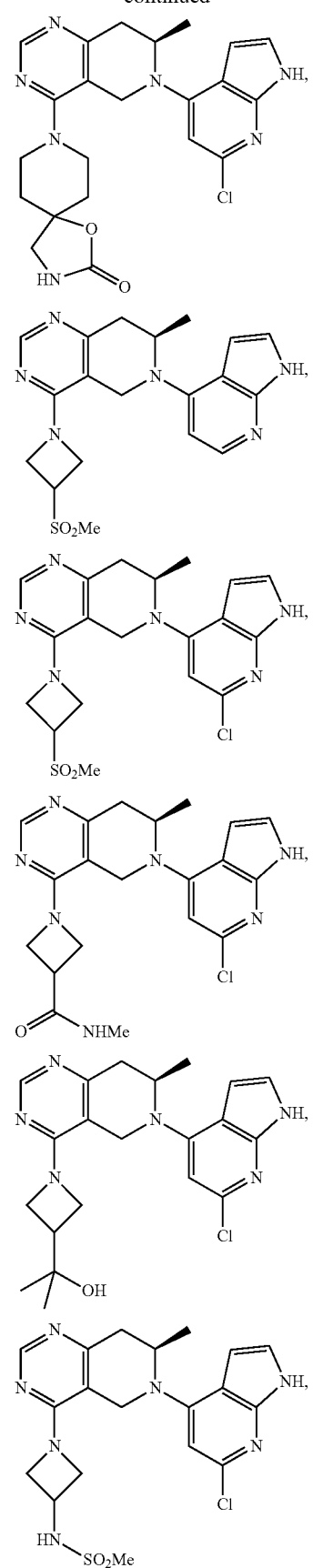

-continued
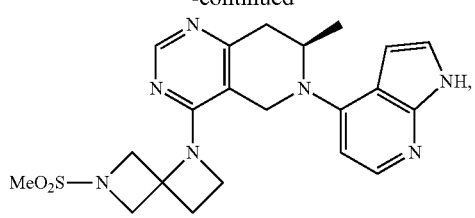
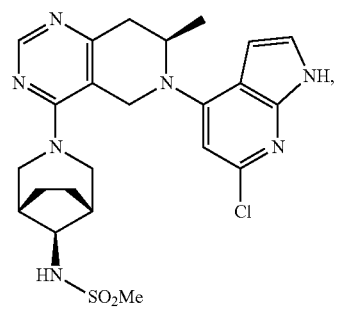
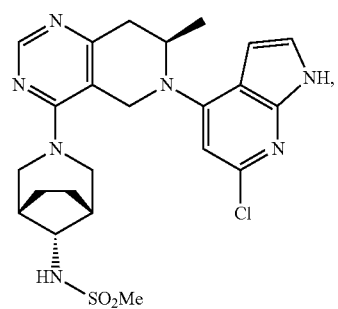
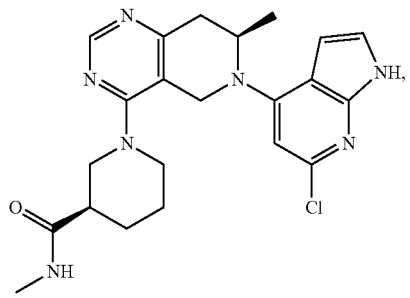
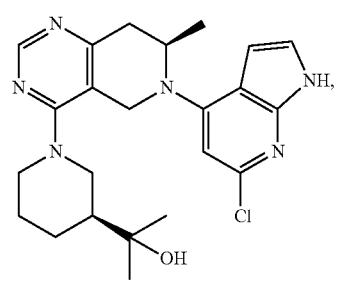
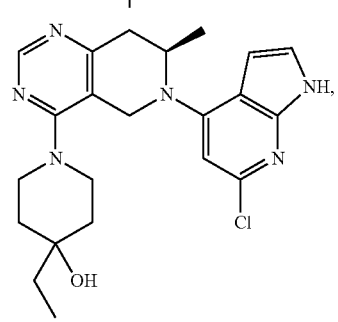
-continued
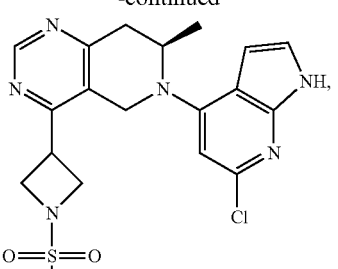
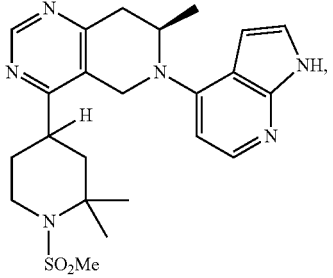
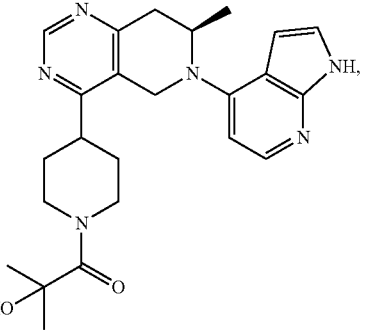
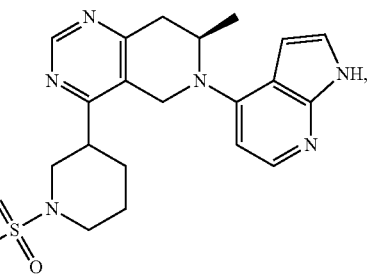
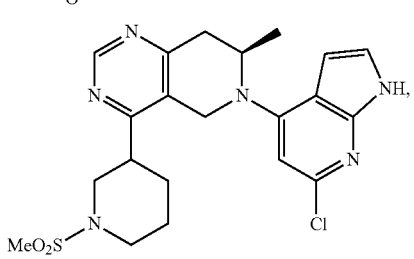

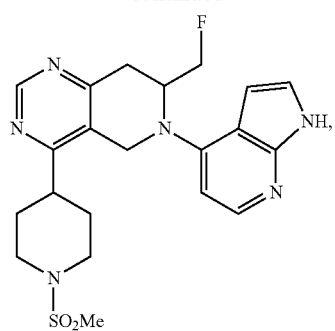
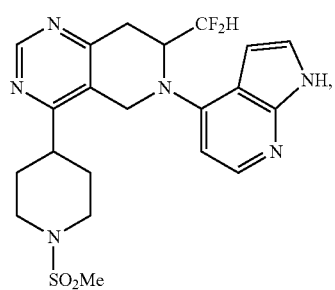
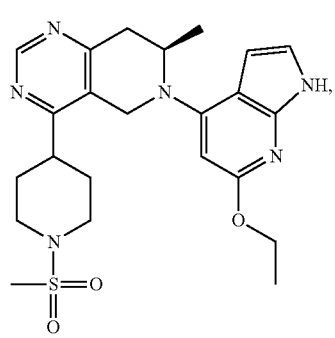
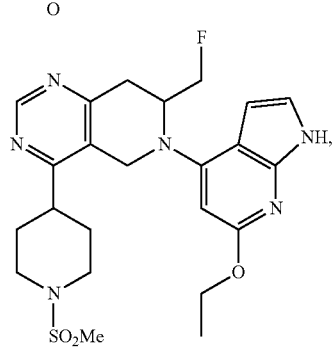
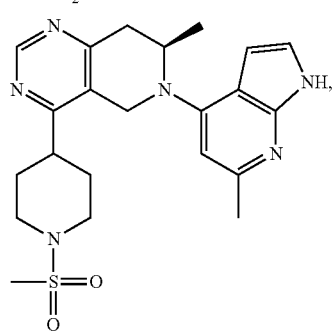
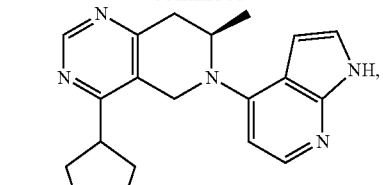
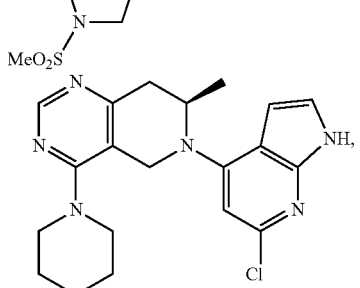
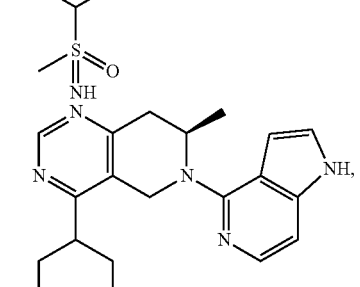
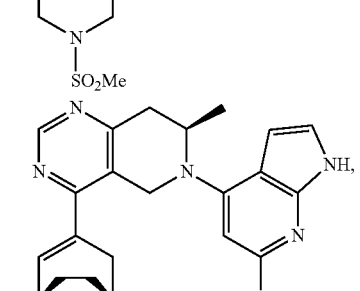
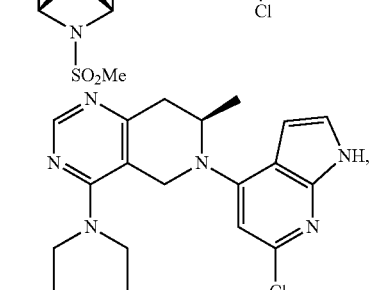
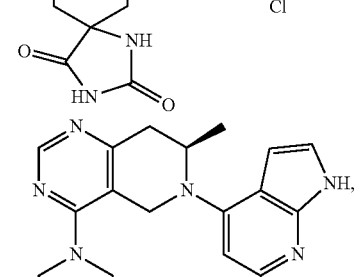

31
-continued
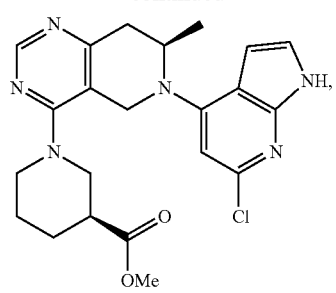
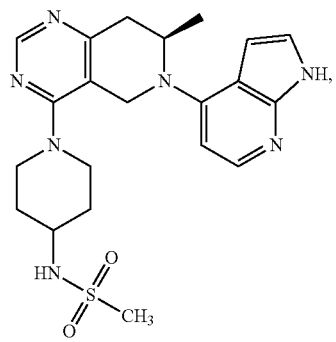
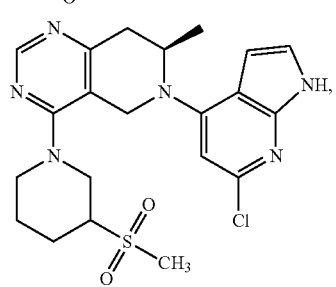
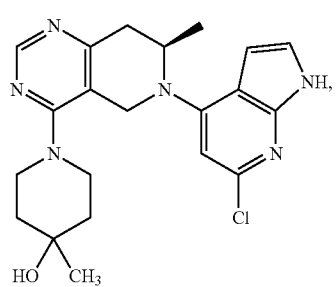
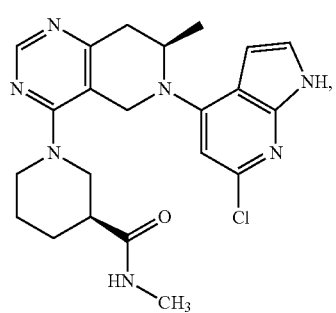
32
-continued
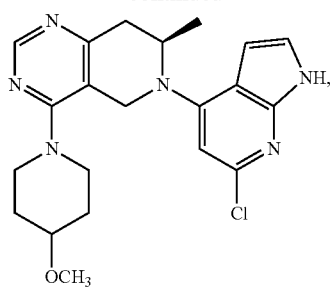
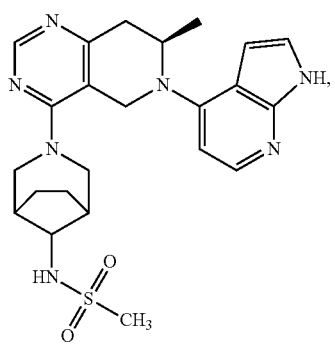
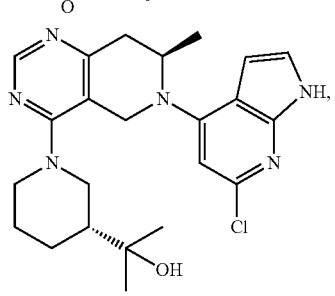
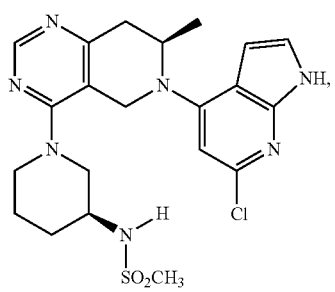
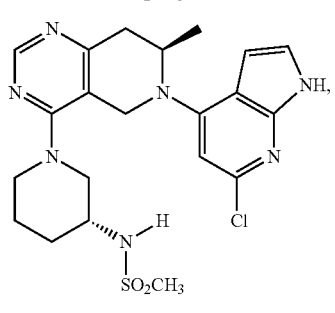

-continued
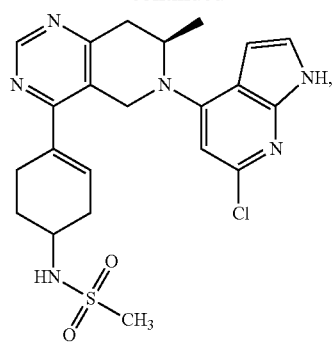
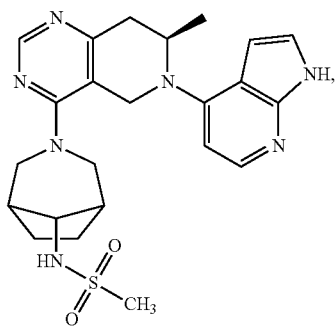
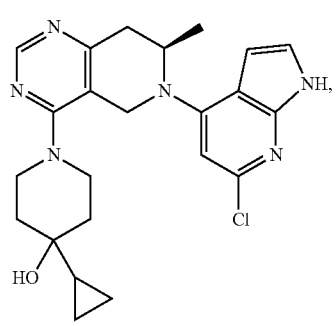
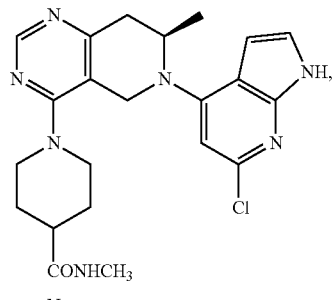
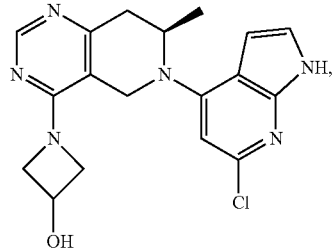
-continued
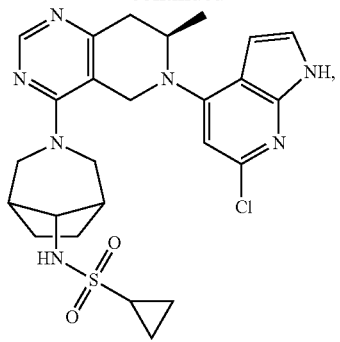
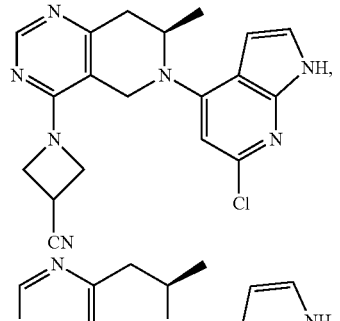
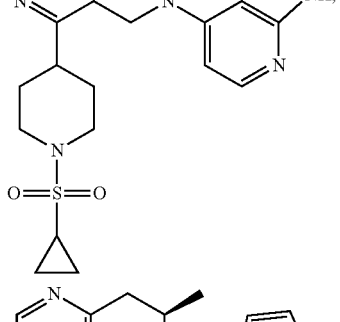
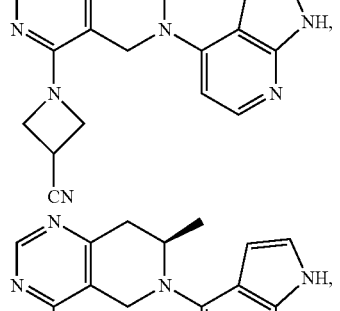
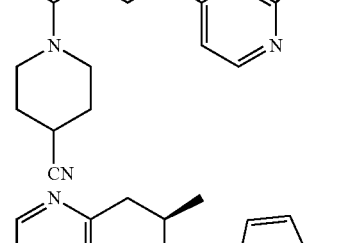

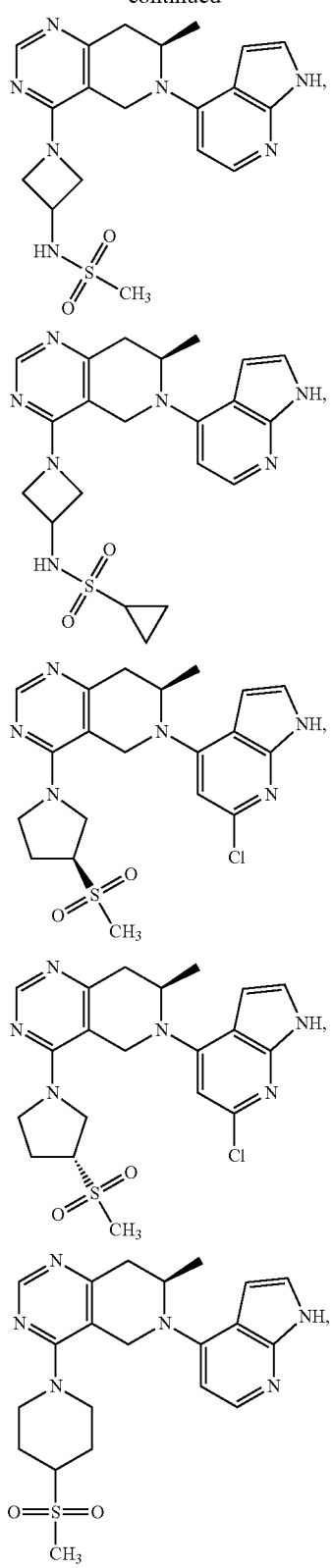
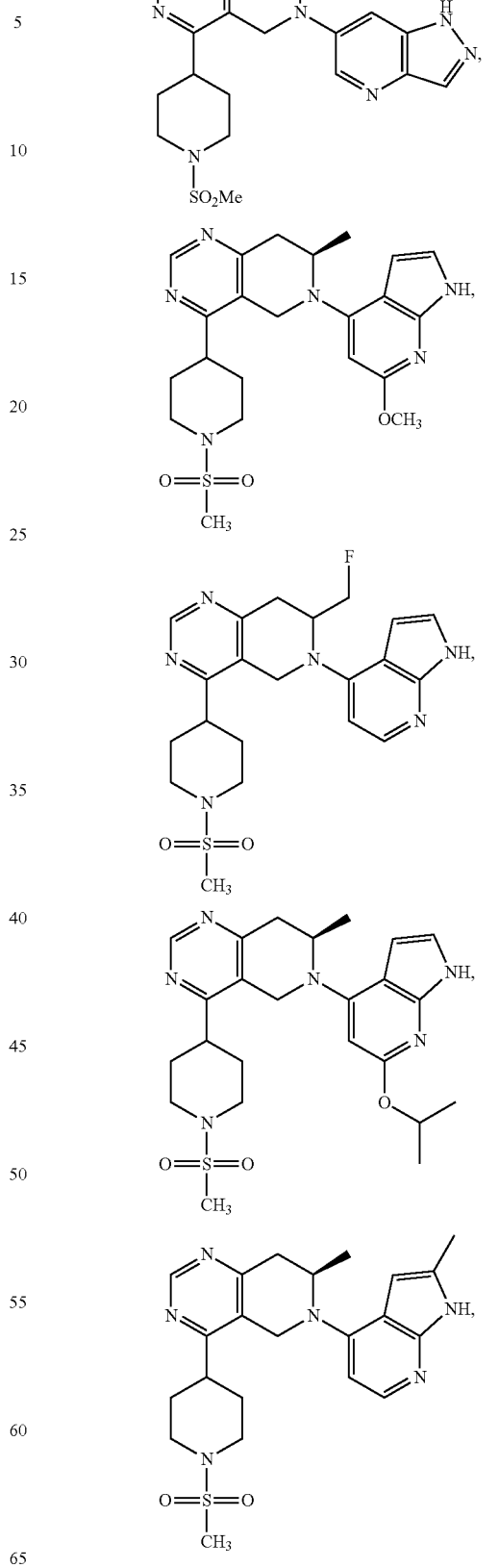

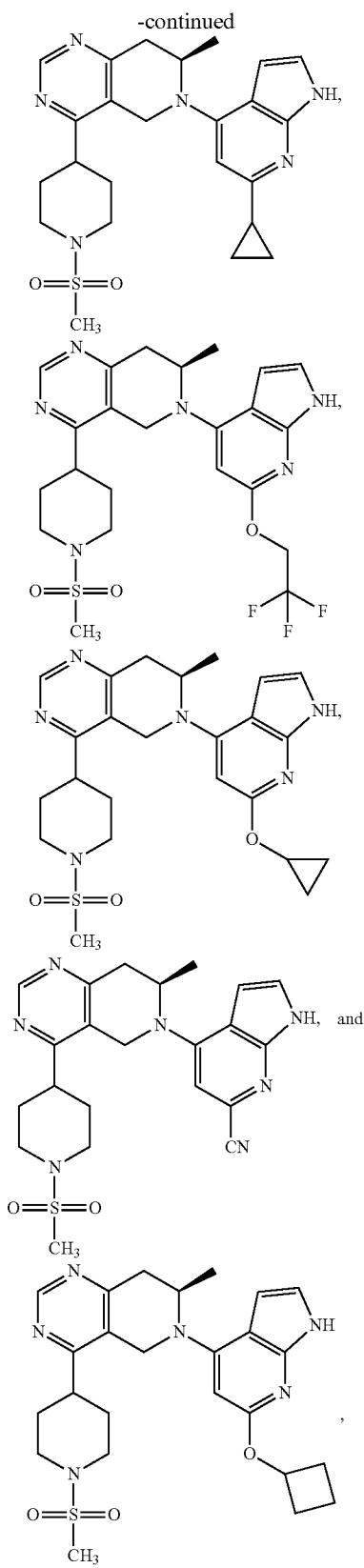
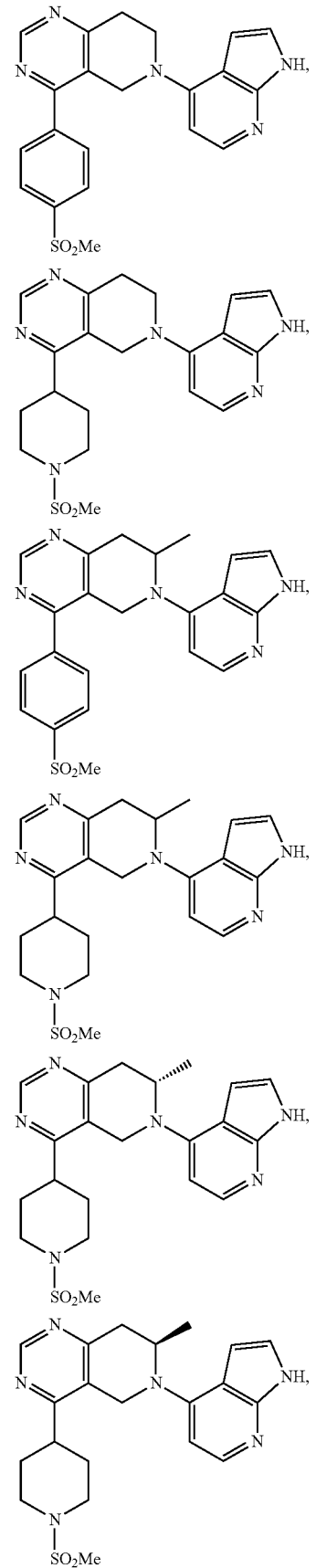
or a salt thereof.
Also provided herein is a compound as disclosed herein, chosen from:

-continued
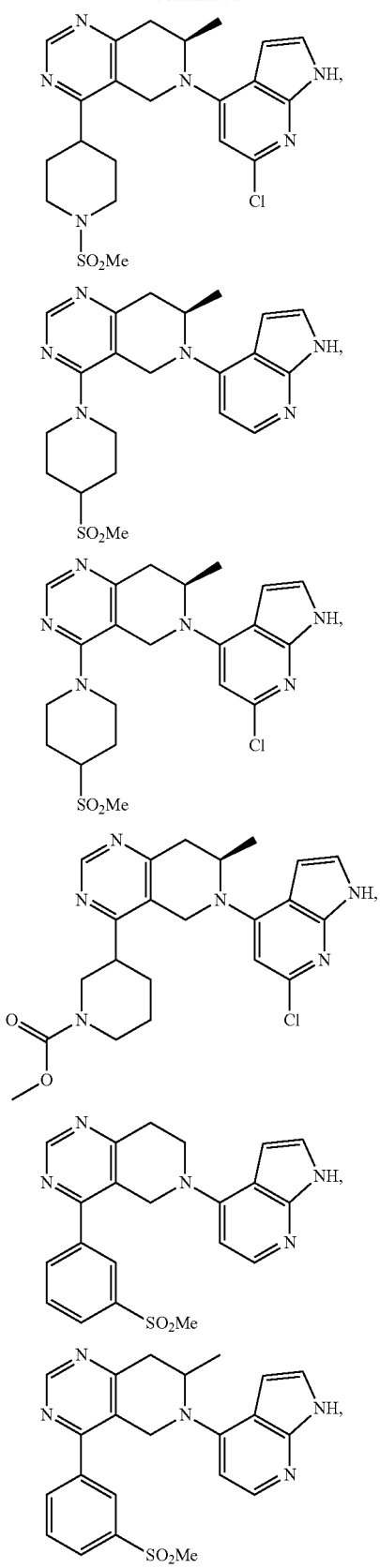
-continued
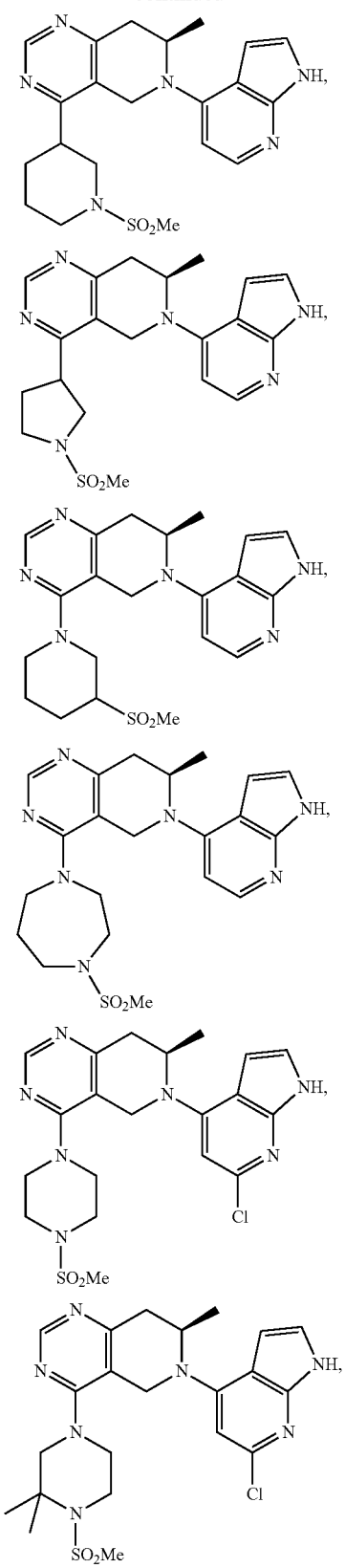

-continued
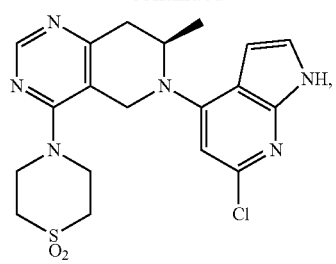
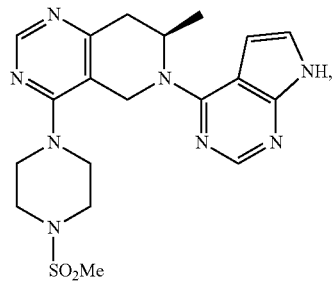
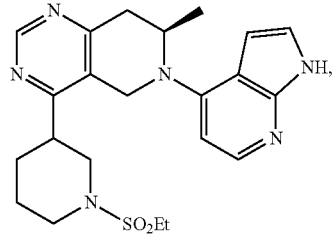
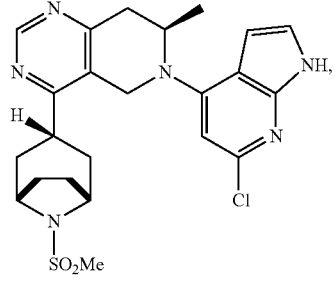
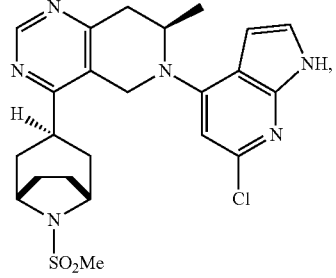
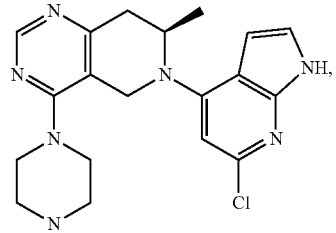
-continued
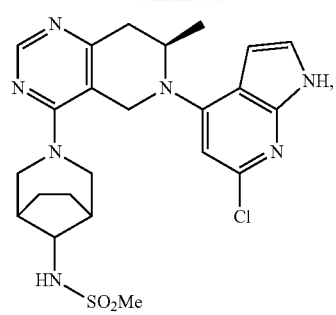
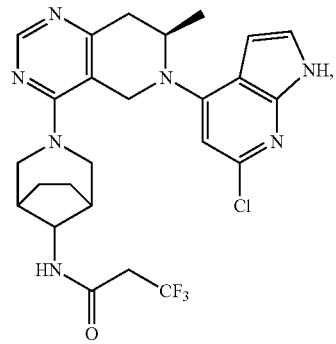
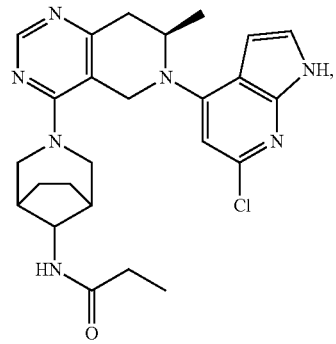
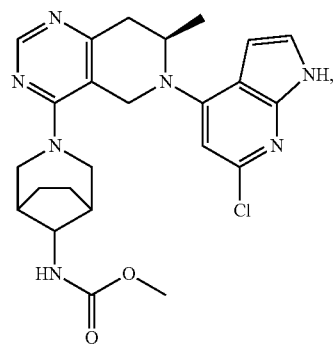
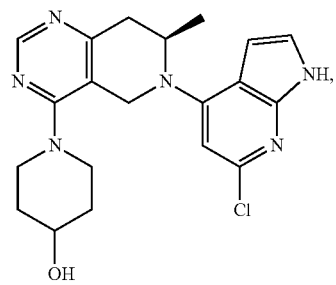

-continued
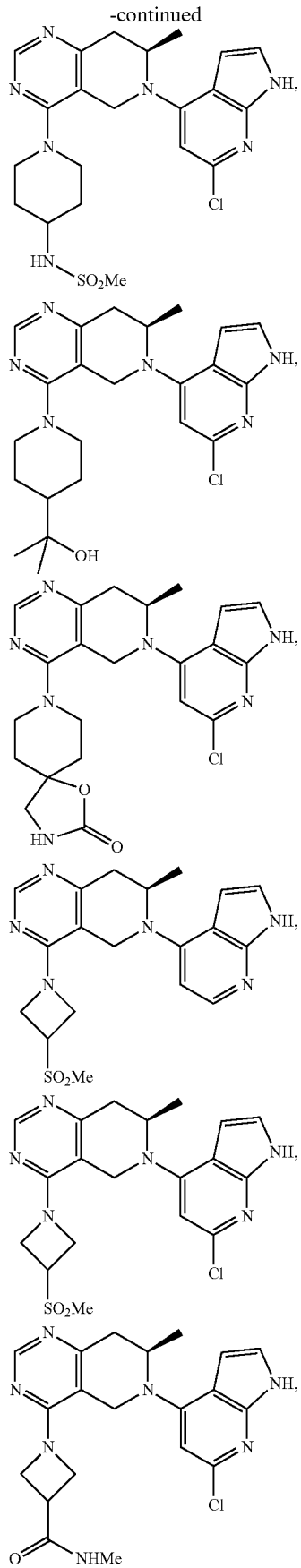
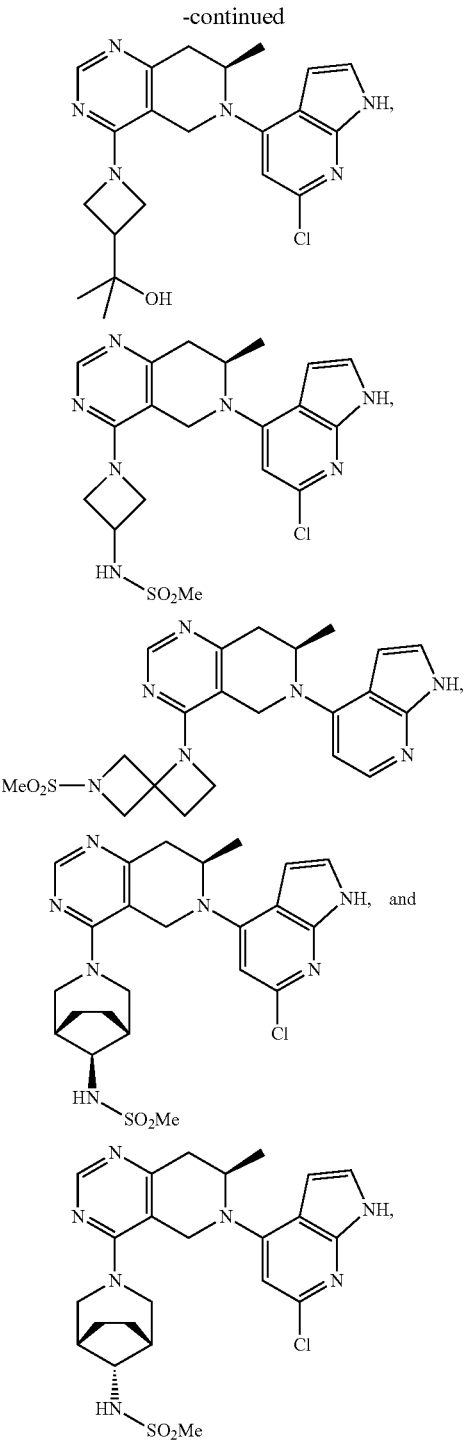
or a salt thereof.
Also provided herein is a compound as disclosed herein, chosen from:

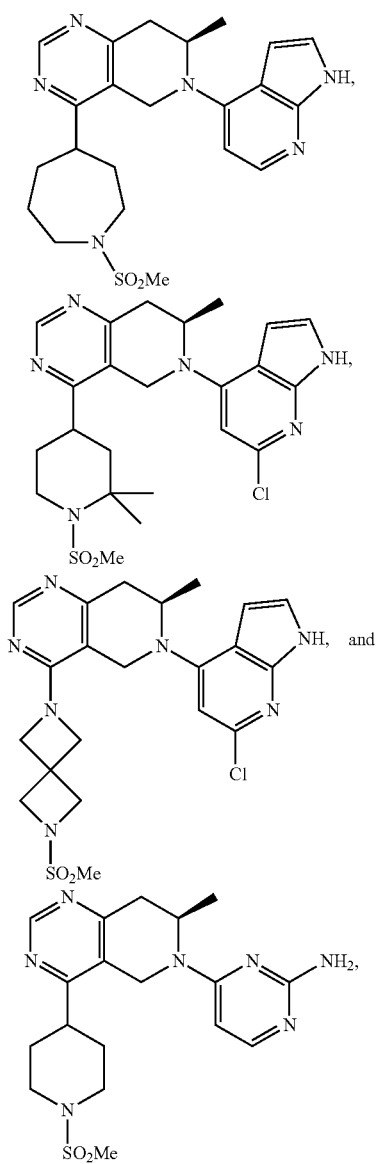

or a salt thereof.

The present invention also relates to a method of inhibiting at least one ATR kinase function comprising the step of contacting ATR kinase with a compound as described herein. The cell phenotype, cell proliferation, activity of ATR kinase, change in biochemical output produced by active ATR kinase, expression of ATR kinase, or binding of ATR kinase with a natural binding partner may be monitored. Such methods may be modes of treatment of disease, biological assays, cellular assays, biochemical assays, or the like.

Also provided herein is a method of treatment of an ATR kinase-mediated disease comprising the administration of a therapeutically effective amount of a compound as disclosed herein, or a salt thereof, to a patient in need thereof.

In certain embodiments, the ATR kinase-mediated disease is a proliferative disease.

In certain embodiments, the proliferative disease is a myeloproliferative disorder.

In certain embodiments, the proliferative disease is cancer.

In some embodiments, the cancer is a chemotherapy-resistant cancer.

In some embodiments, the cancer is a radiotherapy-resistant cancer.

In some embodiments, the cancer is an ALT-positive cancer.

In some embodiments, the cancer is a sarcoma. In some embodiments, the sarcoma is selected from osteosarcoma and glioblastoma.

In some embodiments, the cancer is selected from lung cancer, head and neck cancer, pancreatic cancer, gastric cancer, and brain cancer.

In some embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the cancer has a defect in a base excision repair protein.

In some embodiments, the cancer has defects in the ATM signaling cascade. In some embodiments, the defect is altered expression or activity of one or more of the following: TM, p53, CHK2, MRE11, RAD50, NBS 1, 53BP1, MDC1, H2AX, MCPH1/BRIT1, CTIP, or SMC1.

In certain embodiments, the cancer is lymphoma.

In certain embodiments, the cancer is B cell lymphoma.

In certain embodiments, the cancer is pancreatic cancer.

Also provided herein is a compound as disclosed herein for use as a medicament.

Also provided herein is a compound as disclosed herein for use as a medicament for the treatment of an ATR kinase-mediated disease.

Also provided is the use of a compound as disclosed herein as a medicament.

Also provided is the use of a compound as disclosed herein as a medicament for the treatment of an ATR kinase-mediated disease.

Also provided is the use of a compound as disclosed herein for the treatment of an ATR kinase-mediated disease.

Also provided herein is a method of sensitizing cells to DNA-damaging agents comprising administering to a patient a compound as recited in claim 1.

Also provided herein is a method of preventing cell repair from DNA damage comprising administering to a patient a compound as recited in claim 1.

Also provided herein is a method of inhibition of ATR kinase comprising contacting ATR kinase with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

Also provided is a method of modulation of an ATR kinase-mediated function in a subject comprising the administration of a therapeutically effective amount of a compound as disclosed herein.

Also provided is a compound as disclosed herein for use in the manufacture of a medicament for the treatment of an ATR kinase-mediated disease.

In certain embodiments, the ATR kinase mediated disease is cancer. In some embodiments, the cancer is a chemotherapy-resistant cancer. In some embodiments, the cancer is a radiotherapy-resistant cancer. In some embodiments, the cancer is an ALT-positive cancer. In some embodiments, the cancer is a sarcoma. osteosarcoma and glioblastoma. In some embodiments, the cancer is selected from lung cancer, head and neck cancer, pancreatic cancer, gastric cancer, and brain cancer. In some embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer. In some embodiments, the cancer has a defect in a base excision repair protein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

In certain embodiments, the pharmaceutical composition is formulated for parenteral administration.

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that FIGURE as well, taking into account significant FIGURES.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane. "Cycloalkyl", as used herein, alone or in combination, encompasses "bicycloalkyl", "bridged cycloalkyl", and "spirocycloalkyl", as defined below.

The term "bicycloalkyl", as used herein, alone or in combination, refers to a cyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged cycloalkyl", as used herein, alone or in combination, refers to a bicycloalkyl system in which all three of the bond pathways between bridgehead atoms contain at least one atom. "Bridged cycloalkyl" thus encompasses, by way of example, bicyclo[2.2.1]heptane, also known as norbornane, and bicyclo[2.2.2]octane. "Bridged cycloalkyl" thus does not encompass bicyclo[2.2.0]hexane or bicyclo[3.3.0]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, sulfoximines, sulfimides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited. The term "heterocycloalkyl", as used herein, alone or in combination, is understood to encompass "heterobicycloalkyl" and "bridged heterocycloalkyl", as defined below.

The term "heterobicycloalkyl", as used herein, alone or in combination, refers to a heterocyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 1,4-diazabicyclo[2.2.2]octane, also known as DABCO, and 7-azabicyclo[2.2.1]heptane.

Bicyclic ring systems can be described using terminology that will be recognized by the person in the art. A bicyclic compound can be named as the fusion of two ring systems. For example, "benzobenzene" is understood to refer to naphthalene. Unless specifically restricted, any ring fusion isomer will be embraced by this terminology. For example, "benzonaphthalene" is understood to embrace both anthracene and phenanthrene. As a further example, pyrrolopyridine is understood to embrace any compound having pyrrole fused to pyridine, and thus embraces 4-azaindole, 5-azaindole, 6-azaindole, and 7-azaindole.

The term "heterobicycloalkyl", as used herein, alone or in combination, refers to a saturated, partially unsaturated, or fully unsaturated (but nonaromatic) cyclic alkyl system, containing at least one heteroatom as a ring member, that is characterized by the presence of two atoms, termed "bridgehead atoms" that are connected to each other via three bond pathways. "Heterobicycloalkyl" thus encompasses, by way of example, 7-azabicyclo[2.2.1]heptane, 1,4-diazabicyclo[2.2.2]octane, also referred to as "DABCO", 1-azabicyclo[2.2.0]hexane, and 3-azabicyclo [3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 7-azabicyclo[2.2.1]heptane, 1,4-diazabicyclo[2.2.2]octane, also referred to as "DABCO", but not 1-azabicyclo[2.2.0]hexane, or 3-azabicyclo[3.3.0]octane.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group. Examples of hydroxyalkyl groups include hydroxymethyl, 1-hydroxyethyl, 2-hydroxyethyl, and 2-hydroxy-2-propyl.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycloakyl", as used herein, alone or in combination, refers to an alkyl group having two rings that has a single atom common to both rings. Examples of spirocycloalkyl systems include spiro[3.3]heptanyl and spiro[4.4]nonanyl.

The term "spiroheterocycloakyl", as used herein, alone or in combination, refers to a heteroalkyl group having two rings that has a single atom common to both rings. Examples of spirocycloalkyl systems include 2-azaspiro[3.3]heptanyl and 3-azaspiro[4.4]nonanyl.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "sulfimide" refers to a RS(=NR')R" group with R, R', and R" as defined herein.

The term "sulfoximine" refers to a RS(=O)(=NR')R" group with R, R', and R" as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', or the term R", appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R, R' and R" groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "enantiomer", as used herein, alone or in combination, refers to one of a pair of compounds that differ in absolute stereochemistry at every stereocenter. Each enantiomer in a pair of compounds is thus the mirror image of the other enantiomer.

The term "epimer", as used herein, alone or in combination, refers to one of a pair of compounds that differ in absolute stereochemistry at a single stereocenter.

The term "diastereomer", as used herein, alone or in combination, refers to one of a pair of compounds that neither have identical stereochemistry nor are enantiomers of each other.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Certain of the compounds disclosed herein can exist as a mixture of two diastereomers. In some embodiments, the two diastereomers are present in equal amounts. In some embodiments, the compound contains 60% or more of the major diastereomer. In some embodiments, the compound contains 70% or more of the major diastereomer. In some embodiments, the compound contains 80% or more of the major diastereomer. In some embodiments, the compound contains 90% or more of the major diastereomer. In some embodiments, the compound contains 95% or more of the major diastereomer. In some embodiments, the compound contains 98% or more of the major diastereomer.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"ATR kinase inhibitor" is used herein to refer to a compound that exhibits an $IC_{50}$ with respect to ATR kinase activity of no more than about 100 μM and more typically not more than about 50 μM, as measured in the ATR/ATRIP biochemical assay or in the ATR kinase pCHK1 cellular assay described generally herein. "$IC_{50}$" is that concentration of inhibitor which reduces to half-maximal level the activity of an enzyme (e.g., ATR kinase), or the ATR-induced phosphorylation of CHK1 at Serine 345 in cells. Certain compounds disclosed herein have been discovered to exhibit inhibition against ATR kinase. In certain embodiments, compounds will exhibit an $IC_{50}$ with respect to ATR kinase of no more than about 10 μM; in further embodiments, compounds will exhibit an $IC_{50}$ with respect to ATR kinase of no more than about 2 μM; in yet further embodiments, compounds will exhibit an IC50 with respect to ATR kinase of not more than about 1 μM; in yet further embodiments, compounds will exhibit an $IC_{50}$ with respect to ATR kinase of not more than about 500 nM; in yet further embodiments, compounds will exhibit an $IC_{50}$ with respect to ATR kinase of not more than about 200 nM; in yet further embodiments, compounds will exhibit an $IC_{50}$ with respect to ATR kinase of not more than about 100 nM, as measured in the ATR kinase assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Formulations

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Combinations and Combination Therapies

The compounds can be used, alone or in combination with other pharmaceutically active compounds, to treat conditions such as those previously described hereinabove. The compound(s) and other pharmaceutically active compound (s) can be administered simultaneously (either in the same dosage form or in separate dosage forms) or sequentially. Accordingly, in one embodiment, the present invention comprises methods for treating a condition by administering to the subject a therapeutically-effective amount of one or more compounds and one or more additional pharmaceutically active compounds.

In another embodiment, there is provided a pharmaceutical composition comprising one or more compounds, one or more additional pharmaceutically active compounds, and a pharmaceutically acceptable carrier.

In another embodiment, the one or more additional pharmaceutically active compounds is selected from anti-cancer drugs, anti-proliferative drugs, and anti-inflammatory drugs.

ATR inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer an ATR inhibitor compound, as described herein, in combination with another therapeutic agent. By way of example only, the therapeutic effectiveness of an ATR inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an ATR inhibitor as described herein) may be administered in any order, or simultaneously. If simultaneously, the multiple therapeutic agents are optionally provided in a single, unified form, or in multiple forms (by way of example only, either as a single pill or as two separate pills).

In another embodiment, an ATR inhibitor is optionally used in combination with procedures that provide additional benefit to the patient. An ATR inhibitor and any additional therapies are optionally administered before, during or after the occurrence of a disease or condition, and the timing of administering the composition containing an ATR inhibitor varies in some embodiments. Thus, for example, an ATR inhibitor is used as a prophylactic and is administered continuously to subjects with a propensity to develop conditions or diseases in order to prevent the occurrence of the disease or condition. An ATR inhibitor and compositions are optionally administered to a subject during or as soon as possible after the onset of the symptoms. While embodiments have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

An ATR inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases an ATR inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotics, which are often plant alkaloids and terpenoids, or derivatives thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amsacrine, camptothecin (CTP), genisten, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide(NILANDRON);
17) tyrosine kinase inhibitors, including, but not limited to: imatinib (GLEEVEC), erlotinib (TARCEVA), lapatinib (TYKERB), sorafenib (NEXAVAR), and axitinib (INLYTA);
18) mTOR inhibitors, including, but not limited to: everolimus, temsirolimus (TORISEL), and sirolimus;

19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
    a. tetracyclines, including, but not limited to: doxycycline;
    b. erythromycins, including, but not limited to: azithromycin;
    c. glycylglycines, including, but not limited to: tigecyline;
    d. antiparasitics, including, but not limited to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;
24) antibody therapeutical agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone;

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating ATR kinase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of ATR kinase-mediated disorders.

Specific diseases to be treated by the compounds, compositions, and methods disclosed herein include proliferative and hyperproliferative diseases, including cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations

ACN=acetonitrile; Boc=tert-butyloxycarbonyl; BPin=4,4,5,5-tetramethyl-1,3,2-dioxaborolan-2-yl; $Br_2$=bromine; Bu=n-butyl; t-Bu=tert-butyl=2,2-dimethylethyl; °C.=Celsius; $CDCl_3$=deuterated chloroform; $CD_3CN$=deuterated acetonitrile; DBN=1,5-Diazabicyclo(4.3.0)non-5-ene; DBU=1,8-diazabicyclo(5.4.0)undec-7-ene; DCM=dichloromethane; DDTT=3-((dimethylaminomethylidene)amino)-3H-1,2,4-dithiazole-5-thione; DIPEA=$iPr_2NEt$=diisopropylethylamine; DMAP=4-Dimethylaminopyridine; DMF=dimethylformamide; DMF-$d_7$=dimethylformamide-$d_7$; DMSO=dimethyl sulfoxide; DMSO-$d_6$=dimethyl sulfoxide-$d_6$; DMTr=dimethoxytrityl=(4-methoxyphenyl)$_2$(phenyl)methyl; $D_2O$=deuterated water; dppf=1,1'-bis(diphenylphosphino)ferrocene; EA=EtOAc=ethyl acetate; ES+=electrospray positive ionization; ES-=electrospray negative ionization; Et=ethyl; EtOH=ethanol; h=hour; H=hydrogen; HCl=hydrogen chloride; $HCO_2NH_4$=ammonium formate; $H_2O$=water; HPLC=high pressure liquid chromatography, also known as preparative high performance liquid chromatography; int.=intermediate; iPr=isopropyl=2-propyl; M=molar; mCPBA=m-chloroperbenzoic acid; MeCN=$CH_3CN$=acetonitrile; MeOH=methanol; MHz=megahertz; mL=milliliter; min=minute; MS=mass spectrometry; MsCl=methanesulfonyl chloride; MW=microwave; $N_2$=nitrogen; $NH_3$=ammonia; $NH_4OH$=ammonium hydroxide; NMP=N-Methyl-2-pyrrolidone; $^1$H-NMR=proton nuclear magnetic resonance; $^{31}$P-NMR=phosphorous nuclear magnetic resonance; PBS=phosphate buffered saline; PE=petroleum ether; PEPPSI™=pyridine-enhanced precatalyst preparation stabilization and initiation; Pd-PEPPSI™-IPr catalyst=[1,3-bis(2,6-diisopropylphenyl)imidazol-2-ylidene] (3-chloropyridyl)palladium(II) dichloride; Pd-PEPPSI™-IPent catalyst=[1,3-bis(2,6-di-3-pentylphenyl)imidazol-2-ylidene](3-chloropyridyl)palladium(II) dichloride; Piv=pivaloyl=$(CH_3)_3C—C(=O)—$; prep-HPLC=preparative high pressure liquid chromatography, also known as preparative high performance liquid chromatography; RT=room temperature; NaOH=sodium hydroxide; Pd(dppf)$Cl_2$=[1,1'-bis(diphenylphosphino)ferrocene]palladium(II) dichloride; RuPhos=dicyclohexyl(2',6'-diisopropoxy-[1,1'-biphenyl]-2-yl)phosphine; THF=tetrahydrofuran; Py=pyridine; SFC=supercritical fluid chromatography; TBSCl=tert-butyldimethylsilyl chloride; TEA=triethylamine; TEAB=tetraethyl ammonium bicarbonate; TMSCl=trimethylsilyl chloride; TFA=trifluoroacetic acid; $K_2CO_3$=potassium carbonate; ul=microliter.

General Synthetic Methods for Preparing Compounds

The following schemes can be used to practice the present invention.

SCHEME I

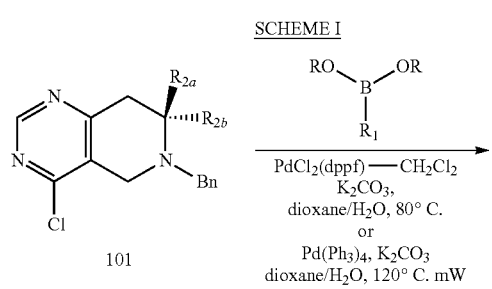

Examples 1 and 3 can be synthesized using the following general synthetic procedure set forth in Scheme I. A Suzuki cross-coupling reaction with chloro-pyrimidine 1 and an aryl or heteroaryl boronate gives the substituted pyrimidine intermediate 102. Subsequent cleavage of the benzyl group gives amine 103, which then undergoes a Buchwald coupling with an aryl or heteroaryl halide to give the pyrido pyrimidine compound 104.

SCHEME II

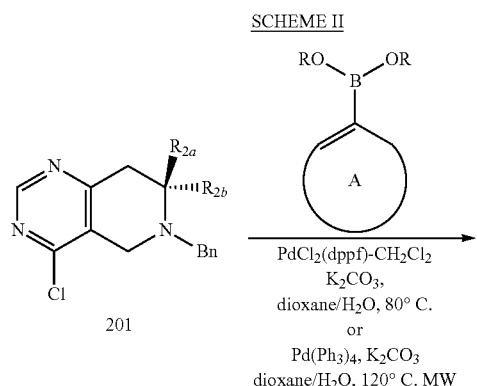

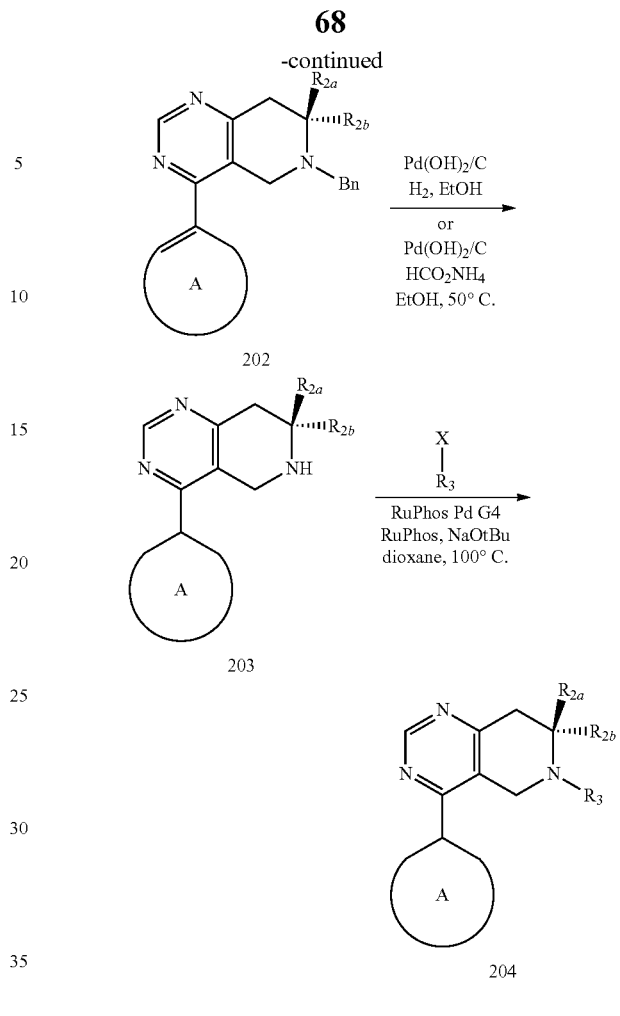

Examples 2, 4, 5, 6, 7, and 10 can be synthesized using the following general synthetic procedure set forth in Scheme II. A Suzuki cross-coupling reaction with chloro-pyrimidine 201 and an unsaturated carbocyclic or heterocyclic boronate gives the substituted pyrimidine intermediate 202. Subsequent cleavage of the benzyl group with concurrent reduction of the alkene gives the saturated amine 203, which then undergoes a Buchwald coupling with an aryl or heteroaryl halide to give the pyrido pyrimidine compound 204.

SCHEME III

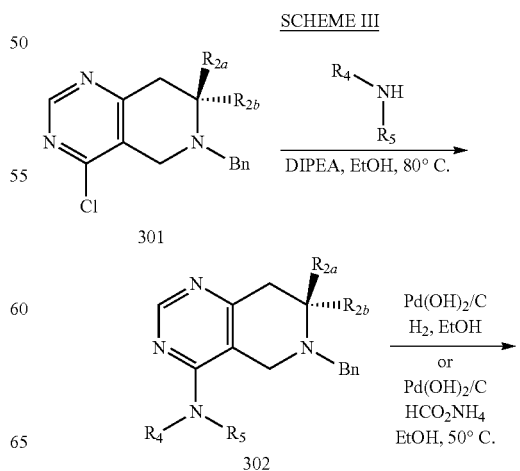

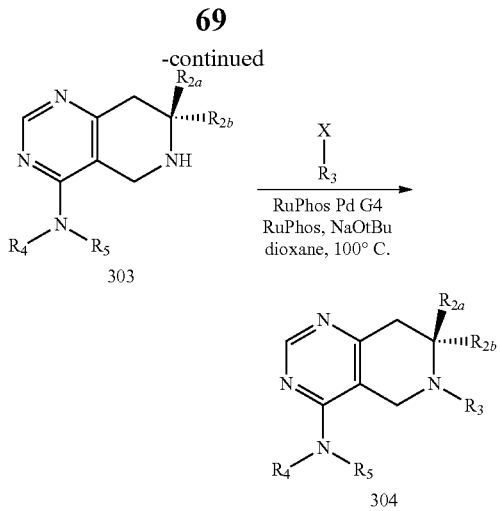

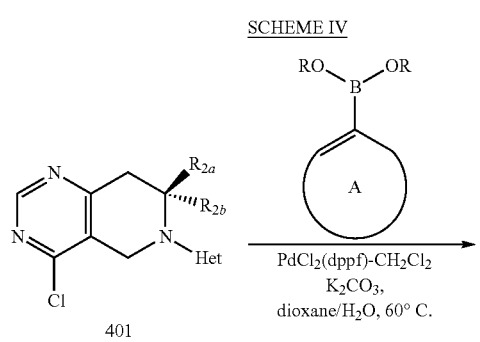

Examples 8 and 9 can be synthesized using the following general synthetic procedure set forth in Scheme III. S$_N$Ar addition reaction with chloro-pyrimidine 301 and an amine gives the substituted pyrimidine intermediate 302. Subsequent cleavage of the benzyl group gives amine 303, which then undergoes a Buchwald coupling with an aryl or heteroaryl halide to give the pyrido pyrimidine compound 304.

SCHEME IV

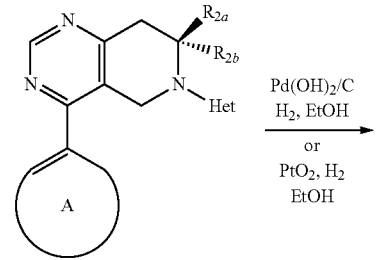

Examples 11 and 25 can be synthesized using the following general synthetic procedure set forth in Scheme IV. A Suzuki cross-coupling reaction with chloro-pyrimidine 401 and an unsaturated carbocyclic or heterocyclic boronate gives the substituted pyrimidine intermediate 402. Subsequent reduction of the alkene gives the saturated carbocyclic or heterocyclic compound 403. In the Scheme above, A is a substituent that is compatible with the reaction conditions, and "Het" is a heteroaromatic substituent that is compatible with the reaction conditions.

SCHEME V

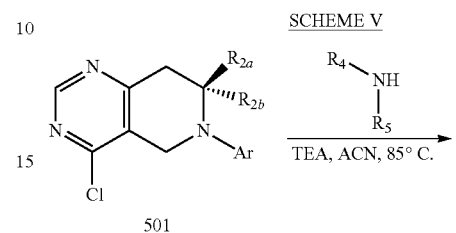

Examples 12, 13, 27, 28, 29, 30, 31 and 32 can be synthesized using the following general synthetic procedure set forth in Scheme V. S$_N$Ar addition reaction with chloro-pyrimidine 501 and an amine gives the substituted pyrimidine the amino pyrimidine compound 502. In the Scheme above, Ar is an aromatic group.

The following intermediates are used to synthesize the example compounds disclosed below.

Intermediate A

6-Benzyl-4-chloro-5,6,7,8-tetrahydropyrido[4,3-d]pyrimidine

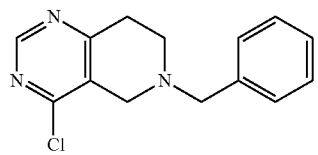 [SMILES: Clc1ncnc2c1CN(Cc1ccccc1)CC2]

Step 1

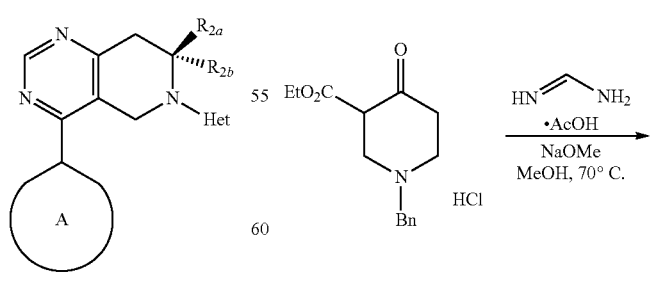

6-Benzyl-5,6,7,8-tetrahydropyrido[4,3-d]pyrimidin-4 (3H)-one To a solution of ethyl 1-benzyl-4-oxopiperidine-3-carboxylate hydrochloride (1.0 g, 3.4 mmol) and formamidine acetate (0.420 g, 4.03 mmol) in MeOH (6.7 mL) was added NaOMe in MeOH (4.6 ml, 20 mmol) and the resulting suspension was stirred at 70° C. for 18 h. The mixture was cooled to RT and concentrated under reduced pressure. The residue was partitioned between water (1 mL) and 3:1 CHCl$_3$:iPrOH (3 mL). The layers were separated and the organic layer was washed with brine (1 mL), dried over Na$_2$SO$_4$ and concentrated under reduced pressure to afford the title compound (444 mg, 55%) as a light yellow solid.

MS (ES$^+$) C$_{14}$H$_{15}$N$_{3}$O requires: 241, found: 242 [M+H]$^+$.

Step 2

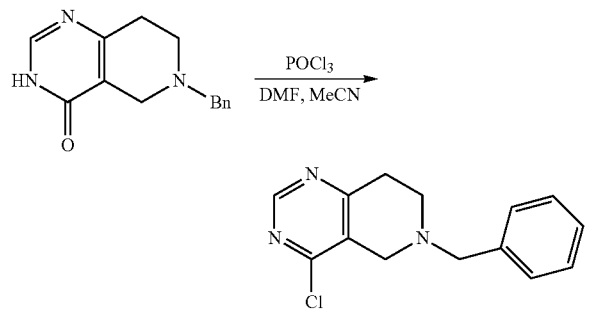

6-Benzyl-4-chloro-5,6,7,8-tetrahydropyrido[4,3-d]pyrimidine To a solution of the product from the previous step (100 mg, 0.414 mmol) in acetonitrile (1.7 mL) was added POCl$_3$ (68 µL, 0.72 mmol) and DMF (13 µL, 0.17 mmol) and the resulting mixture was stirred at 70° C. for 4 h. Additional POCl$_3$ (113 µL, 1.2 mmol) was added and the mixture was stirred at 70° C. for 12 h. The mixture was concentrated and the residue was taken up in CH$_2$Cl$_2$ (10 mL) and partitioned with aqueous sat. NaHCO$_3$ (2 mL). The aqueous layer was extracted with CH$_2$Cl$_2$ (3×3 mL) and the combined organic layers were washed with NaHCO$_3$ (1 mL), brine (1 mL), dried over Na$_2$SO$_4$, filtered and concentrated. The residue was purified via silica gel chromatography (0-10% MeOH in CH$_2$Cl$_2$) to afford the title compound (85 mg, 79% yield) as a brown liquid.

MS (ES$^+$) C$_{14}$H$_{14}$ClN$_3$ requires: 259, found: 260 [M+H]$^+$.

Intermediate B

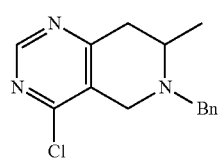

6-Benzyl-4-chloro-7-methyl-5,6,7,8-tetrahydropyrido[4,3-d]pyrimidine

Step 1

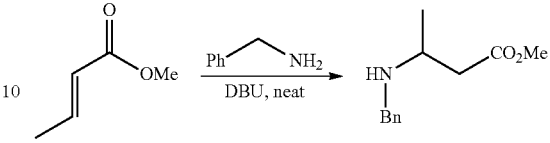

Methyl 3-(benzylamino)butanoate To a mixture of benzylamine (5.1 mL, 47 mmol) and methyl (E)-but-2-enoate at 0° C. was added DBU (0.348 mL, 2.31 mmol) and the mixture was allowed to slowly warm to RT and stirred for 12 h. The mixture was diluted with 90% EtOAc in hexanes (20 mL) and filtered through a short pad of SiO$_2$. The pad was washed with 90% EtOAc in hexanes (300 mL) and concentrated under reduced pressure to afford the title compound (7.4 g, 77% yield) as a pale yellow liquid.

TLC: Rf=0.3 (50% EtOAc/Hexanes).

Step 2

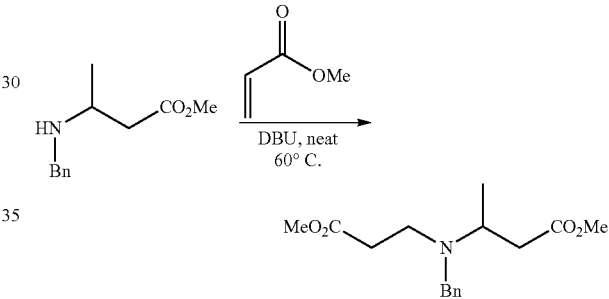

Methyl 3-(benzyl(3-methoxy-3-oxopropyl)amino)butanoate To a mixture of the product from the previous step (7.4 g, 35.7 mmol) and methyl acrylate (3.2 mL, 36 mmol) at 0° C. was added DBU (0.269 mL, 1.79 mmol) and the mixture was allowed to slowly warm to RT then heated at 60° C. for 12 h. The mixture was cooled to RT and concentrated under reduced pressure (70 mbar at 40° C.). The residue was purified via silica gel chromatography (0-40% EtOAc in hexanes) to afford the title compound (7.78 g, 74% yield) as a colorless liquid.

MS (ES$^+$) C$_{16}$H$_{23}$NO$_4$ requires: 293, found 294 [M+H]$^+$.

Step 3

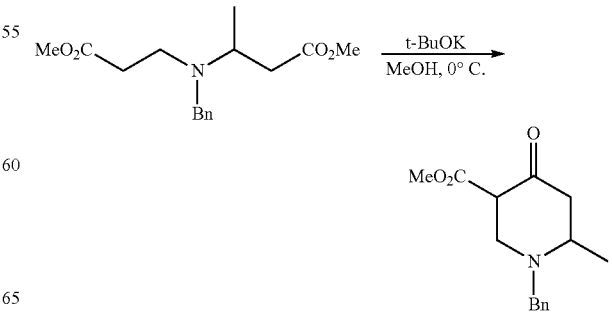

Methyl 1-benzyl-6-methyl-4-oxopiperidine-3-carboxylate To a suspension of potassium tert-butoxide (1.53 g, 13.6 mmol) in THF (34 mL) at 0° C. was added the product from the previous step (2.0 g, 6.8 mmol) and the resulting mixture was stirred at 0° C. for 2 h. Water (20 mL) was added, the layers were separated, and the aqueous phase was extracted with EtOAc (3×20 mL). The combined organic layers were washed with sat NaCl (10 mL), dried over Na$_2$SO$_4$, filtered and concentrated under reduced pressure. The residue was purified via silica gel chromatography (0-40% EtOAc in hexanes) to afford the title compound (1.62 g, 91% yield) as a colorless liquid.

MS (ES+) C$_{15}$H$_{19}$NO$_3$ requires: 261, found 262 [M+H]$^+$.

Step 4

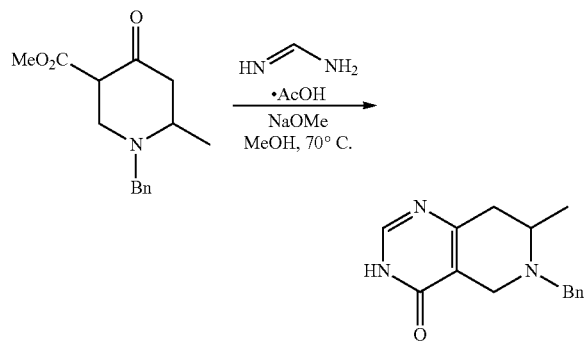

6-Benzyl-7-methyl-5,6,7,8-tetrahydropyrido[4,3-d]pyrimidin-4(3H)-one To a suspension of the product from the previous step (1.60 g, 6.12 mmol) in a solution of NaOMe in MeOH (7.0 mL, 31 mmol) was added formamidine acetate (0.765 g, 7.35 mmol), and the resulting thick mixture was stirred at 70° C. for 16 h, during which time the mixture became yellow then solidified to afford an orange mixture. MeOH (7 mL) was added and the mixture as heating at 70° C. for an additional 16 h, during which time it became a thick orange mixture. The mixture was purified by mass-triggered preparative HPLC (Mobile phase: A=0.1% TFA/H$_2$O, B=0.1% TFA/MeCN; Gradient: B=0-30%; 26 min; Column: XBridge C18, 5 μm, 19 mm×150 mm) to afford the title compound (938 mg, 60% yield) as a light yellow liquid.

MS (ES+) C$_{15}$H$_{17}$N$_3$O requires: 255, found 256 [M+H]$^+$.

Step 5

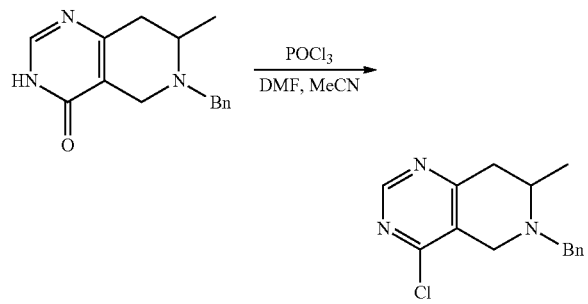

6-Benzyl-4-chloro-7-methyl-5,6,7,8-tetrahydropyrido[4,3-d]pyrimidine To a solution of the product from the previous step (200 mg, 0.783 mmol) in acetonitrile (3.1 mL) were added POCl$_3$ (128 μL, 1.37 mmol) and DMF (6.1 μL, 0.078 mmol) and the resulting mixture was stirred at 70° C. for 4 h. Additional POCl$_3$ (364 uL, 3.9 mmol) and DMF (31 uL, 0.392 mmol) were added and the mixture was stirred at 70° C. for 12 h. The mixture was concentrated and the residue was taken up in CH$_2$Cl$_2$ (10 mL) and poured over ice. The mixture was then carefully neutralized with the addition of solid NaHCO$_3$. The organic layer was separated, dried over Na$_2$SO$_4$ and concentrated. The residue was purified via silica gel chromatography (0-100% EtOAc in hexanes, followed by 5% of MeOH in CH$_2$Cl$_2$ with 1% of NH$_4$OH) to afford the title compound (109 mg, 51% yield) as a yellow liquid.

MS (ES+) C$_{15}$H$_{16}$ClN$_3$ requires: 273, found 274 [M+H]$^+$.

Intermediate C (R)-6-Benzyl-4-chloro-7-methyl-5,6,7,8-tetrahydropyrido[4,3-d]pyrimidine

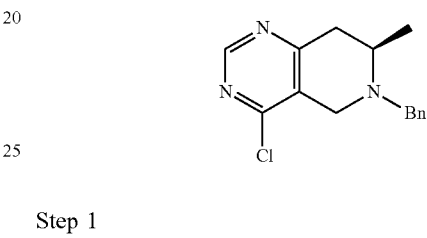

Step 1

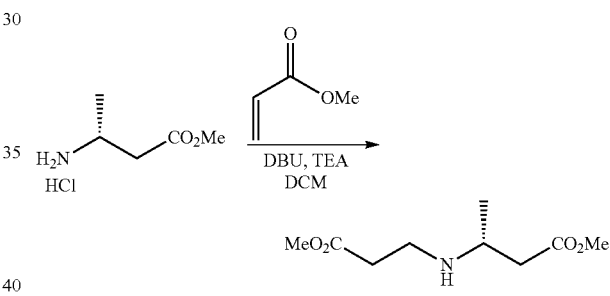

Methyl (R)-3-((3-methoxy-3-oxopropyl)amino)butanoate To a mixture of (R)-methyl 3-aminobutanoate hydrochloride (5.0 g, 33 mmol) and methyl acrylate (3.2 ml, 36 mmol) were added TEA (4.5 mL, 33 mmol) and DBU (0.25 mL, 1.6 mmol) and the mixture was stirred for 12 h at 40° C. The mixture was cooled to RT. Et$_2$O (100 mL) was slowly poured in with rapid stirring, the mixture was stirred for 10 min, then filtered. The filtrate was washed with Et$_2$O (2×50 mL) and concentrated under reduced pressure to afford the title compound (5.4 g, 82% yield) as a colorless oil.

TLC: Rf=0.4 (10% MeOH in CH$_2$Cl$_2$).

Step 2

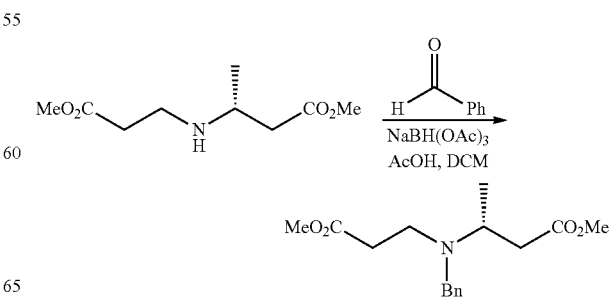

Methyl (R)-3-(benzyl(3-methoxy-3-oxopropyl)amino)butanoate To a solution of the product from the previous step (5.1 g, 25 mmol) in CH$_2$Cl$_2$ (100 mL) were added benzaldehyde (5.1 mL, 50 mmol) and AcOH (1.7 mL, 30 mmol) and the resulting mixture was stirred at RT for 15 min. NaBH(OAc)$_3$ (10.6 g, 50.2 mmol) was added and the mixture was stirred for 12 h at RT. Sat NaHCO$_3$ (30 mL) was added, the layers were separated and the aqueous phase was extracted with CH$_2$Cl$_2$ (3×30 mL). The combined organic layers were dried over Na$_2$SO$_4$, filtered and concentrated under reduced pressure. The residue was purified via silica gel chromatography (0-40% EtOAc in hexanes) to give afford the title compound (3.5 g, 48% yield) as a colorless liquid.

TLC: Rf=0.5 (30% EtOAc in hexanes).

Step 3

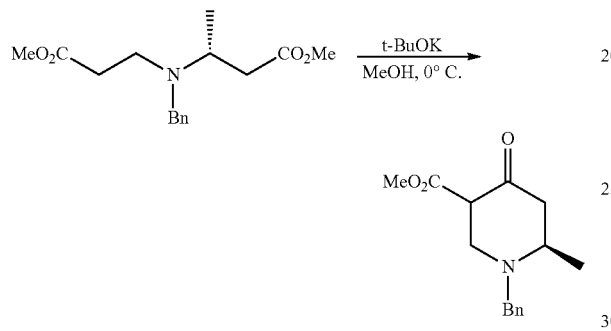

Methyl (6R)-1-benzyl-6-methyl-4-oxopiperidine-3-carboxylate To a solution of the product from the previous step (3.5 g, 12 mmol) in THF (60 mL) at 0° C. was added potassium tert-butoxide (15.5 mL, 1.0 M in THF) and the resulting mixture was stirred at 0° C. for 4 h. Water (10 mL) was added, the layers were separated and the aqueous layer was extracted with EtOAc (3×10 mL). The combined organic layers were washed with brine (4 mL), dried over Na$_2$SO$_4$, filtered and concentrated under reduced pressure. The residue was purified via silica gel chromatography (0-50% EtOAc in hexanes) to afford the title compound (1.87 g, 60% yield) as a colorless liquid.

MS (ES$^+$) C$_{15}$H$_{19}$NO$_3$ requires: 261, found 262 [M+H]$^+$.

Step 4

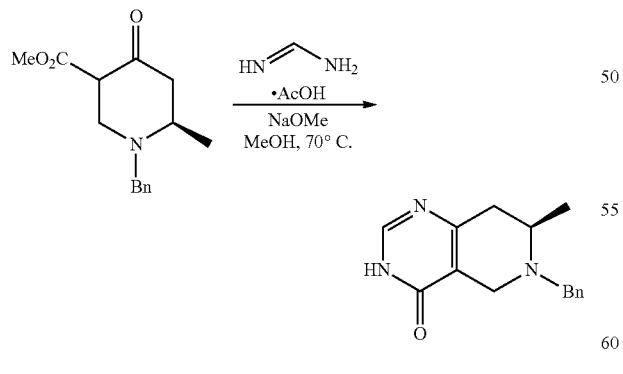

(R)-6-Benzyl-7-methyl-5,6,7,8-tetrahydropyrido[4,3-d]pyrimidin-4(3H)-one

To a solution of the product from the previous step (1.87 g, 7.16 mmol) in MeOH (7.2 mL) were added NaOMe in MeOH (8.2 mL, 36 mmol) and formamidine acetate (2.23 g, 21.4 mmol) and the resulting thick mixture was stirred at 70° C. for 16 h. The mixture was cooled to RT and concentrated. The crude residue was partitioned between NaHCO$_3$ (15 mL) and CH$_2$Cl$_2$ (20 mL), the layers were separated and the aqueous layer was extracted with CH$_2$Cl$_2$ (5×20 mL). The combined organic layers were dried over Na$_2$SO$_4$, filtered and concentrated under reduced pressure. The residue was purified via silica gel chromatography (0-15% MeOH in CH$_2$Cl$_2$) to afford the title compound (1.2 g, 66% yield) as an off-white solid.

MS (ES$^+$) C$_{13}$H$_{19}$N$_3$O$_3$ requires: 265, found: 266 [M+H]$^+$.

Step 5

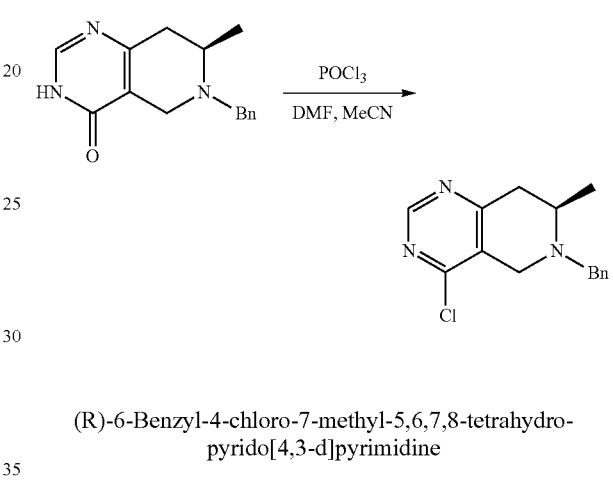

(R)-6-Benzyl-4-chloro-7-methyl-5,6,7,8-tetrahydropyrido[4,3-d]pyrimidine

To a solution of the product from the previous step (1.2 g, 4.7 mmol) in Acetonitrile (19 mL) were added POCl$_3$ (1.3 mL, 14 mmol) and DMF (0.182 mL, 2.35 mmol) and the resulting mixture was stirred at 70° C. for 4 h. The mixture was concentrated and the residue was partitioned between CH$_2$Cl$_2$ (20 mL) and NaHCO$_3$ (20 mL) and the layers were separated. The aqueous layer was extracted with CH$_2$Cl$_2$ (5×20 mL). The combined organic layers were dried over Na$_2$SO$_4$, filtered and concentrated under reduced pressure. The residue was purified via silica gel chromatography (0-15% MeOH in CH$_2$Cl$_2$) to afford the title compound (1.12 g, 87% yield) as an orange liquid.

MS (ES$^+$) C$_{15}$H$_{16}$ClN$_3$ requires: 273, found 274 [M+H]$^+$.

Intermediate D

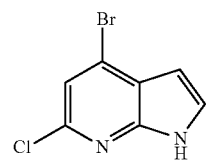 [SMILES: Clc1cc(Br)c2cc[nH]c2n1]

4-Bromo-6-chloro-1H-pyrrolo[2,3-b]pyridine

Step 1

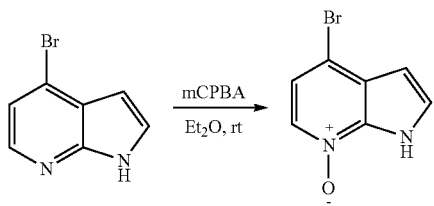

4-Bromo-1H-pyrrolo[2,3-b]pyridine 7-oxide To a solution of 4-bromo-1H-pyrrolo[2,3-b]pyridine (10.0 g, 50.8 mmol) in Et$_2$O (800 mL) at 25° C. was added mCPBA (17 g, 85 mmol) portion wise. The reaction mixture was stirred at room temperature for 16 h. The reaction was filtered to collect the solid. The solid was washed with Et$_2$O (3×100 mL), then dried under vacuum to afford the title compound (9.1 g, 84%) as white solid.

MS (ES$^+$) C$_7$H$_5$BrN$_2$O requires: 212, found 213 [M+H]$^+$.

Step 2

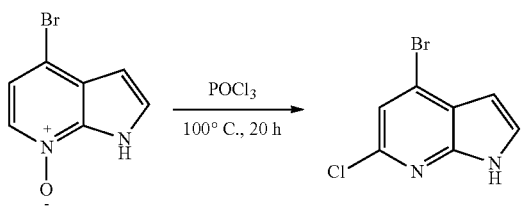

4-Bromo-6-chloro-1H-pyrrolo[2,3-b]pyridine A mixture of the product from the previous step (8.6 g, 41 mmol) in POCl$_3$ (250 mL) was stirred at 100° C. for 16 h. The mixture was cooled to RT and concentrated under reduced pressure. The residue was diluted in CH$_2$Cl$_2$ (50 mL) and added dropwise to a solution of aqueous sat. NaHCO$_3$ (300 mL) at 0° C. with stirring. The layers were separated and the aqueous layer was extracted with CH$_2$Cl$_2$ (5×300 mL). The combined organic layers were dried over Na$_2$SO$_4$, filtered and concentrated under reduced pressure. The residue was purified via silica gel chromatography (10% EtOAc in petroleum ether) to afford the title compound (3.5 g, 37%) as a white solid.

MS (ES$^+$) C$_7$H$_4$BrClN$_2$ requires 230, found 231.0 [M+H]$^+$.

Intermediate E

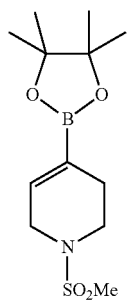

1-(Methylsulfonyl)-4-(4,4,5,5-tetramethyl-1,3,2-dioxaborolan-2-yl)-1,2,3,6-tetrahydropyridine Step 1

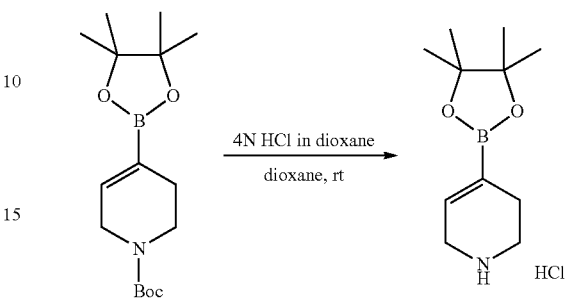

4-(4,4,5,5-Tetramethyl-1,3,2-dioxaborolan-2-yl)-1,2,3,6-tetrahydropyridine hydrochloride To a solution of tert-butyl 4-(4,4,5,5-tetramethyl-1,3,2-dioxaborolan-2-yl)-5,6-dihydropyridine-1(2H)-carboxylate (5 g, 16 mmol) in dioxane (10 mL) was added 4N HCl dioxane solution (24.2 mL, 97 mmol) at RT, and the reaction was stirred at RT for 4 h. The mixture was concentrated under reduced pressure to afford the title compound (4 g, yield 100%) as a white solid.

MS (ES$^+$) C$_{11}$H$_{21}$BClNO$_2$ requires: 209, found 210 [M+H]$^+$.

Step 2

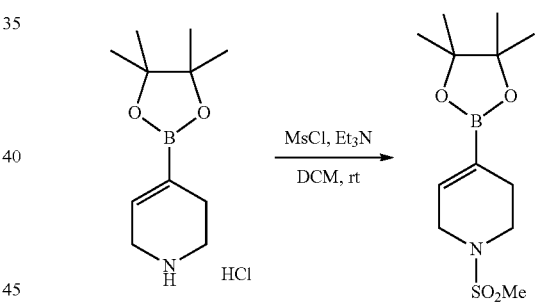

1-(Methylsulfonyl)-4-(4,4,5,5-tetramethyl-1,3,2-dioxaborolan-2-yl)-1,2,3,6-tetrahydropyridine To a mixture of the product from the previous step (4.0 g, 16 mmol) and TEA (6.3 mL, 48 mmol) in CH$_2$Cl$_2$ (60 mL) at RT was added methanesulfonyl chloride (1.5 mL, 20 mmol) dropwise and the reaction was stirred at RT overnight. The reaction mixture was diluted with CH$_2$Cl$_2$ (60 mL), washed with 1N HCl to pH=5, then with brine (50 mL), and then dried over Na$_2$SO$_4$, filtered and concentrated under reduced pressure. The residue was washed with petroleum ether (100 mL) to afford the title compound (3.5 g, 75% yield) as a white solid.

MS (ES$^+$) C$_{12}$H$_{22}$BNO$_4$S, requires: 287, found 288 [M+H]$^+$.

Intermediate F

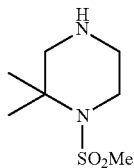

2,2-Dimethyl-1-(methylsulfonyl)piperazine hydrochloride

Step 1

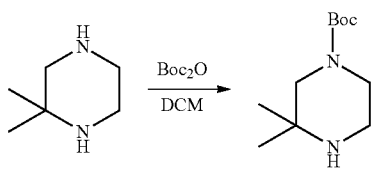

tert-Butyl 3,3-dimethylpiperazine-1-carboxylate To a solution of 2,2-dimethylpiperazine (1.50 g, 13.1 mmol) in CH$_2$Cl$_2$ (119 mL) at 0° C. was added Boc$_2$O (2.8 mL, 12 mmol) and the resulting mixture was stirred at RT for 14 h. The mixture was concentrated under reduced pressure and taken on to the next step without purification.

Step 2

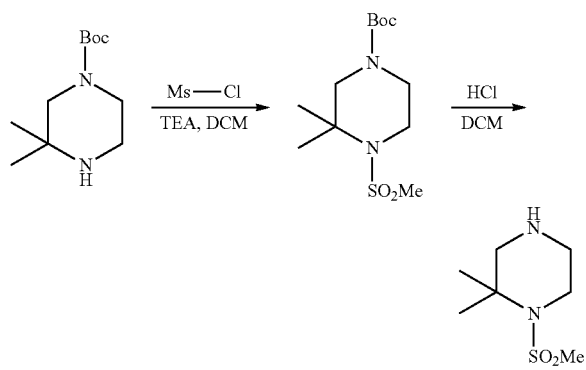

2,2-Dimethyl-1-(methylsulfonyl)piperazine hydrochloride: To a solution of the product from the previous step (1.0 g, 4.7 mmol) in CH$_2$Cl$_2$ (20 mL) at 0° C. were added TEA (2.0 ml, 14 mmol) and methanesulfonyl chloride (0.641 g, 5.60 mmol) and the resulting mixture was stirred RT for 3 h. The mixture was concentrated under reduced pressure. The residue was purified via silica gel chromatography (5-100% EtOAc in hexanes) to afford a colorless liquid. The residue was taken up in CH$_2$Cl$_2$ (20 mL), 4 N HCl in dioxane (3.5 mL, 14 mmol) was added and the mixture was stirred at RT for 14 h. A white ppt was collected by vacuum filtration to afford the title compound (716 mg, 80% yield).

$^1$H NMR (600 MHz, Methanol-d$_4$) δ 3.69-3.66 (m, 2H), 3.29-3.25 (m, 2H), 3.12 (s, 2H), 3.07 (s, 3H), 1.59 (s, 6H).

Intermediate G

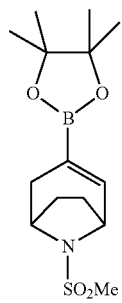

8-(Methylsulfonyl)-3-(4,4,5,5-tetramethyl-1,3,2-dioxaborolan-2-yl)-8-azabicyclo[3.2.1]-oct-2-ene Step 1

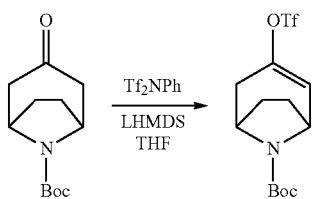 [SMILES: "Tf2NPh" ; CC(C)(C)OC(=O)N1C2CCC1CC(=O)C2 ; "LHMDSTHF" ; CC(C)(C)OC(=O)N1C2C=C(OS(=O)(=O)C(F)(F)F)CC1CC2]

Tert-butyl 3-(((trifluoromethyl)sulfonyl)oxy)-8-azabicyclo[3.2.1]oct-2-ene-8-carboxylate: To a solution of tert-butyl 3-oxo-8-azabicyclo[3.2.1]octane-8-carboxylate (1.0 g, 4.2 mmol) in THF (21.1 mL) was added LHMDS (4.64 mL, 4.64 mmol) dropwise under N$_2$ at −50° C. and the solution was warmed to −30° C. and stirred for 1 h. 1,1,1-trifluoro-N-phenyl-N-((trifluoromethyl)sulfonyl)methanesulfonamide (1.66 g, 4.64 mmol) in THF (1.0 mL) was added dropwise at −30° C. and the resulting mixture was warmed to 25° C. and stirred for 4 h. Aqueous sat. NH$_4$Cl (10 mL) was added to the reaction mixture and the aqueous layer was extracted with DCM (3×10 mL). The combined organic layers were dried over Na$_2$SO$_4$, filtered and concentrated under reduced pressure. The residue was purified via silica gel chromatography (0-30%) EtOAc in hexanes to afford the title compound (2.2 g, 95% yield)

MS (ES$^+$) C$_{13}$H$_{18}$F$_3$NO$_5$S requires: 357, found 358 [M+H]$^+$.

Step 2

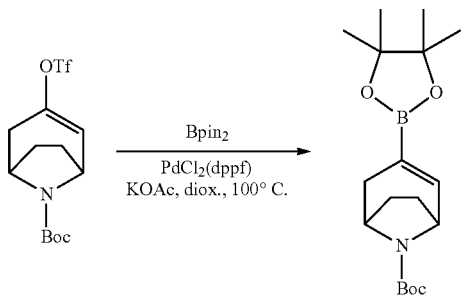

Tert-butyl 3-(4,4,5,5-tetramethyl-1,3,2-dioxaborolan-2-yl)-8-azabicyclo[3.2.1]oct-2-ene-8-carboxylate: To a solution of the product from the previous step (2.20 g, 4.00 mmol) in dioxane (13.3 mL) under N₂ were added KOAc (1.257 g, 12.81 mmol), PdCl₂(dppf) (0.293 g, 0.400 mmol) and 4,4,4',4',5,5,5',5'-octamethyl-2,2'-bi(1,3,2-dioxaborolane) (2.34 g, 9.20 mmol) and the resulting mixture was stirred at 100° C. for 4 h. The reaction was cooled to RT, water (10 mL) was added and the aqueous layer was extracted with EtOAc (3×10 mL). The combined organic layers were washed with brine (5 mL), dried over Na₂SO₄, filtered, and concentrated under reduced pressure. The residue was purified via silica gel chromatography (0-50%) EtOAc in hexanes to afford the title compound (1.12 g, 42% yield) as a colorless liquid.

MS (ES⁺) $C_{18}H_{30}BNO_4$ requires: 335, found 336 [M+H]⁺.

Step 3

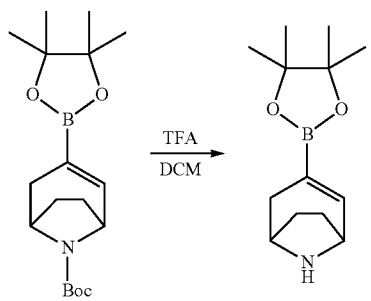

3-(4,4,5,5-Tetramethyl-1,3,2-dioxaborolan-2-yl)-8-azabicyclo[3.2.1]oct-2-ene 2,2,2-trifluoroacetate: To a solution of the product from the previous step (1.1 g, 1.6 mmol) in DCM (8.2 mL) was added TFA (0.632 mL, 8.20 mmol) and the resulting mixture was stirred at 22° C. for 2 h. The reaction mixture was concentrated under reduced pressure to afford the title compound (0.50 g, 87% yield) as a colorless liquid.

MS (ES⁺) $C_{13}H_{22}BNO_2$ requires: 235, found 236 [M+H]⁺.

Step 4

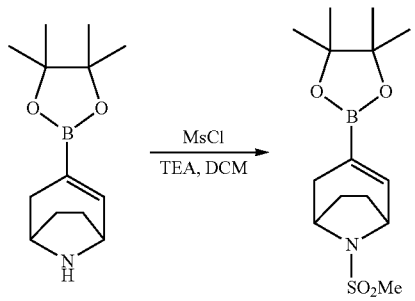

8-(Methylsulfonyl)-3-(4,4,5,5-tetramethyl-1,3,2-dioxaborolan-2-yl)-8-azabicyclo[3.2.1]oct-2-ene: To a solution of the product from the previous step (0.50 g, 0.72 mmol) in DCM (7.2 mL) were added TEA (0.249 mL, 1.79 mmol) and Ms-Cl (0.061 mL, 0.79 mmol) and the resulting mixture was stirred at 23° C. for 2 h. The reaction mixture was concentrated under reduced pressure. The residue was purified via silica gel chromatography (10-50% EtOAc in hexanes) to afford the title compound (181 mg, 81% yield) as a white solid.

MS (ES⁺) $C_{14}H_{24}BNO_4S$ requires: 313, found 314 [M+H]⁺.

Intermediate H

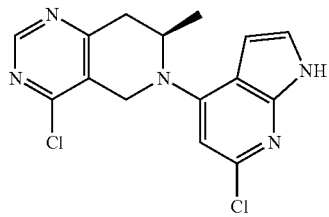 [SMILES: C[C@@H]1Cc2ncnc(Cl)c2CN1c1cc(Cl)nc2[nH]ccc12]

(R)-4-Chloro-6-(6-chloro-1H-pyrrolo[2,3-b]pyridin-4-yl)-7-methyl-5,6,7,8-tetrahydropyrido[4,3-d]pyrimidine Step 1

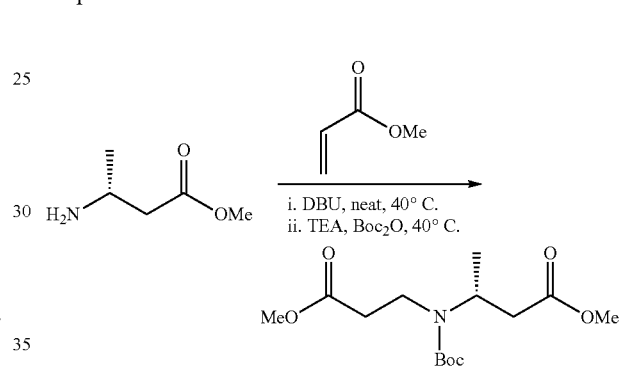

Methyl (R)-3-((tert-butoxycarbonyl)(3-methoxy-3-oxopropyl)amino)butanoate: To a mixture of (R)-methyl 3-aminobutanoate hydrochloride (5.0 g, 33 mmol) and methyl acrylate (3.2 mL, 36 mmol) in DCM (0.5 M) were added TEA (4.5 mL, 33 mmol) and DBU (0.245 mL, 1.63 mmol) and the mixture was stirred for 12 h at 40° C. TEA (9.0 mL, 66 mmol) and Boc₂O (8.5 g, 39 mmol) were added and the mixture was stirred for an additional 24 h at 40° C. The mixture was cooled to RT and concentrated under reduced pressure. Et₂O (50 mL) was added and the mixture was stirred for 5 min. The mixture was filtered, washed with Et₂O (2×10 mL) and the filtrate was concentrated under reduced pressure. The residue was taken up in Et₂O, filtered, washed with Et₂O (2×10 mL) and the filtrate was concentrated under reduced pressure. The residue was purified via silica gel chromatography (0-60% EtOAc in hexanes) to afford the title compound (7.36 g, 75% yield) as a colorless liquid.

¹H NMR (600 MHz, Chloroform-d) δ 4.27 (d, J=127.4 Hz, 1H), 3.67 (d, J=10.6 Hz, 6H), 3.52-3.28 (m, 2H), 2.73-2.64 (m, 1H), 2.64-2.59 (m, 1H), 2.56 (s, 1H), 2.46 (dd, J=14.9, 6.7 Hz, 1H), 1.46 (s, 9H), 1.24 (d, J=6.9 Hz, 3H).

Step 2

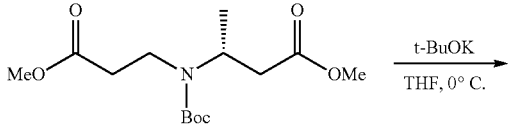

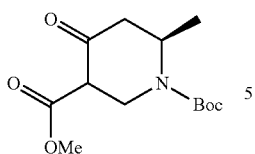

1-(Tert-butyl) 3-methyl (6R)-6-methyl-4-oxopiperidine-1,3-dicarboxylate: To a solution of the product from the previous step (10.6 g, 34.9 mmol) in THF (175 mL) at 0° C. was added t-BuOK 1.0 M in THF (41.9 mL, 41.9 mmol), slowly down the sides of the flask submerged in an ice water bath, and the resulting mixture was stirred at 0° C. for 3 h. Aqueous sat. NaHCO$_3$ (30 mL) was added and the layers were separated. The aqueous layer was extracted with EtOAc (4×50 mL). The combined organic layers were washed with brine (10 mL), dried over Na$_2$SO$_4$, filtered and concentrated under reduced pressure. The residue was filtered through a short pad of SiO$_2$ (80 mL) with 30% EtOAc in hexanes (200 mL) to afford the title compound (9.6 g, assumed quantitative yield) as a yellow liquid.

Step 3

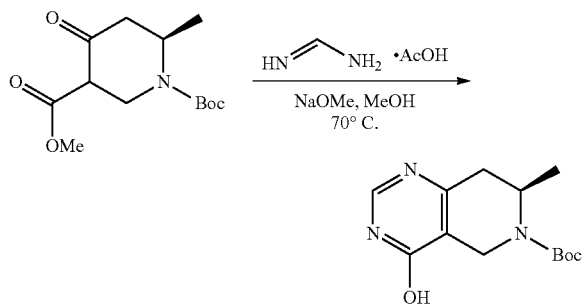

Tert-butyl (R)-4-hydroxy-7-methyl-7,8-dihydropyrido[4,3-d]pyrimidine-6(5H)-carboxylate: To a solution of the product from the previous step (9.55 g, 35.2 mmol) in MeOH (70.4 mL) was added formamidine acetate (11.0 g, 106 mmol) followed by sodium methoxide in MeOH (24.1 mL, 106 mmol) and the resulting mixture was stirred at 70° C. for 16 h. The mixture was cooled to RT and concentrated under reduced pressure. The residue was partitioned between EtOAc (50 mL) and aq. sat. NaHCO$_3$ (30 mL) and the aqueous layer was extracted with EtOAc (4×60 mL). The combined organic fractions were washed with brine (10 mL), dried over Na$_2$SO$_4$, filtered and concentrated under reduced pressure to afford the title compound (9.4 g, assumed quantitative yield) as a brown amorphous solid.

MS (ES$^+$) C$_{13}$H$_{19}$N$_3$O$_3$ requires: 265, found: 266 [M+H]$^+$.

Step 4

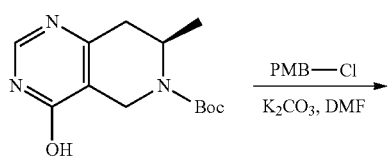

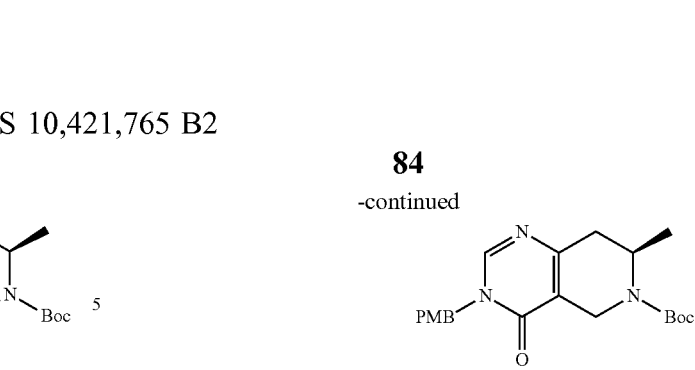

Tert-butyl (R)-3-(4-methoxybenzyl)-7-methyl-4-oxo-3,5,7,8-tetrahydropyrido[4,3-d]pyrimidine-6(4H)-carboxylate: To a solution of the product from the previous step (9.3 g, 35 mmol) in DMF (117 mL) were added K$_2$CO$_3$ (9.69 g, 70.1 mmol) and 4-methoxybenzyl chloride (5.25 mL, 38.6 mmol) and the resulting mixture was stirred at 40° C. for 12 h. The reaction mixture was cooled to RT, diluted with EtOAc (100 mL) and partitioned with H$_2$O (100 mL). The layers were separated, and the aqueous layer was extracted with EtOAc (3×150 mL). The combined organic layers were washed with H2O (4×60 mL) and brine (60 mL), dried over Na$_2$SO$_4$, filtered and concentrated under reduced pressure. The residue was purified via silica gel chromatography (50-100% EtOAc in hexanes) to afford the title compound (6.48 g, 48% yield) as a yellow liquid.

MS (ES$^+$) C$_{21}$H$_{27}$N$_3$O$_4$ requires: 385, found: 386 [M+H]$^+$.

Step 5

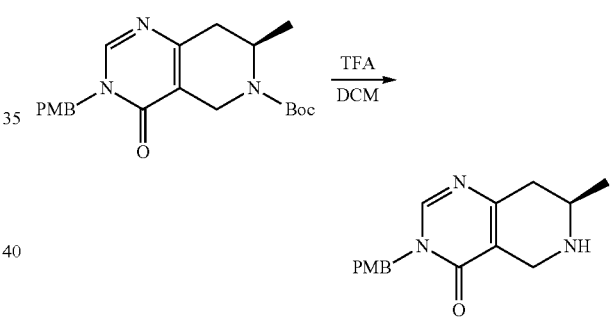

(R)-3-(4-Methoxybenzyl)-7-methyl-5,6,7,8-tetrahydropyrido[4,3-d]pyrimidin-4(3H)-one: To a solution of the product from the previous step (4.84 g, 12.6 mmol) in DCM (62.8 mL) were added TFA (9.67 mL, 126 mmol) and the resulting mixture was stirred at RT for 16 h. The mixture was diluted with DCM (150 mL) and partitioned with aq. sat. NaHCO$_3$ (150 mL). The layers were separated and the aqueous layer was extracted with DCM (4×100 mL). The combined organic layers were washed with brine (30 mL), dried over Na$_2$SO$_4$, filtered and concentrated under reduced pressure to afford the title compound (3.53 g, 99% yield) as an off-white solid.

MS (ES$^+$) C$_{16}$H$_{19}$N$_3$O$_2$ requires: 285, found: 286 [M+H]$^+$.

Step 6

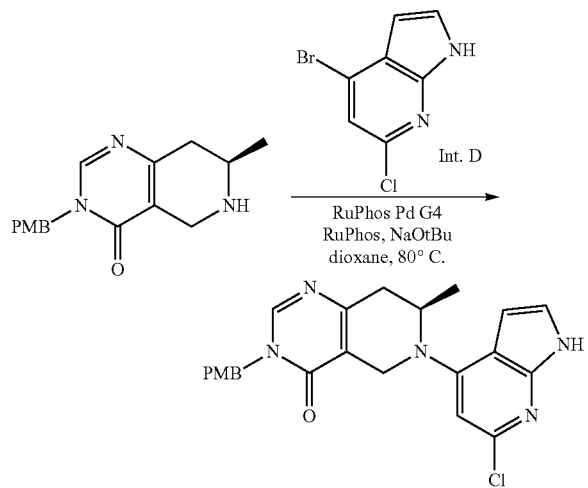

(R)-6-(6-Chloro-1H-pyrrolo[2,3-b]pyridin-4-yl)-3-(4-methoxybenzyl)-7-methyl-5,6,7,8-tetrahydropyrido[4,3-d]pyrimidin-4(3H)-one: A solution of the product from the previous step (6.1 g, 21.38 mmol) and Int. D (4.95 g, 21.38 mmol) in Dioxane (107 mL) was sonicated to give a heterogenous mixture then degassed with $N_2$ for 5 minutes. RuPhos (0.998 g, 2.14 mmol), RuPhos Pd G4 (1.66 g, 2.14 mmol) and sodium tert-butoxide (6.16 g, 64.1 mmol) were added and the mixture was sonicated for 1 minute then degassed with $N_2$ for an additional 2 minutes. The reaction mixture was heated at 80° C. and stirred for 16 h. The mixture was cooled to RT, diluted with EtOAc (20 mL), filtered through CELITE® and concentrated under reduced pressure. The residue was purified via silica gel chromatography (0-10% MeOH in DCM) to afford the title compound (6.1 g, 66% yield) as a pale yellow solid.

MS (ES$^+$) $C_{23}H_{22}ClN_5O_2$ requires: 435, found: 436 [M+H]$^+$.

Step 7

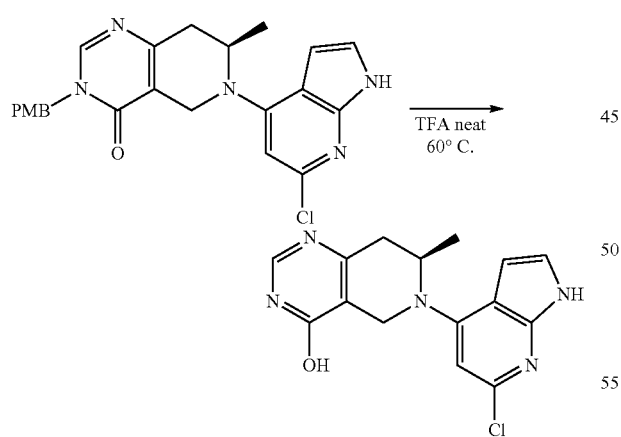

(R)-6-(6-Chloro-1H-pyrrolo[2,3-b]pyridin-4-yl)-7-methyl-5,6,7,8-tetrahydropyrido[4,3-d]pyrimidin-4-ol bis(2,2,2-trifluoroacetate): A solution of the product from the previous step (5.1 g, 12 mmol) in TFA (11.7 mL) was heated at 60° C. for 72 h. The mixture was cooled to RT, diluted with DCM (50 mL) and concentrated under reduced pressure. The residue was re-concentrated from DCM (4×50 mL) to afford the title compound (6.4 g, assumed quantitative yield) as a brown solid.

MS (ES$^+$) $C_{15}H_{14}ClN_5O$ requires: 315, found: 316 [M+H]$^+$.

Step 8

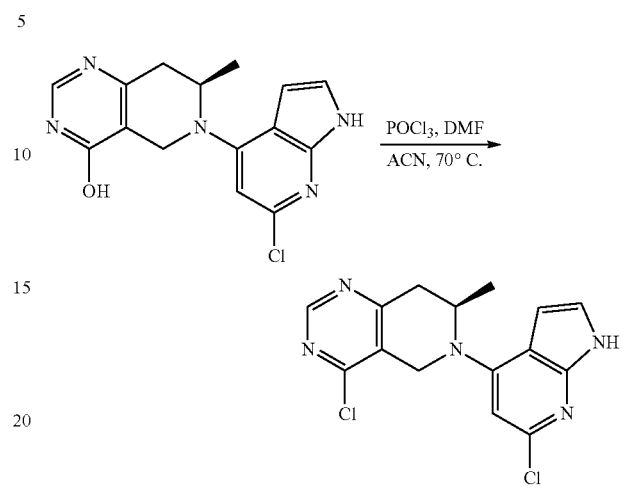

(R)-4-Chloro-6-(6-chloro-1H-pyrrolo[2,3-b]pyridin-4-yl)-7-methyl-5,6,7,8-tetrahydropyrido[4,3-d]pyrimidine: To a solution the product from the previous step (1.4 g, 2.6 mmol) in ACN (25.7 mL) was added POCl$_3$ (0.72 mL, 7.7 mmol) and DMF (20 µL, 0.26 mmol) and the mixture was heated at 70° C. for 6 h. The mixture was cooled to RT and concentrated under reduced pressure. The residue was partitioned between DCM (20 mL) and aq. sat. NaHCO$_3$ (20 mL) and the aqueous layer was extracted with DCM (3×20 mL). The combined organic layers were dried over Na$_2$SO$_4$, filtered and concentrated under reduced pressure. The residue was purified via silica gel chromatography (0-10% MeOH in DCM) to afford the title compound (522 mg, 61% yield) as a yellow solid.

$^1$H NMR (600 MHz, Chloroform-d) δ 10.50 (s, 1H), 8.88 (s, 1H), 7.24 (dd, J=3.6, 2.5 Hz, 1H), 6.58-6.53 (m, 1H), 6.54 (s, 1H), 5.00-4.92 (m, 1H), 4.72 (d, J=17.0 Hz, 1H), 4.51 (d, J=17.0 Hz, 1H), 3.52 (dd, J=17.5, 6.1 Hz, 1H), 2.95 (d, J=17.4 Hz, 1H), 1.20 (d, J=6.8 Hz, 3H); MS (ES$^+$) $C_{15}H_{13}Cl_2N_5$ requires: 333, found: 334 [M+H]$^+$.

Intermediate I

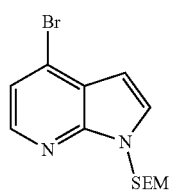

87

4-Bromo-1-((2-(trimethylsilyl)ethoxy)methyl)-1H-pyrrolo[2,3-b]pyridine

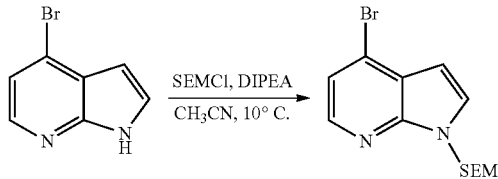 [SMILES: Brc1ccnc2[nH]ccc12 ; C[Si](C)(C)CCOCn1ccc2c(Br)ccnc21]

4-bromo-1-((2-(trimethylsilyl)ethoxy)methyl)-1H-pyrrolo[2,3-b]pyridine: To a solution of 4-bromo-1H-pyrrolo[2,3-b]pyridine (800 mg, 4.06 mmol) in CH₃CN (20 mL) at 10° C. was added 2-(trimethylsilyl)ethoxymethyl chloride (1.0 mL, 5.7 mmol) and DIPEA (1.0 mL, 5.74 mmol) dropwise and the resulting mixture was stirred at 10° C. for 2 h. H₂O (20 mL) was added, the layers were separated and the aqueous layer was extracted with EtOAc (3×30 mL). The combined organic layers were dried over MgSO₄, filtered and concentrated under reduced pressure The residue was purified via silica gel chromatography (75% EtOAc in petroleum ether) to afford the title compound (1.2 g, 92% yield).

MS (ES⁺) $C_{13}H_{19}BrN_2OSi$ requires: 326, found: 327 $[M+H]^+$.

Intermediate J

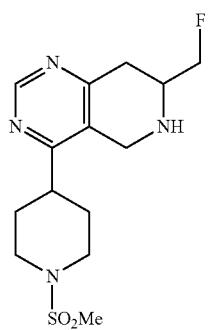 [SMILES: CS(=O)(=O)N1CCC(c2ncnc3c2CNC(CF)C3)CC1]

7-(Fluoromethyl)-4-(1-(methylsulfonyl)piperidin-4-yl)-5,6,7,8-tetrahydropyrido[4,3-d]-pyrimidine Step 1

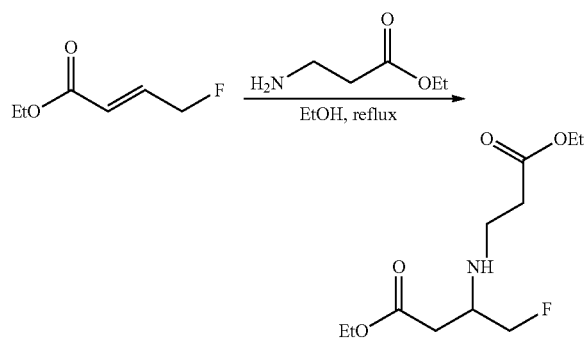

88

Ethyl 3-((3-ethoxy-3-oxopropyl)amino)-4-fluorobutanoate: To a solution of ethyl (E)-4-fluorobut-2-enoate (1.0 g, 7.57 mmol) in EtOH (15 mL) was added ethyl 3-aminopropanoate (1.12 g, 9.46 mmol) and the resulting mixture was heated to 85° C. and stirred for 14 h. The mixture was cooled to RT and concentrated under reduced pressure. The residue was partitioned between EtOAc (50 mL) and water (50 mL), the layers were separated, and the aqueous layer was extracted with EtOAc (3×50 mL). The combined organic layers were dried over MgSO₄, filtered and concentrated under reduced pressure to afford the title compound (0.93 g, 49% yield) as colorless oil.

MS (ES⁺) $C_{11}H_{20}FNO_4$ requires: 249, found: 250 $[M+H]^+$.

Step 2

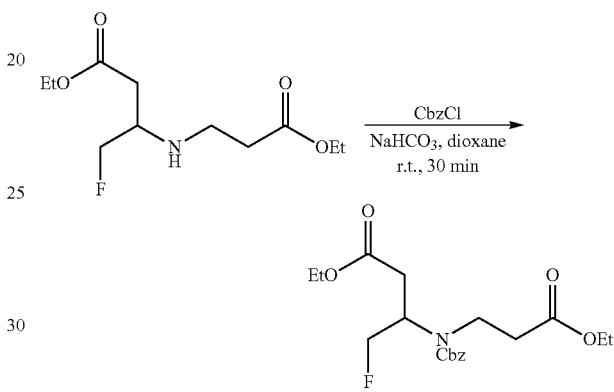

Ethyl 3-(((benzyloxy)carbonyl)(3-ethoxy-3-oxopropyl)amino)-4-fluorobutanoate: To a suspension of the product from the previous step (1.0 g, 4.0 mmol) and NaHCO₃ (506 mg, 6.02 mmol) in dioxane (10 mL) at 0° C. was added CbzCl (1.15 g, 6.79 mmol) and the resulting mixture was stirred warmed to RT and stirred for 30 min. H₂O (20 mL) was added dropwise, the layers are separated and the aqueous layer was extracted with EtOAc (3×30 mL). The combined organic layers were dried over MgSO₄, filtered and concentrated under reduced pressure. The residue was purified via silica gel chromatography (8% EtOAc in petroleum ether) to afford the title compound (1.0 g, 85% yield).

MS (ES⁺) $C_{19}H_{26}FNO_6$ requires: 383, found: 384 $[M+H]^+$.

Step 3

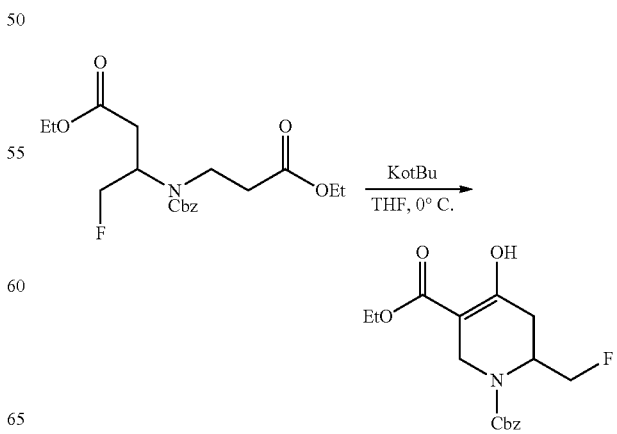

1-Benzyl 3-ethyl 6-(fluoromethyl)-4-hydroxy-5,6-dihydropyridine-1,3(2H)-dicarboxylate: To a solution of the product from the previous step (1.0 g, 2.6 mmol) in THF (10 mL) at 0° C. was added t-BuOK (1 mmol/mL in THF, 5.7 mL, 6.3 mmol) dropwise and the resulting mixture was stirred at 0° C. for 30 min. H$_2$O (50 mL) was added dropwise, the layers were separated and the aqueous layer was extracted with EtOAc (3×50 mL). The combined organic layers were dried over MgSO$_4$, filtered and concentrated under reduced pressure. The residue was purified via silica gel chromatography (8% EtOAc in petroleum ether) to afford the title compound (300 mg, 36% yield) as colorless liquid.

$^1$H NMR (400 MHz, CDCl$_3$): δ 12.15 (s, 1H), 7.47-7.28 (m, 5H), 5.25-5.13 (m, 2H), 4.99-3.98 (m, 6H), 3.86-3.17 (m, 1H), 2.77-2.21 (m, 2H), 1.34-1.27 (m, 3H).
Step 4

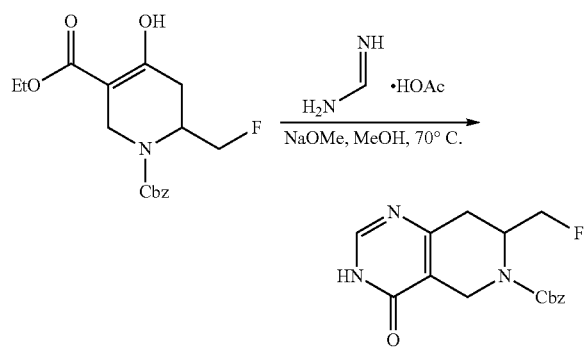

Benzyl 7-(fluoromethyl)-4-oxo-3,5,7,8-tetrahydropyrido[4,3-d]pyrimidine-6(4H)-carboxylate: To a solution of the product from the previous step (1.5 g, 4.5 mmol) in MeOH (26 mL) at 0° C. was added NaOMe (5.5 mL, 29 mmol) and the resulting mixture was stirred at 0° C. for 30 min. Formamidine acetate (2.315 g, 28.9 mmol) was added and the reaction mixture was heated to 70° C. and stirred for 14 h. The mixture was cooled to RT and concentrated under reduced pressure. The residue was partitioned between H$_2$O (20 mL) and EtOAc (20 mL), the layers were separated and the aqueous layer was extracted with EtOAc (3×20 mL). The combined organic layers were dried over MgSO$_4$, filtered and concentrated under reduced pressure. The residue was purified via silica gel chromatography (50% EtOAc in petroleum ether) to afford the title compound (0.9 g, 64% yield).

MS (ES$^+$) C$_{16}$H$_{16}$FN$_3$O$_3$ requires: 317, found: 318 [M+H]$^+$.
Step 5

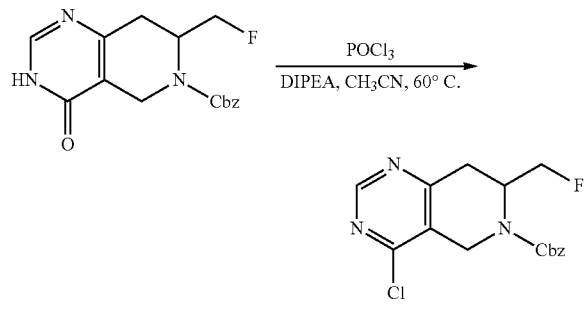

Benzyl 4-chloro-7-(fluoromethyl)-7,8-dihydropyrido[4,3-d]pyrimidine-6(5H)-carboxylate: To a solution of the product from the previous step (6.1 g, 19 mmol) in CH$_3$CN (64 mL) at 0° C. were added POCl$_3$ (26.88 mL, 288.4 mmol) and DIPEA (49.6 mL, 288.4 mmol) slowly. The mixture was heated at 60° C. and stirred for 14 h. The mixture was poured into ice water (10 mL), neutralized with aq. sat. NaHCO$_3$ and extracted EtOAc (3×50 mL). The combined organic layers were dried over MgSO$_4$, filtered and concentrated under reduced pressure. The residue was purified via silica gel chromatography (66% DCM in MeOH) to afford the title compound (1.9 g, 33% yield).

MS (ES$^+$) C$_{16}$H$_{15}$ClFN$_3$O$_2$ requires: 335, found: 336 [M+H]$^+$.
Step 6

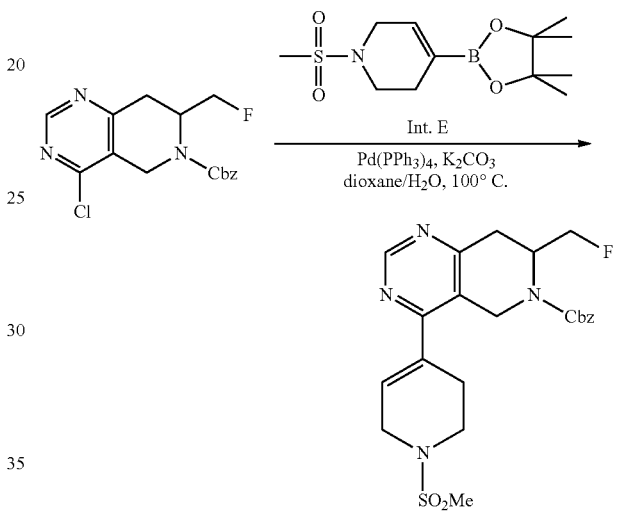

Benzyl 7-(fluoromethyl)-4-(1-(methylsulfonyl)-1,2,3,6-tetrahydropyridin-4-yl)-7,8-dihydropyrido[4,3-d]pyrimidine-6(5H)-carboxylate: To a suspension of the product from the previous step (1.3 g, 3.9 mmol), Int. E (1.2 g, 4.3 mmol), K$_2$CO$_3$ (1.1 g, 4.0 mmol) and Pd(PPh$_3$)$_4$(447 mg, 10 mol %) in dioxane (20 mL) and H$_2$O (1 mL) was degassed with N$_2$ for 3 minutes. The reaction mixture was heated to 100° C. and stirred for 14 h under Ar. The mixture was cooled to RT, filtered through CELITE® and concentrated under reduced pressure. The residue was purified via silica gel chromatography (50% EtOAc in petroleum ether) to afford the title compound (0.8 g, 61% yield).

MS (ES$^+$) C$_{22}$H$_{25}$FN$_4$O$_4$S requires: 460, found: 461 [M+H]$^+$.
Step 7

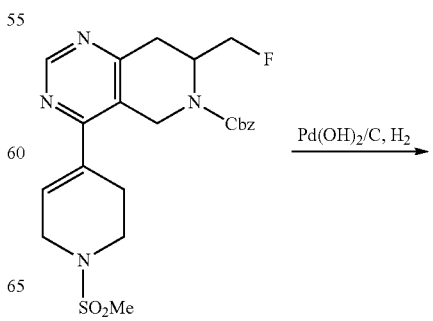

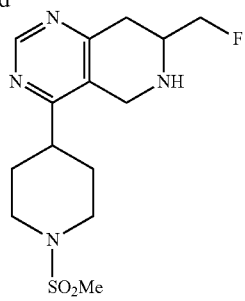

7-(Fluoromethyl)-4-(1-(methylsulfonyl)piperidin-4-yl)-5,6,7,8-tetrahydro-pyrido[4,3-d]pyrimidine: A reaction vessel was charged with the product from the previous step (700 mg, 1.52 mmol), 10% Pd/C (350 mg, 20 mol %) and MeOH (9 mL) under an atmosphere of $N_2$. The suspension was degassed with $N_2$ for 1 minute and purged with $H_2$ for 3 minutes. The reaction mixture was stirred under an atmosphere of $H_2$ at 1 atm for 16 h. The reaction mixture was purged with $N_2$, filtered through CELITE® and concentrated under reduced pressure to afford the title compound (367 mg, 73% yield).

MS (ES$^+$) $C_{14}H_{21}FN_4O_2S$ requires: 328, found: 329 $[M+H]^+$.

Intermediate K

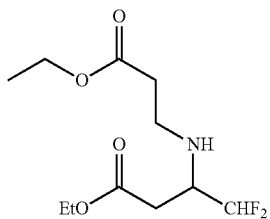 [SMILES: CCOC(=O)CCNC(CC(=O)OCC)C(F)F]

Ethyl 3-((3-ethoxy-3-oxopropyl)amino)-4,4-difluorobutanoate

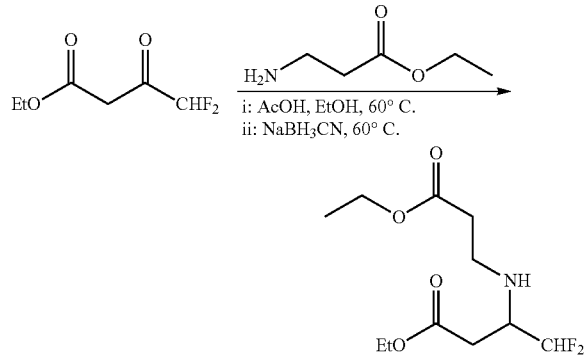

Ethyl 3-((3-ethoxy-3-oxopropyl)amino)-4,4-difluorobutanoate: To a solution of ethyl 3-aminopropanoate (4.0 g, 34 mmol) in EtOH (100 mL) was added glacial acetic acid (2 mL) and the resulting mixture was stirred at RT for 10 mins. Ethyl 4,4-difluoro-3-oxobutanoate (5.1 g, 31 mmol) was added and the mixture was heated at reflux for 1 h. The mixture was cooled to RT, NaBH$_3$CN (2.0 g, 31 mmol) was added in small portions and the mixture was heated at 60° C. and stirred for 2 h. The mixture was cooled to RT and concentrated under reduced pressure. The residue was partitioned with H$_2$O (30 mL) and EtOAc (30 mL), the layers were separated and the aqueous layer was extracted with EtOAc (3×50 mL). The combined organic layers were dried over MgSO$_4$, filtered and concentrated under reduced pressure to afford the title compound (3.0 g, 63% yield) as colorless liquid.

MS (ES$^+$) $C_{11}H_{19}F_2NO_4$ requires: 267, found: 268 $[M+H]^+$.

Intermediate L

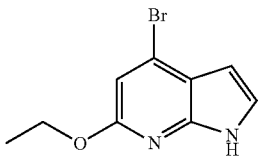

4-Bromo-6-ethoxy-1H-pyrrolo[2,3-b]pyridine

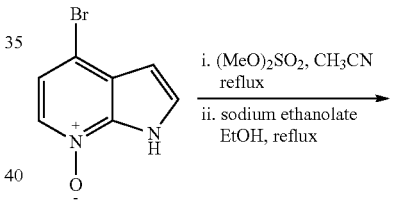

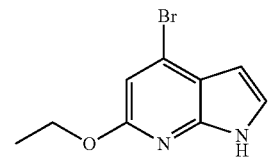

4-Bromo-6-ethoxy-1H-pyrrolo[2,3-b]pyridine: A mixture of 4-bromo-1H-pyrrolo[2,3-b]pyridine 7-oxide (426 mg, 2.0 mmol) and dimethyl sulfate (303 mg, 2.4 mmol) in CH$_3$CN (10 mL) was heated to 70° C. for 24 h. The reaction mixture was cooled to RT, sodium ethanolate (40 mg, 6.0 mmol) was added and the mixture was heated at 70° C. for 24 h. The reaction mixture was cooled to RT, neutralized with AcOH to pH=7 and then concentrated under reduced pressure. The residue was dissolved in CH$_2$Cl$_2$ (50 mL), washed with aq. sat. NaHCO$_3$ (20 mL) and brine (15 mL), dried over Na$_2$SO$_4$, filtered and concentrated under reduced pressure. The residue was purified via silica gel chromatography (0-20% EtOAc in petroleum ether) to afford the title compound (151 mg, 31% yield) as a white solid.

MS (ES$^+$) $C_9H_9BrN_2O$ requires: 240, found: 241 $[M+H]^+$.

93

Intermediate M

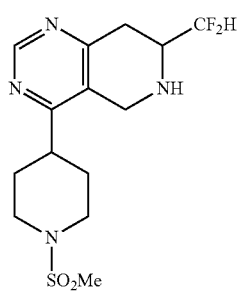

7-(Difluoromethyl)-4-(1-(methylsulfonyl)piperidin-4-yl)-5,6,7,8-tetrahydropyrido[4,3-d]pyrimidine 7-(Difluoromethyl)-4-(1-(methylsulfonyl)piperidin-4-yl)-5,6,7,8-tetrahydropyrido[4,3-d]pyrimidine: Synthesized as described for Int. J by substituting Int. K in place of ethyl 3-((3-ethoxy-3-oxopropyl)amino)-4-fluorobutanoate.

MS (ES$^+$) $C_{14}H_{20}F_2N_4O_2S$ requires: 346, found: 347 [M+H]$^+$.

Intermediate N

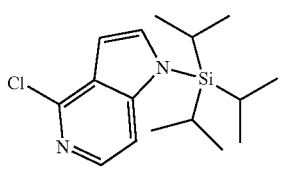 [SMILES: CC(C)[Si](C(C)C)(C(C)C)n1ccc2c(Cl)nccc21]

4-Chloro-1-(triisopropylsilyl)-1H-pyrrolo[3,2-c]pyridine

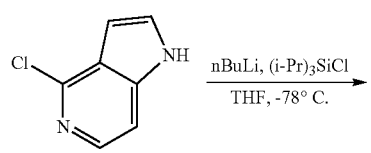

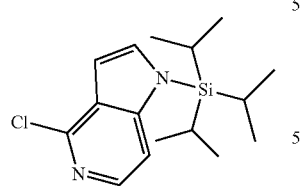

4-Chloro-1-(triisopropylsilyl)-1H-pyrrolo[3,2-c]pyridine: To a solution of 4-chloro-1H-pyrrolo[3,2-c]pyridine (150 mg, 0.98 mmol) in THF (10 mL) at −78° C. was added 2.5N n-BuLi (0.6 mL, 1.5 mmol) and the reaction was stirred at −78° C. for 30 min. Chlorotriisopropylsilane (284 mg, 1.47 mmol) was added and the mixture was stirred at −78° C. for an additional 2 h. Water (400 μL) was added followed by THF (20 mL) and the mixture was dried over Na$_2$SO$_4$, filtered and concentrated under reduced pressure. The residue was purified via silica gel chromatography (0-40% acetone in petroleum ether) to afford the title compound (150 mg, 49% yield) as a colorless oil.

MS (ES$^+$) $C_{16}H_{25}ClN_2Si$ requires: 308, found: 309 [M+H]$^+$.

The invention is further illustrated by the following examples, which may be synthesized and isolated as free bases or as TFA salts.

EXAMPLE 1

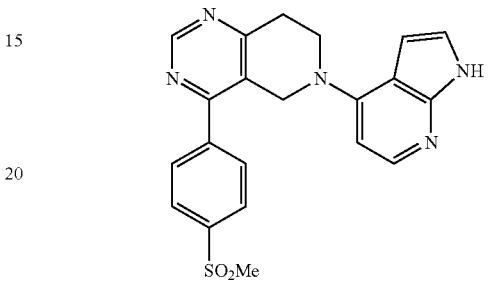

4-(4-(Methylsulfonyl)phenyl)-6-(1H-pyrrolo[2,3-b]pyridin-4-yl)-5,6,7,8-tetrahydropyrido[4,3-d]pyrimidine bis(trifluoroacetate)

Step 1

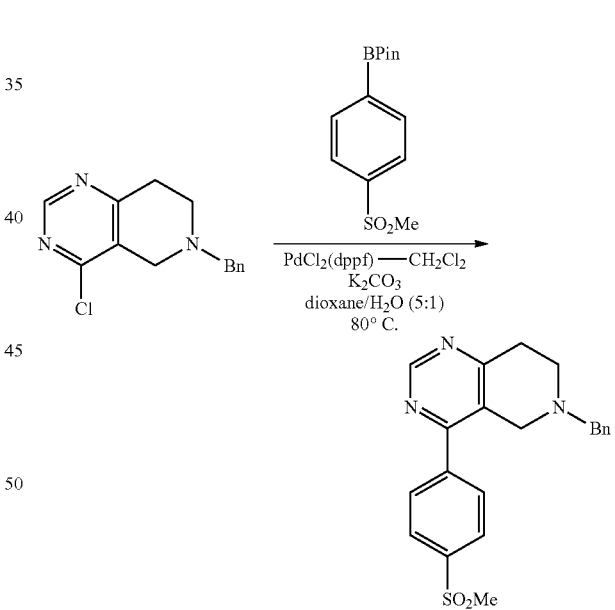

6-Benzyl-4-(4-(methylsulfonyl)phenyl)-5,6,7,8-tetrahydropyrido[4,3-d]-pyrimidine A suspension of Intermediate A (40 mg, 0.15 mmol), 4,4,5,5-tetramethyl-2-(4-(methylsulfonyl)phenyl)-1,3,2-dioxaborolane (48 mg, 0.17 mmol) and K$_2$CO$_3$ (64 mg, 0.46 mmol) in dioxane (642 μL) and water (128 μL) was degassed with N$_2$ for 1 minute. PdCl$_2$(dppf)-CH$_2$Cl$_2$ Adduct (13 mg, 0.015 mmol) was added and the mixture was degassed with N$_2$ for an additional 1 minute. The reaction mixture was heated at 80° C. and stirred for 16 h. The mixture was cooled to RT, filtered through CELITE® and concentrated under reduced pressure. The residue was purified by mass-triggered preparative HPLC (Mobile phase: A=0.1% TFA/H₂O, B=0.1% TFA/MeCN; Gradient: B=10-40%; 12 min; Column: XBridge C18, 5 µm, 19 mm×150 mm) to afford the title compound (45 mg, 48% yield) as an off-white solid.

MS (ES$^+$) $C_{21}H_{21}N_3O_2S$ requires: 379, found: 380 [M+H]$^+$.

Step 2

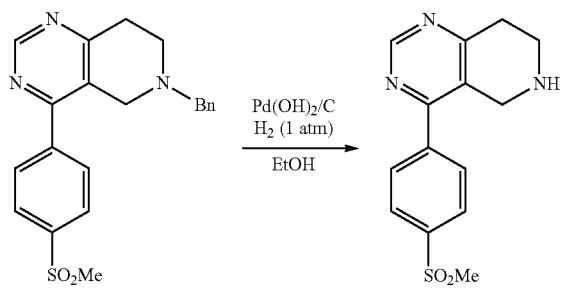 [SMILES: "EtOH" ; CS(=O)(=O)c1ccc(-c2ncnc3c2CN(Cc2ccccc2)CC3)cc1 ; "Pd(OH)2/CH2 (1 atm)" ; CS(=O)(=O)c1ccc(-c2ncnc3c2CNCC3)cc1]

4-(4-(Methylsulfonyl)phenyl)-5,6,7,8-tetrahydropyrido[4,3-d]pyrimidine bis(trifluoroacetate) A reaction vessel was charged with the product from the previous step (100 mg, 0.165 mmol), Pd/C (35 mg, 0.033 mmol) and EtOH (1.6 mL) under an atmosphere of N₂. The suspension was degassed with N₂ for 1 minute and purged with H₂ for 1 minute. The reaction mixture was stirred under an atmosphere of H₂ at 50 psi for 16 h. The reaction mixture was purged with N₂, and filtered through CELITE® and concentrated under reduced pressure. The residue was purified by mass-triggered preparative HPLC (Mobile phase: A=0.1% TFA/H₂O, B=0.1% TFA/MeCN; Gradient: B=0-30%; 20 min; Column: XBridge C18, 5 µm, 19 mm×150 mm) to afford the title compound (69 mg, 81% yield) as a pale yellow liquid.

MS (ES$^+$) $C_{14}H_{15}N_3O_2S$ requires: 289, found 290 [M+H]$^+$.

Step 3

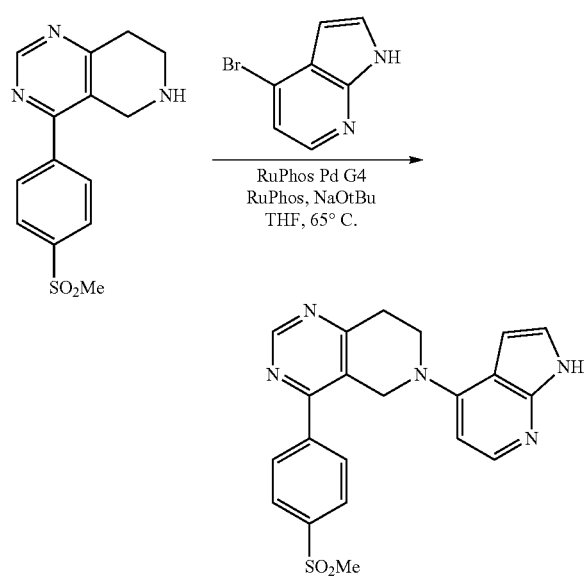

4-(4-(Methylsulfonyl)phenyl)-6-(1H-pyrrolo[2,3-b]pyridin-4-yl)-5,6,7,8-tetra-hydropyrido[4,3-d]pyrimidine bis(trifluoroacetate): A reaction vial was charged with the product from the previous step (25 mg, 0.086 mmol), 4-bromo-1H-pyrrolo[2,3-b]pyridine (20 mg, 0.10 mmol), dicyclohexyl(2',6'-diisopropoxy-[1,1'-biphenyl]-2-yl)phosphine (20 mg, 0.043 mmol) and sodium tert-butoxide (25 mg, 0.26 mmol). RuPhos Pd G4 (7.4 mg, 8.6 µmol) was added under N₂, the mixture was degassed with N₂ for 30 seconds, the vial was sealed and heated at 65° C. for 12 h. The mixture was cooled to RT, 1.0 M HCl in MeOH (1.5 mL) was added to give a homogeneous solution and the mixture was concentrated under reduced pressure. The residue was purified by mass-triggered preparative HPLC (Mobile phase: A=0.1% TFA/H₂O, B=0.1% TFA/MeCN; Gradient: B=0-30%; 12 min; Column: XBridge C18, 5 µm, 19 mm×150 mm) to afford the title compound (3.7 mg, 6.8% yield) as a yellow amorphous material.

$^1$H NMR (600 MHz, Methanol-d₄) δ 9.13 (s, 1H), 8.19 (d, J=8.3 Hz, 2H), 7.95 (d, J=8.3 Hz, 2H), 7.91 (d, J=7.2 Hz, 1H), 7.29 (d, J=3.7 Hz, 1H), 6.75 (d, J=7.3 Hz, 1H), 6.71 (d, J=3.7 Hz, 1H), 5.14 (s, 2H), 4.28 (t, J=6.1 Hz, 2H), 3.39 (t, J=6.0 Hz, 2H), 3.23 (s, 3H); MS (ES$^+$) $C_{21}H_{19}N_5O_2S$ requires: 405, found: 406 [M+H]$^+$.

EXAMPLE 2

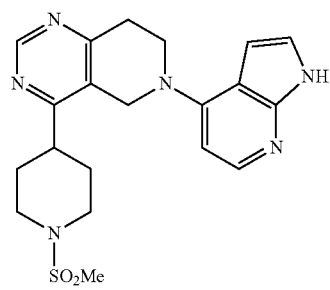 [SMILES: CS(=O)(=O)N1CCC(c2ncnc3c2CN(c2ccnc4[nH]ccc24)CC3)CC1]

4-(1-(Methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate)

Step 1

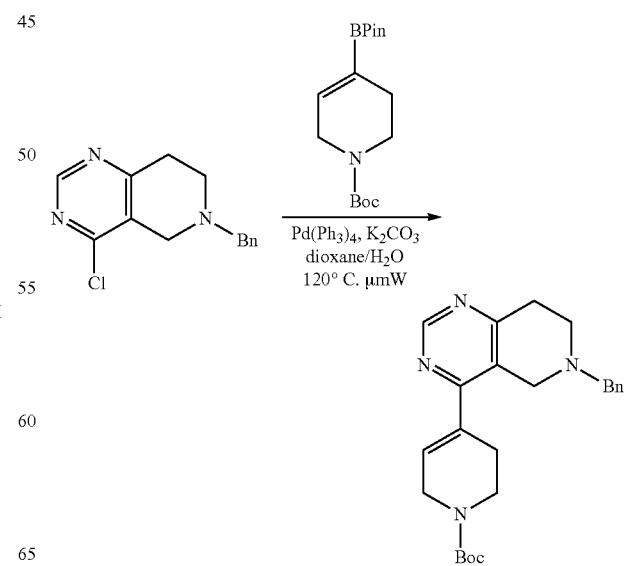

tert-Butyl 4-(6-benzyl-5,6,7,8-tetrahydropyrido[4,3-d]pyrimidin-4-yl)-3,6-dihydropyridine-1(2H)-carboxylate bis(trifluoroacetate) To a solution of Intermediate A (200 mg, 0.770 mmol) in dioxane (3.5 mL) and water (350 μL) under $N_2$ were added Pd(PPh$_3$)$_4$(178 mg, 0.154 mmol), $K_2CO_3$ (319 mg, 2.31 mmol) and tert-butyl 4-(4,4,5,5-tetramethyl-1,3,2-dioxaborolan-2-yl)-5,6-dihydropyridine-1(2H)-carboxylate (310 mg, 1.00 mmol) and the resulting mixture was at 120° C. in a microwave reactor for 1 h. The mixture was filtered through CELITE® and concentrated under reduced pressure. The residue was purified via mass-triggered preparative HPLC (Mobile phase: A=0.1% TFA/H$_2$O, B=0.1% TFA/MeCN; Gradient: B=10-40%; 26 min; Column: XBridge C18, 5 μm, 19 mm×150 mm) to afford the title compound (263 mg, 54% yield) as an orange liquid.

MS (ES$^+$) C$_{24}$H$_{30}$N$_4$O$_2$ requires: 406, found 407 [M+H]$^+$.

Step 2

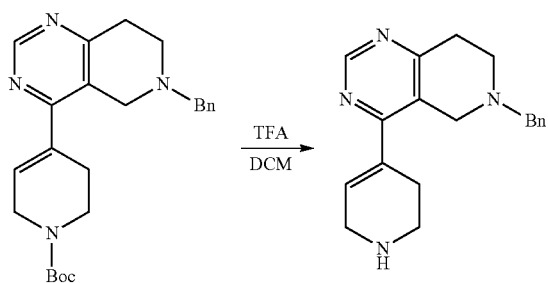

6-Benzyl-4-(1,2,3,6-tetrahydropyridin-4-yl)-5,6,7,8-tetrahydropyrido[4,3-d]-pyrimidine bis(trifluoroacetate) To a solution of the product from the previous step (250 mg, 0.394 mmol) in CH$_2$Cl$_2$ (2.0 mL) was added TFA (304 μL, 3.94 mmol) and the resulting mixture was stirred at 22° C. for 2 h. The reaction solution was concentrated and the residue was purified by mass-triggered preparative HPLC (Mobile phase: A=0.1% TFA/H$_2$O, B=0.1% TFA/MeCN; Gradient: B=0-30%; 16 min; Column: XBridge C18, 5 μm, 19 mm×150 mm) to afford the title compound (133 mg, 63% yield) as a brown liquid.

MS (ES$^+$) C$_{19}$H$_{22}$N$_4$ requires: 306, found 307 [M+H]$^+$.

Step 3

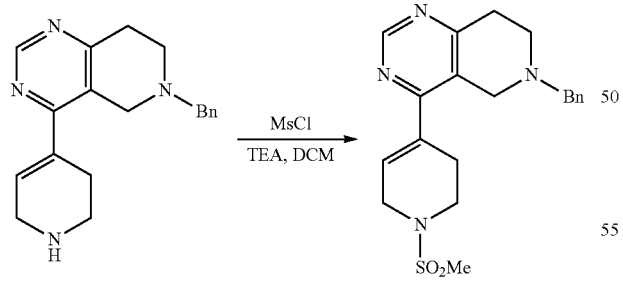

6-Benzyl-4-(1-(methylsulfonyl)-1,2,3,6-tetrahydropyridin-4-yl)-5,6,7,8-tetra-hydropyrido[4,3-d]pyrimidine bis(trifluoroacetate) To a solution of the product from the previous step (133 mg, 0.205 mmol) in CH$_2$Cl$_2$ (2.1 mL) were added TEA (143 μL, 1.03 mmol) and methanesulfonyl chloride (19 μL, 0.25 mmol) and the resulting mixture was stirred at 23° C. for 1 h. The mixture was purified by mass-triggered preparative HPLC (Mobile phase: A=0.1% TFA/H$_2$O, B=0.1% TFA/MeCN; Gradient: B=10-40%; 16 min; Column: XBridge C18, 5 μm, 19 mm×150 mm) to afford the title compound (88 mg, 70% yield) as a pale yellow liquid.

MS (ES$^+$) C$_{20}$H$_{24}$N$_4$O$_2$S requires: 384, found 385 [M+H]$^+$.

Step 4

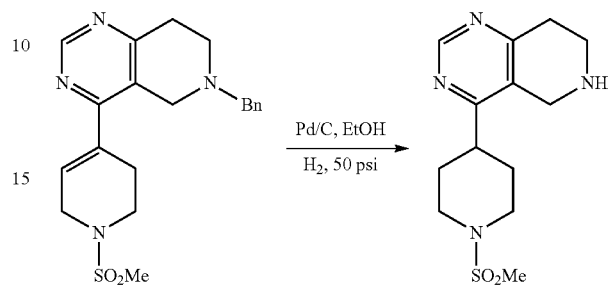

4-(1-(Methylsulfonyl)piperidin-4-yl)-5,6,7,8-tetrahydropyrido[4,3-d]pyrimidine bis(trifluoroacetate) A reaction vessel was charged with the product from the previous step (88 mg, 0.14 mmol), Pd/C (31 mg, 0.029 mmol) and EtOH (1.4 mL) under an atmosphere of N$_2$. The suspension was degassed with N$_2$ for 1 minute and purged with H$_2$ for 1 minute. The reaction mixture was stirred under an atmosphere of H$_2$ at 50 psi for 16 h. The reaction mixture was purged with N$_2$, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=0-30%; 20 min; Column: XBridge C18, 5 μm, 19 mm×150 mm) afford the title compound (36 mg, 48% yield) as a pale yellow liquid.

MS (ES$^+$) C$_{13}$H$_{20}$N$_4$O$_2$S requires: 296, found 297 [M+H]$^+$.

Step 5

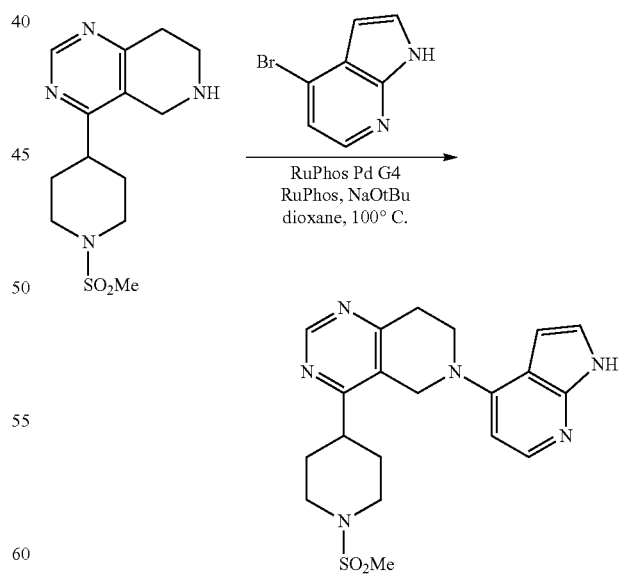

4-(1-(Methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate) A reaction vial was charged with the product from the previous step (36 mg, 0.069 mmol), RuPhos Pd G4 (11 mg, 0.014 mmol), RuPhos (6.4 mg, 0.014 mmol) and 4-bromo-1H-pyrrolo[2,3-b]pyridine (16 mg, 0.082 mmol). Sodium tert-butoxide (33.0 mg, 0.34 mmol) in dioxane (686 µL) was added under $N_2$, the mixture was degassed with $N_2$ for 30 seconds, the vial was sealed and heated at 100° C. for 12 h. The mixture was cooled to RT, 1.0 M HCl in MeOH (1 mL) was added to give a homogeneous solution and the mixture was concentrated under reduced pressure. The residue was purified by mass-triggered preparative HPLC (Mobile phase: A=0.1% TFA/$H_2O$, B=0.1% TFA/MeCN; Gradient: B=10-40%; 20 min; Column: XBridge C18, 5 µm, 19 mm×150 mm) to afford the title compound (5.7 mg, 13% yield) as an off-white solid.

$^1$H NMR (600 MHz, Methanol-$d_4$) δ 8.94 (s, 1H), 7.99 (d, J=7.2 Hz, 1H), 7.39 (d, J=3.6 Hz, 1H), 7.05 (d, J=3.7 Hz, 1H), 7.01 (d, J=7.2 Hz, 1H), 5.16 (s, 2H), 4.26 (t, J=5.9 Hz, 2H), 3.89 (d, J=12.2 Hz, 1H), 3.25 (t, J=5.9 Hz, 2H), 3.16-3.09 (m, 1H), 3.02-2.96 (m, 2H), 2.91 (s, 3H), 2.09-2.01 (m, 2H), 1.92 (d, J=13.3 Hz, 3H); MS (ES$^+$) $C_{20}H_{24}N_6O_2S$ requires: 412, found: 413 [M+H]$^+$.

EXAMPLE 3

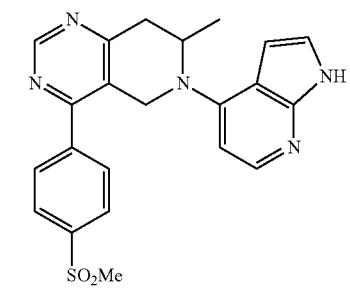 [SMILES: CC1Cc2ncnc(-c3ccc(S(C)(=O)=O)cc3)c2CN1c1ccnc2[nH]ccc12]

7-Methyl-4-(4-(methylsulfonyl)phenyl)-6-(1H-pyrrolo[2,3-b]pyridin-4-yl)-5,6,7,8-tetrahydropyrido[4,3-d]pyrimidine bis(trifluoroacetate)

Step 1

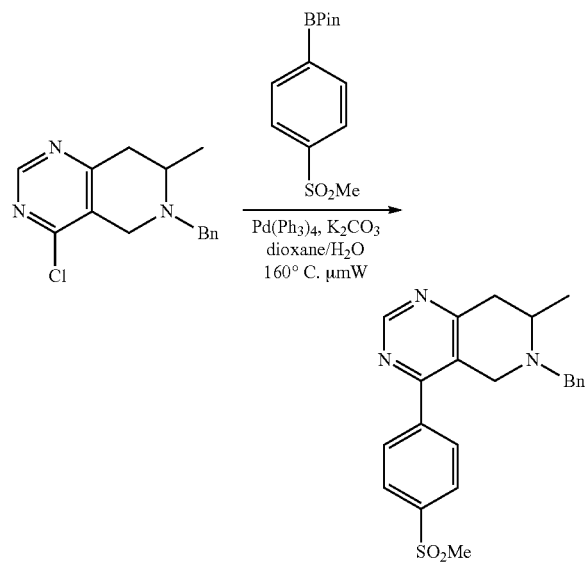

6-Benzyl-7-methyl-4-(4-(methylsulfonyl)phenyl)-5,6,7,8-tetrahydropyrido[4,3-d]pyrimidine bis(trifluoroacetate) To a solution of Intermediate B (50 mg, 0.18 mmol) in dioxane (830 µL) and water (83 µL) under $N_2$ were added Pd(PPh$_3$)$_4$ (42 mg, 0.037 mmol), $K_2CO_3$ (76 mg, 0.55 mmol) and 4,4,5,5-tetramethyl-2-(4-(methylsulfonyl)phenyl)-1,3,2-dioxaborolane (67 mg, 0.24 mmol) and the resulting mixture was at 160° C. in a microwave reactor for 1.5 h. The mixture was filtered through CELITE® and concentrated under reduced pressure. The residue was purified via silica gel chromatography (0-5%) MeOH in $CH_2Cl_2$ with 1% of $NH_4OH$ followed by mass-triggered preparative HPLC (Mobile phase: A=0.1% TFA/$H_2O$, B=0.1% TFA/MeCN; Gradient: B=10-40%; 20 min; Column: XBridge C18, 5 µm, 19 mm×150 mm) to afford the title compound (73 mg, 64% yield) as a white solid.

MS (ES$^+$) $C_{22}H_{23}N_3O_2S$ requires: 393, found 394 [M+H]$^+$.

Step 2

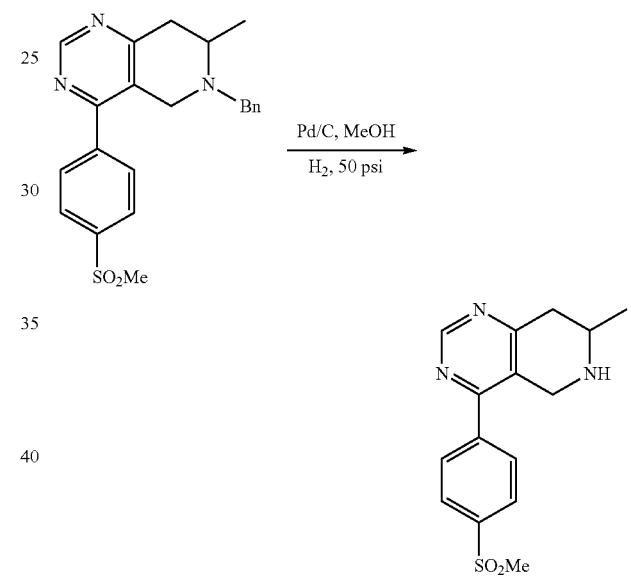

7-Methyl-4-(4-(methylsulfonyl)phenyl)-5,6,7,8-tetrahydropyrido[4,3-d]-pyrimidine bis(trifluoroacetate) A reaction vessel was charged with the product from the previous step (158 mg, 0.254 mmol), Pd/C (54 mg, 0.051 mmol) and MeOH (2.5 mL) under an atmosphere of $N_2$. The suspension was degassed with $N_2$ for 1 minutes and purged with $H_2$ for 1 minutes. The reaction mixture was stirred under an atmosphere of $H_2$ at 50 psi for 4 h. The reaction mixture was purged with $N_2$, filtered through CELITE® and concentrated under reduced pressure. The residue was purified by mass-triggered preparative HPLC (Mobile phase: A=0.1% TFA/$H_2O$, B=0.1% TFA/MeCN; Gradient: B=0-20%; 26 min; Column: XBridge C18, 5 µm, 19 mm×150 mm) to afford the title compound (78 mg, 58% yield) as an off-white solid.

MS (ES$^+$) $C_{15}H_{17}N_3O_2S$ requires: 303, found 304 [M+H]$^+$.

Step 3

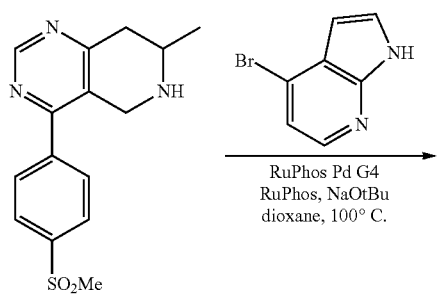

7-Methyl-4-(4-(methylsulfonyl)phenyl)-6-(1H-pyrrolo[2,3-b]pyridin-4-yl)-5,6,7,8-tetrahydropyrido[4,3-d]pyrimidine bis(trifluoroacetate) A reaction vial was charged with the product from the previous step (25 mg, 0.047 mmol), RuPhos Pd G4 (3.7 mg, 4.7 mol), RuPhos (2.2 mg, 4.7 μmol) and 4-bromo-1H-pyrrolo[2,3-b]pyridine (12 mg, 0.061 mmol). Sodium tert-butoxide (23 mg, 0.24 mmol) in dioxane (235 μL) was added under $N_2$, the mixture was degassed with $N_2$ for 30 seconds, the vial was sealed and heated at 100° C. for 12 h. The mixture was cooled to RT, 1.0 M HCl in MeOH (1 mL) was added to give a homogeneous solution and the mixture was concentrated under reduced pressure. The residue was purified by mass-triggered preparative HPLC (Mobile phase: A=0.1% TFA/$H_2O$, B=0.1% TFA/MeCN; Gradient: B=10-40%; 20 min; Column: XBridge C18, 5 μm, 19 mm×150 mm) to afford the title compound (8.7 mg, 29% yield) as an off-white solid.

$^1$H NMR (600 MHz, Methanol-$d_4$) δ 9.17 (s, 1H), 8.20 (d, J=8.4 Hz, 2H), 7.98 (d, J=8.4 Hz, 2H), 7.92 (d, J=7.3 Hz, 1H), 7.30 (d, J=3.7 Hz, 1H), 6.76 (d, J=7.3 Hz, 1H), 6.72 (d, J=3.8 Hz, 1H), 5.26 (d, J=16.3 Hz, 1H), 5.19-5.13 (m, 1H), 5.01 (d, J=16.3 Hz, 1H), 3.58 (dd, J=16.9, 5.8 Hz, 1H), 3.23 (s, 3H), 3.17 (dd, J=16.9, 2.5 Hz, 1H), 1.35 (d, J=6.7 Hz, 3H); MS (ES$^+$) $C_{22}H_{21}N_5O_2S$ requires: 419, found: 420[M+H]$^+$.

EXAMPLE 4

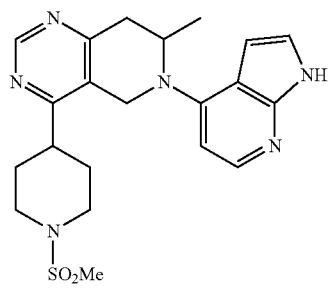 [SMILES: CC1Cc2ncnc(C3CCN(S(C)(=O)=O)CC3)c2CN1c1ccnc2[nH]ccc12]

7-Methyl-4-(1-(methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate)

Step 1

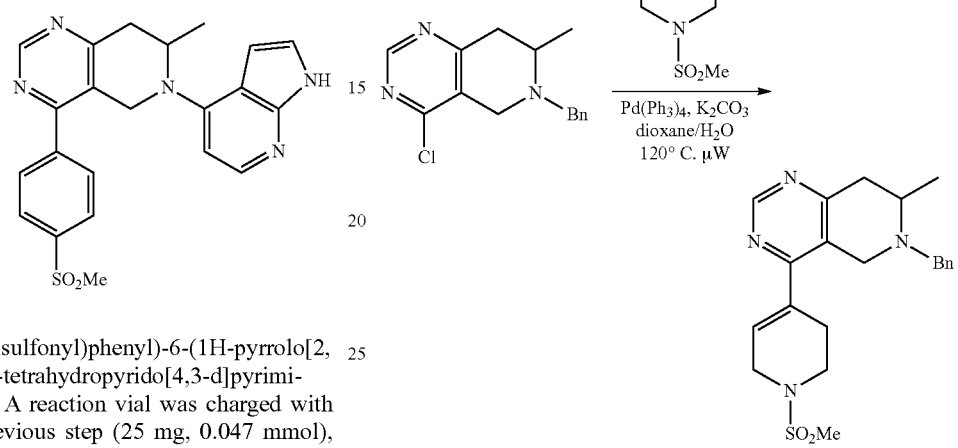

6-Benzyl-7-methyl-4-(1-(methylsulfonyl)-1,2,3,6-tetrahydropyridin-4-yl)-5,6,7,8-tetrahydropyrido[4,3-d]pyrimidine To a solution of Intermediate B (300 mg, 1.10 mmol) in dioxane (10 mL) and water (1 mL) under $N_2$ were added Pd(PPh$_3$)$_4$(253 mg, 0.219 mmol), $K_2CO_3$ (454 mg, 3.29 mmol) and 1-(methylsulfonyl)-4-(4,4,5,5-tetramethyl-1,3,2-dioxaborolan-2-yl)-1,2,3,6-tetrahydropyridine (409 mg, 1.43 mmol) and the resulting mixture was heated at 120° C. in a microwave reactor for 2 h. The mixture was filtered through CELITE® and concentrated under reduced pressure. The residue was purified via silica gel chromatography (0-10% MeOH in $CH_2Cl_2$) to afford the title compound (417 mg, 95% yield) as a yellow liquid.

MS (ES$^+$) $C_{21}H_{26}N_4O_2S$ requires: 398, found 399 [M+H]$^+$.

Step 2

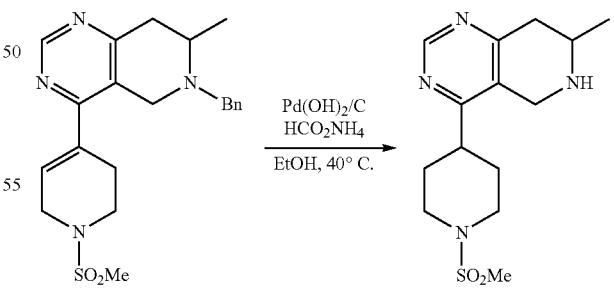

7-Methyl-4-(1-(methylsulfonyl)piperidin-4-yl)-5,6,7,8-tetrahydropyrido[4,3-d]-pyrimidine bis(trifluoroacetate) To a solution of the product from the previous step (100 mg, 0.251 mmol) in EtOH (1.3 mL) were added HCO$_2$NH$_4$ (79 mg, 1.3 mmol) and Pd(OH)$_2$/C (18 mg, 0.025 mmol) and the resulting mixture was stirred at room temperature for 30 min, then heated at 40° C. for 16 h. The mixture was cooled to RT, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=0-30%; 20 min; Column: XBridge C18, 5 μm, 19 mm×150 mm) to afford the title compound (63 mg, 47% yield) as a white solid.

MS (ES$^+$) C$_{14}$H$_{22}$N$_4$O$_2$S requires: 310, found 311 [M+H]$^+$.

Step 3

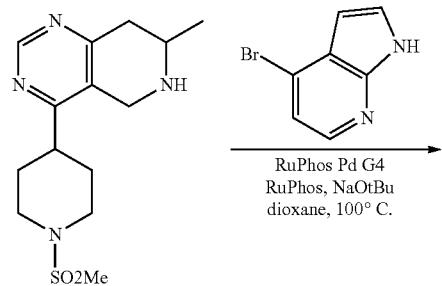

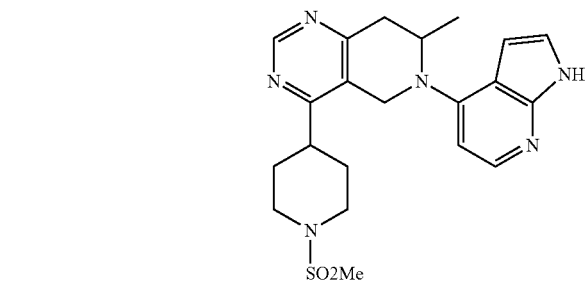

7-Methyl-4-(1-(methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate) A reaction vial was charged with the product from the previous step (30 mg, 0.056 mmol), RuPhos Pd G4 (8.7 mg, 0.011 mmol), RuPhos (5.2 mg, 0.011 mmol) and 4-bromo-1H-pyrrolo[2,3-b]pyridine (14 mg, 0.067 mmol). Sodium tert-butoxide (27 mg, 0.28 mmol) in dioxane (557 μL) was added under N$_2$, the mixture was degassed with N$_2$ for 30 seconds, the vial was sealed and heated at 100° C. for 12 h. The mixture was cooled to RT, 1.0 M HCl in MeOH (1 mL) was added to give a homogeneous solution and the mixture was concentrated under reduced pressure. The residue was purified by mass-triggered preparative HPLC (Mobile phase: A=0.1% TFA/H$_2$O, B=0.1% TFA/MeCN; Gradient: B=0-30%; 20 min; Column: XBridge C18, 5 μm, 19 mm×150 mm) afford the title compound (3.8 mg, 10% yield) as an off-white solid.

$^1$H NMR (500 MHz, Methanol-d$_4$) δ 8.98 (s, 1H), 8.01 (d, J=7.2 Hz, 1H), 7.40 (d, J=3.8 Hz, 1H), 7.05 (d, J=3.7 Hz, 1H), 7.02 (d, J=7.3 Hz, 1H), 5.30-5.24 (m, 1H), 5.27-5.02 (m, 2H), 3.95-3.86 (m, 2H), 3.49 (dd, J=17.1, 5.7 Hz, 1H), 3.15 (tt, J=11.5, 3.7 Hz, 1H), 3.06-2.94 (m, 3H), 2.91 (s, 3H), 2.13-2.00 (m, 2H), 1.98-1.89 (m, 2H), 1.31 (d, J=6.7 Hz, 3H); MS (ES$^+$) C$_{21}$H$_{26}$N$_6$O$_2$S requires: 426, found: 427 [M+H]$^+$.

EXAMPLE 5

This example was intentionally left empty.

EXAMPLE 6

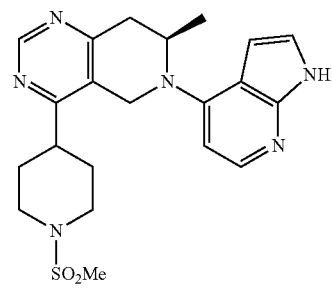

(R)-7-Methyl-4-(1-(methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate)

Step 1

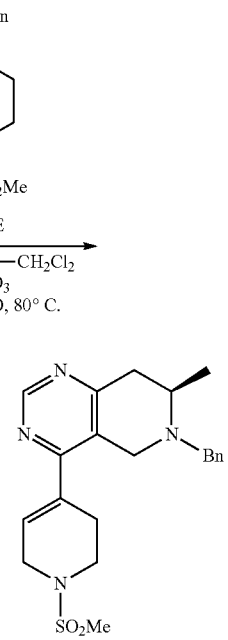

(R)-6-Benzyl-7-methyl-4-(1-(methylsulfonyl)-1,2,3,6-tetrahydropyridin-4-yl)-5,6,7,8-tetrahydropyrido[4,3-d]pyrimidine To a solution of Intermediate C (40 mg, 0.15 mmol) in dioxane (1.2 mL) and water (244 μL) under N$_2$ were added Intermediate E (50.4 mg, 0.175 mmol), K$_2$CO$_3$ (61 mg, 0.44 mmol) and PdCl$_2$(dppf)-CH$_2$Cl$_2$ Adduct (12 mg, 0.015 mmol) and the resulting mixture was degassed by bubbling N$_2$ for 1 minute then heated at 80° C. for 16 h. The mixture was cooled to RT, water (1 mL) was added, and the layers were separated. The aqueous phase was extracted with EtOAc (3×1 mL). The combined organic layers were washed with sat NaCl (1 mL), dried over Na$_2$SO$_4$, filtered and concentrated under reduced pressure. The residue was purified via silica gel chromatography (0-10% MeOH in CH$_2$Cl$_2$) to afford the title compound (54 mg, 93% yield) as a brown liquid.

MS (ES$^+$) C$_{21}$H$_{26}$N$_4$O$_2$S requires: 398, found 399 [M+H]$^+$.

Step 2

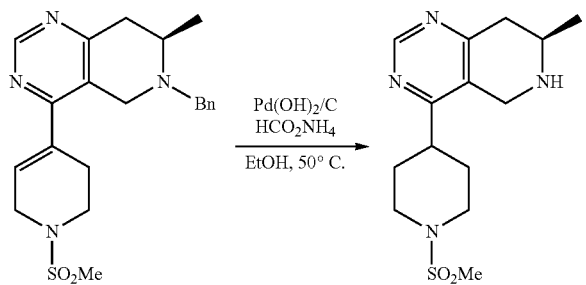 [SMILES: C[C@@H]1Cc2ncnc(C3=CCN(S(C)(=O)=O)CC3)c2CN1Cc1ccccc1 ; "EtOH, 50° C." ; "Pd(OH)2/CHCO2NH4" ; C[C@@H]1Cc2ncnc(C3CCN(S(C)(=O)=O)CC3)c2CN1]

(R)-7-Methyl-4-(1-(methylsulfonyl)piperidin-4-yl)-5,6,7,8-tetrahydropyrido[4,3-d]pyrimidine bis(trifluoroacetate) To a solution of the product from the previous step (157 mg, 0.251 mmol) in EtOH (1.3 mL) were added HCO$_2$NH$_4$ (79 mg, 1.25 mmol) and Pd(OH)$_2$/C (35 mg, 0.025 mmol) and the resulting mixture was stirred at RT for 30 min, then at 50° C. for 5 h. The mixture was cooled to RT, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=0-30%; 12 min; Column: XBridge C18, 5 μm, 19 mm×150 mm) to afford the title compound (100 mg, 74% yield) as a white solid.

MS (ES$^+$) C$_{14}$H$_{22}$N$_4$O$_2$S requires: 310, found 311 [M+H]$^+$.

Step 3

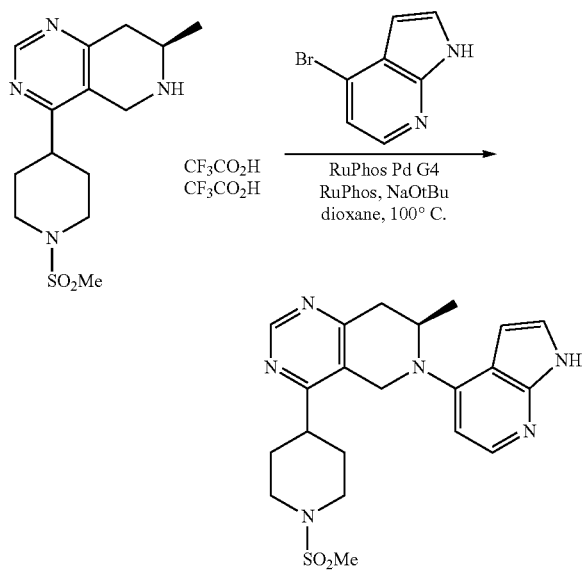

(R)-7-Methyl-4-(1-(methylsulfonyl)piperidin-4-yl)-6-(1H-pyrrolo[2,3-b]pyridin-4-yl)-5,6,7,8-tetrahydropyrido[4,3-d]pyrimidine bis(trifluoroacetate) A reaction vial was charged with the product from the previous step (68 mg, 0.13 mmol), RuPhos Pd G4 (20 mg, 0.025 mmol), RuPhos (12 mg, 0.025 mmol) and 4-bromo-1H-pyrrolo[2,3-b]pyridine (31 mg, 0.15 mmol). Sodium tert-butoxide (61 mg, 0.63 mmol) in dioxane (1.3 mL) was added under N$_2$, the mixture was degassed with N$_2$ for 30 seconds, the vial was sealed and heated at 100° C. for 12 h. The mixture was cooled to RT, 1.0 M HCl in MeOH (1 mL) was added to give a homogeneous solution and the mixture was concentrated under reduced pressure. The residue was purified by mass-triggered preparative HPLC (Mobile phase: A=0.1% TFA/H$_2$O, B=0.1% TFA/MeCN; Gradient: B=0-30%; 20 min; Column: XBridge C18, 5 μm, 19 mm×150 mm) to afford the title compound (5 mg, 6% yield) as an off-white solid.

$^1$H NMR (500 MHz, Methanol-d$_4$) δ 8.98 (s, 1H), 8.01 (d, J=7.2 Hz, 1H), 7.40 (d, J=3.8 Hz, 1H), 7.05 (d, J=3.7 Hz, 1H), 7.02 (d, J=7.3 Hz, 1H), 5.30-5.24 (m, 1H), 5.27-5.02 (m, 2H), 3.95-3.86 (m, 2H), 3.49 (dd, J=17.1, 5.7 Hz, 1H), 3.15 (tt, J=11.5, 3.7 Hz, 1H), 3.06-2.94 (m, 3H), 2.91 (s, 3H), 2.13-2.00 (m, 2H), 1.98-1.89 (m, 2H), 1.31 (d, J=6.7 Hz, 3H); MS (ES$^+$) C$_{21}$H$_{26}$N$_6$O$_2$S requires: 426, found: 427 [M+H]$^+$.

EXAMPLE 7

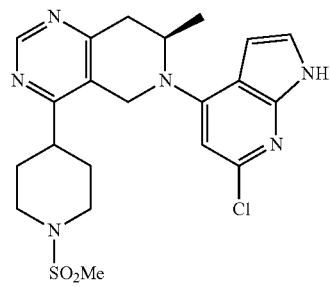

(R)-6-(6-Chloro-1H-pyrrolo[2,3-b]pyridin-4-yl)-7-methyl-4-(1-(methylsulfonyl)-piperidin-4-yl)-5,6,7,8-tetrahydropyrido[4,3-d]pyrimidine bis(trifluoroacetate)

Synthesized using analogous chemistry to Example 6 with the following modification: Intermediate D was used in place of 4-bromo-1H-pyrrolo[2,3-b]pyridine.

$^1$H NMR (600 MHz, Methanol-d$_4$) δ 8.95 (s, 1H), 7.23 (d, J=3.6 Hz, 1H), 6.73 (s, 1H), 6.66 (d, J=3.6 Hz, 1H), 5.10-5.02 (m, 1H), 4.80-4.67 (m, 2H), 3.90-3.83 (m, 2H), 3.53 (dd, J=17.4, 6.0 Hz, 1H), 3.17 (tt, J=11.6, 3.6 Hz, 1H), 3.00 (tdd, J=12.1, 4.5, 2.5 Hz, 2H), 2.93-2.88 (m, 4H), 2.13-1.99 (m, 2H), 1.93 (d, J=13.2 Hz, 2H), 1.16 (d, J=6.8 Hz, 3H); MS (ES$^+$) C$_{21}$H$_{25}$ClN$_6$O$_2$S requires: 460, found: 461 [M+H]$^+$.

EXAMPLE 8

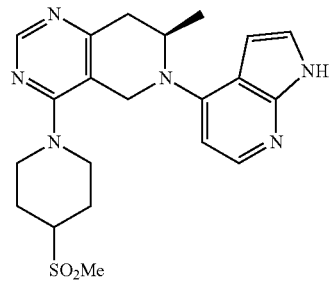

(R)-7-Methyl-4-(4-(methylsulfonyl)piperidin-1-yl)-6-(1H-pyrrolo[2,3-b]pyridin-4-yl)-5,6,7,8-tetrahydropyrido[4,3-d]pyrimidine bis(trifluoroacetate)

Step 1

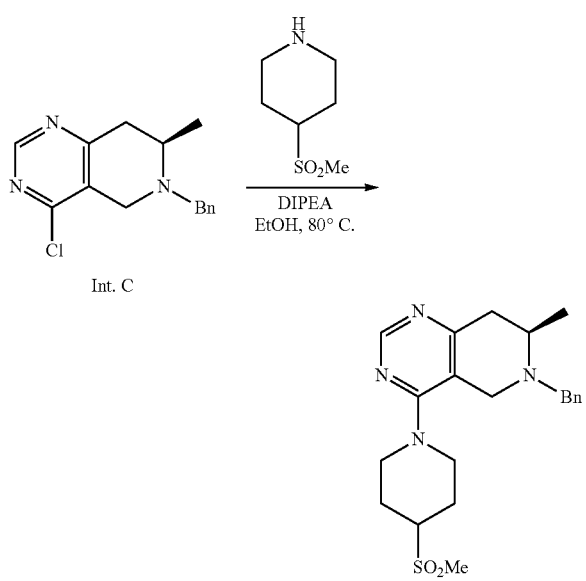

(R)-6-Benzyl-7-methyl-4-(4-(methylsulfonyl)piperidin-1-yl)-5,6,7,8-tetrahydro-pyrido[4,3-d]pyrimidine bis(trifluoroacetate) To a suspension of Intermediate C (100 mg, 0.365 mmol) in EtOH (1.2 mL) were added 4-(methylsulfonyl)piperidine (89 mg, 0.55 mmol) and DIPEA (128 µL, 0.731 mmol) and the resulting mixture was stirred at 80° C. for 16 h. The mixture was cooled to RT and concentrated under reduced pressure. The residue was purified by mass-triggered preparative HPLC (Mobile phase: A=0.1% TFA/H$_2$O, B=0.1% TFA/MeCN; Gradient: B=0-30%; 12 min; Column: XBridge C18, 5 µm, 19 mm×150 mm) to afford the title compound (189 mg, 82% yield) as a white solid.

MS (ES$^+$) C$_{21}$H$_{28}$N$_4$O$_2$S requires: 400, found: 401 [M+H]$^+$.

Step 2

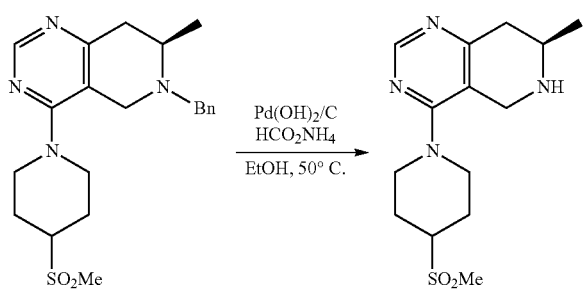 [SMILES: C[C@@H]1Cc2ncnc(N3CCC(S(C)(=O)=O)CC3)c2CN1Cc1ccccc1 ; "EtOH, 50° C." ; "Pd(OH)2/CHCO2NH4" ; C[C@@H]1Cc2ncnc(N3CCC(S(C)(=O)=O)CC3)c2CN1]

(R)-7-Methyl-4-(4-(methylsulfonyl)piperidin-1-yl)-5,6,7,8-tetrahydropyrido[4,3-d]pyrimidine bis(trifluoroacetate) To a solution of the product from the previous reaction (189 mg, 0.301 mmol) in EtOH (1.5 mL) were added HCO$_2$NH$_4$ (95 mg, 1.5 mmol) and Pd(OH)$_2$/C (42 mg, 0.030 mmol) and the resulting mixture was stirred at room temperature for 30 min, then at 50° C. for 2 h. The mixture was cooled to RT, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=0-30%; 12 min; Column: XBridge C18, 5 µm, 19 mm×150 mm) to afford the title compound (50 mg, 31% yield) as a white solid. MS (ES$^+$) C$_{14}$H$_{22}$N$_4$O$_2$S requires: 310, found 311 [M+H]$^+$.

Step 3

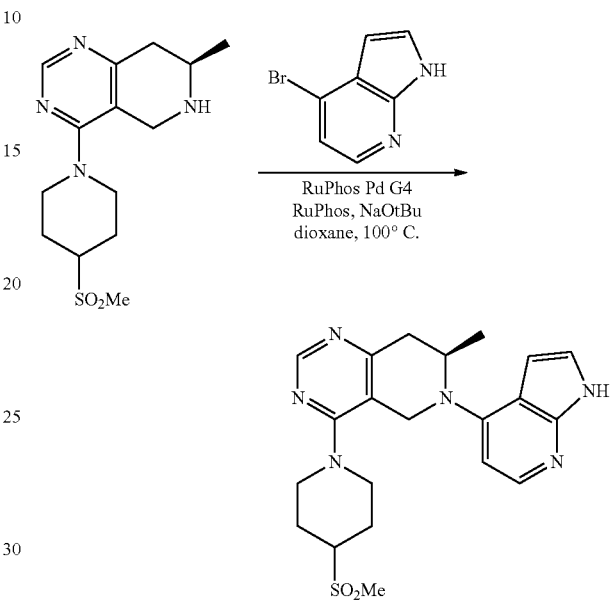

(R)-7-Methyl-4-(4-(methylsulfonyl)piperidin-1-yl)-6-(1H-pyrrolo[2,3-b]pyridin-4-yl)-5,6,7,8-tetrahydropyrido[4,3-d]pyrimidine bis(trifluoroacetate) A reaction vial was charged with the product from the previous reaction (40 mg, 0.074 mmol), RuPhos Pd G4 (5.8 mg, 7.4 µmol), dicyclohexyl(2',6'-diisopropoxy-[1,1'-biphenyl]-2-yl)phosphine (3.5 mg, 7.4 µmol) and 4-bromo-1H-pyrrolo[2,3-b]pyridine (15 mg, 0.074 mmol). Sodium tert-butoxide (36 mg, 0.37 mmol) in dioxane (743 µL) was added under N$_2$, the mixture was degassed with N$_2$ for 30 seconds, and the vial was sealed and heated at 100° C. for 2 h. The mixture was cooled to RT, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=0-30%; 30 min; Column: XBridge C18, 5 µm, 19 mm×150 mm) afford the title compound (11 mg, 23% yield) as an off-white solid.

$^1$H NMR (600 MHz, Methanol-d$_4$) δ 8.68 (s, 1H), 8.02 (d, J=7.2 Hz, 1H), 7.42 (d, J=3.7 Hz, 1H), 6.93 (d, J=3.7 Hz, 1H), 6.91 (d, J=7.2 Hz, 1H), 5.13-4.99 (m, 3H), 4.61 (dd, J=18.0, 14.1 Hz, 2H), 3.55 (tt, J=12.0, 4.4 Hz, 1H), 3.52-3.38 (m, 3H), 3.02-2.96 (m, 4H), 2.41-2.31 (m, 2H), 2.08-1.89 (m, 2H), 1.46 (d, J=6.7 Hz, 3H); MS (ES$^+$) C$_{21}$H$_{26}$N$_6$O$_2$S requires: 426, found: 427 [M+H]$^+$.

EXAMPLE 9

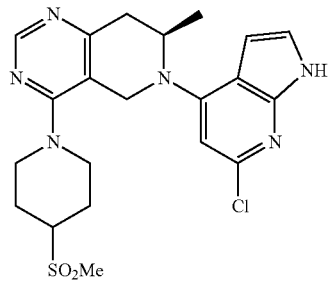

(R)-6-(6-Chloro-1H-pyrrolo[2,3-b]pyridin-4-yl)-7-methyl-4-(4-(methylsulfonyl)-piperidin-1-yl)-5,6,7,8-tetrahydropyrido[4,3-d]pyrimidine bis(trifluoroacetate)

Synthesized using analogous chemistry to Example 8 with the following modification: Intermediate D was used in place of 4-bromo-1H-pyrrolo[2,3-b]pyridine.

$^1$H NMR (600 MHz, Methanol-$d_4$) δ 8.65 (s, 1H), 7.24 (d, J=3.6 Hz, 1H), 6.59 (s, 1H), 6.55 (d, J=3.6 Hz, 1H), 4.85 (t, J=6.8 Hz, 1H), 4.82-4.75 (m, 2H), 4.67 (d, J=13.4 Hz, 1H), 4.55 (d, J=15.5 Hz, 1H), 3.63-3.52 (m, 2H), 3.48-3.40 (m, 1H), 3.38 (ddd, J=14.3, 12.2, 2.7 Hz, 1H), 2.98 (s, 3H), 2.84 (d, J=18.0 Hz, 1H), 2.35 (d, J=11.9 Hz, 2H), 2.03 (qd, J=12.0, 4.0 Hz, 1H), 1.91 (qd, J=12.3, 4.4 Hz, 1H), 1.39 (d, J=6.8 Hz, 3H); MS (ES$^+$) $C_{21}H_{25}ClN_6O_2S$ requires: 460, found: 461 [M+H]$^+$.

EXAMPLE 10

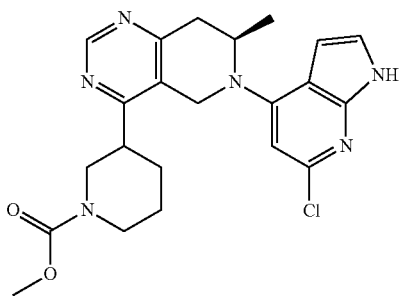 [SMILES: COC(=O)N1CCCC(c2ncnc3c2CN(c2cc(Cl)nc4[nH]ccc24)[C@H](C)C3)C1]

Methyl 3-((R)-6-(6-chloro-1H-pyrrolo[2,3-b]pyridin-4-yl)-7-methyl-5,6,7,8-tetrahydro-pyrido[4,3-d]pyrimidin-4-yl)piperidine-1-carboxylate bis(trifluoroacetate)

Step 1

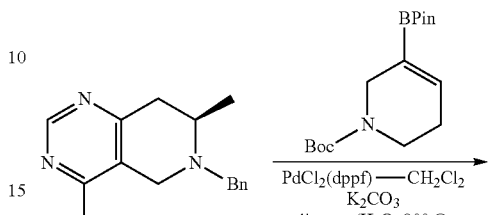

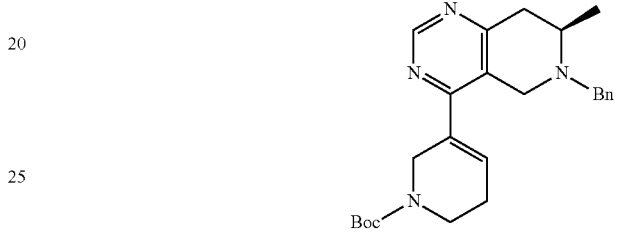

tert-Butyl (R)-5-(6-benzyl-7-methyl-5,6,7,8-tetrahydropyrido[4,3-d]pyrimidin-4-yl)-3,6-dihydropyridine-1(2H)-carboxylate bis(trifluoroacetate) To a solution of Intermediate C (600 mg, 2.19 mmol) in dioxane (13 mL) and water (1.2 mL) were added Pd(PPh$_3$)$_4$(507 mg, 0.438 mmol) and K$_2$CO$_3$ (909 mg, 6.58 mmol), then followed by tert-butyl 5-(4,4,5,5-tetramethyl-1,3,2-dioxaborolan-2-yl)-3,6-dihydropyridine-1(2H)-carboxylate (881 mg, 2.85 mmol) and the resulting mixture was heated at 120° C. in a microwave reactor for 2 h. The mixture was filtered through CELITE® and concentrated under reduced pressure. The residue was purified by mass-triggered preparative HPLC (Mobile phase: A=0.1% TFA/H$_2$O, B=0.1% TFA/MeCN; Gradient: B=20-60%; 16 min; Column: XBridge C18, 5 μm, 19 mm×150 mm) to afford the title compound (1.13 g, 79% yield) as a yellow liquid.

MS (ES$^+$) $C_{25}H_{32}N_4O_2$ requires: 420, found 421 [M+H]$^+$.

Step 2

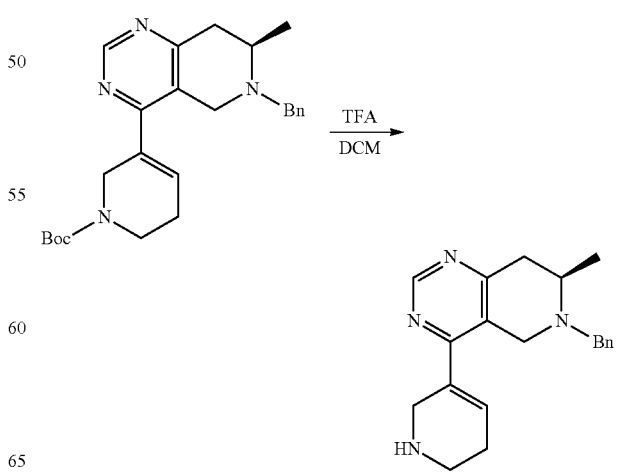

(R)-6-Benzyl-7-methyl-4-(1,2,5,6-tetrahydropyridin-3-yl)-5,6,7,8-tetrahydro-pyrido[4,3-d]pyrimidine bis(trifluoroacetate) To a solution of the product from the previous reaction (1.13 g, 1.74 mmol) in CH$_2$Cl$_2$ (8.7 mL) was added TFA (1.3 mL, 17 mmol) and the resulting mixture was stirred at 22° C. for 2 h. The reaction solution was concentrated under reduced pressure then reconcentrated from toluene (3×5 mL) to afford the title compound (1.45 g, 100% yield) with 20% of toluene as a yellow liquid, which was taken on to the next step without purification.

MS (ES$^+$) C$_{20}$H$_{24}$N$_4$ requires: 320, found 321 [M+H]$^+$.

Step 3

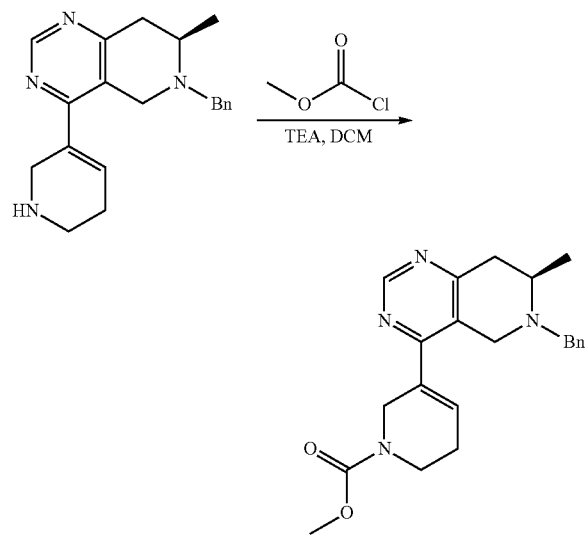

Methyl (R)-5-(6-benzyl-7-methyl-5,6,7,8-tetrahydropyrido[4,3-d]pyrimidin-4-yl)-3,6-dihydropyridine-1(2H)-carboxylate bis(trifluoroacetate) To a solution of the product from the previous reaction (120 mg, 0.145 mmol) in CH$_2$Cl$_2$ (1.5 mL) were added TEA (101 μL, 0.725 mmol) and methyl chloroformate (16 mg, 0.17 mmol) and the resulting mixture was stirred at 23° C. for 1 h. The mixture was concentrated under reduced pressure. The residue was purified by mass-triggered preparative HPLC (Mobile phase: A=0.1% TFA/H$_2$O, B=0.1% TFA/MeCN; Gradient: B=10-40%; 12 min; Column: XBridge C18, 5 μm, 19 mm×150 mm) afford the title compound (74 mg, 84% yield) as a pale yellow liquid.

MS (ES$^+$) C$_{22}$H$_{26}$N$_4$O$_2$ requires: 378, found 379 [M+H]$^+$.

Step 4

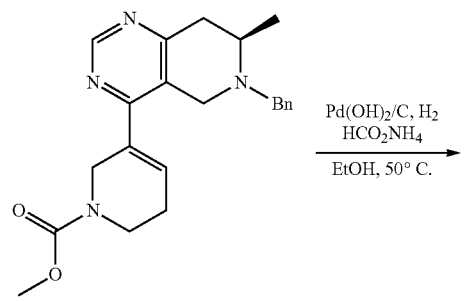

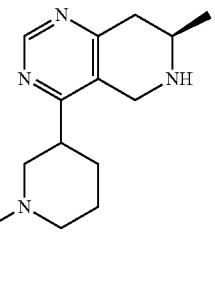

Methyl 3-((R)-7-methyl-5,6,7,8-tetrahydropyrido[4,3-d]pyrimidin-4-yl)-piperidine-1-carboxylate To a solution of the product from the previous reaction (74 mg, 0.12 mmol) in EtOH (610 μL) were added HCO$_2$NH$_4$ (39 mg, 0.61 mmol) and Pd(OH)$_2$/C (8.6 mg, 0.012 mmol) and the resulting mixture was stirred at room temperature for 30 min, then at 50° C. for 16 h. The mixture was cooled to RT, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=10-30%; 12 min; Column: XBridge C18, 5 μm, 19 mm×150 mm) to afford the bis-TFA salt of the title compound (43 mg, 0.083 mmol, 68.0% yield) as a pale yellow liquid. The bis-TFA salt was taken up in MeOH (829 μL), MP-Carbonate resin (100 mg, 0.29 mmol) was added and the resulting mixture was stirred at 25° C. for 1 h. The mixture was filtered, washed with MeOH (2 mL) and concentrated under reduced pressure to afford the title compound (24 mg, 69% yield) as a white solid.

MS (ES$^+$) C$_{15}$H$_{22}$N$_4$O$_2$ requires: 290, found 291 [M+H]$^+$.

Step 5

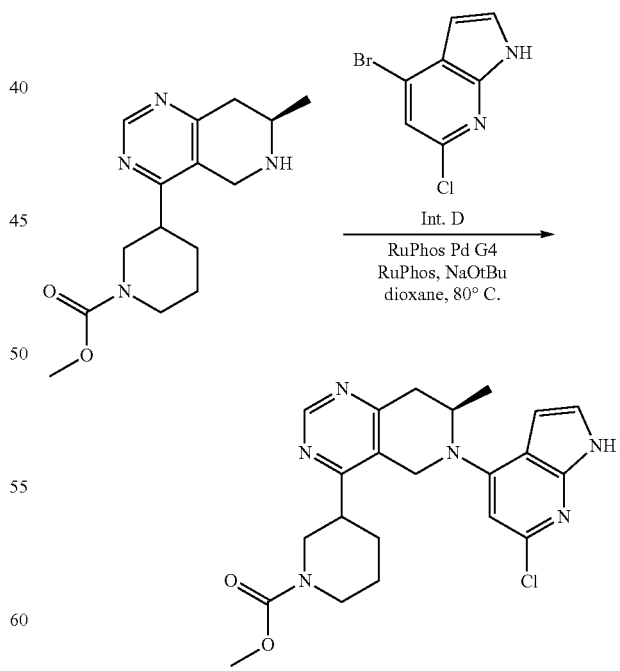

Methyl 3-((R)-6-(6-chloro-1H-pyrrolo[2,3-b]pyridin-4-yl)-7-methyl-5,6,7,8-tetra-hydropyrido[4,3-d]pyrimidin-4-yl)piperidine-1-carboxylate bis(trifluoroacetate) A reaction vial was charged with the product from the previous step (24 mg, 0.083 mmol), RuPhos Pd G4 (13 mg, 0.017 mmol), RuPhos (7.7 mg, 0.017 mmol) and Intermediate D (19 mg, 0.083 mmol). Sodium tert-butoxide (10 mg, 0.41 mmol) in dioxane (827 µL) was added under N$_2$, the mixture was degassed with N$_2$ for 30 seconds, the vial was sealed and heated at 80° C. for 4 h. The mixture was cooled to RT, 1.0 M HCl in MeOH (1 mL) was added to give a homogeneous solution and the mixture was concentrated under reduced pressure. The residue was purified by mass-triggered preparative HPLC (Mobile phase: A=0.1% TFA/H$_2$O, B=0.1% TFA/MeCN; Gradient: B=20-50%; 20 min; Column: XBridge C18, 5 µm, 19 mm×150 mm) to afford the title compound (2.5 mg, 3.74 µmol, 4.52% yield) as a yellow solid.

$^1$H NMR (600 MHz, Methanol-d$_4$) δ 8.94 (s, 1H), 7.24 (d, J=3.6 Hz, 1H), 6.81-6.66 (m, 2H), 5.12-5.03 (m, 1H), 4.74 (t, J=21.5 Hz, 2H), 4.20 (s, 2H), 3.73 (s, 3H), 3.52 (dd, J=17.4, 6.1 Hz, 1H), 3.14 (d, J=8.6 Hz, 2H), 3.01-2.85 (m, 1H), 2.07-1.95 (m, 2H), 1.88-1.79 (m, 1H), 1.77-1.67 (m, 1H), 1.20-1.14 (m, 3H). MS (ES$^+$) C$_{22}$H$_{25}$ClN$_6$O$_2$ requires: 440, found: 441 [M+H]$^+$.

EXAMPLE 11a AND 11b

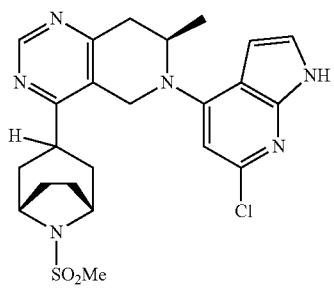 [SMILES: C[C@@H]1Cc2ncnc(C3C[C@H]4CC[C@@H](C3)N4S(C)(=O)=O)c2CN1c1cc(Cl)nc2[nH]ccc12]

(R)-6-(6-Chloro-1H-pyrrolo[2,3-b]pyridin-4-yl)-7-methyl-4-((1S,5R)-(3-exo)-8-(methylsulfonyl)-8-azabicyclo[3.2.1]octan-3-yl)-5,6,7,8-tetrahydropyrido[4,3-d]pyrimidine and (R)-6-(6-Chloro-1H-pyrrolo[2,3-b]pyridin-4-yl)-7-methyl-4-((1S,5R)-(3-endo)-8-(methylsulfonyl)-8-azabicyclo[3.2.1]octan-3-yl)-5,6,7,8-tetrahydropyrido[4,3-d]pyrimidine Step 1

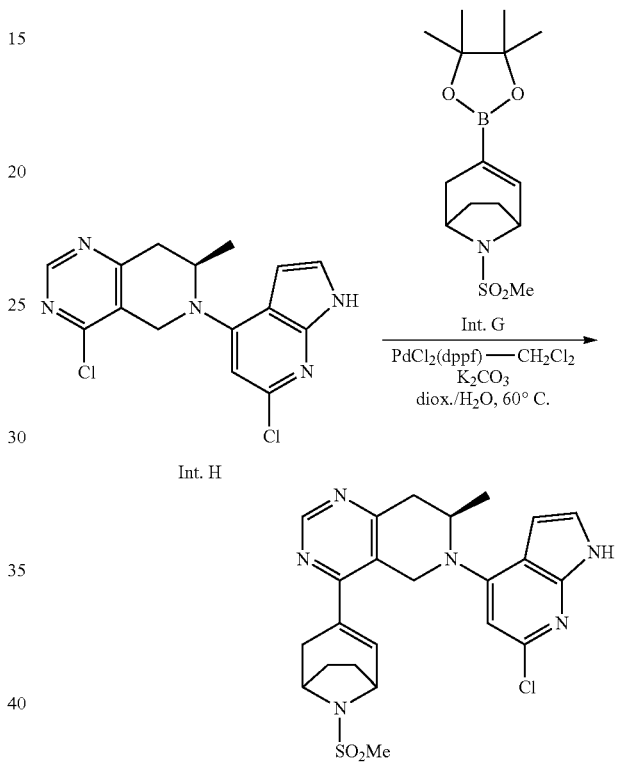

(R)-6-(6-Chloro-1H-pyrrolo[2,3-b]pyridin-4-yl)-7-methyl-4-(-8-(methylsulfonyl)-8-azabicyclo[3.2.1]oct-2-en-3-yl)-5,6,7,8-tetrahydropyrido[4,3-d]pyrimidine bis(2,2,2-trifluoroacetate): A solution of Int. H (166 mg, 0.498 mmol), Int. G (150 mg, 0.383 mmol) and K$_2$CO$_3$ (159 mg, 1.15 mmol) in dioxane (3.2 mL) and water (639 µL) was degassed with N$_2$ for 30 seconds. PdCl$_2$(dppf)-CH$_2$Cl adduct (31 mg, 0.038 mmol) was added and the mixture was degassed with N$_2$ for an additional 30 seconds. The reaction mixture was heated to 60° C. and stirred for 1.5 h. The reaction mixture was allowed to cool to room temperature and partitioned between EtOAc (1 mL) and water (1 mL). The aqueous layer was extracted with EtOAc (3×1 mL). The combined organic layers were washed with brine (0.5 mL), dried over Na$_2$SO$_4$, filtered and concentrated under reduced pressure. The residue was purified by mass-triggered preparative HPLC (Mobile phase: A=0.1% TFA/H2O, B=0.1% TFA/MeCN; Gradient: B=20-60%; 20 min; Column: XBridge C18, 5 µm, 19 mm×150 mm) to afford the title compound (124 mg, 45% yield) as a pale yellow solid.

MS (ES$^+$) C$_{23}$H$_{25}$ClN$_6$O$_2$S requires: 484, found: 485 [M+H]$^+$.

Step 2

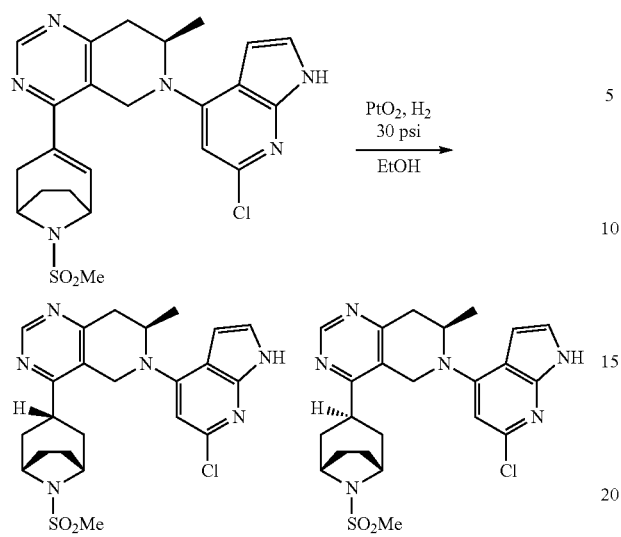 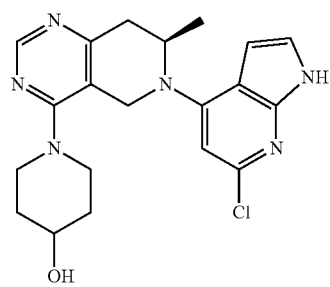 [SMILES: C[C@@H]1Cc2ncnc(N3CCC(O)CC3)c2CN1c1cc(Cl)nc2[nH]ccc12]

(R)-6-(6-Chloro-1H-pyrrolo[2,3-b]pyridin-4-yl)-7-methyl-4-((1R,5S)-(3-exo)-8-(methylsulfonyl)-8-azabicyclo[3.2.1]octan-3-yl)-5,6,7,8-tetrahydropyrido[4,3-d]pyrimidine bis(2,2,2-trifluoroacetate) and (R)-6-(6-Chloro-1H-pyrrolo[2,3-b]pyridin-4-yl)-7-methyl-4-((1R,5S)-(3-endo)-8-(methylsulfonyl)-8-azabicyclo[3.2.1]octan-3-yl)-5,6,7,8-tetrahydropyrido[4,3-d]pyrimidine bis(2,2,2-trifluoroacetate): A reaction vessel was charged with the product from the previous step (110 mg, 0.154 mmol), platinum(IV) oxide (7.0 mg, 0.031 mmol) and ethanol (1.5 mL) under an atmosphere of $N_2$. The suspension was degassed with $N_2$ for 1 minute and purged with $H_2$ for 1 minute. The reaction mixture was shaken under an atmosphere of $H_2$ at 15 psi for 16 h. Additional platinum(IV) oxide (7.0 mg, 0.031 mmol) was added and the mixture was shaken under an atmosphere of $H_2$ at 30 psi for 4 h. The reaction mixture was purged with $N_2$, filtered through CELITE® and concentrated under reduced pressure. The residue was purified by mass-triggered preparative HPLC (Mobile phase: A=0.1% TFA/$H_2O$, B=0.1% TFA/MeCN; Gradient: B=20-50%; 40 min; Column: XBridge C18, 5 μm, 19 mm×150 mm) to afford the title compounds 11a (5.9 mg, 5% yield) and 11b (4.0 mg, 4% yield) as white solids.

Example 11a (3-exo or 3-endo): $^1$H NMR (600 MHz, Methanol-$d_4$) δ 8.96 (s, 1H), 7.23 (d, J=3.6 Hz, 1H), 6.73 (d, J=3.7 Hz, 1H), 6.71 (s, 1H), 5.05-4.97 (m, 1H), 4.87 (d, J=16.2 Hz, 1H), 4.75 (d, J=16.4 Hz, 1H), 4.36-4.29 (m, 2H), 3.52-3.41 (m, 2H), 3.02 (s, 3H), 2.91 (d, J=17.1 Hz, 1H), 2.57-2.48 (m, 2H), 2.14-2.05 (m, 2H), 2.03-1.95 (m, 2H), 1.97-1.88 (m, 2H), 1.19 (d, J=6.7 Hz, 3H); MS (ES$^+$) $C_{23}H_{27}ClN_6O_2S$ requires: 486, found: 487 [M+H]$^+$; $R_t$=15.2 minutes; Example 11b (3-endo or 3-exo): $^1$H NMR (600 MHz, Methanol-$d_4$) δ 8.97 (s, 1H), 7.29 (d, J=3.6 Hz, 1H), 6.83 (s, 1H), 6.78 (d, J=3.7 Hz, 1H), 5.07-4.99 (m, 2H), 4.91 (d, J=16.3 Hz, 1H), 4.41-4.34 (m, 2H), 3.55-3.46 (m, 2H), 3.01 (s, 3H), 2.95 (d, J=17.6 Hz, 1H), 2.29-2.16 (m, 4H), 2.12-2.04 (m, 2H), 1.89-1.80 (m, 2H), 1.22 (d, J=6.7 Hz, 3H); $R_t$=16.6 minutes; MS (ES$^+$) $C_{23}H_{27}ClN_6O_2S$ requires: 486, found: 487 [M+H]$^+$.

EXAMPLE 12

(R)-1-(6-(6-Chloro-1H-pyrrolo[2,3-b]pyridin-4-yl)-7-methyl-5,6,7,8-tetrahydropyrido[4,3-d]pyrimidin-4-yl)piperidin-4-ol Step 1

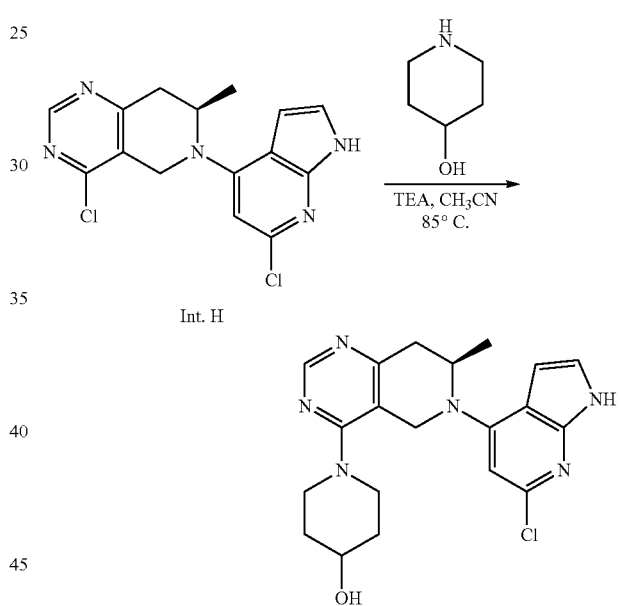

(R)-1-(6-(6-Chloro-1H-pyrrolo[2,3-b]pyridin-4-yl)-7-methyl-5,6,7,8-tetrahydropyrido[4,3-d]pyrimidin-4-yl)piperidin-4-ol: To a suspension of Int. H (20 mg, 0.060 mmol) in ACN (598 μL) were added piperidin-4-ol (6.1 mg, 0.060 mmol) and TEA (25 μL, 0.18 mmol) and the resulting mixture was stirred at 85° C. for 1 h. The residue was purified by mass-triggered preparative HPLC (Mobile phase: A=0.1% TFA/H2O, B=0.1% TFA/MeCN; Gradient: B=10-50%; 20 min; Column: XBridge C18, 5 μm, 19 mm×150 mm) to afford the title compound (14 mg, 45% yield) as a white solid.

$^1$H NMR (600 MHz, DMSO-$d_6$) δ 7.80 (s, 1H), 6.46 (d, J=3.5 Hz, 1H), 5.79 (s, 1H), 5.76 (d, J=3.6 Hz, 1H), 4.06 (t, J=6.7 Hz, 1H), 4.00 (d, J=15.5 Hz, 1H), 3.75 (d, J=15.5 Hz, 1H), 3.61-3.45 (m, 3H), 3.29-3.23 (m, 1H), 3.02 (dtd, J=70.7, 10.0, 9.4, 4.5 Hz, 2H), 2.64 (dd, J=17.8, 7.1 Hz, 1H), 2.03 (d, J=18.0 Hz, 1H), 1.35-1.24 (m, 2H), 1.03-0.87 (m, 2H), 0.60 (d, J=6.8 Hz, 3H); MS (ES$^+$) $C_{20}H_{23}ClN_6O$ requires: 398, found: 399 [M+H]$^+$.

EXAMPLE 13

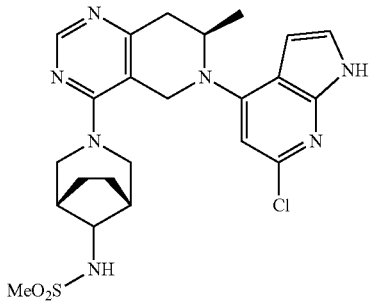 [SMILES: C[C@@H]1Cc2ncnc(N3C[C@H]4CC[C@@H](C3)C4NS(C)(=O)=O)c2CN1c1cc(Cl)nc2[nH]ccc12]

N-((1R,5S)-3-((R)-6-(6-Chloro-1H-pyrrolo[2,3-b]pyridin-4-yl)-7-methyl-5,6,7,8-tetrahydropyrido[4,3-d]pyrimidin-4-yl)-3-azabicyclo[3.2.1]octan-8-yl)methanesulfonamide Step 1

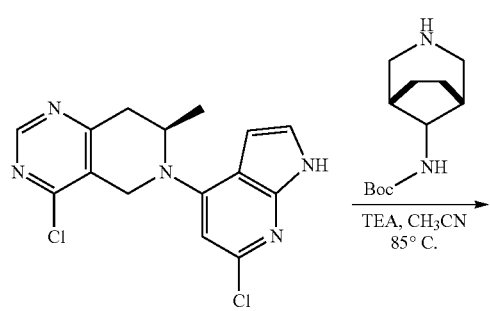

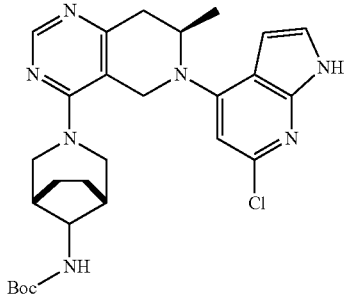

Tert-butyl ((1R,5S)-3-((R)-6-(6-chloro-1H-pyrrolo[2,3-b]pyridin-4-yl)-7-methyl-5,6,7,8-tetrahydropyrido[4,3-d]pyrimidin-4-yl)-3-azabicyclo[3.2.1]octan-8-yl)carbamate: To a solution of Int. H (30 mg, 0.090 mmol) in ACN (898 µL) were added tert-butyl (1R,5S)-3-azabicyclo[3.2.1]octan-8-ylcarbamate (31 mg, 0.14 mmol) and TEA (38 µL, 0.27 mmol) and the resulting mixture was stirred at 85° C. for 16 h. The mixture was cooled to RT. The residue was purified by mass-triggered preparative HPLC (Mobile phase: A=0.1% TFA/H$_2$O, B=0.1% TFA/MeCN; Gradient: B=30-70%; 20 min; Column: XBridge C18, 5 µm, 19 mm×150 mm) to afford the title compound (48 mg, 71% yield) as an orange solid.

MS (ES$^+$) C$_{27}$H$_{34}$ClN$_7$O$_2$ requires: 523, found: 524 [M+H]$^+$.

Step 2

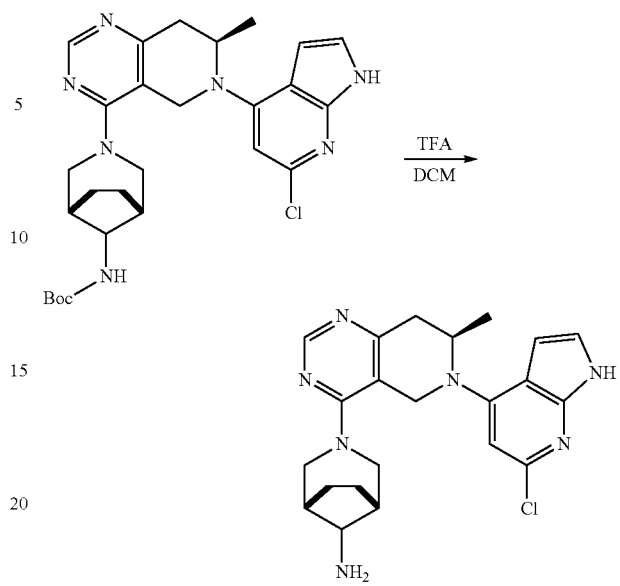

(1R,5S)-3-((R)-6-(6-chloro-1H-pyrrolo[2,3-b]pyridin-4-yl)-7-methyl-5,6,7,8-tetrahydropyrido[4,3-d]pyrimidin-4-yl)-3-azabicyclo[3.2.1]octan-8-amine: To a solution of the product from the previous step (48 mg, 0.064 mmol) in DCM (319 µL) was added TFA (98 µL, 1.2 mmol) and the resulting mixture was stirred at RT for 6 h. The mixture was concentrated under reduced pressure to give an orange oil.

MS (ES$^+$) C$_{22}$H$_{26}$ClN$_7$ requires: 424, found: 423 [M+H]$^+$.

Step 3

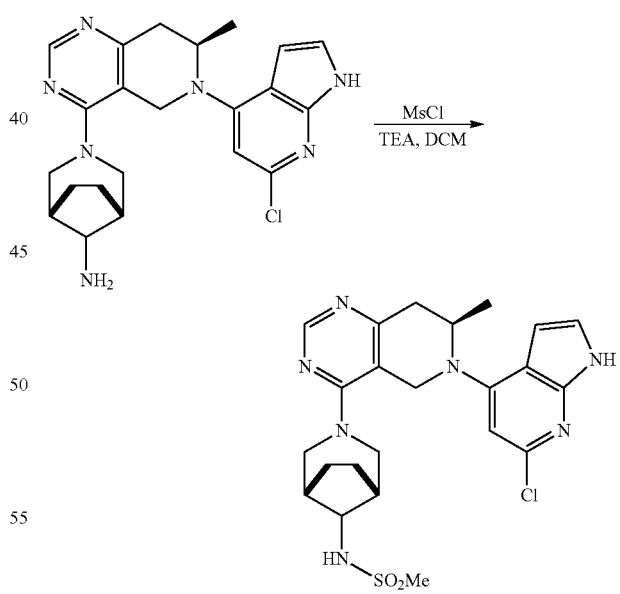

N-((1R,5S)-3-((R)-6-(6-chloro-1H-pyrrolo[2,3-b]pyridin-4-yl)-7-methyl-5,6,7,8-tetrahydropyrido[4,3-d]pyrimidin-4-yl)-3-azabicyclo[3.2.]octan-8-yl)methanesulfonamide: To a solution of the product from the previous step (10 mg, 0.019 mmol) in DCM (186 µL) at 0° C. were added TEA (13 µL, 0.093 mmol) and Ms-Cl (1.5 µL, 0.019 mmol) and the resulting mixture was stirred at 0° C. for 5 minutes. The reaction mixture was concentrated under reduced pressure.

The residue was purified by mass-triggered preparative HPLC (Mobile phase: A=0.1% TFA/H2O, B=0.1% TFA/MeCN; Gradient: B=20-50%; 20 min; Column: XBridge C18, 5 μm, 19 mm×150 mm) to afford the title compound (3.5 mg, 31% yield) as an off-white solid.

$^1$H NMR (600 MHz, DMSO-d$_6$) δ 11.73 (s, 1H), 8.71 (s, 1H), 7.57 (d, J=4.8 Hz, 1H), 7.32 (t, J=3.0 Hz, 1H), 6.56 (dd, J=3.6, 2.0 Hz, 1H), 6.51 (s, 1H), 4.79-4.71 (m, 1H), 4.70 (d, J=15.7 Hz, 1H), 4.55 (s, 1H), 4.43 (d, J=15.6 Hz, 1H), 4.00 (d, J=12.4 Hz, 1H), 3.80 (s, 1H), 3.36 (dd, J=18.2, 6.8 Hz, 2H), 3.04 (s, 3H), 2.75 (d, J=18.1 Hz, 1H), 2.33 (s, 2H), 1.80-1.69 (m, 2H), 1.64-1.56 (m, 1H), 1.51-1.42 (m, 1H), 1.25 (d, J=6.7 Hz, 3H); MS (ES$^+$) C$_{23}$H$_{28}$ClN$_7$O$_2$S requires: 501, found: 502 [M+H]$^+$.

The compounds reported in Table 1 were synthesized using one of the methods described for Examples 1-10, as specified for each case. The appropriate boronates and amines were prepared as described for Intermediates E, F and G.

TABLE 1

Examples 14-43.

| Ex | Structure | IUPAC Name | MWt | [M + H] | Ex. Method |
|---|---|---|---|---|---|
| 14 | 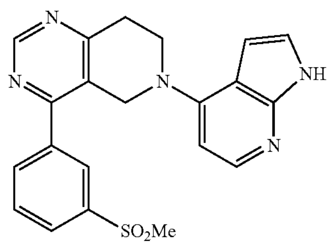 [SMILES: CS(=O)(=O)c1cccc(-c2ncnc3c2CN(c2ccnc4[nH]ccc24)CC3)c1] | 4-(3-methanesulfonyl-phenyl)-6-{1H-pyrrolo-[2,3-b]pyridin-4-yl}-5H,6H,7H,8H-pyrido[4,3-d]pyrimidine | 405 | 406 | 1 |
| 15 | 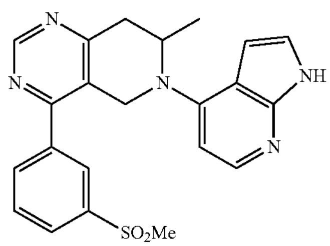 [SMILES: CC1Cc2ncnc(-c3cccc(S(C)(=O)=O)c3)c2CN1c1ccnc2[nH]ccc12] | 4-(3-methanesulfonyl-phenyl)-7-methyl-6-{1H-pyrrolo[2,3-b]pyridin-4-yl}-5H,6H,7H,8H-pyrido[4,3-d]pyrimidine | 419 | 420 | 3 |
| 16 | 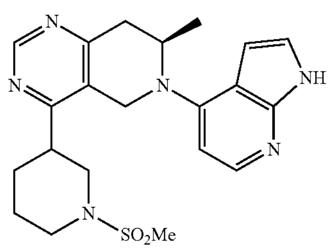 | 1-methanesulfonyl-3-[(7R)-7-methyl-6-{1H-pyrrolo[2,3-b]pyridin-4-yl}-5H,6H,7H,8H-pyrido[4,3-d]pyrimidin-4-yl]piperidine | 426 | 427 | 6 |
| 17 | 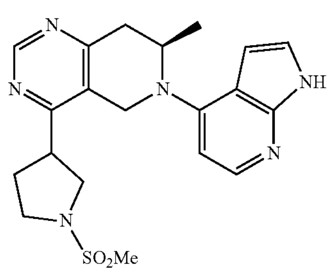 [SMILES: C[C@@H]1Cc2ncnc(C3CCN(S(C)(=O)=O)C3)c2CN1c1ccnc2[nH]ccc12] | 1-methanesulfonyl-3-[(7R)-7-methyl-6-{1H-pyrrolo[2,3-b]pyridin-4-yl}-5H,6H,7H,8H-pyrido[4,3-d]pyrimidin-4-yl]pyrrolidine | 412 | 413 | 6 |
| 18 | 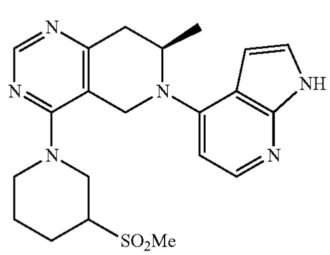 [SMILES: C[C@@H]1Cc2ncnc(N3CCCC(S(C)(=O)=O)C3)c2CN1c1ccnc2[nH]ccc12] | 3-methanesulfonyl-1-[(7R)-7-methyl-6-{1H-pyrrolo[2,3-b]pyridin-4-yl}-5H,6H,7H,8H-pyrido[4,3-d]pyrimidin-4-yl]piperidine | 426 | 427 | 8 |

TABLE 1-continued

Examples 14-43.

| Ex | Structure | IUPAC Name | MWt | [M + H] | Ex. Method |
|---|---|---|---|---|---|
| 19 | 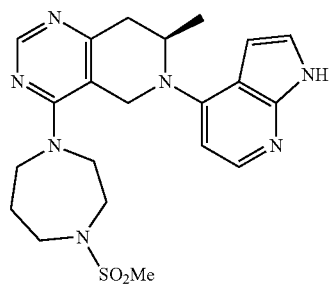 [SMILES: C[C@@H]1Cc2ncnc(N3CCCN(S(C)(=O)=O)CC3)c2CN1c1ccnc2[nH]ccc12] | 1-methanesulfonyl-4-[(7R)-7-methyl-6-{1H-pyrrolo[2,3-b]pyridin-4-yl}-5H,6H,7H,8H-pyrido[4,3-d]pyrimidin-4-yl]-1,4-diazepane | 441 | 442 | 8 |
| 20 | 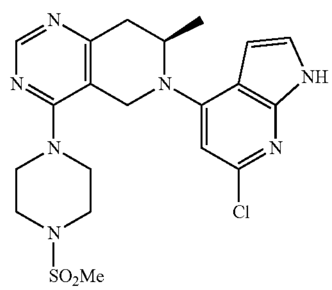 | 1-[(7R)-6-{6-chloro-1H-pyrrolo[2,3-b]pyridin-4-yl}-7-methyl-5H,6H,7H,8H-pyrido[4,3-d]pyrimidin-4-yl]-4-methanesulfonyl-piperazine | 461 | 462 | 9 |
| 21 | 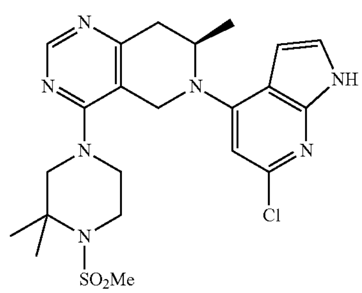 [SMILES: C[C@@H]1Cc2ncnc(N3CCN(S(C)(=O)=O)C(C)(C)C3)c2CN1c1cc(Cl)nc2[nH]ccc12] | 4-[(7R)-6-{6-chloro-1H-pyrrolo[2,3-b]pyridin-4-yl}-7-methyl-5H,6H,7H,8H-pyrido[4,3-d]pyrimidin-4-yl]-1-methanesulfonyl-2,2-dimethylpiperazine | 490 | 491 | 9 |
| 22 | 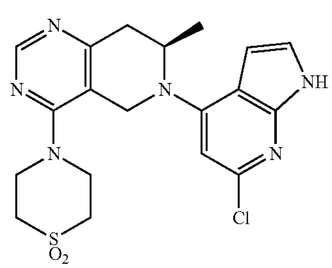 [SMILES: C[C@@H]1Cc2ncnc(N3CCS(=O)(=O)CC3)c2CN1c1cc(Cl)nc2[nH]ccc12] | 4-[(7R)-6-{6-chloro-1H-pyrrolo[2,3-b]pyridin-4-yl}-7-methyl-5H,6H,7H,8H-pyrido[4,3-d]pyrimidin-4-yl]-1$\lambda^6$-thiomorpholine-1,1-dione | 432 | 433 | 9 |
| 23 | 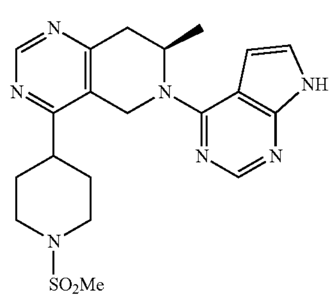 | 1-methanesulfonyl-4-[(7R)-7-methyl-6-{7H-pyrrolo[2,3-d]pyrimidin-4-yl}-5H,6H,7H,8H-pyrido[4,3-d]pyrimidin-4-yl]piperidine | 427 | 428 | 6 |

TABLE 1-continued

Examples 14-43.

| Ex | Structure | IUPAC Name | MWt | [M + H] | Ex. Method |
|---|---|---|---|---|---|
| 24 | 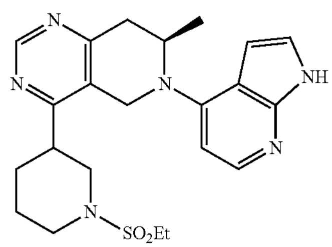 | 3-[(7R)-6-{6-chloro-1H-pyrrolo[2,3-b]pyridin-4-yl}-7-methyl-5H,6H,7H,8H-pyrido[4,3-d]pyrimidin-4-yl]-1-(ethanesulfonyl)-piperidine | 475 | 476 | 10 |
| 25 | 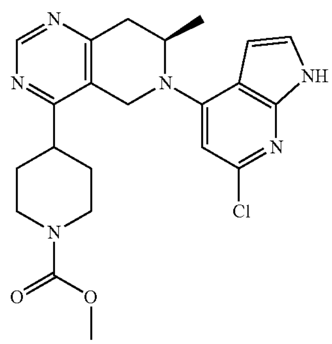 [SMILES: COC(=O)N1CCC(c2ncnc3c2CN(c2cc(Cl)nc4[nH]ccc24)[C@H](C)C3)CC1] | methyl 4-[(7R)-6-{6-chloro-1H-pyrrolo[2,3-b]pyridin-4-yl}-7-methyl-5H,6H,7H,8H-pyrido[4,3-d]pyrimidin-4-yl]piperidine-1-carboxylate | 440 | 441 | 10 |
| 26 | 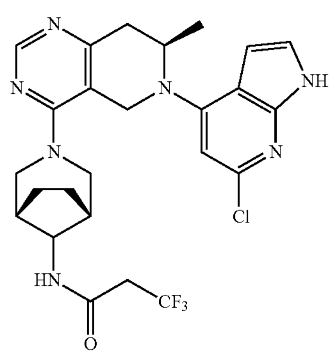 [SMILES: C[C@@H]1Cc2ncnc(N3C[C@H]4CC[C@@H](C3)C4NC(=O)CC(F)(F)F)c2CN1c1cc(Cl)nc2[nH]ccc12] | N-{3-[(7R)-6-{6-chloro-1H-pyrrolo[2,3-b]pyridin-4-yl}-7-methyl-5H,6H,7H,8H-pyrido[4,3-d]pyrimidin-4-yl]-3-azabicyclo[3.2.1]octan-8-yl}-3,3,3-trifluoropropanamide | 533 | 534 | 13 |
| 27 | 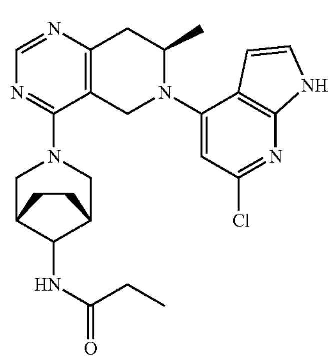 [SMILES: CCC(=O)NC1[C@@H]2CC[C@H]1CN(c1ncnc3c1CN(c1cc(Cl)nc4[nH]ccc14)[C@H](C)C3)C2] | N-[3-[(7R)-6-{6-chloro-1H-pyrrolo[2,3-b]pyridin-4-yl}-7-methyl-5H,6H,7H,8H-pyrido[4,3-d]pyrimidin-4-yl]-3-azabicyclo[3.2.1]octan-8-yl}propanamide | 479 | 480 | 13 |

TABLE 1-continued

Examples 14-43.

| Ex | Structure | IUPAC Name | MWt | [M + H] | Ex. Method |
|---|---|---|---|---|---|
| 28 | 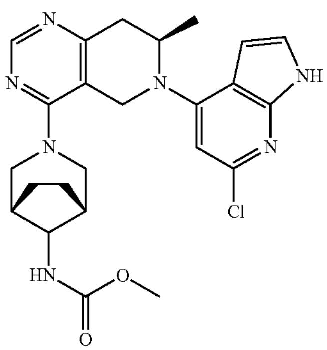 [SMILES: COC(=O)NC1[C@@H]2CC[C@H]1CN(c1ncnc3c1CN(c1cc(Cl)nc4[nH]ccc14)[C@H](C)C3)C2] | methyl N-{3-[(7R)-6-{6-chloro-1H-pyrrolo[2,3-b]-pyridin-4-yl}-7-methyl-5H,6H,7H,8H-pyrido[4,3-d]pyrimidin-4-yl]-3-azabicyclo[3.2.1]octan-8-yl}carbamate | 481 | 482 | 13 |
| 29 | 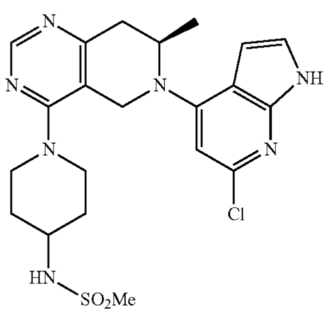 [SMILES: C[C@@H]1Cc2ncnc(N3CCC(NS(C)(=O)=O)CC3)c2CN1c1cc(Cl)nc2[nH]ccc12] | N-{1-[(7R)-6-{6-chloro-1H-pyrrolo[2,3-b]pyridin-4-yl}-7-methyl-5H,6H,7H,8H-pyrido[4,3-d]pyrimidin-4-yl]piperidin-4-yl}methanesulfonamide | 475 | 476 | 13 |
| 30 | 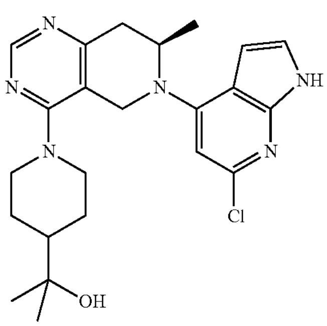 [SMILES: C[C@@H]1Cc2ncnc(N3CCC(C(C)(C)O)CC3)c2CN1c1cc(Cl)nc2[nH]ccc12] | 2-{1-[(7R)-6-{6-chloro-1H-pyrrolo[2,3-b]pyridin-4-yl}-7-methyl-5H,6H,7H,8H-pyrido[4,3-d]pyrimidin-4-yl]-piperidin-4-yl}propan-2-ol | 440 | 441 | 12 |
| 31 | 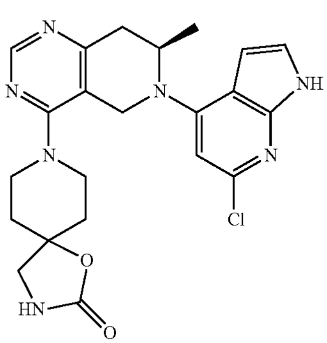 [SMILES: C[C@@H]1Cc2ncnc(N3CCC4(CC3)CNC(=O)O4)c2CN1c1cc(Cl)nc2[nH]ccc12] | 8-[(7R)-6-{6-chloro-1H-pyrrolo[2,3-b]pyridin-4-yl}-7-methyl-5H,6H,7H,8H-pyrido[4,3-d]pyrimidin-4-yl]-1-oxa-3,8-diazaspiro[4.5]decan-2-one | 453 | 454 | 12 |

TABLE 1-continued

Examples 14-43.

| Ex | Structure | IUPAC Name | MWt | [M + H] | Ex. Method |
|---|---|---|---|---|---|
| 32 | 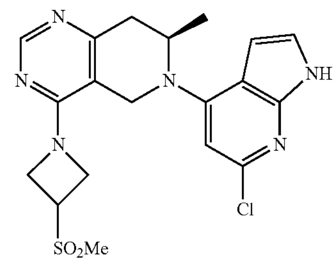 [SMILES: C[C@@H]1Cc2ncnc(N3CC(S(C)(=O)=O)C3)c2CN1c1cc(Cl)nc2[nH]ccc12] | 1-[(7R)-6-{6-chloro-1H-pyrrolo[2,3-b]pyridin-4-yl}-7-methyl-5H,6H,7H,8H-pyrido[4,3-d]pyrimidin-4-yl]-3-methanesulfonylazetidine | 432 | 433 | 12 |
| 33 | 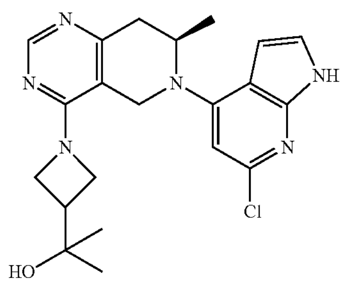 [SMILES: C[C@@H]1Cc2ncnc(N3CC(C(C)(C)O)C3)c2CN1c1cc(Cl)nc2[nH]ccc12] | 2-{1-[(7R)-6-{6-chloro-1H-pyrrolo[2,3-b]pyridin-4-yl}-7-methyl-5H,6H,7H,8H-pyrido[4,3-d]pyrimidin-4-yl]azetidin-3-yl}propan-2-ol | 412 | 413 | 12 |
| 34 | 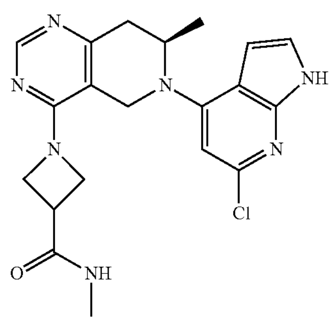 [SMILES: CNC(=O)C1CN(c2ncnc3c2CN(c2cc(Cl)nc4[nH]ccc24)[C@H](C)C3)C1] | 1-[(7R)-6-{6-chloro-1H-pyrrolo[2,3-b]pyridin-4-yl}-7-methyl-5H,6H,7H,8H-pyrido[4,3-d]pyrimidin-4-yl]-N-methylazetidine-3-carboxamide | 411 | 412 | 12 |
| 35 | 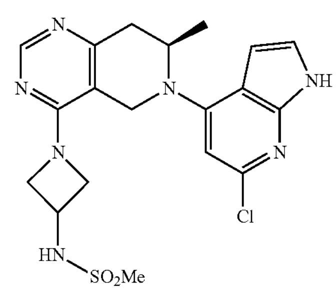 [SMILES: C[C@@H]1Cc2ncnc(N3CC(NS(C)(=O)=O)C3)c2CN1c1cc(Cl)nc2[nH]ccc12] | N-{1-[(7R)-6-{6-chloro-1H-pyrrolo[2,3-b]pyridin-4-yl}-7-methyl-5H,6H,7H,8H-pyrido[4,3-d]pyrimidin-4-yl]azetidin-3-yl}methanesulfonamide | 447 | 448 | 13 |
| 36 | 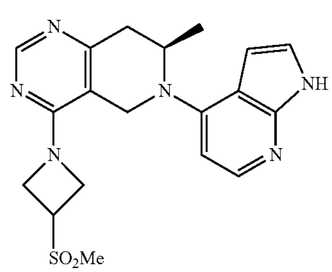 [SMILES: C[C@@H]1Cc2ncnc(N3CC(S(C)(=O)=O)C3)c2CN1c1ccnc2[nH]ccc12] | 3-methanesulfonyl-1-[(7R)-7-methyl-6-{1H-pyrrolo[2,3-b]pyridin-4-yl}-5H,6H,7H,8H-pyrido[4,3-d]pyrimidin-4-yl]azetidine | 398 | 399 | 12 |

TABLE 1-continued

Examples 14-43.

| Ex | Structure | IUPAC Name | MWt | [M + H] | Ex. Method |
|---|---|---|---|---|---|
| 37 | 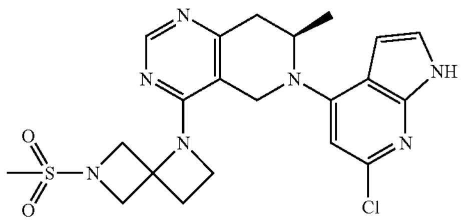 [SMILES: C[C@@H]1Cc2ncnc(N3CCC34CN(S(C)(=O)=O)C4)c2CN1c1cc(Cl)nc2[nH]ccc12] | (R)-6-(6-chloro-1H-pyrrolo[2,3-b]pyridin-4-yl)-7-methyl-4-(6-(methylsulfonyl)-1,6-diazaspiro[3.3]heptan-1-yl)-5,6,7,8-tetrahydropyrido[4,3-d]pyrimidine | 473 | 474 | 13 |
| 38 | 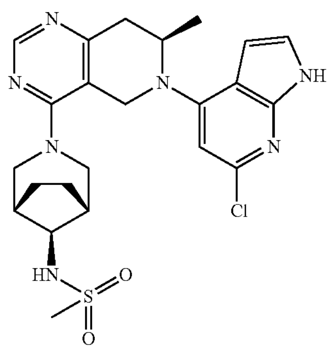 [SMILES: C[C@@H]1Cc2ncnc(N3C[C@H]4CC[C@@H](C3)[C@@H]4NS(C)(=O)=O)c2CN1c1cc(Cl)nc2[nH]ccc12] | N-((1R,5S)-(8-anti)-3-((R)-6-(6-chloro-1H-pyrrolo[2,3-b]pyridin-4-yl)-7-methyl-5,6,7,8-tetrahydropyrido[4,3-d]pyrimidin-4-yl)-3-azabicyclo[3.2.1]octan-8-yl)methanesulfonamide | 501 | 502 | 13 |
| 39 | 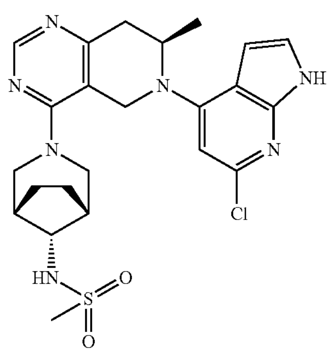 [SMILES: C[C@@H]1Cc2ncnc(N3C[C@H]4CC[C@@H](C3)[C@H]4NS(C)(=O)=O)c2CN1c1cc(Cl)nc2[nH]ccc12] | N-((1R,5S)-(8-syn)-3-((R)-6-(6-chloro-1H-pyrrolo[2,3-b]pyridin-4-yl)-7-methyl-5,6,7,8-tetrahydropyrido[4,3-d]pyrimidin-4-yl)-3-azabicyclo[3.2.1]octan-8-yl)methanesulfonamide | 501 | 502 | 13 |
| 40 | 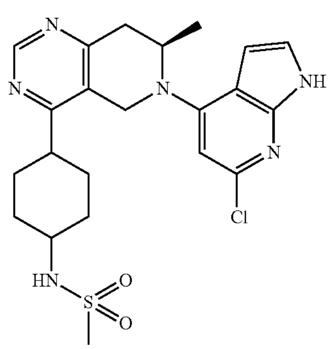 [SMILES: C[C@@H]1Cc2ncnc(C3CCC(NS(C)(=O)=O)CC3)c2CN1c1cc(Cl)nc2[nH]ccc12] | (R)-N-(4-(6-(6-chloro-1H-pyrrolo[2,3-b]pyridin-4-yl)-7-methyl-5,6,7,8-tetrahydropyrido[4,3-d]pyrimidin-4-yl)cyclohexyl)methanesulfonamide | 474 | 475 | 11 |
| 41 | 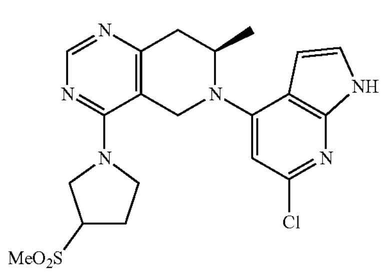 [SMILES: C[C@@H]1Cc2ncnc(N3CCC(S(C)(=O)=O)C3)c2CN1c1cc(Cl)nc2[nH]ccc12] | (7R)-6-(6-chloro-1H-pyrrolo[2,3-b]pyridin-4-yl)-7-methyl-4-(3-(methylsulfonyl)pyrrolidin-1-yl)-5,6,7,8-tetrahydropyrido[4,3-d]pyrimidine | 446 | 447 | 12 |

TABLE 1-continued

Examples 14-43.

| Ex | Structure | IUPAC Name | MWt | [M + H] | Ex. Method |
|---|---|---|---|---|---|
| 42 | 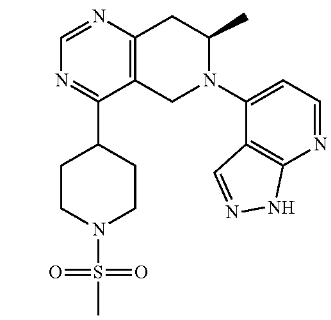 [SMILES: C[C@@H]1Cc2ncnc(C3CCN(S(C)(=O)=O)CC3)c2CN1c1ccnc2[nH]ncc12] | (R)-7-methyl-4-(1-(methylsulfonyl)piperidin-4-yl)-6-(1H-pyrazolo[3,4-b]pyridin-4-yl)-5,6,7,8-tetrahydropyrido[4,3-d]pyrimidine | 427 | 428 | 6 |
| 43 | 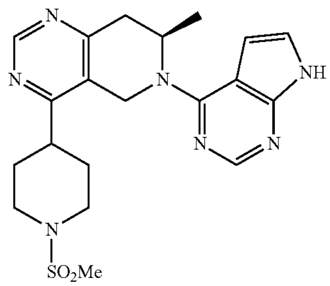 | (R)-7-methyl-4-(1-(methylsulfonyl)piperidin-4-yl)-6-(7H-pyrrolo[2,3-d]pyrimidin-4-yl)-5,6,7,8-tetrahydropyrido[4,3-d]pyrimidine | 427 | 428 | 6 |

EXAMPLE 44

(R)-1-((R)-6-(6-Chloro-1H-pyrrolo[2,3-b]pyridin-4-yl)-7-methyl-5,6,7,8-tetrahydropyrido[4,3-d]pyrimidin-4-yl)-N-methylpiperidine-3-carboxamide

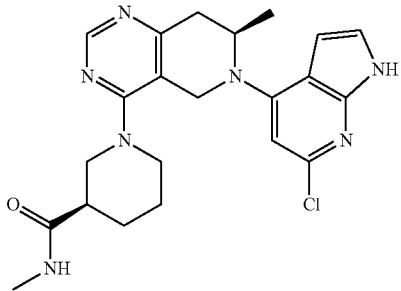 [SMILES: CNC(=O)[C@@H]1CCCN(c2ncnc3c2CN(c2cc(Cl)nc4[nH]ccc24)[C@H](C)C3)C1]

Step 1

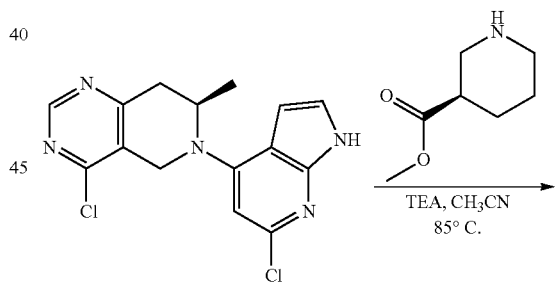

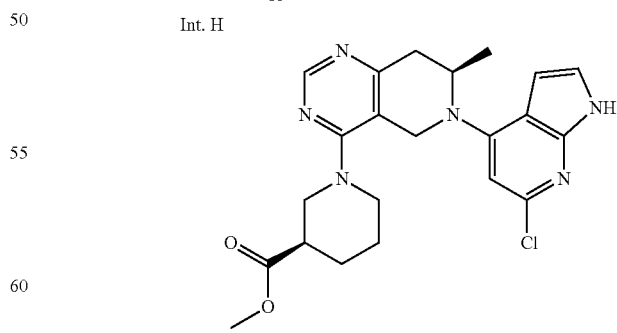

Methyl (R)-1-((R)-6-(6-chloro-1H-pyrrolo[2,3-b]pyridin-4-yl)-7-methyl-5,6,7,8-tetrahydropyrido[4,3-d]pyrimidin-4-yl)piperidine-3-carboxylate: To a solution of Int. H (50 mg, 0.15 mmol) in acetonitrile (1.5 mL) were added TEA (63 µL, 0.45 mmol) and (R)-methyl piperidine-3-carboxylate (34 mg, 0.22 mmol) and the resulting mixture was stirred at 85° C. for 16 h. The mixture was cooled to RT, filtered and concentrated under reduced pressure. The residue was purified by mass-triggered preparative HPLC (Mobile phase: A=0.1% TFA/H$_2$O, B=0.1% TFA/MeCN; Gradient: B=10-60%; 16 min; Column: XBridge C18, 5 µm, 50 mm×100 mm) to afford the title compound (61 mg, 61% yield) as a pale yellow solid.

MS (ES$^+$) C$_{22}$H$_{25}$ClN$_6$O$_2$ requires: 440, found: 441 [M+H]$^+$.

Step 2

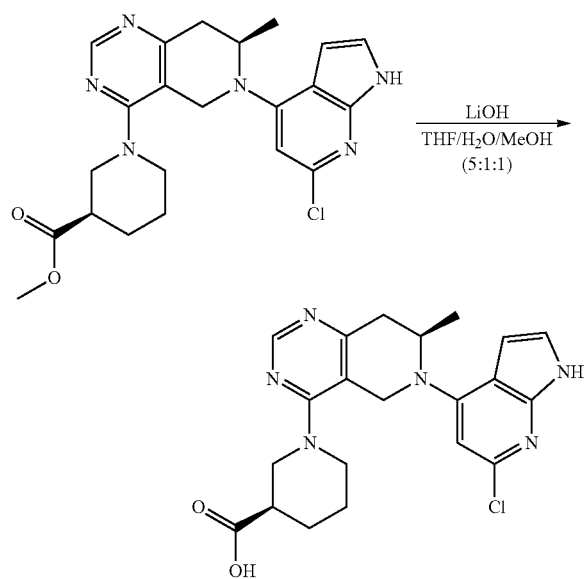

(R)-1-((R)-6-(6-Chloro-1H-pyrrolo[2,3-b]pyridin-4-yl)-7-methyl-5,6,7,8-tetrahydropyrido[4,3-d]pyrimidin-4-yl)piperidine-3-carboxylic acid: To a solution of the product from the previous step (61 mg, 0.091 mmol) in THF (326 µL), MeOH (65 µL), and water (65 µL) was added LiOH (7.0 mg, 0.27 mmol) and the resulting mixture was stirred at 20° C. for 4 h. The mixture was filtered and purified by mass-triggered preparative HPLC (Mobile phase: A=0.1% TFA/H$_2$O, B=0.1% TFA/MeCN; Gradient: B=10-40%; 20 min; Column: XBridge C18, 5 µm, 19 mm×150 mm) to afford the title compound (37 mg, 62% yield) as a pale yellow solid.

MS (ES$^+$) C$_{21}$H$_{23}$ClN$_6$O$_2$ requires: 426, found: 427 [M+H]$^+$.

Step 3

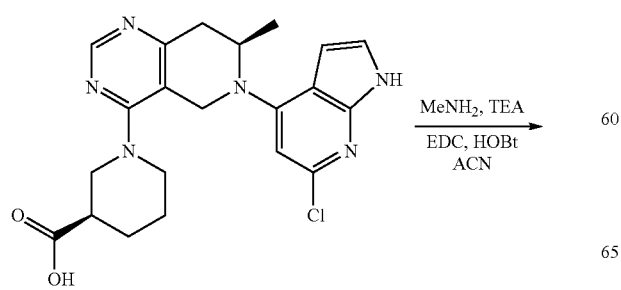

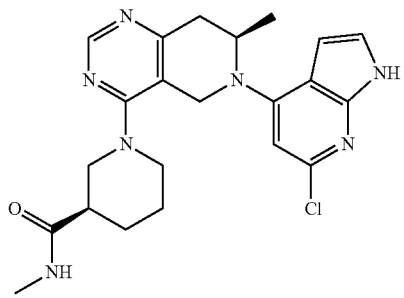

(R)-1-((R)-6-(6-Chloro-1H-pyrrolo[2,3-b]pyridin-4-yl)-7-methyl-5,6,7,8-tetrahydropyrido[4,3-d]pyrimidin-4-yl)-N-methylpiperidine-3-carboxamide: To a suspension of the product from the previous step (33 mg, 0.050 mmol) in acetonitrile (504 µL) were added methylamine hydrochloride (17 mg, 0.25 mmol), EDC (39 mg, 0.20 mmol), and HOBt (31 mg, 0.20 mmol) and the resulting mixture was stirred at 60° C. for 24 h. The mixture was cooled to RT, filtered and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: XBridge C18, 5 µm, 19 mm×150 mm) to afford the title compound (20 mg, 58% yield) as a pale yellow solid.

$^1$H NMR (600 MHz, Methanol-d$_4$) δ 8.60 (s, 1H), 7.24 (d, J=3.6 Hz, 1H), 6.58 (s, 1H), 6.56 (d, J=3.6 Hz, 1H), 4.84-4.81 (m, overlap H$_2$O, 1H), 4.76 (d, J=15.3 Hz, 1H), 4.63 (d, J=15.5 Hz, 1H), 4.56 (d, J=13.3 Hz, 1H), 4.38 (d, J=13.9 Hz, 1H), 3.66 (dd, J=13.3, 10.1 Hz, 1H), 3.53 (ddd, J=13.9, 11.0, 2.9 Hz, 1H), 3.42 (dd, J=17.9, 6.8 Hz, 1H), 2.83 (d, J=17.9 Hz, 1H), 2.73 (s, 3H), 2.63-2.55 (m, 1H), 2.12-2.06 (m, 1H), 2.06-2.01 (m, 1H), 1.96-1.86 (m, 1H), 1.85-1.76 (m, 1H), 1.37 (d, J=6.8 Hz, 3H).

MS (ES$^+$) C$_{22}$H$_{26}$ClN$_7$O requires: 439, found: 440 [M+H]$^+$.

EXAMPLE 45

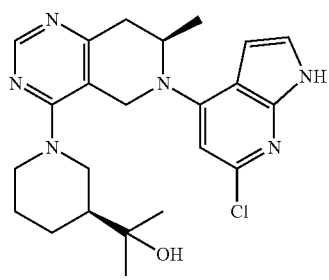 [SMILES: C[C@@H]1Cc2ncnc(N3CCC[C@H](C(C)(C)O)C3)c2CN1c1cc(Cl)nc2[nH]ccc12]

2-((R)-1-((R)-6-(6-Chloro-1H-pyrrolo[2,3-b]pyridin-4-yl)-7-methyl-5,6,7,8-tetrahydropyrido[4,3-d]pyrimidin-4-yl)piperidin-3-yl)propan-2-ol Step 1

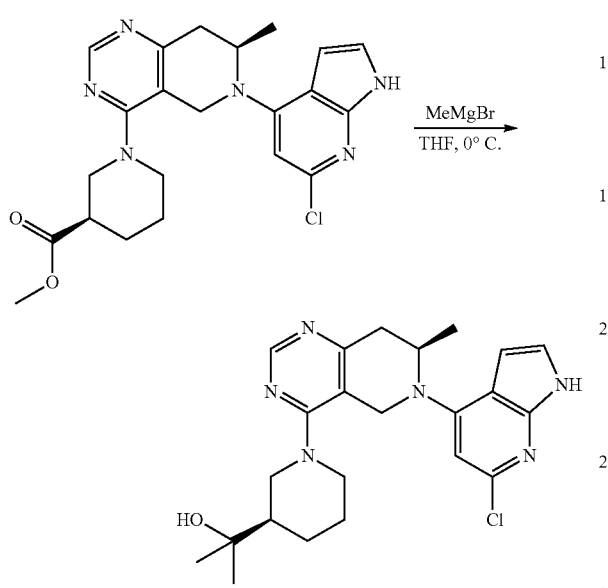

2-((R)-1-((R)-6-(6-Chloro-1H-pyrrolo[2,3-b]pyridin-4-yl)-7-methyl-5,6,7,8-tetrahydropyrido[4,3-d]pyrimidin-4-yl)piperidin-3-yl)propan-2-ol: To a suspension of (R)-methyl 1-((R)-6-(6-chloro-1H-pyrrolo[2,23-b]pyridin-4-yl)-7-methyl-5,6,7,8-tetrahydropyrido-[4,3-d]pyrimidin-4-yl) piperidine-3-carboxylate (20 mg, 0.03 mmol) in THF (299 µL) was added methylmagnesium bromide (100 µL, 3.0 M in THF, 0.299 mmol) dropwise at 0° C. and the resulting mixture was allowed to slowly warm to RT and stirred for 2 hr. The mixture was cooled to 0° C. and additional methylmagnesium bromide (50 µL, 3.0 M in THF, 0.15 mmol) was added and the resulting mixture was allowed to slowly warm to RT and stirred for 16 hr. MeOH (500 uL) was added to the mixture followed by a few drops of TFA and the mixture was concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: XBridge C18, 5 µm, 19 mm×150 mm) to afford the title compound (0.4 mg, 2% yield) as an off-white solid.

$^1$H NMR (600 MHz, Methanol-d$_4$) δ 8.56 (s, 1H), 7.23 (d, J=3.6 Hz, 1H), 6.57 (s, 1H), 6.56 (d, J=3.6 Hz, 1H), 4.74 (d, J=15.7 Hz, 1H), 4.58 (d, J=15.5 Hz, 1H), 3.42 (p, J=1.6 Hz, 1H), 3.39 (d, J=11.4 Hz, 1H), 3.34-3.32 (m, 1H), 3.21-3.12 (m, 3H), 2.87-2.75 (m, 2H), 2.05-1.99 (m, 3H), 1.37 (d, J=6.7 Hz, 3H), 1.25 (s, 3H), 1.22 (s, 3H).

MS (ES$^+$) C$_{23}$H$_{29}$ClN$_6$O requires: 440, found: 441 [M+H]$^+$.

EXAMPLE 46

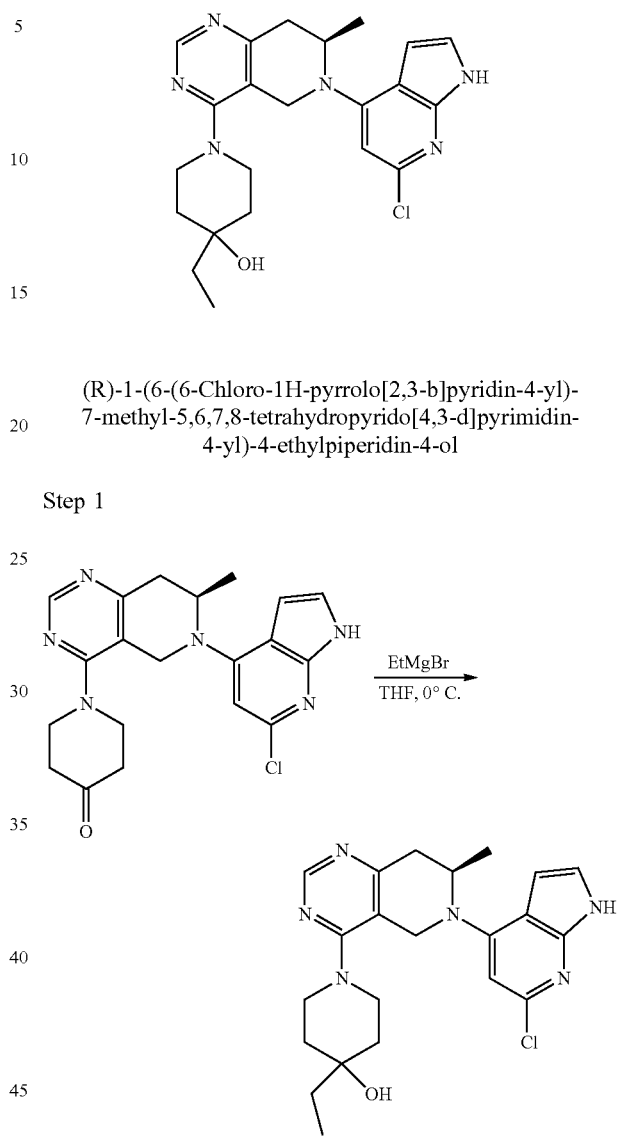

(R)-1-(6-(6-Chloro-1H-pyrrolo[2,3-b]pyridin-4-yl)-7-methyl-5,6,7,8-tetrahydropyrido[4,3-d]pyrimidin-4-yl)-4-ethylpiperidin-4-ol Step 1

(R)-1-(6-(6-Chloro-1H-pyrrolo[2,3-b]pyridin-4-yl)-7-methyl-5,6,7,8-tetrahydropyrido[4,3-d]pyrimidin-4-yl)-4-ethylpiperidin-4-ol: To a solution of (R)-1-(6-(6-chloro-1H-pyrrolo [2,3-b]pyridin-4-yl)-7-methyl-5,6,7,8-tetrahydropyrido [4,3-d]pyrimidin-4-yl)piperidin-4-one (7 mg, 0.011 mmol, prepared via a procedure similar to that disclosed for Example 12) in THF (112 µL) was added ethylmagnesium bromide (56 µL, 1.0 M in THF, 0.056 mmol) at 0° C. and the resulting mixture was warmed to 20° C. and stirred for 2 h. The mixture was filtered and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: XBridge C18, 5 µm, 19 mm×150 mm) to afford the title compound (5 mg, 64% yield) as a white solid.

$^1$H NMR (600 MHz, Methanol-d$_4$) δ 8.56 (s, 1H), 7.24 (d, J=3.6 Hz, 1H), 6.56 (s, 1H), 6.54 (d, J=3.6 Hz, 1H), 4.85-4.75 (m, 2H), 4.56 (d, J=15.5 Hz, 1H), 4.50-4.39 (m, 2H), 3.82-3.74 (m, 1H), 3.69 (dt, J=14.4, 7.5 Hz, 1H), 3.41

(dd, J=17.9, 7.0 Hz, 1H), 2.81 (d, J=18.0 Hz, 1H), 1.81 (dt, J=10.0, 4.7 Hz, 3H), 1.70 (ddd, J=14.0, 12.2, 4.5 Hz, 1H), 1.57 (q, J=7.5 Hz, 2H), 1.39 (d, J=6.7 Hz, 3H), 0.97 (t, J=7.5 Hz, 3H).

MS (ES+) $C_{22}H_{27}ClN_6O$ requires: 426, found 427 [M+H]+.

EXAMPLE 47

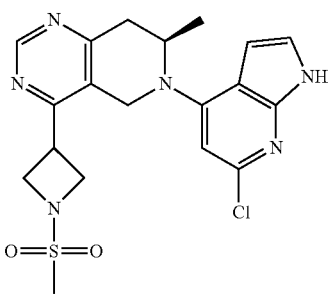 [SMILES: C[C@@H]1Cc2ncnc(C3CN(S(C)(=O)=O)C3)c2CN1c1cc(Cl)nc2[nH]ccc12]

(R)-6-(6-Chloro-1H-pyrrolo[2,3-b]pyridin-4-yl)-7-methyl-4-(1-(methylsulfonyl)azetidin-3-yl)-5,6,7,8-tetrahydropyrido[4,3-d]pyrimidine Step 1

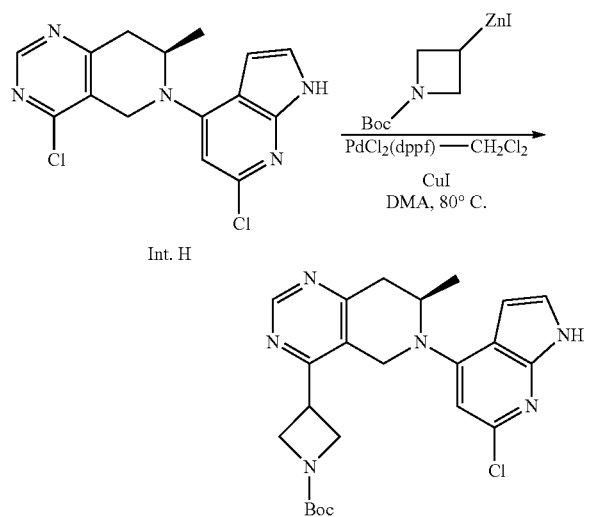

Tert-butyl (R)-3-(6-(6-chloro-1H-pyrrolo[2,3-b]pyridin-4-yl)-7-methyl-5,6,7,8-tetrahydropyrido[4,3-d]pyrimidin-4-yl)azetidine-1-carboxylate: Zinc (231 mg, 3.53 mmol) was added to an oven-dried nitrogen-filled flask with DMA (2.5 mL). The suspension was heated to 50° C. with vigorous stirring, 1,2-dibromoethane (50 µL, 0.58 mmol) and TMS-Cl (84 µL, 0.65 mmol) were added concurrently to the suspension while maintaining the temperature below 50° C. The resulting mixture was allowed to stir for 30 min at 50° C. Tert-butyl 3-iodoazetidine-1-carboxylate (307 µL, 1.77 mmol) was added to the reaction maintaining a temperature below 50° C. and the resulting solution was stirred for 30 min at 50° C. In a separate oven-dried nitrogen filled flask, a solution of Int. H (50 mg, 0.15 mmol), PdCl$_2$(dppf)-CH$_2$Cl$_2$ (12 mg, 0.015 mmol) and copper(I) iodide (3.4 mg, 0.018 mmol) in DMA (150 µL) was degassed with N$_2$ for 1 minute. The prepared solution of (1-(tert-butoxycarbonyl)azetidin-3-yl)zinc(II) iodide (2.2 mL, 0.45 mmol) was added and the reaction mixture was heated to 80° C. and stirred for 2 h. The reaction mixture was cooled to RT, 1 M HCl (1 mL) was added, the layers were separated and the aqueous phase was extracted with EtOAc (3×2 mL). The aqueous layer was then extracted with 4:1 CHCl$_3$/iPrOH (4×20 mL). The combined CHCl$_3$/iPrOH layers were dried over MgSO$_4$, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=20-50%; 12 min; Column: XBridge C18, 5 µm, 19 mm×150 mm) to afford the title compound (20 mg, 20% yield) as a yellow solid.

MS (ES+) $C_{23}H_{27}ClN_6O_2$ requires: 454, found: 455 [M+H]+.

Step 2

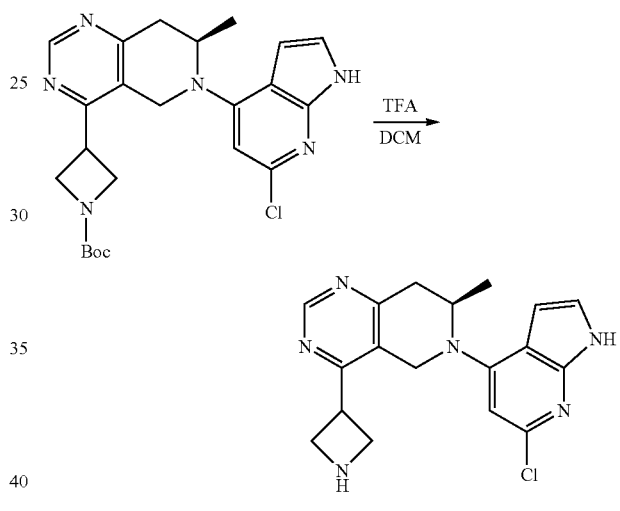

(R)-4-(Azetidin-3-yl)-6-(6-chloro-1H-pyrrolo[2,3-b]pyridin-4-yl)-7-methyl-5,6,7,8-tetrahydropyrido[4,3-d]pyrimidine: To a solution of the product from the previous step in DCM (146 µL) was added TFA (23 µL, 0.29 mmol) and the resulting mixture was stirred at RT for 6 h. The mixture was concentrated under reduced pressure to afford the title compound (assumed quantitative yield) as a brown liquid, which was used immediately in the subsequent reaction.

MS (ES+) $C_{18}H_{19}ClN_6$ requires: 354, found: 355[M+H]+.

Step 3

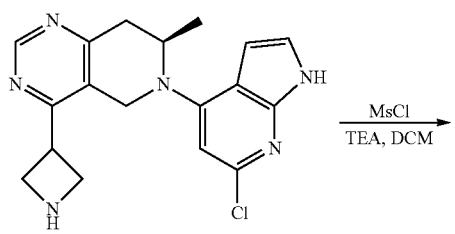

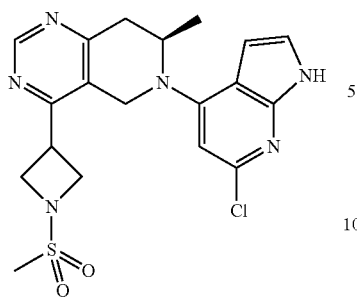

(R)-6-(6-Chloro-1H-pyrrolo[2,3-b]pyridin-4-yl)-7-methyl-4-(1-(methylsulfonyl)azetidin-3-yl)-5,6,7,8-tetrahydropyrido[4,3-d]pyrimidine: To a solution of the product form the previous step (17 mg, 0.031 mmol) in DCM (310 μL) at 0° C. were added TEA (43 μL, 0.31 mmol) and Ms-Cl (2.7 μL, 0.034 mmol) and the resulting mixture was stirred at 0° C. for 1 minute. The reaction mixture was concentrated under reduced pressure. The residue was purified by mass-triggered preparative HPLC (Mobile phase: A=0.1% TFA/H$_2$O, B=0.1% TFA/MeCN; Gradient: B=20-60%; 16 min; Column: XBridge C18, 5 μm, 19 mm×150 mm) to afford the title compound (7.4 mg, 38%) as an off-white solid.

$^1$H NMR (600 MHz, Methanol-d$_4$) δ 9.09 (s, 1H), 8.01 (d, J=7.2 Hz, 1H), 7.41 (d, J=3.7 Hz, 1H), 7.05 (d, J=3.7 Hz, 1H), 6.99 (d, J=7.3 Hz, 1H), 5.30-5.24 (m, 1H), 5.11 (d, J=16.5 Hz, 1H), 4.91 (d, J=16.4 Hz, 1H), 4.46-4.41 (m, 1H), 4.36-4.29 (m, 4H), 3.49 (dd, J=17.2, 5.8 Hz, 1H), 3.09-3.01 (m, 4H), 1.29 (d, J=6.8 Hz, 3H).

MS (ES$^+$) C$_{19}$H$_{22}$N$_6$O$_2$S requires: 398, found: 399 [M+H]$^+$.

EXAMPLE 48a AND 48b

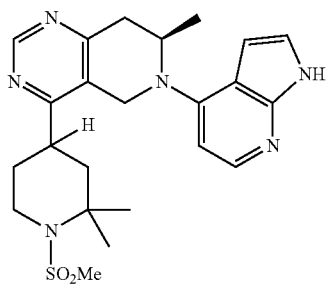 [SMILES: C[C@@H]1Cc2ncnc(C3CCN(S(C)(=O)=O)C(C)(C)C3)c2CN1c1ccnc2[nH]ccc12]

(R)-4-((R)-2,2-Dimethyl-1-(methylsulfonyl)piperidin-4-yl)-7-methyl-6-(1H-pyrrolo[2,3-b]pyridin-4-yl)-5,6,7,8-tetrahydropyrido[4,3-d]pyrimidine and (R)-4-((S)-2,2-Dimethyl-1-(methylsulfonyl)piperidin-4-yl)-7-methyl-6-(H-pyrrolo[2,3-b]pyridin-4-yl)-5,6,7,8-tetrahydropyrido[4,3-d]pyrimidine Step 1

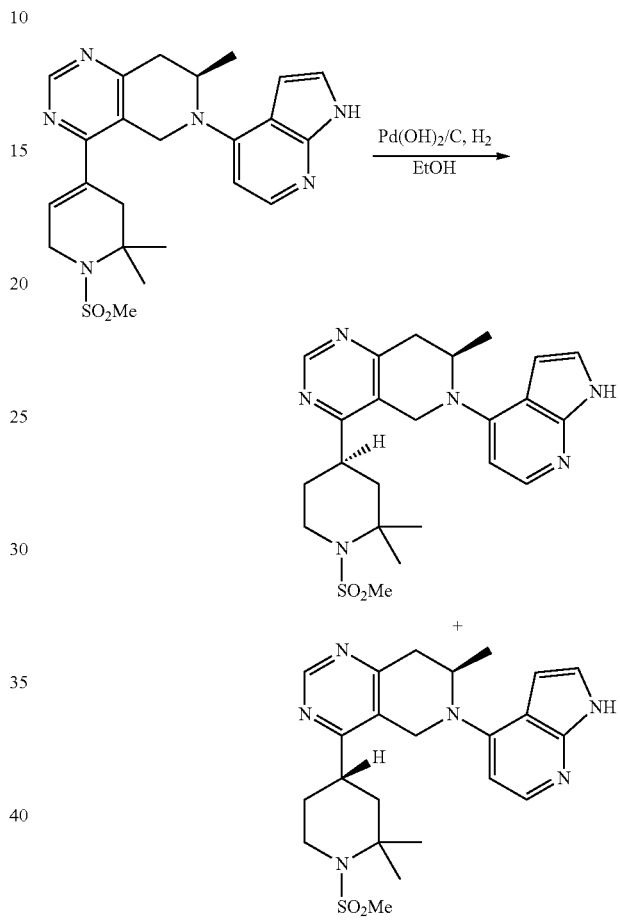

(R)-4-((R)-2,2-Dimethyl-1-(methylsulfonyl)piperidin-4-yl)-7-methyl-6-(1H-pyrrolo[2,3-b]pyridin-4-yl)-5,6,7,8-tetrahydropyrido[4,3-d]pyrimidine and (R)-4-((S)-2,2-Dimethyl-1-(methylsulfonyl)piperidin-4-yl)-7-methyl-6-(1H-pyrrolo[2,3-b]pyridin-4-yl)-5,6,7,8-tetrahydropyrido[4,3-d]pyrimidine: A reaction vessel was charged with (R)-4-(2,2-dimethyl-1-(methylsulfonyl)-1,2,3,6-tetrahydropyridin-4-yl)-7-methyl-6-(1H-pyrrolo[2,3-b]pyridin-4-yl)-5,6,7,8-tetrahydropyrido[4,3-d]pyrimidine (57 mg, 0.084 mmol, prepared via a procedure similar to that disclosed for Example 11a/b), palladium hydroxide on carbon (12 mg, 0.017 mmol) and MeOH (422 μL) under an atmosphere of N$_2$. The suspension was degassed with N$_2$ for 1 minute and purged with H$_2$ for 1 minute. The reaction mixture was stirred under an atmosphere of H$_2$ at 15 psi for 6 h. The reaction mixture was purged with N$_2$, filtered through CELITE® and concentrated under reduced pressure. The residue was purified by mass-triggered preparative HPLC (Mobile phase: A=0.1% TFA/H$_2$O, B=0.1% TFA/MeCN; Gradient: B=10-50%; 26 min; Column: XBridge C18, 5 μm, 19 mm×150 mm) to afford the title compounds 48a (9.5 mg, 34% yield) and 48b (9.0 mg, 32% yield) as off-white solids.

Example 48a ((R) or (S)-2,2-Dimethyl-1-(methylsulfonyl)piperidin-4-yl): $^{1}$H NMR (600 MHz, Methanol-d$_{4}$) δ 8.97 (s, 1H), 8.01 (d, J=7.2 Hz, 1H), 7.40 (d, J=3.7 Hz, 1H), 7.05 (d, J=3.7 Hz, 1H), 6.98 (d, J=7.3 Hz, 1H), 5.31-5.15 (m, 3H), 3.94 (dt, J=13.3, 4.0 Hz, 1H), 3.48 (dd, J=17.1, 5.8 Hz, 1H), 3.42 (tt, J=12.4, 3.8 Hz, 1H), 3.34 (ddd, J=13.2, 12.0, 2.9 Hz, 1H), 3.04-3.00 (m, 4H), 2.08 (qd, J=12.2, 4.4 Hz, 1H), 2.01-1.91 (m, 2H), 1.70-1.63 (m, 1H), 1.64 (s, 3H), 1.61 (s, 3H), 1.31 (d, J=6.7 Hz, 3H); MS (ES$^{+}$) C$_{23}$H$_{30}$N$_{6}$O$_{2}$S requires: 454, found 455 [M+H]$^{+}$; R$_{t}$=17.0 minutes.

Example 48b ((R) or (S)-2,2-Dimethyl-1-(methylsulfonyl)piperidin-4-yl): $^{1}$H NMR (600 MHz, Methanol-d$_{4}$) δ 8.98 (s, 1H), 8.01 (d, J=7.3 Hz, 1H), 7.41 (d, J=3.7 Hz, 1H), 7.05 (d, J=3.7 Hz, 1H), 7.01 (d, J=7.3 Hz, 1H), 5.30 (d, J=16.3 Hz, 1H), 5.25 (t, J=7.0 Hz, 1H), 5.03 (d, J=16.3 Hz, 1H), 3.95 (dt, J=13.3, 4.1 Hz, 1H), 3.48 (dd, J=17.0, 5.7 Hz, 1H), 3.44-3.31 (m, 2H), 3.03 (s, 4H), 2.08-1.98 (m, 2H), 1.97-1.91 (m, 1H), 1.72-1.67 (m, 1H), 1.66 (s, 3H), 1.58 (s, 3H), 1.30 (d, J=6.7 Hz, 3H); MS (ES$^{+}$) C$_{23}$H$_{30}$N$_{6}$O$_{2}$S requires: 454, found 455 [M+H]$^{+}$; R$_{t}$=18.1 minutes.

EXAMPLE 49

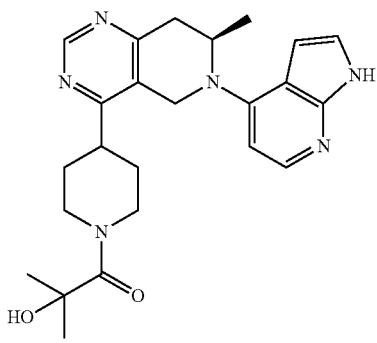 [SMILES: C[C@@H]1Cc2ncnc(C3CCN(C(=O)C(C)(C)O)CC3)c2CN1c1ccnc2[nH]ccc12]

(R)-2-Hydroxy-2-methyl-1-(4-(7-methyl-6-(1H-pyrrolo[2,3-b]pyridin-4-yl)-5,6,7,8-tetrahydropyrido[4,3-d]pyrimidin-4-yl)piperidin-1-yl)propan-1-one Step 1

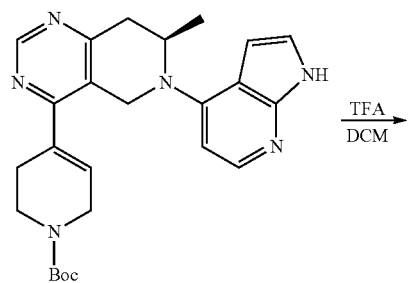

(R)-7-Methyl-6-(1H-pyrrolo[2,3-b]pyridin-4-yl)-4-(1,2,3,6-tetrahydropyridin-4-yl)-5,6,7,8-tetrahydropyrido[4,3-d]pyrimidine: To a solution of (R)-tert-butyl 4-(7-methyl-6-(1H-pyrrolo[2,3-b]pyridin-4-yl)-5,6,7,8-tetrahydropyrido[4,3-d]pyrimidin-4-yl)-5,6-dihydropyridine-1(2H)-carboxylate (300 mg, 0.445 mmol, prepared via a procedure similar to that disclosed for Example 2) in DCM (2.2 mL) was added TFA (343 μL, 4.45 mmol) and the resulting mixture was stirred at 22° C. for 2 h. The reaction solution was concentrated under reduced pressure then re-concentrated from toluene (3×5 mL) to afford the title compound (assumed quantitative yield) as a colorless liquid.

MS (ES$^{+}$) C$_{20}$H$_{22}$N$_{6}$ requires: 346, found 347 [M+H]$^{+}$.

Step 2

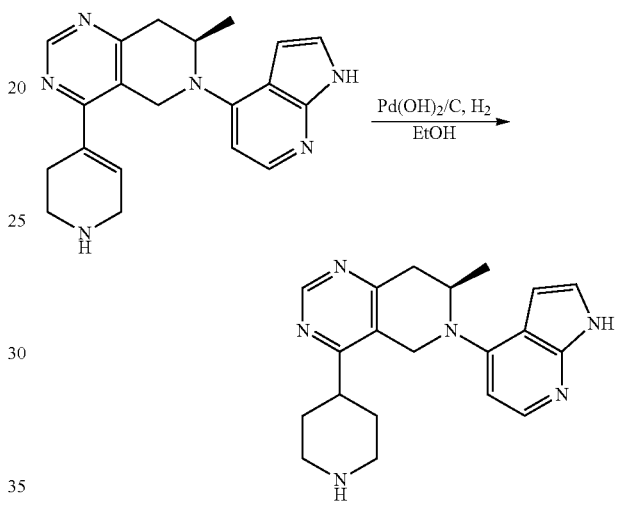

(R)-7-Methyl-4-(piperidin-4-yl)-6-(1H-pyrrolo[2,3-b]pyridin-4-yl)-5,6,7,8-tetrahydropyrido[4,3-d]pyrimidine: A reaction vessel was charged with the product from the previous step (306 mg, 0.444 mmol), palladium hydroxide on carbon (62 mg, 0.089 mmol) and ethanol (2.2 mL) under an atmosphere of N$_{2}$. The suspension was degassed with N$_{2}$ for 1 minute and purged with H$_{2}$ for 1 minute. The reaction mixture was stirred under an atmosphere of H$_{2}$ at 15 psi for 2 h. The mixture was filtered through CELITE® and concentrated under reduced pressure. The residue was purified by mass-triggered preparative HPLC (Mobile phase: A=0.1% TFA/H$_{2}$O, B=0.1% TFA/MeCN; Gradient: B=0-20%; 16 min; Column: XBridge C18, 5 μm, 19 mm×150 mm) to afford the title compound (56 mg, 18% yield) as a yellow solid.

MS (ES$^{+}$) C$_{20}$H$_{24}$N$_{6}$ requires: 348, found 349 [M+H]$^{+}$.

Step 3

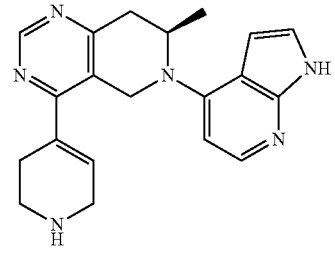

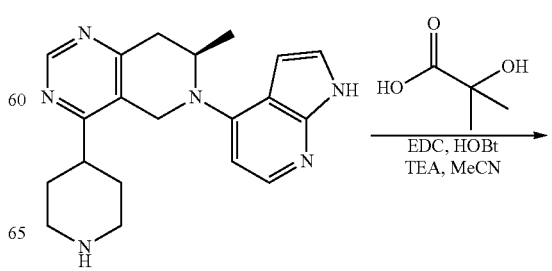

143
-continued

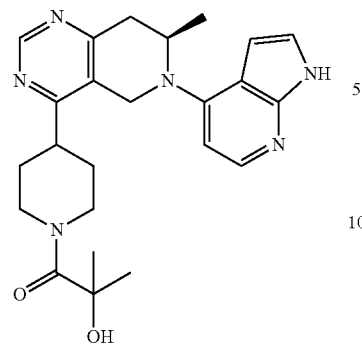

(R)-2-Hydroxy-2-methyl-1-(4-(7-methyl-6-(1H-pyrrolo[2,3-b]pyridin-4-yl)-5,6,7,8-tetrahydropyrido[4,3-d]pyrimidin-4-yl)piperidin-1-yl)propan-1-one: To a suspension of the product from the previous step (9 mg, 0.013 mmol) in acetonitrile (130 μL) were added 2-hydroxy-2-methylpropanoic acid (2.0 mg, 0.02 mmol) EDC (5.0 mg, 0.026 mmol), and HOBt (4.0 mg, 0.026 mmol) and the resulting mixture was stirred at 20° C. for 4 h. The mixture was filtered and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: XBridge C18, 5 μm, 19 mm×150 mm) to afford the title compound (3.0 mg, 35% yield) as an off-white solid.

$^1$H NMR (600 MHz, Methanol-d$_4$) δ 8.96 (s, 1H), 8.01 (d, J=7.2 Hz, 1H), 7.41 (d, J=3.7 Hz, 1H), 7.06 (d, J=3.7 Hz, 1H), 7.03 (d, J=7.3 Hz, 1H), 5.31-5.22 (m, 2H), 5.08 (d, J=16.5 Hz, 1H), 3.48 (dd, J=17.2, 5.8 Hz, 1H), 3.36-3.32 (m, 2H), 3.02 (dd, J=17.1, 1.8 Hz, 1H), 2.05-1.79 (m, 5H), 1.47 (d, J=5.7 Hz, 8H), 1.31 (d, J=6.7 Hz, 3H).

MS (ES$^+$) C$_{24}$H$_{30}$N$_6$O$_2$ requires: 434, found: 435 [M+H]$^+$.

EXAMPLE 50a AND 50b

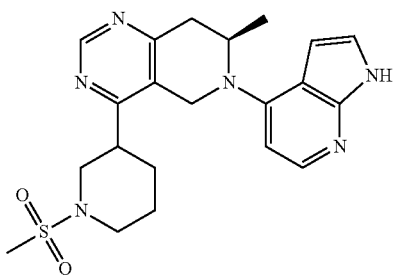 [SMILES: C[C@@H]1Cc2ncnc(C3CCCN(S(C)(=O)=O)C3)c2CN1c1ccnc2[nH]ccc12]

144

(R)-7-methyl-4-((R)-1-(methylsulfonyl)piperidin-3-yl)-6-(1H-pyrrolo[2,3-b]pyridin-4-yl)-5,6,7,8-tetrahydropyrido[4,3-d]pyrimidine and (R)-7-methyl-4-((S)-1-(methylsulfonyl)piperidin-3-yl)-6-(1H-pyrrolo[2,3-b]pyridin-4-yl)-5,6,7,8-tetrahydropyrido[4,3-d]pyrimidine Step 1

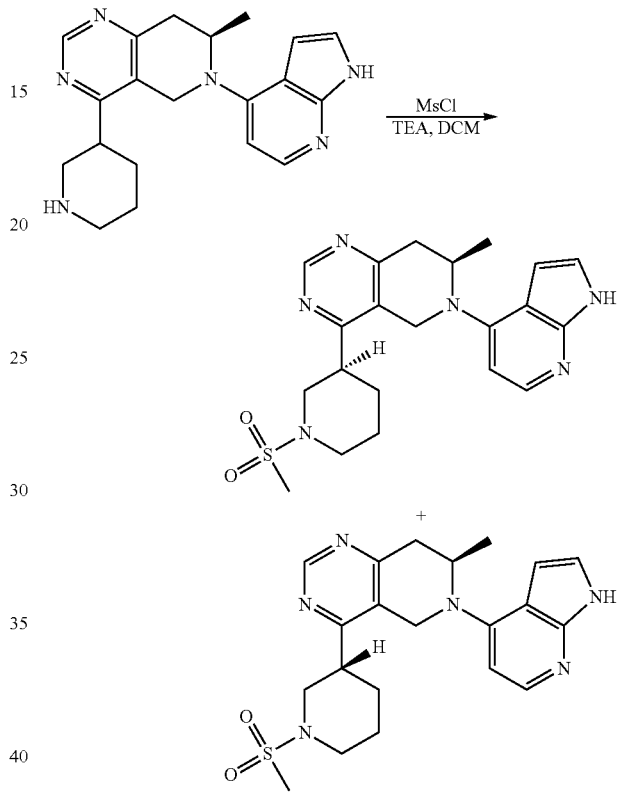

(R)-7-methyl-4-((R)-1-(methylsulfonyl)piperidin-3-yl)-6-(1H-pyrrolo[2,3-b]pyridin-4-yl)-5,6,7,8-tetrahydropyrido[4,3-d]pyrimidine and (R)-7-methyl-4-((S)-1-(methylsulfonyl)piperidin-3-yl)-6-(1H-pyrrolo[2,3-b]pyridin-4-yl)-5,6,7,8-tetrahydropyrido[4,3-d]pyrimidine: To a solution of (7R)-7-methyl-4-(piperidin-3-yl)-6-(1H-pyrrolo[2,3-b]pyridin-4-yl)-5,6,7,8-tetrahydropyrido[4,3-d]pyrimidine (47 mg, 0.14 mmol, prepared via a procedure similar to that disclosed for Example 49), in DCM (1.3 mL) were added TEA (28 μL, 0.20 mmol) and Ms-Cl (13 μL, 0.16 mmol) and the resulting mixture was stirred at 23° C. for 2 hr. The mixture was concentrated under reduced pressure. The residue was purified by mass-triggered preparative HPLC (Mobile phase: A=0.1% TFA/H$_2$O, B=0.1% TFA/MeCN; Gradient: B=0-30%; 26 min; Column: XBridge C18, 5 μm, 19 mm×150 mm) to afford the title compounds 50a (16 mg, 18% yield) and 50b (13 mg, 15% yield) as off-white solids.

Example 50a ((R) or (S)-1-(methylsulfonyl)piperidin-3-yl): $^1$H NMR (600 MHz, Methanol-d$_4$) δ 8.98 (s, 1H), 8.00 (d, J=7.2 Hz, 1H), 7.40 (d, J=3.7 Hz, 1H), 7.04 (d, J=3.7 Hz, 1H), 7.01 (d, J=7.3 Hz, 1H), 5.29-5.19 (m, 2H), 5.08 (d, J=16.4 Hz, 1H), 3.89-3.83 (m, 2H), 3.49 (dd, J=17.1, 5.8 Hz, 1H), 3.31-3.23 (m, 1H), 3.18 (t, J=11.3 Hz, 1H), 3.03 (dd, J=17.1, 1.9 Hz, 1H), 2.90 (s, 3H), 2.88-2.80 (m, 1H), 2.05-1.93 (m, 2H), 1.91-1.79 (m, 2H), 1.31 (d, J=6.7 Hz, 3H); MS (ES+) $C_{21}H_{26}N_6O_2S$ requires: 426, found 427 [M+H]+; $R_t$=22.0 minutes.

Example 50b ((R) or (S)-1-(methylsulfonyl)piperidin-3-yl): $^1$H NMR (600 MHz, Methanol-$d_4$) δ 8.98 (s, 1H), 8.00 (d, J=7.2 Hz, 1H), 7.38 (d, J=3.7 Hz, 1H), 7.06 (d, J=3.7 Hz, 1H), 7.00 (d, J=7.2 Hz, 1H), 5.32-5.23 (m, 2H), 5.07 (d, J=16.5 Hz, 1H), 3.92-3.83 (m, 2H), 3.49 (dd, J=17.1, 5.8 Hz, 1H), 3.31-3.23 (m, 1H), 3.09 (t, J=11.5 Hz, 1H), 3.03 (dd, J=17.1, 2.0 Hz, 1H), 2.89 (s, 3H), 2.88-2.80 (m, 1H), 2.07-2.01 (m, 1H), 2.00-1.77 (m, 3H), 1.31 (d, J=6.7 Hz, 3H); MS (ES+) $C_{21}H_{26}N_6O_2S$ requires: 426, found 427 [M+H]+; $R_t$=23.1 minutes.

EXAMPLE 51a AND 51b

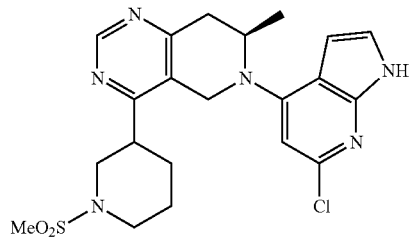 [SMILES: C[C@@H]1Cc2ncnc(C3CCCN(S(C)(=O)=O)C3)c2CN1c1cc(Cl)nc2[nH]ccc12]

((R)-6-(6-chloro-1H-pyrrolo[2,3-b]pyridin-4-yl)-7-methyl-4-((R)-1-(methylsulfonyl)piperidin-3-yl)-5,6,7,8-tetrahydropyrido[4,3-d]pyrimidine and (((R)-6-(6-chloro-1H-pyrrolo[2,3-b]pyridin-4-yl)-7-methyl-4-((S)-1-(methylsulfonyl)piperidin-3-yl)-5,6,7,8-tetrahydropyrido[4,3-d]pyrimidine Step 1

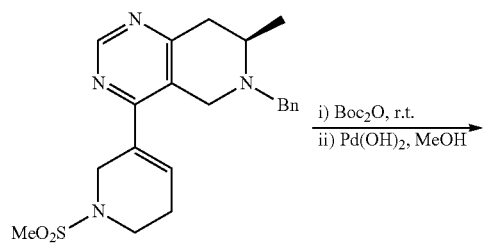

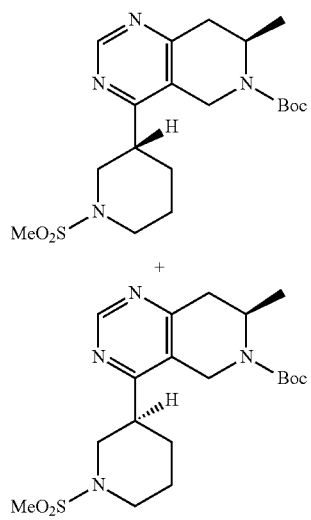

Tert-butyl (R)-7-methyl-4-((R)-1-(methylsulfonyl)piperidin-3-yl)-7,8-dihydropyrido[4,3-d]pyrimidine-6(5H)-carboxylate and tert-butyl (R)-7-methyl-4-((S)-1-(methylsulfonyl)piperidin-3-yl)-7,8-dihydropyrido[4,3-d]pyrimidine-6(5H)-carboxylate (Isomers 1a/b): A reaction vessel was charged with (R)-6-benzyl-7-methyl-4-(1-(methylsulfonyl)-1,2,5,6-tetrahydropyridin-3-yl)-5,6,7,8-tetrahydropyrido[4,3-d]pyrimidine (synthesized as described for Example 10, steps 1-3) (0.55 g, 1.38 mmol), $Boc_2O$ (0.60 g, 2.76 mmol), 20% Pd(OH)$_2$ on carbon (0.20 g, 0.28 mmol) and MeOH (50 mL) under an atmosphere of $N_2$. The suspension was degassed with $N_2$ for 1 minute and purged with $H_2$ for 1 minute. The reaction mixture was stirred under an atmosphere of $H_2$ at 1 atm for 16 h. The reaction mixture was purged with $N_2$, filtered through CELITE® and concentrated under reduced pressure. The residue was purified by mass-triggered preparative HPLC (Mobile phase: A=10 mM $NH_4HCO_3/H_2O$, B=MeCN; Gradient: B=25-55%; 18 min; Column: Welch XB C18, 10 μm, 21.2 mm×250 mm) to afford the title compounds as a mixture of diastereomers (0.4 g, 71% yield) as a white solid. MS (ES+) $C_{19}H_{30}N_4O_4S$ requires: 410, found: 411 [M+H]+.

The mixture of diastereomers was separated by chiral SFC (Mobile phase: $CO_2$/Methanol (0.2% Methanol Ammonia)=85/15; Flow rate: 80 g/min; 12 min; Column temperature: 35° C.; Back pressure: 100 bar; Column: Daicel CHIRALPAK® AD, 10 μm, 20 mm×250 mm) to afford Isomer 1a (0.2 g, >99% ee) as a white solid and Isomer 1b (0.2 g, 100% yield, >99% ee) as a white solid.

Isomer 1a: $R_t$=6.7 min; MS (ES+) $C_{19}H_{30}N_4O_4S$ requires: 410, found: 411 [M+H]+.

Isomer 1b: $R_t$=9.5 min; MS (ES+) $C_{19}H_{30}N_4O_4S$ requires: 410, found: 411 [M+H]+.

Step 2a

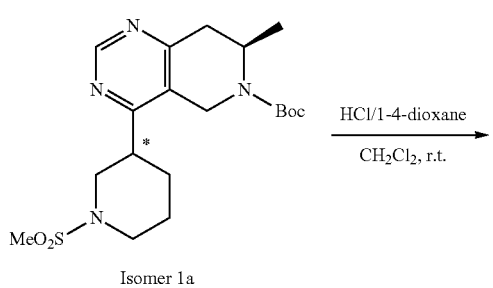

Isomer 1a

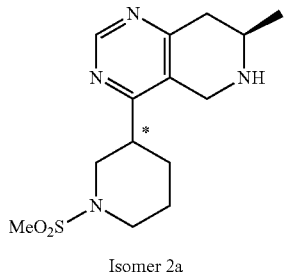

Isomer 2a (R)-7-methyl-4-((R)-1-(methylsulfonyl)piperidin-3-yl)-5,6,7,8-tetrahydro-pyrido[4,3-d]pyrimidine or (R)-7-methyl-4-((S)-1-(methylsulfonyl)piperidin-3-yl)-5,6,7,8-tetrahydropyrido[4,3-d]pyrimidine (Isomer 2a): A solution of Isomer 1a from the previous step (0.2 g, 0.49 mmol) in 4N HCl dioxane (1.8 mL, 7.3 mmol) and CH$_2$Cl$_2$(10 mL) was stirred at RT for 4 h. The mixture was concentrated under reduced pressure. The residue was purified by mass-triggered preparative HPLC (Mobile phase: A=10 mM NH$_4$HCO$_3$/H$_2$O, B=MeCN; Gradient: B=10-40%; 18 min; Column: Welch XB C18, 10 μm, 21.2 mm×250 mm) to afford Isomer 2a of title compound (116 mg, 77% yield, >99% ee) as a white solid.

$^1$H NMR (500 MHz, DMSO-d$_6$) δ 8.83 (s, 1H), 4.04 (d, J=16.3 Hz, 1H), 3.88 (d, J=16.4 Hz, 1H), 3.63 (d, J=10.8 Hz, 1H), 3.55 (d, J=7.7 Hz, 1H), 3.00-2.83 (m, 6H), 2.80-2.66 (m, 2H), 2.47-2.39 (m, 1H), 1.93-1.55 (m, 4H), 1.15 (d, J=6.3 Hz, 3H). MS (ES$^+$) C$_{14}$H$_{22}$N$_4$O$_2$S requires: 310, found: 311 [M+H]$^+$.

Step 2b

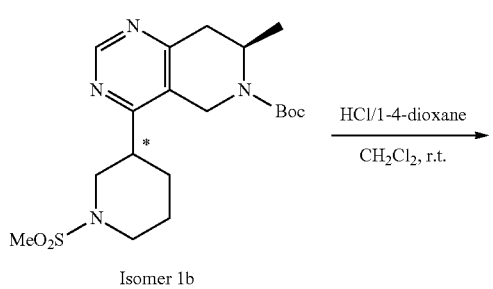

Isomer 1b

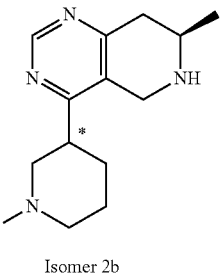

Isomer 2b (R)-7-methyl-4-((R)-1-(methylsulfonyl)piperidin-3-yl)-5,6,7,8-tetrahydropyrido[4,3-d]pyrimidine or (R)-7-methyl-4-((S)-1-(methylsulfonyl)piperidin-3-yl)-5,6,7,8-tetrahydropyrido[4,3-d]pyrimidine (Isomer 2b): A solution of Isomer 1b from the previous step (0.2 g, 0.49 mmol) in 4N HCl dioxane (1.8 mL, 7.3 mmol) and CH$_2$Cl$_2$ (10 mL) was stirred at RT for 4 hr. The mixture was concentrated under reduced pressure. The residue was purified by mass-triggered preparative HPLC (Mobile phase: A=10 mM NH$_4$HCO$_3$/H$_2$O, B=MeCN; Gradient: B=10-40%; 18 min; Column: Welch XB C18, 10 μm, 21.2 mm×250 mm) to afford Isomer 2b of the title compound (100 mg, 66% yield, >99% ee) as a white solid.

$^1$H NMR (500 MHz, DMSO-d6) δ 8.83 (s, 1H), 4.04 (d, J=16.3 Hz, 1H), 3.88 (d, J=16.4 Hz, 1H), 3.63 (d, J=10.8 Hz, 1H), 3.55 (d, J=7.7 Hz, 1H), 3.00-2.83 (m, 6H), 2.80-2.66 (m, 2H), 2.47-2.39 (m, 1H), 1.93-1.55 (m, 4H), 1.15 (d, J=6.3 Hz, 3H). MS (ES$^+$) C$_{14}$H$_{22}$N$_4$O$_2$S requires: 310, found: 311 [M+H]$^+$.

Step 3a

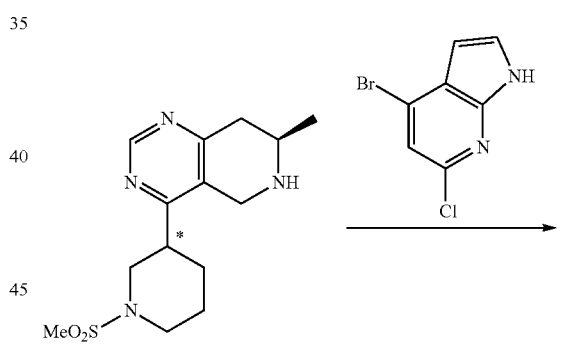

Isomer 2a

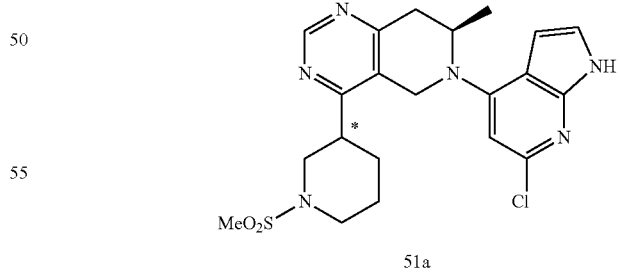

51a ((R)-6-(6-chloro-1H-pyrrolo[2,3-b]pyridin-4-yl)-7-methyl-4-((R)-1-(methylsulfonyl)piperidin-3-yl)-5,6,7,8-tetrahydropyrido[4,3-d]pyrimidine or (((R)-6-(6-chloro-1H-pyrrolo[2,3-b]pyridin-4-yl)-7-methyl-4-((S)-1-(methylsulfonyl)piperidin-3-yl)-5,6,7,8-tetrahydropyrido[4,3-d]pyrimidine (Example 51a): A suspension of Isomer 2a (50 mg, 0.16 mmol), Int. D (37.3 mg, 0.16 mmol) and sodium tert-butoxide (46 mg, 0.48 mmol) in dioxane (805 µL) was sonicated to give a heterogeneous mixture then degassed with N$_2$ for 1 minute. RuPhos (7.5 mg, 0.016 mmol) and RuPhos Pd G4 (12.5 mg, 0.016 mmol) were added and the mixture was degassed with N$_2$ for an additional 1 minute. The reaction mixture was heated to 80° C. and stirred for 16 h. The mixture was cooled to RT, diluted with EtOAc (2 mL), filtered through CELITE® and concentrated under reduced pressure. The residue was purified by mass-triggered preparative HPLC (Mobile phase: A=0.1% TFA/H$_2$O, B=0.1% TFA/MeCN; Gradient: B=20-50%; 30 min; Column: C18) to afford the title compound (1.2 mg, 1% yield) as an off-white solid.

$^1$H NMR (600 MHz, Methanol-d$_4$) δ 8.96 (s, 1H), 7.27 (d, J=3.6 Hz, 1H), 6.83 (s, 1H), 6.75 (d, J=3.6 Hz, 1H), 5.11-5.04 (m, 1H), 4.93-4.81 (m, overlap H$_2$O, 2H), 3.88-3.79 (m, 2H), 3.51 (dd, J=17.3, 6.0 Hz, 1H), 3.30-3.26 (m, overlap MeOH, 1H), 3.21-3.14 (m, 1H), 2.94 (d, J=16.9 Hz, 1H), 2.90 (s, 3H), 2.83 (td, J=11.8, 2.6 Hz, 1H), 2.02 (d, J=12.5 Hz, 1H), 1.98-1.93 (m, 1H), 1.92-1.79 (m, 2H), 1.21 (d, J=6.7 Hz, 3H); MS (ES$^+$) C$_{21}$H$_{25}$ClN$_6$O$_2$S requires: 460, found: 461 [M+H]$^+$.

Step 3b

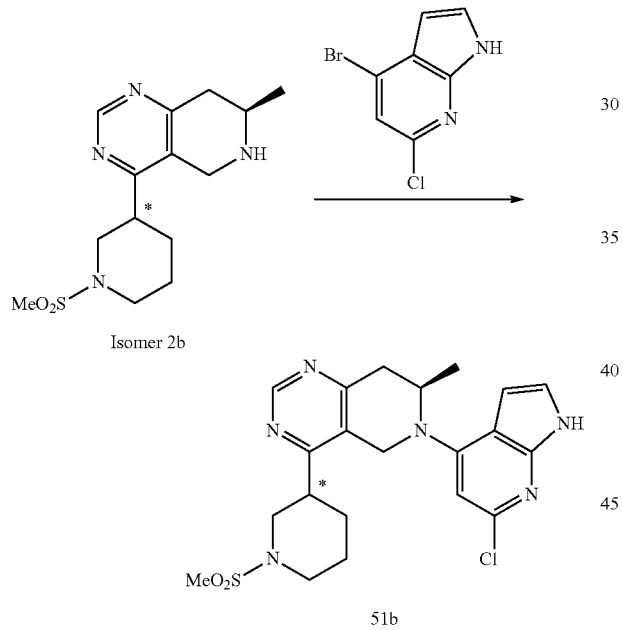

Isomer 2b

51b ((R)-6-(6-chloro-1H-pyrrolo[2,3-b]pyridin-4-yl)-7-methyl-4-((R)-1-(methylsulfonyl)piperidin-3-yl)-5,6,7,8-tetrahydropyrido[4,3-d]pyrimidine or (((R)-6-(6-chloro-1H-pyrrolo[2,3-b]pyridin-4-yl)-7-methyl-4-((S)-1-(methylsulfonyl)piperidin-3-yl)-5,6,7,8-tetrahydropyrido[4,3-d]pyrimidine (Example 51b): A suspension of Isomer 2b (50 mg, 0.16 mmol), Int. D (37.3 mg, 0.16 mmol) and sodium tert-butoxide (46 mg, 0.48 mmol) in dioxane (805 µL) was sonicated to give a heterogeneous mixture then degassed with N$_2$ for 1 minute. RuPhos (7.5 mg, 0.016 mmol) and RuPhos Pd G4 (12.5 mg, 0.016 mmol) were added and the mixture was degassed with N$_2$ for an additional 1 minute. The reaction mixture was heated to 80° C. and stirred for 16 h. The mixture was cooled to RT, diluted with EtOAc (2 mL), filtered through CELITE® and concentrated under reduced pressure. The residue was purified by mass-triggered preparative HPLC (Mobile phase: A=0.1% TFA/H$_2$O, B=0.1% TFA/MeCN; Gradient: B=20-50%; 30 min; Column: C18) to afford the title compound (3.0 mg, 3% yield) as an off-white solid.

$^1$H NMR (500 MHz, Methanol-d$_4$) δ 8.94 (s, 1H), 7.23 (d, J=3.6 Hz, 1H), 6.77 (s, 1H), 6.72 (d, J=3.7 Hz, 1H), 5.09-5.01 (m, 1H), 4.95-4.71 (m, overlap H$_2$O, 2H), 3.89-3.82 (m, 2H), 3.50 (dd, J=17.4, 6.0 Hz, 1H), 3.31-3.24 (m, overlap MeOH, 1H), 3.12 (t, J=11.5 Hz, 1H), 2.95-2.87 (m, 4H), 2.83 (td, J=12.6, 11.9, 3.9 Hz, 1H), 2.02 (d, J=9.1 Hz, 1H), 1.98-1.91 (m, 1H), 1.91-1.80 (m, 2H), 1.18 (d, J=6.8 Hz, 3H); MS (ES$^+$) C$_{21}$H$_{25}$ClN$_6$O$_2$S requires: 460, found: 461 [M+H]$^+$.

EXAMPLE 52a AND 52b

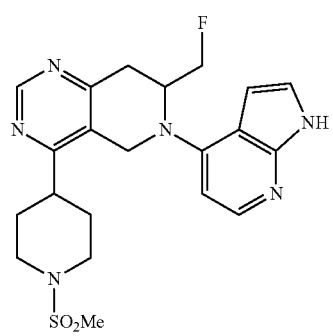

(S)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine and (R)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine Step 1

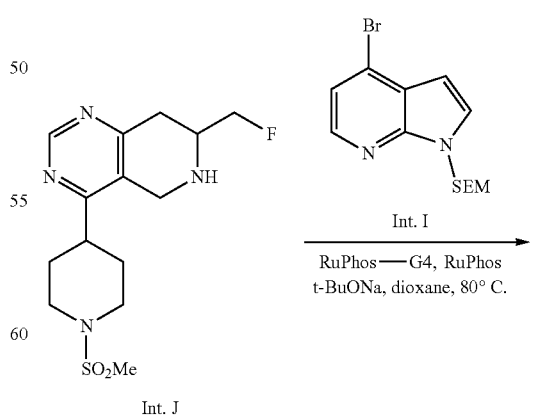

Int. J

Int. I

RuPhos—G4, RuPhos
t-BuONa, dioxane, 80° C.

-continued

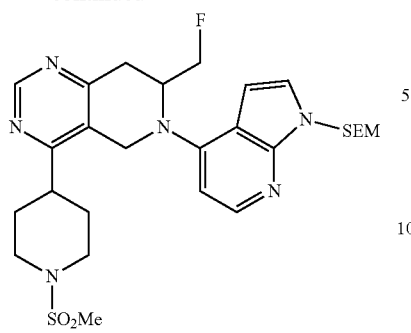

7-(Fluoromethyl)-4-(1-(methylsulfonyl)piperidin-4-yl)-6-(1-((2-(trimethylsilyl)ethoxy)methyl)-1H-pyrrolo[2,3-b]pyridin-4-yl)-5,6,7,8-tetrahydropyrido[4,3-d]pyrimidine: A mixture of Int. J (356 mg, 1.08 mmol), Int. I (390 mg, 1.19 mmol), RuPhos Pd G4 (50 mg, 5 mmol %), RuPhos (50 mg, 10 mol %) and t-BuONa (210 mg, 2.16 mmol) in dioxane (5 mL) was degassed with $N_2$ for 3 minutes. The reaction mixture was heated to 80° C. and stirred for 14 h under $N_2$. The mixture was cooled to RT, $H_2O$ (3 mL) was added and the aqueous layer was extracted with EtOAc (2×30 mL). The combined organic layers were dried over $MgSO_4$, filtered, and concentrated under reduced pressure. The residue was purified via silica gel chromatography (EtOAc in petroleum ether, 0 to 100%) to afford the title compound (360 mg, 58% yield).

MS (ES⁺) $C_{27}H_{39}FN_6O_3SSi$ requires: 574, found: 575 [M+H]⁺.

Step 2

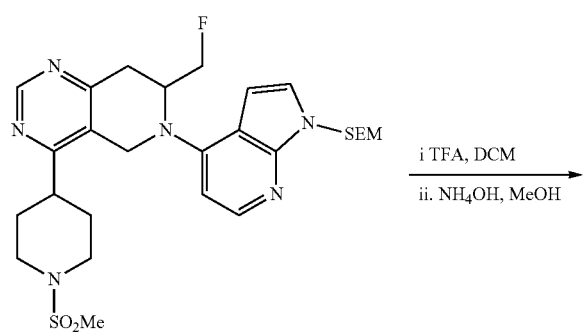

-continued

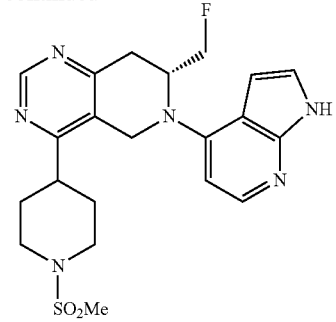 [SMILES: CS(=O)(=O)N1CCC(c2ncnc3c2CN(c2ccnc4[nH]ccc24)C(CF)C3)CC1]

52a

+

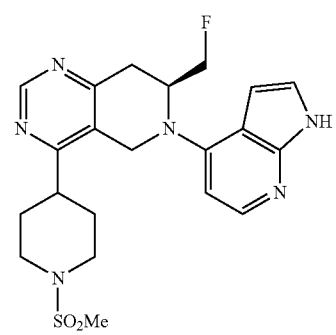

52b (R)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine and (S)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine: A mixture of the product from the previous step (340 mg, 0.59 mmol) and TFA (2 mL) in DCM (2 mL) was stirred at RT for 2 h. The reaction mixture was concentrated under reduced pressure. The residue was dissolved in MeOH (3.5 mL), $NH_4OH$ (3 mL) was added and the mixture was stirred at RT for 2 h. The mixture was filtered and concentrated under reduced pressure to afford a mixture of the title compounds (104 mg, 40% yield). The mixture of enantiomers was separated by Chiral SFC (Mobile phase: $CO_2$/methanol (0.2% Methanol Ammonia)=30/70; Flow rate: 80 g/min; 12 min; Column temperature: 35° C.; Back pressure: 100 bar; Column: Daicel CHIRALPAK® OZ, 10 μm, 20 mm×250 mm) to afford the title compounds 52a (28 mg, 54% yield, >99% ee) as a white solid and 52b (27 mg, 52% yield, 98% ee) as a white solid.

Example 52a ((R)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine): ¹H NMR (500 MHz, DMSO-d6) δ 11.51 (s, 1H), 8.95 (s, 1H), 8.03 (d, J=5.4 Hz, 1H), 7.59-7.04 (m, 1H), 6.88-6.39 (m, 2H), 5.17-4.91 (m, 1H), 4.60 (d, J=75.8 Hz, 4H), 3.68 (d, J=12.1 Hz, 2H), 3.61-3.45 (m, 1H), 3.16-3.06 (m, 1H), 2.99-2.83 (m, 6H), 1.86 (dd, J=18.2, 14.9 Hz, 4H); MS (ES⁺) $C_{21}H_{25}FN_6O_2S$ requires: 444, found: 445 [M+H]⁺; $R_t$=3.68 min.

Example 52b ((S)-7-(fluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine): ¹H NMR (500 MHz, DMSO-d6) δ 11.51 (s, 1H), 9.30-8.39 (m, 1H), 8.28-7.70 (m, 1H), 7.50-7.06 (m, 1H), 6.95-6.37 (m, 2H), 5.16-4.98

(m, 1H), 4.76-4.32 (m, 4H), 3.69 (t, J=12.2 Hz, 2H), 3.59-3.47 (m, 1H), 3.17-3.07 (m, 1H), 3.00-2.82 (m, 6H), 1.86 (dd, J=18.3, 15.0 Hz, 4H); MS (ES+) C21H25FN6O2S requires: 444, found: 445 [M+H]+; Rf=5.82 min.

Assignment of absolute stereochemistry for Examples 52a and 52b is made based on potency observed for enantiomeric pairs of known stereochemistry in this series of compounds.

EXAMPLE 53a AND 53b

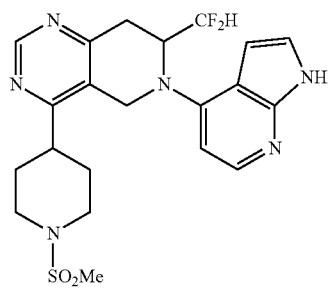

(R)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine and ((S)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine Step 1

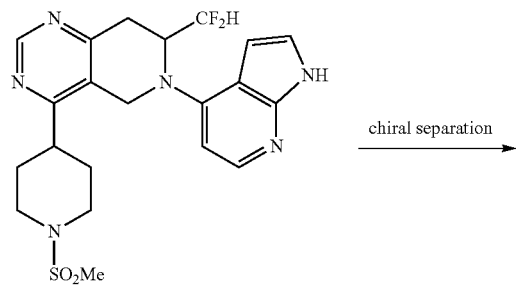

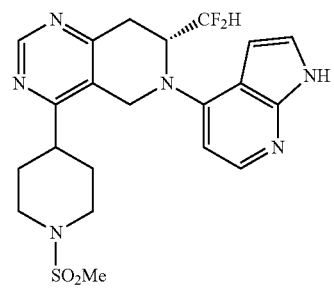 [SMILES: CS(=O)(=O)N1CCC(c2ncnc3c2CN(c2ccnc4[nH]ccc24)C(C(F)F)C3)CC1]

53a

+

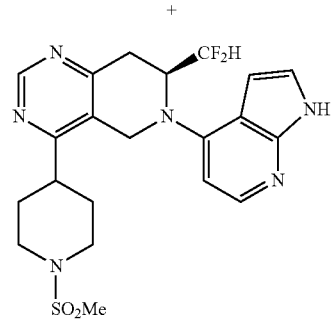

53b (R)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine and ((S)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine:

The mixture of enantiomers (140 mg, synthesized as described for Example 52 using Int. M), was separated by Chiral SFC (Mobile phase: CO2/methanol (0.2% Methanol Ammonia)=30/70; Flow rate: 80 g/min; 12 min; Column temperature: 35° C.; Back pressure: 100 bar; Column: Daicel CHIRALPAK® OZ, 10 μm, 20 mm×250 mm) to afford the title compounds 53a (53 mg, 76% yield, >99% ee) as a white solid and 53b (43 mg, 61% yield, >99% ee) as a white solid.

53a ((R)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine): $^1$H NMR (500 MHz, DMSO-d6) δ 11.58 (s, 1H), 8.97 (s, 1H), 8.07 (d, J=5.4 Hz, 1H), 7.52-7.20 (m, 1H), 6.72 (dd, J=89.1, 3.6 Hz, 2H), 6.26 (s, 1H), 5.06-4.91 (m, 1H), 4.72 (d, J=12.1 Hz, 2H), 3.67 (d, J=12.7 Hz, 3H), 3.03 (d, J=18.3 Hz, 2H), 2.99-2.83 (m, 5H), 1.86 (d, J=8.4 Hz, 4H); MS (ES+) C21H24F2N6O2S requires: 462, found: 463 [M+H]+; Rf=2.13 min.

53b (((S)-7-(difluoromethyl)-4-(1-(methylsulfonyl)piperidin-4-yl)-6-(1H-pyrrolo[2,3-b]pyridin-4-yl)-5,6,7,8-tetrahydropyrido[4,3-d]pyrimidine): $^1$H NMR (500 MHz, DMSO-d6) δ 11.58 (s, 1H), 8.97 (s, 1H), 8.07 (d, J=5.4 Hz, 1H), 7.34 (d, J=3.5 Hz, 1H), 6.72 (dd, J=89.3, 4.5 Hz, 3H), 5.15-4.89 (m, 1H), 4.72 (d, J=12.1 Hz, 2H), 3.66 (s, 3H), 3.14-3.07 (m, 1H), 3.05 (s, 1H), 2.93 (s, 5H), 1.86 (d, J=8.6 Hz, 4H); MS (ES+) C21H24F2N6O2S requires: 462, found: 463 [M+H]+; Rf=3.96 min.

EXAMPLE 54

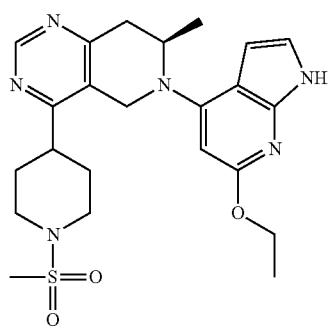 [SMILES: CCOc1cc(N2Cc3c(ncnc3C3CCN(S(C)(=O)=O)CC3)C[C@H]2C)c2cc[nH]c2n1]

(R)-6-(6-ethoxy-1H-pyrrolo[2,3-b]pyridin-4-yl)-7-methyl-4-(1-(methylsulfonyl)piperidin-4-yl)-5,6,7,8-tetrahydropyrido[4,3-d]pyrimidine Step 1

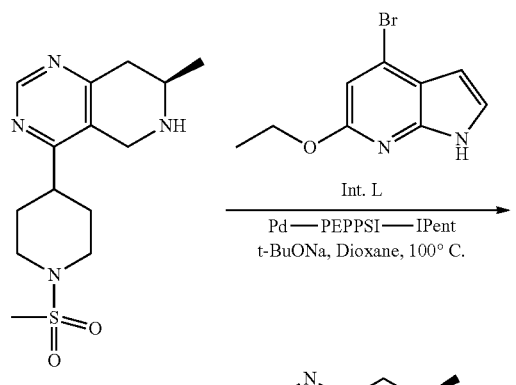

(R)-6-(6-ethoxy-1H-pyrrolo[2,3-b]pyridin-4-yl)-7-methyl-4-(1-(methylsulfonyl)piperidin-4-yl)-5,6,7,8-tetrahydropyrido[4,3-d]pyrimidine: A mixture of (R)-7-methyl-4-(1-(methylsulfonyl)piperidin-4-yl)-5,6,7,8-tetrahydropyrido[4,3-d]pyrimidine (Example 6, step 2) (150 mg, 0.483 mmol), Int. L (128 mg, 0.531 mmol) and t-BuONa (139 mg, 1.45 mmol) in dioxane (9.6 mL) was bubbled with $N_2$ for 1 min. Pd-PEPPSI™-IPent (38.0 mg, 0.048 mmol) was added and the mixture was bubbled with $N_2$ for 1 min. and heated to 90° C. for 16 hr. The mixture was cooled to RT, diluted with THF (20 mL), filtered through CELITE®, and concentrated under reduced pressure. The residue was purified by mass-triggered preparative HPLC (Mobile phase: A=10 mM $NH_4HCO_3/H_2O$, B=MeCN; Gradient: B=35-65%; 18 min; Column: Welch XB C18, 10 μm, 21.2 mm×250 mm) to afford the title compound (30 mg, 13% yield) as a white solid.

$^1$H NMR (500 MHz, DMSO-d6) δ 11.30 (s, 1H), 8.95 (s, 1H), 7.09-6.94 (m, 1H), 6.45 (s, 1H), 6.08 (s, 1H), 4.95-4.79 (m, 1H), 4.47 (s, 2H), 4.29 (q, J=7.0 Hz, 2H), 3.69 (s, 2H), 3.48 (dd, J=17.5, 5.7 Hz, 1H), 3.18 (s, 1H), 3.00-2.83 (m, 6H), 2.77 (d, J=17.5 Hz, 1H), 1.92-1.77 (m, 4H), 1.33 (t, J=7.0 Hz, 3H), 0.98 (d, J=6.7 Hz, 3H); MS (ES$^+$) $C_{23}H_{30}N_6O_3S$ requires: 470, found: 471 [M+H]$^+$.

EXAMPLE 55a AND 55b

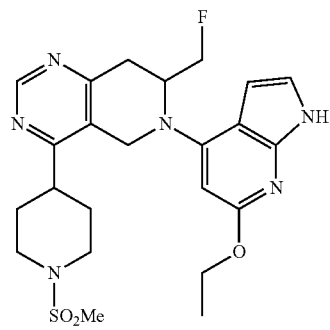 [SMILES: CCOc1cc(N2Cc3c(ncnc3C3CCN(S(C)(=O)=O)CC3)CC2CF)c2cc[nH]c2n1]

(R)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine and (R)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine Step 1

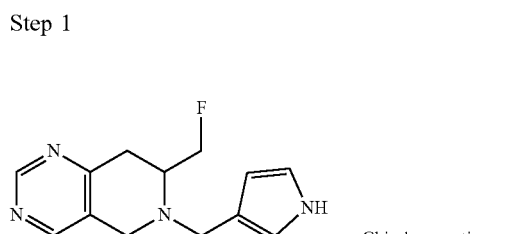

Chiral separation

157
-continued

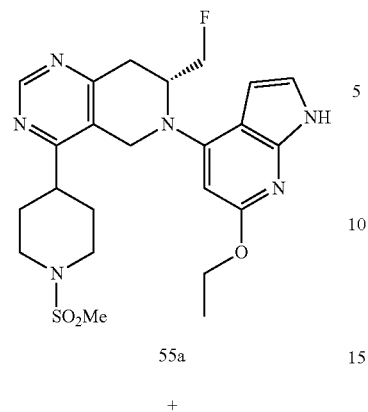

55a

+

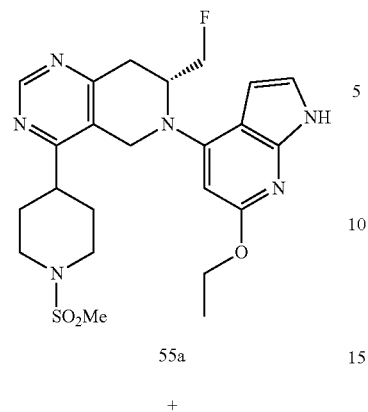

55b (R)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine and (R)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine: The mixture of enantiomers (420 mg; synthesized as described for Example 52 was separated by Chiral SFC (Mobile phase: CO$_2$/ethanol (1% Methanol Ammonia)=30/70; Flow rate: 80 g/min; 7 min; Column temperature: 35° C.; Back pressure: 100 bar; Column: Daicel WHELK, 10 μm, 20 mm×250 mm) to afford the title compounds 55a (107 mg, 51% yield, >99% ee) and 55b (157 mg, 74% yield, 92% ee).

55a ((R)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine): $^1$H NMR (500 MHz, DMSO-d6) δ 11.33 (s, 1H), 8.94 (s, 1H), 7.05 (s, 1H), 6.47 (s, 1H), 6.14 (s, 1H), 5.03 (s, 1H), 4.50 (d, J=67.2 Hz, 4H), 4.29 (q, J=7.0 Hz, 2H), 3.68 (s, 2H), 3.56 (s, 1H), 3.15 (s, 1H), 3.03-2.83 (m, 6H), 1.86 (s, 4H), 1.34 (t, J=7.0 Hz, 3H); MS (ES+) C$_{23}$H$_{29}$FN$_6$O$_3$S requires: 488, found: 489 [M+H]$^+$; R$_t$=3.26 min.

55b ((S)-6-(6-ethoxy-1H-pyrrolo[2,3-b]pyridin-4-yl)-7-(fluoromethyl)-4-(1-(methylsulfonyl)piperidin-4-yl)-5,6,7,8-tetrahydropyrido[4,3-d]pyrimidine): $^1$H NMR (500 MHz, DMSO-d6) δ 11.33 (s, 1H), 8.94 (s, 1H), 7.08-7.02 (m, 1H), 6.47 (s, 1H), 6.14 (s, 1H), 5.03 (s, 1H), 4.64-4.40 (m, 4H), 4.29 (q, J=7.0 Hz, 2H), 3.68 (s, 2H), 3.54 (d, J=19.2 Hz, 1H), 3.15 (s, 1H), 3.02-2.82 (m, 6H), 1.84 (d, J=26.2 Hz, 4H), 1.34 (t, J=7.1 Hz, 3H); MS (ES$^+$) C$_{23}$H$_{29}$FN$_6$O$_3$S requires: 488, found: 489 [M+H]$^+$; R$_t$=3.91 min.

158

EXAMPLE 56

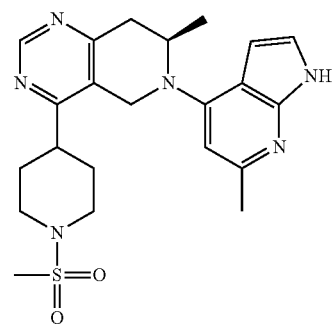 [SMILES: Cc1cc(N2Cc3c(ncnc3C3CCN(S(C)(=O)=O)CC3)C[C@H]2C)c2cc[nH]c2n1]

(R)-7-methyl-6-(6-methyl-1H-pyrrolo[2,3-b]pyridin-4-yl)-4-(1-(methylsulfonyl)piperidin-4-yl)-5,6,7,8-tetrahydropyrido[4,3-d]pyrimidine Step 1

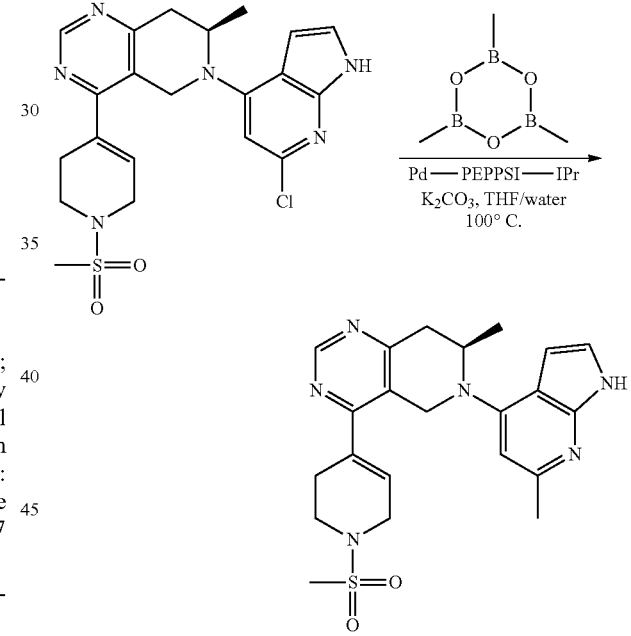

(R)-7-methyl-6-(6-methyl-1H-pyrrolo[2,3-b]pyridin-4-yl)-4-(1-(methylsulfonyl)-1,2,3,6-tetrahydropyridin-4-yl)-5,6,7,8-tetrahydropyrido[4,3-d]pyrimidine: A mixture of (R)-6-(6-chloro-1H-pyrrolo[2,3-b]pyridin-4-yl)-7-methyl-4-(1-(methylsulfonyl)-1,2,3,6-tetrahydropyridin-4-yl)-5,6,7,8-tetrahydropyrido[4,3-d]pyrimidine (synthesized as described for Example 11; 100 mg, 0.218 mmol), 2,4,6-trimethyl-1,3,5,2,4,6-trioxatriborinane (3.5 M in THF, 0.19 mL, 0.65 mmol), K$_2$CO$_3$ (109 mg, 0.785 mmol) in THF (4 mL) and H$_2$O (1 mL) was degassed with N$_2$ for 1 min. Pd-PEPPSI™-IPr (15 mg, 0.022 mmol) was added, the mixture was degassed with N$_2$ for 1 min. and heated to 100° C. for 16 h. The mixture was cooled to RT and concentrated under reduced pressure. The residue was purified by Biotage Isolera system (Mobile Phase: A=10 mM NH$_4$HCO$_3$ in water, B=MeCN; Gradient: 5-95% B in 20 min; 40 mL/min;

Column: Agela C18, 40 g, 20-35 μm, 100 Å) to afford the title compound (50 mg, 52% yield) as a yellow solid.

MS (ES+) $C_{22}H_{26}N_6O_2S$ requires: 438, found: 439 [M+H]+.

Step 2

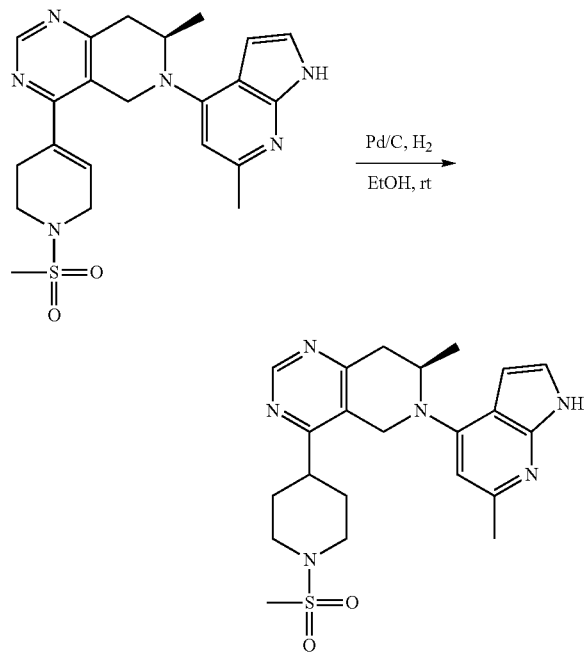

(R)-7-methyl-6-(6-methyl-1H-pyrrolo[2,3-b]pyridin-4-yl)-4-(1-(methylsulfonyl)piperidin-4-yl)-5,6,7,8-tetrahydropyrido[4,3-d]pyrimidine: A mixture of the product from the previous step (50 mg, 0.11 mmol), 30% Pd/C (43 mg, 0.011 mmol) and EtOH (10 mL) under an atmosphere of $N_2$. The suspension was degassed with $N_2$ for 1 minute and purged with $H_2$ for 1 minute. The reaction mixture was stirred under an atmosphere of $H_2$ at 1 atm for 16 h. The reaction mixture was purged with $N_2$, filtered through CELITE® and concentrated under reduced pressure. The residue was purified by mass-triggered preparative HPLC (Mobile phase: A=10 mM $NH_4HCO_3/H_2O$, B=MeCN; Gradient: B=25-55%; 18 min; Column: Welch XB C18, 10 μm, 21.2 mm×250 mm) to afford the title compound (2.2 mg, 5% yield) as a white solid.

1H NMR (500 MHz, DMSO-d6) δ 11.28 (s, 1H), 8.96 (s, 1H), 7.24-7.12 (m, 1H), 6.53 (s, 1H), 6.49 (s, 1H), 4.92-4.75 (m, 1H), 4.55 (d, J=17.7 Hz, 2H), 3.70 (s, 2H), 3.47 (dd, J=17.6, 5.7 Hz, 1H), 3.13 (d, J=7.7 Hz, 1H), 2.93 (d, J=8.3 Hz, 5H), 2.78 (d, J=17.5 Hz, 1H), 2.47 (s, 3H), 1.88 (d, J=2.7 Hz, 4H), 1.01 (d, J=6.7 Hz, 3H); MS (ES+) $C_{22}H_{28}N_6O_2S$ requires: 440, found: 441 [M+H]+.

EXAMPLE 57a AND 57b

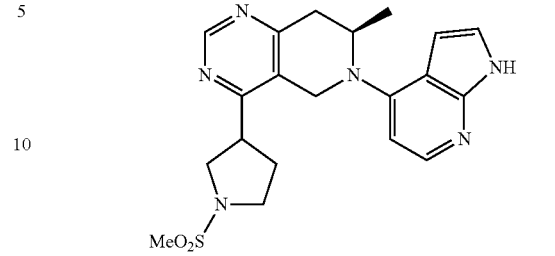

(R)-7-methyl-4-((R)-1-(methylsulfonyl)pyrrolidin-3-yl)-6-(1H-pyrrolo[2,3-b]pyridin-4-yl)-5,6,7,8-tetrahydropyrido[4,3-d]pyrimidine and (R)-7-methyl-4-((S)-1-(methylsulfonyl)pyrrolidin-3-yl)-6-(1H-pyrrolo[2,3b]-pyridin-4-yl)-5,6,7,8-tetrahydropyrido[4,3-d]pyrimidine Synthesis is similar to that described for Example 50.

57a (4-(S) or 4-(R)-1-(methylsulfonyl)pyrrolidin-3-yl)): 1H NMR (500 MHz, DMSO-d6) δ 11.48 (s, 1H), 8.97 (s, 1H), 8.02 (d, J=5.4 Hz, 1H), 7.28 (s, 1H), 6.67 (d, J=5.5 Hz, 1H), 6.58 (d, J=3.1 Hz, 1H), 4.94-4.81 (m, 1H), 4.73-4.46 (m, 2H), 3.95-3.85 (m, 1H), 3.74-3.69 (m, 1H), 3.58-3.45 (m, 3H), 3.40 (dd, J=17.2, 7.5 Hz, 1H), 3.00 (d, J=9.6 Hz, 3H), 2.80 (d, J=17.1 Hz, 1H), 2.36 (s, 1H), 2.17-2.05 (m, 1H), 1.02 (d, J=6.7 Hz, 3H); MS (ES+) $C_{20}H_{24}N_6O_2S$ requires: 412, found: 413 [M+H]+.

57b (4-(S) or 4-(R)-1-(methylsulfonyl)pyrrolidin-3-yl)): 1H NMR (500 MHz, DMSO-d6) δ 11.48 (s, 1H), 8.97 (s, 1H), 8.02 (d, J=5.4 Hz, 1H), 7.29 (d, J=3.3 Hz, 1H), 6.67 (dd, J=5.4, 3.1 Hz, 1H), 6.58 (t, J=4.8 Hz, 1H), 4.95-4.81 (m, 1H), 4.73-4.45 (m, 2H), 3.95-3.82 (m, 1H), 3.72 (dt, J=19.0, 9.6 Hz, 1H), 3.58-3.43 (m, 3H), 3.40 (dd, J=16.2, 8.5 Hz, 1H), 3.00 (d, J=9.7 Hz, 3H), 2.80 (d, J=17.5 Hz, 1H), 2.40-2.28 (m, 1H), 2.13 (qd, J=16.0, 7.9 Hz, 1H), 1.03 (d, J=6.7 Hz, 3H); MS (ES+) $C_{20}H_{24}N_6O_2S$ requires: 412, found: 413 [M+H]+.

EXAMPLE 58

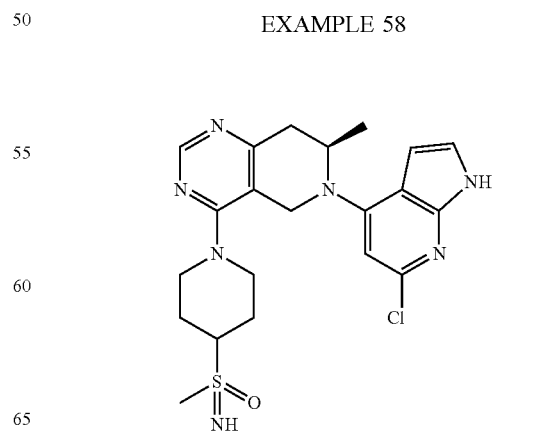

(1-((R)-6-(6-chloro-1H-pyrrolo[2,3-b]pyridin-4-yl)-7-methyl-5,6,7,8-tetrahydropyrido[4,3-d]pyrimidin-4-yl)piperidin-4-yl)(imino)(methyl)-λ⁶-sulfanone Step 1

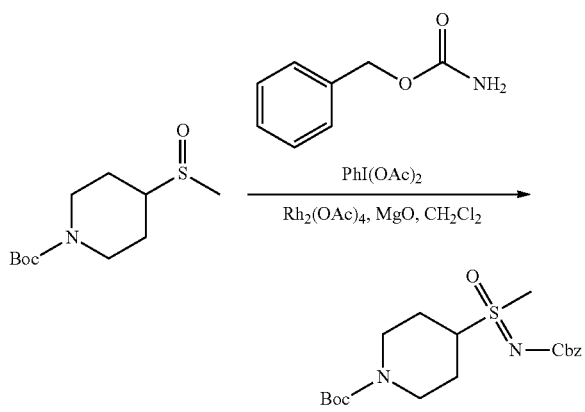

Tert-butyl 4-(N-((benzyloxy)carbonyl)-methylsulfonimidoyl)piperidine-1-carboxylate: To a solution of tert-butyl 4-(methylsulfinyl)piperidine-1-carboxylate (1.3 g, 5.3 mmol) in CH₂Cl₂ (17.5 mL) were added benzyl carbamate (1.2 g, 7.9 mmol), Rh₂(OAc)₄ (116 mg, 0.263 mmol), MgO (631 mg, 15.8 mmol) and PhI(OAc)₂ (2.54 g, 7.88 mmol) and the resulting mixture was heated to reflux for 36 h. The mixture was cooled to RT, diluted with CH₂Cl₂ (50 mL), filtered through CELITE® and concentrated under reduced pressure. The residue was purified via silica gel chromatography (0-100% CH₂Cl₂ in petroleum ether, then 0-10% MeOH in CH₂Cl₂). The residue was further purified by Biotage Isolera system (Mobile Phase: A=10 mM NH₄HCO₃ in water, B=CH₃OH; 75 mL/min; Gradient: 0-95%; 24.0 min; Column: Agela C18, 20-35 μm, 100 Å) to afford the title compound (240 mg, 11% yield) as a white solid.

MS (ES⁺) $C_{19}H_{28}N_2O_5S$ requires: 396, found: 397 [M+H]⁺.

Step 2

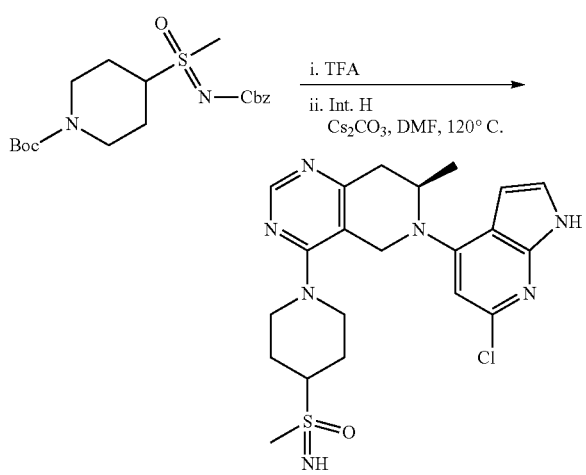

(1-((R)-6-(6-chloro-1H-pyrrolo[2,3-b]pyridin-4-yl)-7-methyl-5,6,7,8-tetrahydropyrido[4,3-d]pyrimidin-4-yl)piperidin-4-yl)(imino)(methyl)-λ⁶-sulfanone: A mixture of the product from the previous step (160 mg, 0.104 mmol) in TFA (4 mL) was stirred at RT for 4 h. The mixture was concentrated under reduced pressure and dissolved in DMF (6 mL). Int. H (81 mg, 0.241 mmol) and Cs₂CO₃ (313 mg, 0.962 mmol) were added and the resulting mixture was stirred at 120° C. for 4 h. The reaction was cooled to RT, filtered through CELITE® and concentrated under reduced pressure. The residue was purified by mass-triggered preparative HPLC (Mobile phase: A=10 mM NH₄HCO₃/H₂O, B=MeCN; Gradient: B=25-55%; 18 min; Column: Welch XB C18, 10 μm, 21.2 mm×250 mm) to afford the title compound (17.5 mg, 16% yield) as a yellow solid.

¹H NMR (500 MHz, DMSO-d6) δ 11.64 (s, 1H), 8.55 (s, 1H), 7.31 (d, J=46.0 Hz, 1H), 6.55 (s, 1H), 6.42 (s, 1H), 4.76-4.63 (m, 1H), 4.51 (dd, J=41.9, 15.8 Hz, 2H), 4.03 (dd, J=28.7, 12.4 Hz, 2H), 3.67 (d, J=2.3 Hz, 1H), 3.30-3.21 (m, 2H), 3.10 (t, J=13.3 Hz, 1H), 2.96 (t, J=12.5 Hz, 1H), 2.86 (s, 3H), 2.72 (d, J=17.2 Hz, 1H), 2.23-2.07 (m, 2H), 1.93-1.75 (m, 1H), 1.77-1.58 (m, 1H), 1.22 (dd, J=6.5, 3.5 Hz, 3H); MS (ES⁺) $C_{21}H_{26}ClN_7OS$ requires: 459, found: 460 [M+H]⁺.

EXAMPLE 59

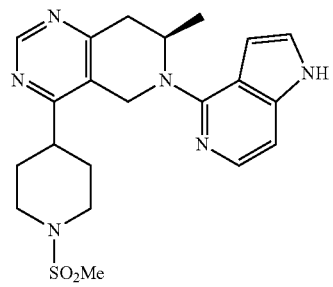

(R)-7-methyl-4-(1-(methylsulfonyl)piperidin-4-yl)-6-(1H-pyrrolo[3,2-c]pyridin-4-yl)-5,6,7,8-tetrahydropyrido[4,3-d]pyrimidine Step 1

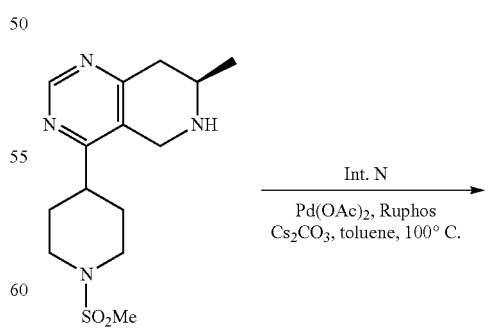

163

-continued

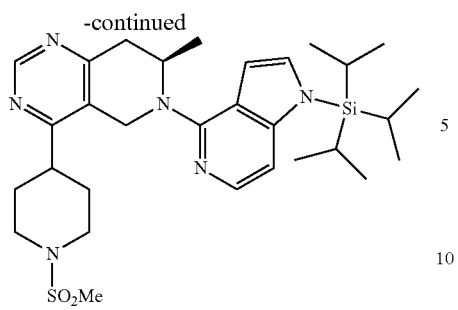

164

-continued

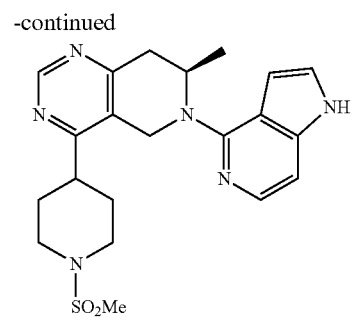

(R)-7-methyl-4-(1-(methylsulfonyl)piperidin-4-yl)-6-(1-(triisopropylsilyl)-1H-pyrrolo[3,2-c]pyridin-4-yl)-5,6,7,8-tetrahydropyrido[4,3-d]pyrimidine: A mixture of (R)-7-methyl-4-(1-(methylsulfonyl)piperidin-4-yl)-5,6,7,8-tetrahydropyrido[4,3-d]pyrimidine (Example 6, step 2) (100 mg, 0.32 mmol), Int. N (300 mg, 0.97 mmol), Pd(OAc)$_2$ (7.0 mg, 0.03 mmol), Cs$_2$CO$_3$ (315 mg, 0.97 mmol), Ruphos (6.0 mg, 0.016 mmol) and toluene (5.2 mL) was bubbled with argon for 1 min., sealed in a tube and heated to 100° C. for 16 h. The reaction mixture was diluted with toluene (20 mL), filtered through CELITE® and concentrated under reduced pressure. The residue was purified via silica gel chromatography (0-100% acetone in petroleum ether) to afford the title compound (70 mg, 37% yield) as a yellow oil.

MS (ES$^+$) C$_{30}$H$_{46}$N$_6$O$_2$SSi requires: 582, found: 583 [M+H]$^+$.

Step 2

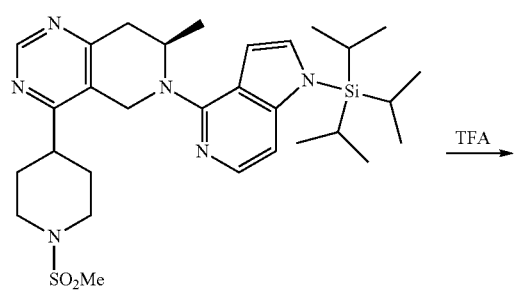

TFA (R)-7-methyl-4-(1-(methylsulfonyl)piperidin-4-yl)-6-(1H-pyrrol[3,2-c]pyridin-4-yl)-5,6,7,8-tetrahydropyrido[4,3-d]pyrimidine: A solution of the product from the previous step (70 mg, 0.12 mmol) in TFA (5 mL) was stirred at RT for 16 h. The mixture was concentrated under reduced pressure. The residue was purified by preparative HPLC (Mobile phase: A=10 mM NH$_4$HCO$_3$/H$_2$O, B=MeCN; Gradient: B=25-55%; 18 min; Column: Welch XB C18, 10 μm, 21.2 mm×250 mm) to afford the title compound (7.8 mg, 13% yield) as a white solid.

$^1$H NMR (500 MHz, DMSO-d6) δ 11.42 (s, 1H), 8.93 (s, 1H), 7.78 (d, J=5.7 Hz, 1H), 7.39-7.19 (m, 1H), 6.92 (d, J=5.7 Hz, 1H), 6.65 (s, 1H), 5.11-4.96 (m, 2H), 4.56 (d, J=17.4 Hz, 1H), 3.68 (d, J=7.4 Hz, 2H), 3.41 (dd, J=17.4, 6.0 Hz, 1H), 3.15-3.00 (m, 1H), 2.98-2.88 (m, 5H), 2.76 (d, J=17.4 Hz, 1H), 1.96-1.77 (m, 4H), 1.08 (d, J=6.8 Hz, 3H); MS (ES$^+$) C$_{21}$H$_{26}$N$_6$O$_2$S requires: 426, found: 427 [M+H]$^+$.

The compounds reported in Table 1 were synthesized using one of the methods described for Examples 1-59, as specified for each case. The appropriate boronates and amines were prepared as described for Intermediates E, F and G.

TABLE 2

Examples 60-99.

| Ex | Structure | IUPAC Name | MWt | [M + H] | Ex. Method |
|---|---|---|---|---|---|
| 60 | 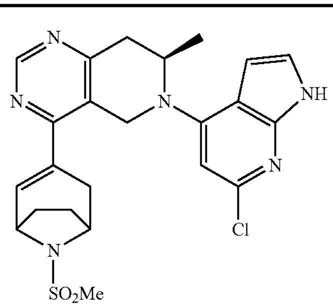 | (R)-6-(6-chloro-1H-pyrrolo[2,3-b]pyridin-4-yl)-7-methyl-4-((1S,5R)-8-(methylsulfonyl)-8-azabicyclo[3.2.1]oct-2-en-3-yl)-5,6,7,8-tetrahydropyrido[4,3-d]-pyrimidine | 485 | 486 | 11 |

TABLE 2-continued

Examples 60-99.

| Ex | Structure | IUPAC Name | MWt | [M + H] | Ex. Method |
|---|---|---|---|---|---|
| 61 | 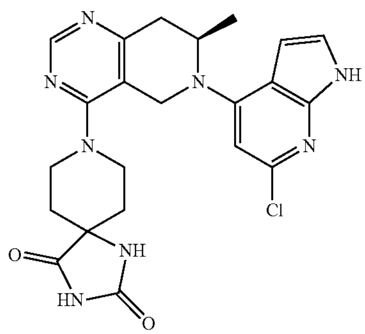 [SMILES: C[C@@H]1Cc2ncnc(N3CCC4(CC3)NC(=O)NC4=O)c2CN1c1cc(Cl)nc2[nH]ccc12] | (R)-8-(6-(6-chloro-1H-pyrrolo[2,3-b]pyridin-4-yl)-7-methyl-5,6,7,8-tetrahydropyrido[4,3-d]pyrimidin-4-yl)-1,3,8-triazaspiro[4.5]decane-2,4-dione | 466 | 467 | 12 |
| 62 | 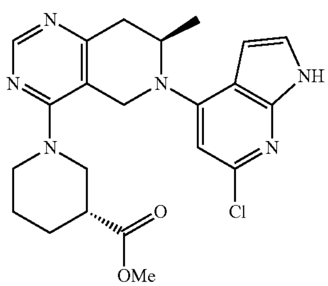 [SMILES: COC(=O)[C@@H]1CCCN(c2ncnc3c2CN(c2cc(Cl)nc4[nH]ccc24)[C@H](C)C3)C1] | Methyl (R)-1-((R)-6-(6-chloro-1H-pyrrolo[2,3-b]pyridin-4-yl)-7-methyl-5,6,7,8-tetrahydropyrido-[4,3-d]pyrimidin-4-yl)-piperidine-3-carboxylate | 440 | 441 | 12 |
| 63 | 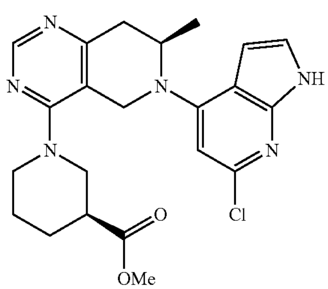 [SMILES: COC(=O)[C@H]1CCCN(c2ncnc3c2CN(c2cc(Cl)nc4[nH]ccc24)[C@H](C)C3)C1] | Methyl (S)-1-((R)-6-(6-chloro-1H-pyrrolo[2,3-b]pyridin-4-yl)-7-methyl-5,6,7,8-tetrahydropyrido-[4,3-d]pyrimidin-4-yl)-piperidine-3-carboxylate | 440 | 441 | 12 |
| 64 | 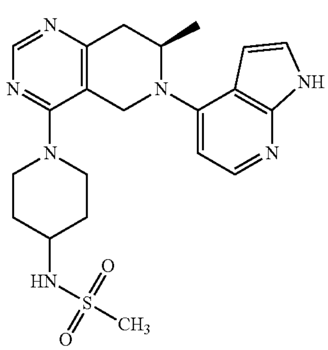 [SMILES: C[C@@H]1Cc2ncnc(N3CCC(NS(C)(=O)=O)CC3)c2CN1c1ccnc2[nH]ccc12] | (R)-N-(1-(7-methyl-6-(1H-pyrrolo[2,3-b]-pyridin-4-yl)-5,6,7,8-tetrahydropyrido[4,3-d]-pyrimidin-4-yl)piperidin-4-yl)methanesulfonamide | 441 | 442 | 13 |
| 65 | 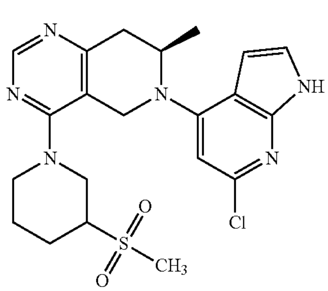 [SMILES: C[C@@H]1Cc2ncnc(N3CCCC(S(C)(=O)=O)C3)c2CN1c1cc(Cl)nc2[nH]ccc12] | (7R)-6-(6-chloro-1H-pyrrolo[2,3-b]pyridin-4-yl)-7-methyl-4-(3-(methylsulfonyl)-piperidin-1-yl)-5,6,7,8-tetrahydropyrido[4,3-d]-pyrimidine | 460 | 461 | 12 |

TABLE 2-continued

Examples 60-99.

| Ex | Structure | IUPAC Name | MWt | [M + H] | Ex. Method |
|---|---|---|---|---|---|
| 66 | 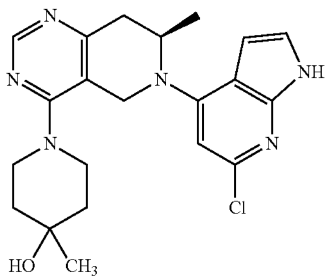 [SMILES: C[C@@H]1Cc2ncnc(N3CCC(C)(O)CC3)c2CN1c1cc(Cl)nc2[nH]ccc12] | (R)-1-(6-(6-chloro-1H-pyrrolo[2,3-b]pyridin-4-yl)-7-methyl-5,6,7,8-tetrahydropyrido[4,3-d]pyrimidin-4-yl)-4-methyl-piperidin-4-ol | 412 | 413 | 12 |
| 67 | 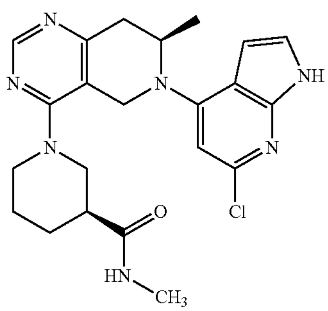 [SMILES: CNC(=O)[C@H]1CCCN(c2ncnc3c2CN(c2cc(Cl)nc4[nH]ccc24)[C@H](C)C3)C1] | (S)-1-((R)-6-(6-chloro-1H-pyrrolo[2,3-b]pyridin-4-yl)-7-methyl-5,6,7,8-tetrahydropyrido[4,3-d]-pyrimidin-4-yl)-N-methylpiperidine-3-carboxamide | 412 | 413 | 12 |
| 68 | 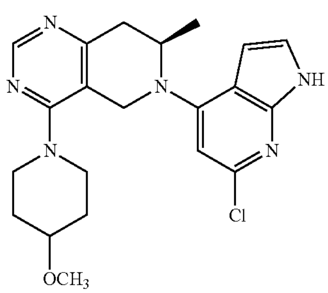 [SMILES: COC1CCN(c2ncnc3c2CN(c2cc(Cl)nc4[nH]ccc24)[C@H](C)C3)CC1] | (R)-6-(6-chloro-1H-pyrrolo[2,3-b]pyridin-4-yl)-4-(4-methoxy-piperidin-1-yl)-7-methyl-5,6,7,8-tetrahydro-pyrido[4,3-d]pyrimidine | 412 | 413 | 12 |
| 69 | 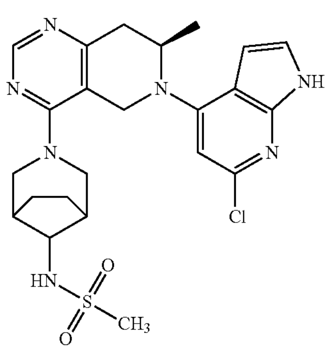 [SMILES: C[C@@H]1Cc2ncnc(N3CC4CCC(C3)C4NS(C)(=O)=O)c2CN1c1cc(Cl)nc2[nH]ccc12] | N-(3-((R)-7-methyl-6-(1H-pyrrolo[2,3-b]-pyridin-4-yl)-5,6,7,8-tetrahydropyrido[4,3-d]-pyrimidin-4-yl)-3-aza-bicyclo[3.2.1]octan-8-yl)-methanesulfonamide | 467 | 468 | 13 |
| 70 | 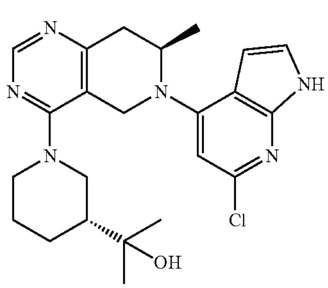 [SMILES: C[C@@H]1Cc2ncnc(N3CCC[C@@H](C(C)(C)O)C3)c2CN1c1cc(Cl)nc2[nH]ccc12] | 2-((R)-1-((R)-6-(6-chloro-1H-pyrrolo[2,3-b]-pyridin-4-yl)-7-methyl-5,6,7,8-tetrahydropyrido-[4,3-d]pyrimidin-4-yl)-piperidin-3-yl)propan-2-ol | 440 | 441 | 45 |

TABLE 2-continued

Examples 60-99.

| Ex | Structure | IUPAC Name | MWt | [M + H] | Ex. Method |
|---|---|---|---|---|---|
| 71 | 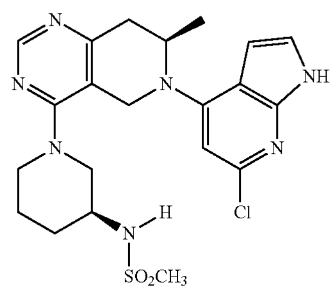 [SMILES: C[C@@H]1Cc2ncnc(N3CCC[C@H](NS(C)(=O)=O)C3)c2CN1c1cc(Cl)nc2[nH]ccc12] | N-((S)-1-((R)-6-(6-chloro-1H-pyrrolo[2,3-b]-pyridin-4-yl)-7-methyl-5,6,7,8-tetrahydropyrido-[4,3-d]pyrimidin-4-yl)-piperidin-3-yl)-methanesulfonamide | 475 | 476 | 13 |
| 72 | 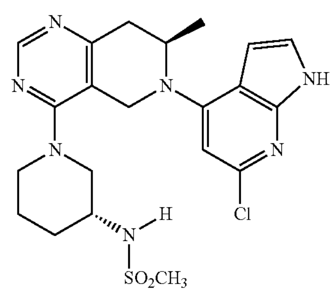 [SMILES: C[C@@H]1Cc2ncnc(N3CCC[C@@H](NS(C)(=O)=O)C3)c2CN1c1cc(Cl)nc2[nH]ccc12] | N-((R)-1-((R)-6-(6-chloro-1H-pyrrolo[2,3-b]-pyridin-4-yl)-7-methyl-5,6,7,8-tetrahydropyrido-[4,3-d]pyrimidin-4-yl)-piperidin-3-yl)-methanesulfonamide | 475 | 476 | 13 |
| 73 | 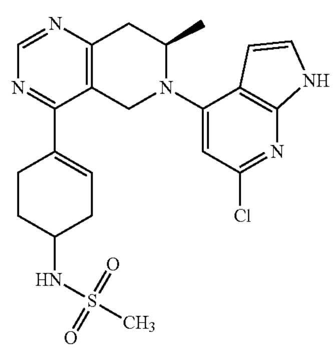 [SMILES: C[C@@H]1Cc2ncnc(C3=CCC(NS(C)(=O)=O)CC3)c2CN1c1cc(Cl)nc2[nH]ccc12] | N-(4-((R)-6-(6-chloro-1H-pyrrolo[2,3-b]pyridin-4-yl)-7-methyl-5,6,7,8-tetrahydropyrido[4,3-d]-pyrimidin-4-yl)cyclohex-3-en-1-yl)methane-sulfonamide | 472 | 473 | 11 |
| 74 | 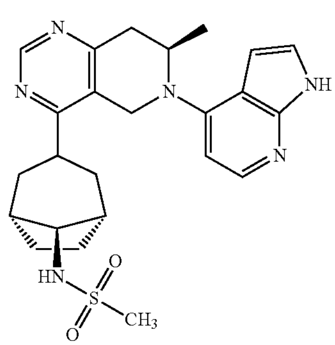 [SMILES: C[C@@H]1Cc2ncnc(C3C[C@H]4CC[C@@H](C3)[C@H]4NS(C)(=O)=O)c2CN1c1ccnc2[nH]ccc12] | N-((1R,5S,8R)-3-((R)-7-methyl-6-(1H-pyrrolo-[2,3-b]pyridin-4-yl)-5,6,7,8-tetrahydropyrido-[4,3-d]pyrimidin-4-yl)-3-azabicyclo[3.2.1]octan-8-yl)methanesulfonamide | 467 | 468 | 13 |

TABLE 2-continued

Examples 60-99.

| Ex | Structure | IUPAC Name | MWt | [M + H] | Ex. Method |
|---|---|---|---|---|---|
| 75 | 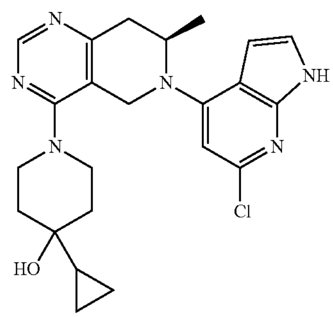 [SMILES: C[C@@H]1Cc2ncnc(N3CCC(O)(C4CC4)CC3)c2CN1c1cc(Cl)nc2[nH]ccc12] | (R)-1-(6-(6-chloro-1H-pyrrolo[2,3-b]pyridin-4-yl)-7-methyl-5,6,7,8-tetrahydropyrido[4,3-d]pyrimidin-4-yl)-4-cyclopropylpiperidin-4-ol | 438 | 439 | 46 |
| 76 | 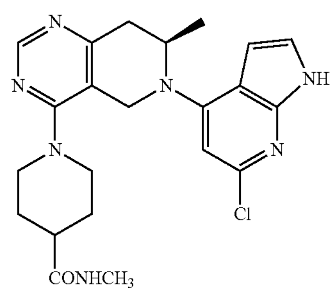 | (R)-1-(6-(6-chloro-1H-pyrrolo[2,3-b]pyridin-4-yl)-7-methyl-5,6,7,8-tetrahydropyrido[4,3-d]-pyrimidin-4-yl)-N-methylpiperidine-4-carboxamide | 439 | 440 | 44 |
| 77 | 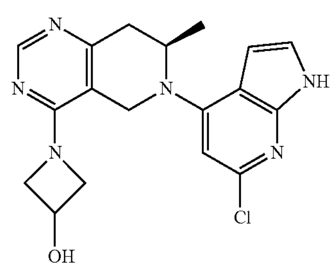 [SMILES: C[C@@H]1Cc2ncnc(N3CC(O)C3)c2CN1c1cc(Cl)nc2[nH]ccc12] | (R)-1-(6-(6-chloro-1H-pyrrolo[2,3-b]pyridin-4-yl)-7-methyl-5,6,7,8-tetrahydropyrido[4,3-d]-pyrimidin-4-yl)azetidin-3-ol | 370 | 371 | 12 |
| 78 | 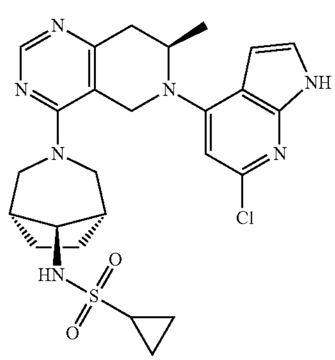 [SMILES: C[C@@H]1Cc2ncnc(N3C[C@H]4CC[C@@H](C3)[C@H]4NS(=O)(=O)C3CC3)c2CN1c1cc(Cl)nc2[nH]ccc12] | N-((1R,5S,8R)-3-((R)-6-(6-chloro-1H-pyrrolo[2,3-b]pyridin-4-yl)-7-methyl-5,6,7,8-tetrahydropyrido-[4,3-d]pyrimidin-4-yl)-3-azabicyclo[3.2.1]-octan-8-yl)cyclopropane-sulfonamide | 527 | 528 | 13 |
| 79 | 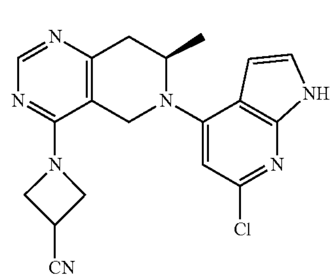 [SMILES: C[C@@H]1Cc2ncnc(N3CC(C#N)C3)c2CN1c1cc(Cl)nc2[nH]ccc12] | (R)-1-(6-(6-chloro-1H-pyrrolo[2,3-b]pyridin-4-yl)-7-methyl-5,6,7,8-tetrahydropyrido[4,3-d]-pyrimidin-4-yl)azetidine-3-carbonitrile | 379 | 380 | 12 |

TABLE 2-continued

Examples 60-99.

| Ex | Structure | IUPAC Name | MWt | [M + H] | Ex. Method |
|---|---|---|---|---|---|
| 80 | 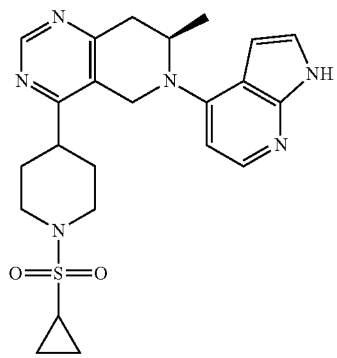 [SMILES: C[C@@H]1Cc2ncnc(C3CCN(S(=O)(=O)C4CC4)CC3)c2CN1c1ccnc2[nH]ccc12] | (R)-4-(1-(cyclopropyl-sulfonyl)piperidin-4-yl)-7-methyl-6-(1H-pyrrolo[2,3-b]pyridin-4-yl)-5,6,7,8-tetrahydro-pyrido[4,3-d]pyrimidine | 452 | 453 | 11 |
| 81 | 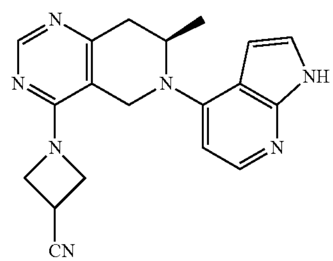 [SMILES: C[C@@H]1Cc2ncnc(N3CC(C#N)C3)c2CN1c1ccnc2[nH]ccc12] | (R)-1-(7-methyl-6-(1H-pyrrolo[2,3-b]pyridin-4-yl)-5,6,7,8-tetrahydro-pyrido[4,3-d]pyrimidin-4-yl)azetidine-3-carbonitrile | 345 | 346 | 12 |
| 82 | 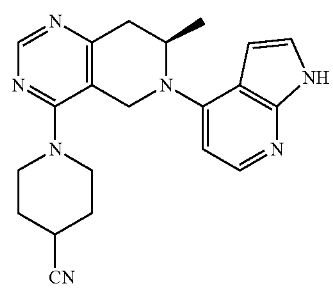 [SMILES: C[C@@H]1Cc2ncnc(N3CCC(C#N)CC3)c2CN1c1ccnc2[nH]ccc12] | (R)-1-(7-methyl-6-(1H-pyrrolo[2,3-b]pyridin-4-yl)-5,6,7,8-tetrahydro-pyrido[4,3-d]pyrimidin-4-yl)piperidine-4-carbonitrile | 373 | 374 | 12 |
| 83 | 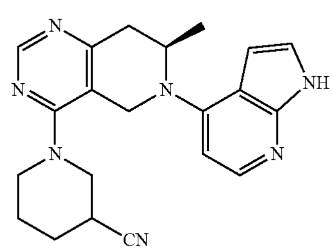 [SMILES: C[C@@H]1Cc2ncnc(N3CCCC(C#N)C3)c2CN1c1ccnc2[nH]ccc12] | 1-((R)-7-methyl-6-(1H-pyrrolo[2,3-b]pyridin-4-yl)-5,6,7,8-tetrahydro-pyrido[4,3-d]pyrimidin-4-yl)piperidine-3-carbonitrile | 373 | 374 | 12 |
| 84 | 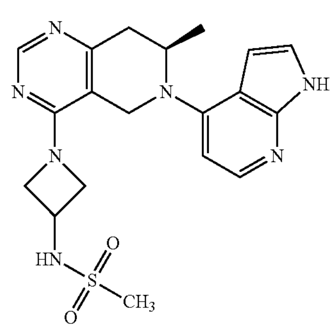 [SMILES: C[C@@H]1Cc2ncnc(N3CC(NS(C)(=O)=O)C3)c2CN1c1ccnc2[nH]ccc12] | (R)-N-(1-(7-methyl-6-(1H-pyrrolo[2,3-b]-pyridin-4-yl)-5,6,7,8-tetrahydropyrido[4,3-d]pyrimidin-4-yl)-azetidin-3-yl)-methanesulfonamide | 413 | 414 | 13 |

TABLE 2-continued

Examples 60-99.

| Ex | Structure | IUPAC Name | MWt | [M + H] | Ex. Method |
|---|---|---|---|---|---|
| 85 | 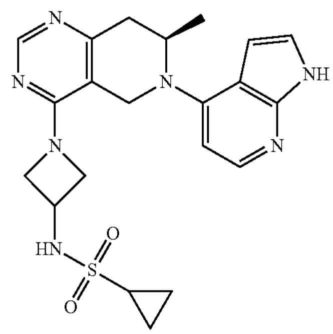 [SMILES: C[C@@H]1Cc2ncnc(N3CC(NS(=O)(=O)C4CC4)C3)c2CN1c1ccnc2[nH]ccc12] | (R)-N-(1-(7-methyl-6-(1H-pyrrolo[2,3-b]-pyridin-4-yl)-5,6,7,8-tetrahydropyrido[4,3-d]-pyrimidin-4-yl)azetidin-3-yl)cyclopropane-sulfonamide | 439 | 440 | 13 |
| 86 | 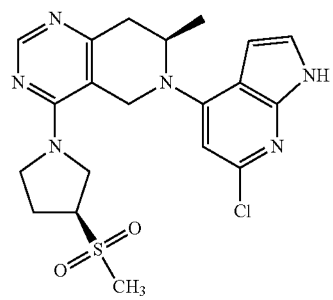 [SMILES: C[C@@H]1Cc2ncnc(N3CC[C@H](S(C)(=O)=O)C3)c2CN1c1cc(Cl)nc2[nH]ccc12] | (R)-6-(6-chloro-1H-pyrrolo[2,3-b]pyridin-4-yl)-7-methyl-4-((S)-3-(methylsulfonyl)-pyrrolidin-1-yl)-5,6,7,8-tetrahydropyrido[4,3-d]-pyrimidine | 446 | 447 | 12 |
| 87 | 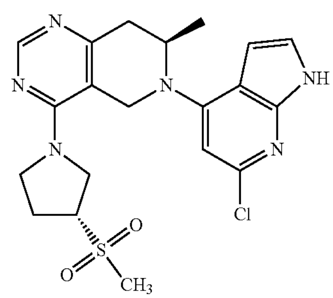 [SMILES: C[C@@H]1Cc2ncnc(N3CC[C@@H](S(C)(=O)=O)C3)c2CN1c1cc(Cl)nc2[nH]ccc12] | (R)-6-(6-chloro-1H-pyrrolo[2,3-b]pyridin-4-yl)-7-methyl-4-((R)-3-(methylsulfonyl)-pyrrolidin-1-yl)-5,6,7,8-tetrahydropyrido[4,3-d]-pyrimidine | 446 | 447 | 12 |
| 88 | 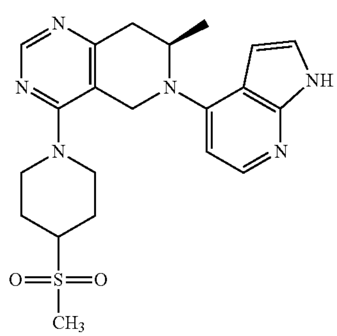 [SMILES: C[C@@H]1Cc2ncnc(N3CCC(S(C)(=O)=O)CC3)c2CN1c1ccnc2[nH]ccc12] | (R)-7-methyl-4-(4-(methylsulfonyl)-piperidin-1-yl)-6-(1H-pyrrolo[2,3-b]pyridin-4-yl)-5,6,7,8-tetrahydro-pyrido[4,3-d]pyrimidine | 425 | 426 | 11 |
| 89 | 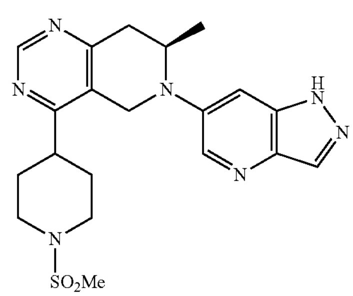 [SMILES: C[C@@H]1Cc2ncnc(C3CCN(S(C)(=O)=O)CC3)c2CN1c1cnc2cn[nH]c2c1] | (R)-7-methyl-4-(1-(methylsulfonyl)piperidin-4-yl)-6-(1H-pyrazolo-[4,3-b]pyridin-6-yl)-5,6,7,8-tetrahydro-pyrido[4,3-d]pyrimidine | 427.527 | 428 | 6 |

TABLE 2-continued

Examples 60-99.

| Ex | Structure | IUPAC Name | MWt | [M + H] | Ex. Method |
|---|---|---|---|---|---|
| 90 | This example intentionally left empty. | | | | |
| 91 | 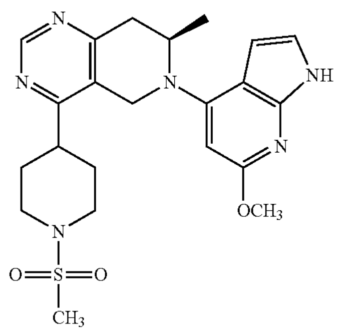 [SMILES: COc1cc(N2Cc3c(ncnc3C3CCN(S(C)(=O)=O)CC3)C[C@H]2C)c2cc[nH]c2n1] | (R)-6-(6-methoxy-1H-pyrrolo[2,3-b]pyridin-4-yl)-7-methyl-4-(1-(methylsulfonyl)-piperidin-4-yl)-5,6,7,8-tetrahydropyrido[4,3-d]-pyrimidine | 456.565 | 457 | 54 |
| 92 | 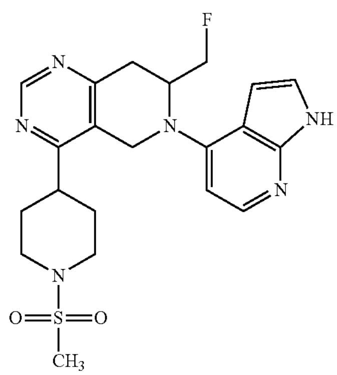 [SMILES: CS(=O)(=O)N1CCC(c2ncnc3c2CN(c2ccnc4[nH]ccc24)C(CF)C3)CC1] | 7-(fluoromethyl-4-(1-(methylsulfonyl)-piperidin-4-yl)-6-(1H-pyrrolo[2,3-b]pyridin-4-yl)-5,6,7,8-tetrahydro-pyrido[4,3-d]pyrimidine | 444.5294 | 445 | 52 |
| 93 | 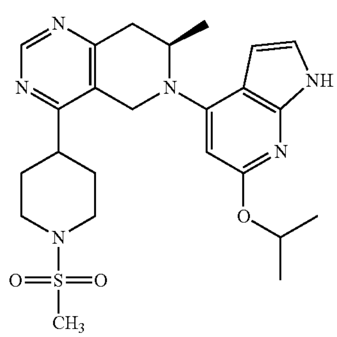 [SMILES: CC(C)Oc1cc(N2Cc3c(ncnc3C3CCN(S(C)(=O)=O)CC3)C[C@H]2C)c2cc[nH]c2n1] | (R)-6-(6-isopropoxy-1H-pyrrolo[2,3-b]pyridin-4-yl)-7-methyl-4-(1-(methylsulfonyl)piperidin-4-yl)-5,6,7,8-tetrahydro-pyrido[4,3-d]pyrimidine | 484.619 | 485 | 54 |
| 94 | 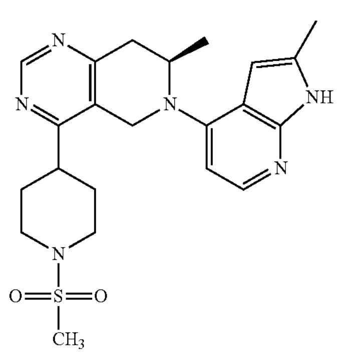 [SMILES: Cc1cc2c(N3Cc4c(ncnc4C4CCN(S(C)(=O)=O)CC4)C[C@H]3C)ccnc2[nH]1] | (R)-7-methyl-6-(2-methyl-1H-pyrrolo[2,3-b]pyridin-4-yl)-4-(1-(methylsulfonyl)piperidin-4-yl)-5,6,7,8-tetrahydro-pyrido[4,3-d]pyrimidine | 440.566 | 441 | 6 |

TABLE 2-continued

Examples 60-99.

| Ex | Structure | IUPAC Name | MWt | [M + H] | Ex. Method |
|---|---|---|---|---|---|
| 95 | 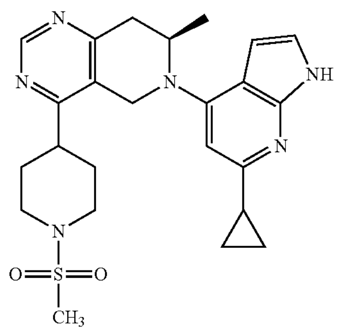 [SMILES: C[C@@H]1Cc2ncnc(C3CCN(S(C)(=O)=O)CC3)c2CN1c1cc(C2CC2)nc2[nH]ccc12] | (R)-6-(6-cyclopropyl-1H-pyrrolo[2,3-b]pyridin-4-yl)-7-methyl-4-(1-(methylsulfonyl)-piperidin-4-yl)-5,6,7,8-tetrahydropyrido[4,3-d]-pyrimidine | 466 | 467 | 56 |
| 96 | 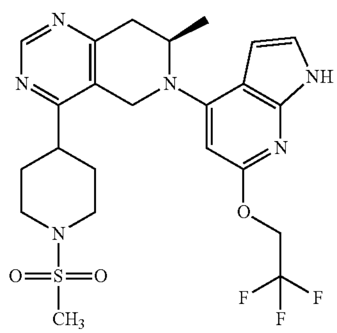 [SMILES: C[C@@H]1Cc2ncnc(C3CCN(S(C)(=O)=O)CC3)c2CN1c1cc(OCC(F)(F)F)nc2[nH]ccc12] | (R)-7-methyl-4-(1-(methylsulfonyl)piperidin-4-yl)-6-(6-(2,2,2-trifluoroethoxy)-1H-pyrrolo[2,3-b]pyridin-4-yl)-5,6,7,8-tetrahydro-pyrido[4,3-d]pyrimidine | 524.5632 | 525 | 54 |
| 97 | 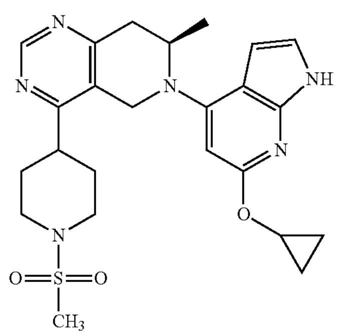 [SMILES: C[C@@H]1Cc2ncnc(C3CCN(S(C)(=O)=O)CC3)c2CN1c1cc(OC2CC2)nc2[nH]ccc12] | (R)-6-(6-cyclopropoxy-1H-pyrrolo[2,3-b]pyridin-4-yl)-7-methyl-4-(1-(methylsulfonyl)piperidin-4-yl)-5,6,7,8-tetrahydro-pyrido[4,3-d]pyrimidine | 482.603 | 483 | 54 |
| 98 | 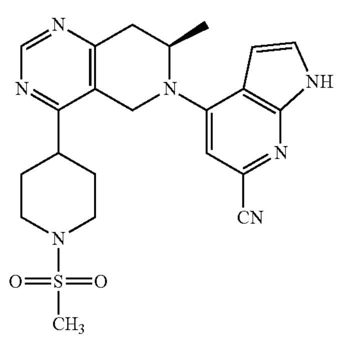 [SMILES: C[C@@H]1Cc2ncnc(C3CCN(S(C)(=O)=O)CC3)c2CN1c1cc(C#N)nc2[nH]ccc12] | (R)-4-(7-methyl-4-(1-(methylsulfonyl)piperidin-4-yl)-7,8-dihydro-pyrido[4,3-d]pyrimidin-6(5H)-yl)-1H-pyrrolo-[2,3-b]pyridine-6-carbonitrile | 451.549 | 452 | 59 |

TABLE 2-continued

Examples 60-99.

| Ex | Structure | IUPAC Name | MWt | [M + H] | Ex. Method |
|----|-----------|------------|-----|---------|------------|
| 99 | 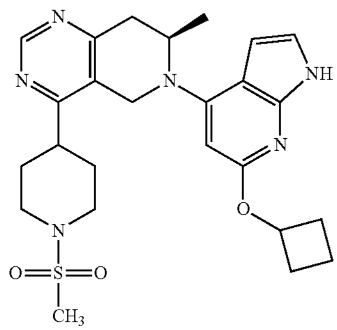 [SMILES: C[C@@H]1Cc2ncnc(C3CCN(S(C)(=O)=O)CC3)c2CN1c1cc(OC2CCC2)nc2[nH]ccc12] | (R)-6-(6-cyclobutoxy-1H-pyrrolo[2,3-b]pyridin-4-yl)-7-methyl-4-(1-(methylsulfonyl)piperidin-4-yl)-5,6,7,8-tetrahydro-pyrido[4,3-d]pyrimidine | 496.63 | 497 | 54 |

The activity of the compounds in Examples 1-99 as ATR kinase inhibitors is illustrated in the following assay). The other compounds listed below, which have not yet been made and/or tested, are predicted to have activity in this assay as well.

| Structure | IUPAC Name |
|-----------|------------|
| 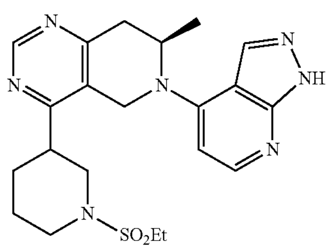 | 1-ethanesulfonyl-3-[(7R)-7-methyl-6-{1H-pyrazolo[3,4-b]pyridin-4-yl}-5H,6H,7H,8H-pyrido[4,3-d]pyrimidin-4-yl]piperidine |
| 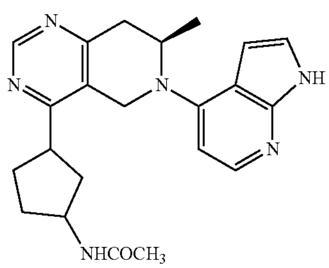 | N-{3-[(7R)-7-methyl-6-{1H-pyrrolo[2,3-b]-pyridin-4-yl}-5H,6H,7H,8H-pyrido[4,3-d]pyrimidin-4-yl]-cyclopentyl}acetamide |
| 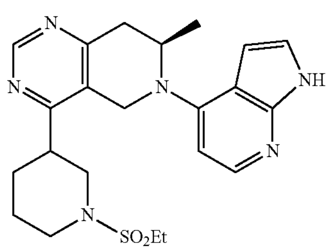 | 3-[(7R)-6-{1H-pyrrolo[2,3-b]pyridin-4-yl}-7-methyl-5H,6H,7H,8H-pyrido[4,3-d]pyrimidin-4-yl]-1-(ethanesulfonyl)-piperidine |
| | 5-[(7R)-6-{6-chloro-1H-pyrrolo[2,3-b]pyridin-4-yl}-7-methyl-5H,6H,7H,8H-pyrido[4,3-d]pyrimidin-4-yl]-2-(methanesulfonyl)-2-azabicyclo[2.2.2]octane |
| | 2-[(7R)-6-{1H-pyrrolo[2,3-b]pyridin-4-yl}-7-methyl-5H,6H,7H,8H-pyrido[4,3-d]pyrimidin-4-yl]-5-(methanesulfonyl)-2-azabicyclo[2.2.2]octane |
| | 4-[(7R)-6-{6-chloro-1H-pyrrolo[2,3-b]pyridin-4-yl}-7-methyl-5H,6H,7H,8H-pyrido[4,3-d]pyrimidin-4-yl]-1-(methanesulfonyl)-cyclohexane |

| Structure | IUPAC Name |
|---|---|
| | 3-[(7R)-6-{6-chloro-1H-pyrrolo[2,3-b]pyridin-4-yl}-7-methyl-5H,6H,7H,8H-pyrido[4,3-d]pyrimidin-4-yl]-6-(methanesulfonylamino)-3-azabicyclo[3.1.0]hexane |
| 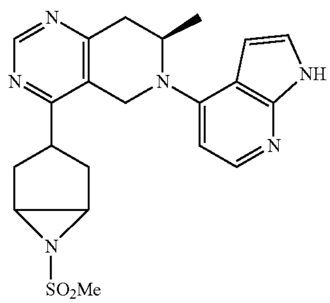 [SMILES: C[C@@H]1Cc2ncnc(C3CC4C(C3)N4S(C)(=O)=O)c2CN1c1ccnc2[nH]ccc12] | 3-[(7R)-6-{1H-pyrrolo[2,3-b]pyridin-4-yl}-7-methyl-5H,6H,7H,8H-pyrido[4,3-d]pyrimidin-4-yl]-6-(methanesulfonyl)-6-azabicyclo[3.1.0]hexane |
| | 6-[(7R)-6-{6-chloro-1H-pyrrolo[2,3-b]pyridin-4-yl}-7-methyl-5H,6H,7H,8H-pyrido[4,3-d]pyrimidin-4-yl]-3-(methanesulfonyl)-3-azabicyclo[3.1.0]hexane |
| | 6-[(7R)-6-{6-chloro-1H-pyrrolo[2,3-b]pyridin-4-yl}-7-methyl-5H,6H,7H,8H-pyrido[4,3-d]pyrimidin-4-yl]-3-(methanesulfonyl)-3-azabicyclo[3.1.0]hexane |
| 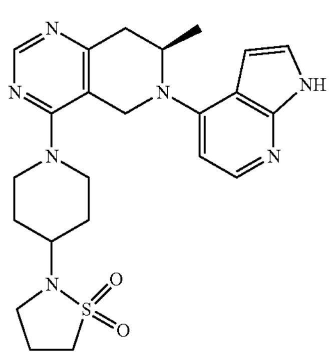 [SMILES: C[C@@H]1Cc2ncnc(N3CCC(N4CCCS4(=O)=O)CC3)c2CN1c1ccnc2[nH]ccc12] | (R)-2-(1-(7-methyl-6-(1H-pyrrolo[2,3-b]-pyridin-4-yl)-5,6,7,8-tetrahydropyrido[4,3-d]-pyrimidin-4-yl)piperidin-4-yl)isothiazolidine 1,1-dioxide |

| Structure | IUPAC Name |
|---|---|
| 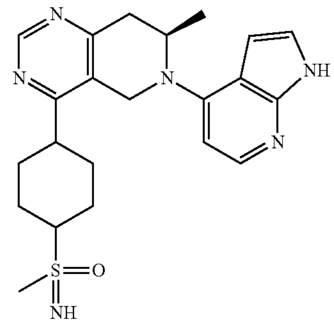 [SMILES: C[C@@H]1Cc2ncnc(C3CCC(S(C)(=N)=O)CC3)c2CN1c1ccnc2[nH]ccc12] | 4-[(7R)-6-{1H-pyrrolo[2,3-b]pyridin-4-yl}-7-methyl-5H,6H,7H,8H-pyrido[4,3-d]pyrimidin-4-yl]-1-(methanesulfonyl)-cyclohexyl methyl sulfoximine |
| 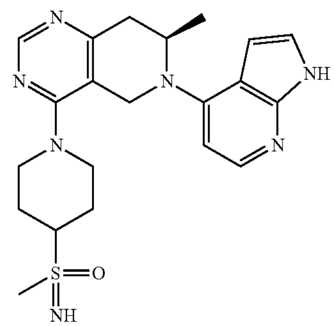 [SMILES: C[C@@H]1Cc2ncnc(N3CCC(S(C)(=N)=O)CC3)c2CN1c1ccnc2[nH]ccc12] | 1-[(7R)-6-{1H-pyrrolo[2,3-b]pyridin-4-yl}-7-methyl-5H,6H,7H,8H-pyrido[4,3-d]pyrimidin-4-yl]-1-(methanesulfonyl)-piperidin-4-yl methyl sulfoximine |
| 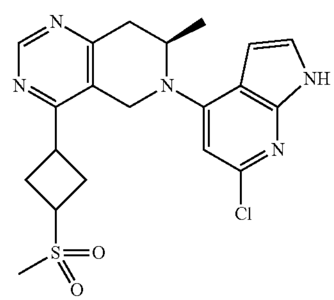 [SMILES: C[C@@H]1Cc2ncnc(C3CC(S(C)(=O)=O)C3)c2CN1c1cc(Cl)nc2[nH]ccc12] | 1-[(7R)-6-{6-chloro-1H-pyrrolo[2,3-b]pyridin-4-yl}-7-methyl-5H,6H,7H,8H-pyrido[4,3-d]pyrimidin-4-yl]-3-(methanesulfonyl)-cyclobutane |
| 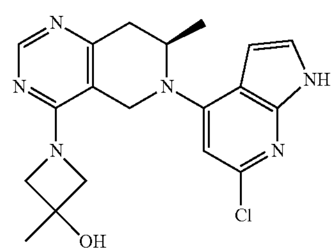 [SMILES: C[C@@H]1Cc2ncnc(N3CC(C)(O)C3)c2CN1c1cc(Cl)nc2[nH]ccc12] | 1-[(7R)-6-{6-chloro-1H-pyrrolo[2,3-b]pyridin-4-yl}-7-methyl-5H,6H,7H,8H-pyrido[4,3-d]pyrimidin-4-yl]-3-hydroxy-3-methylazetidine |
| 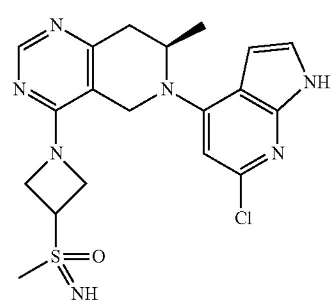 [SMILES: C[C@@H]1Cc2ncnc(N3CC(S(C)(=N)=O)C3)c2CN1c1cc(Cl)nc2[nH]ccc12] | 1-[(7R)-6-{6-chloro-1H-pyrrolo[2,3-b]pyridin-4-yl}-7-methyl-5H,6H,7H,8H-pyrido[4,3-d]pyrimidin-4-yl]-1-hydroxy-3-methylazetidin-3-yl methyl sulfoximine |

| Structure | IUPAC Name |
|---|---|
| (structure) | 1-[(7R)-6-{6-chloro-1H-pyrrolo[2,3-b]pyridin-4-yl}-7-methyl-5H,6H,7H,8H-pyrido[4,3-d]pyrimidin-4-yl]-3-fluoro-3-(methanesulfonyl)azetidine |
| (structure) | 4-[(7R)-6-{6-trifluoromethyl-1H-pyrrolo[2,3-b]pyridin-4-yl}-7-methyl-5H,6H,7H,8H-pyrido[4,3-d]pyrimidin-4-yl]-1-(methanesulfonyl)piperidine | pCHK1 Cellular Assay

Inhibitors of ATR kinase are effective at inhibiting the ATR-driven phosphorylation of the downstream target Chk1 kinase at Serine 345, following the addition of 4-nitroquinoline N-oxide, a chemical used to induce DNA damage. Cellular $IC_{50}$ for the inhibitors of ATR described herein were measured in HT-29 colorectal adenocarcinoma cells. HT-29 cells were routinely maintained in McCoy's 5A media (ATCC Catalog #30-2007) supplemented with 10% fetal bovine serum (Sigma Catalog #F2442) and 1× Penicillin-Streptomycin (Gibco Catalog #15140-122) using a humidified incubator (37° C., 5% $CO_2$, and ambient $O_2$).

In preparation for the CHK1 (p-Ser345) ALPHASCREEN® SUREFIRE® assay, cells were harvested and resuspended in McCoy's 5A media supplemented with 10% fetal bovine serum and 1× Penicillin-Streptomycin. Cells were seeded onto a 384-well black CELLSTAR® Tissue Culture Plate (VWR Catalog #89085-314) at a density of 13,000 cells/well in a volume of 40 uL. The microplate was incubated overnight (approximately 20 hours) at 37° C. with 5% $CO_2$ and ambient $O_2$. Stock solutions of the test compounds were prepared in 100% DMSO (Sigma, Catalog #D2650) and serially diluted 1:3 using 100% DMSO. Compounds were additionally diluted 1:33 in culture medium, and 10 ul/well were transferred to the tissue culture plate. Following the compound addition the microplate was incubated at 37° C. for 90 minutes. 10 uL of 4-nitroquinoline N-oxide (Sigma Aldrich Catalog #N8141-1G) diluted in media (final concentration 12 uM) were added to the tissue culture plate followed by a 120 minute incubation at 37° C. The cells were then washed with PBS and lysed using 10 uL/well SUREFIRE® Kit lysis buffer diluted to 1× in water (PerkinElmer Catalog #TGRCHK1S50K), with mixing on an orbital shaker at 500 rpm for 20 min at RT. Lysates were frozen at −20° C. overnight.

4 uL/well of lysate was then transferred from the tissue culture plate to a 384-well, white, low volume, PROXIPLATE™ (PerkinElmer Catalog #600828). 5 uL/well of the acceptor bead solution, prepared by diluting SUREFIRE® Kit activation buffer (PerkinElmer Catalog #TGRCHK1S50K) and ALPHASCREEN® Protein A acceptor beads (PerkinElmer Catalog #6760617R) in SUREFIRE® Kit reaction buffer (PerkinElmer Catalog #TGRCHK1S50K), were added to the lysates under subdued light and incubated at room temperature for 120 min. 2 uL/well of the donor bead solution, prepared by diluting ALPHASCREEN® Streptavidin donor beads (PerkinElmer Catalog #6760617R) in SUREFIRE® Kit dilution buffer (PerkinElmer Catalog #TGRCHK1S50K), were added under subdued light and incubated at room temperature for an addition 120 minutes. The pCHK1 ALPHASCREEN® signal was measured using an ENVISION® plate reader (PerkinElmer). $IC_{50}$ values were calculated using a four-parameter logistic curve fit using Genedata Screener software. Percent of control for each compound concentration was calculated by the following formula: 100*(Compound−Min)/(Max−Min) where "Max" is the high control, DMSO, and "Min" is the low control, 5 uM ATR inhibitor.

TABLE 3 pCHK1 $IC_{50}$ values

| Example | Cell $IC_{50}$ (nM) |
|---|---|
| 1 | 1879 |
| 2 | 1935 |
| 3 | 183 |
| 4 | 157 |
| 6 | 52 |
| 7 | 32 |
| 8 | 127 |
| 9 | 25 |
| 10 | 39 |
| 11a | 28 |
| 11b | 29 |
| 12 | 28 |
| 13 | 29 |
| 14 | 1606 |
| 15 | 152 |
| 16 | 140 |
| 17 | 362 |
| 18 | 133 |
| 19 | 162 |
| 20 | 97 |
| 21 | 57 |
| 22 | 554 |
| 23 | 611 |
| 24 | 285 |
| 25 | 28 |
| 26 | 88 |
| 27 | 38 |
| 28 | 46 |
| 29 | 13 |
| 30 | 12 |
| 31 | 72 |
| 32 | 21 |
| 33 | 15 |
| 34 | 87 |
| 35 | 34 |
| 36 | 128 |
| 37 | 56 |
| 38 | 83 |
| 39 | 27 |
| 40 | 24 |
| 41 | 36 |
| 42 | 3014 |
| 43 | 611 |
| 44 | 92 |
| 45 | 39 |
| 46 | 21 |
| 47 | 30 |
| 48a | 758 |

TABLE 3-continued pCHK1 IC$_{50}$ values

| Example | Cell IC$_{50}$ (nM) |
|---|---|
| 48b | 79 |
| 49 | 654 |
| 50a | 55 |
| 50b | 579 |
| 51a | 11 |
| 51b | 48 |
| 52a | 10000 |
| 52b | 209 |
| 53a | 10000 |
| 53b | 485 |
| 54 | 10 |
| 55a | 2359 |
| 55b | 30 |
| 56 | 52 |
| 57a | 183 |
| 57b | 394 |
| 58 | 218 |
| 59 | 555 |
| 60 | 22 |
| 61 | 570 |
| 62 | 138 |
| 63 | 57 |
| 64 | 16 |
| 65 | 8 |
| 66 | 25 |
| 67 | 9 |
| 68 | 48 |
| 69 | 48 |
| 70 | 10 |
| 71 | 7 |
| 72 | 119 |
| 73 | 18 |
| 74 | 31 |
| 75 | 34 |
| 76 | 61 |
| 77 | 21 |
| 78 | 50 |
| 79 | 14 |
| 80 | 132 |
| 81 | 38 |
| 82 | 79 |
| 83 | 56 |
| 84 | 79 |
| 85 | 83 |
| 86 | 51 |
| 87 | 20 |
| 88 | 85 |
| 89 | 7390 |
| 91 | 18 |
| 92 | 586 |
| 93 | 15 |
| 94 | 98 |
| 95 | 54 |
| 96 | 22 |
| 97 | 13 |
| 98 | 265 |
| 99 | 9 |

ATR/ATRIP Enzymatic Assay

Human full-length FLAG-TEV-ATR and His$_6$-ATRIP were co-expressed in HEK293 cells. The cell pellet (20 g) was harvested and lysed in 100 mL of lysis buffer (20 mM Tris-HCl pH 7.5 at room temperature, 137 mM NaCl, 10% glycerol, 1 mM DTT, 1% (v/v) Tween-20, 0.1% (v/v) NP-40, complete protease inhibitor cocktail tablets, phosphatase inhibitor cocktail tablets, 2 mM MgCl$_2$, 0.2 mM EDTA, and 1 mM ATP). After sonication and centrifugation, the supernatant was incubated at 4° C. for 3 hours with 1 mL of anti-FLAG resin (Sigma catalog #A2220) that had been pre-equilibrated in buffer A (20 mM Tris-HCl pH 7.5 at room temperature, 137 mM NaCl, 10% glycerol, 1 mM DTT, 2 mM MgCl$_2$, and 0.2 mM EDTA). The sample was loaded into a column, and then washed with buffer A three times. Protein was subsequently eluted with 2 ml of buffer B (buffer A+200 µg/ml 3×FLAG peptide).

The ability of new chemical matter to inhibit the ATR catalytic activity in this ATR/ATRIP complex was assessed using a Caliper-based assay. A 2x enzyme solution (i.e., 4 nM enzyme) was prepared using 1× Kinase Reaction Buffer (25 mM HEPES pH 8, 0.0055% Brij-35, 10 mM MnCl$_2$, and 1 mM DTT). A 2x peptide solution was then prepared consisting of 10 uM FAM-labeled RAD17 peptide (GL Biochem, catalog #524315) in 1× Kinase Reaction Buffer supplemented with 2 µM ATP. 10 µL of the 2× enzyme solution was transferred to an assay plate containing 60 nL of test compound (from a 3× serial dilution) in 100% DMSO. Following a 30 minute incubation at 28° C., 10 µL of the 2× peptide solution was then transferred to the same assay plate. The reaction was allowed to incubate at 28° C. for 6 hours. After adding iL of stop buffer (100 mM HEPES pH 7.5, 0.015% Brij-35, 0.2% Coating-3 Reagent (PerkinElmer, catalog #PN760050), and 50 mM EDTA), data were collected on a Caliper instrument. Conversion values were converted to inhibition values via the following equation: % inhibition=(max−conversion)/(max−min)*100, whereby "max" corresponds to the DMSO control and "min" corresponds to the low control. IC$_{50}$ values were calculated using the following equation in XLFit: Y=Bottom+(Top−Bottom)/1+(IC$_{50}$/X)^HillSlope).

The person of ordinary skill in the art will appreciate that the data disclosed below will suggest that the example compounds are interacting with the target protein, and will further appreciate that factors such as assay quality and protein quality and purity may affect the outcome of given assays.

TABLE 4

ATR/ATRIP Enzyme IC50 values

| Example | ATR/ATRIP Enzyme IC50 (nM) |
|---|---|
| 1 | (a) |
| 2 | (a) |
| 3 | 1966 |
| 4 | 833 |
| 6 | 499 |
| 7 | 163 |
| 8 | 979 |
| 9 | 442 |
| 10 | 408 |
| 11a | 555 |
| 11b | 329 |
| 12 | 518 |
| 13 | 114 |
| 14 | (a) |
| 15 | (a) |
| 16 | 3571 |
| 17 | 936 |
| 18 | 420 |
| 19 | (a) |
| 20 | (a) |
| 21 | (a) |
| 22 | (a) |
| 23 | (a) |
| 24 | (a) |
| 25 | 899 |
| 26 | (a) |
| 27 | (a) |
| 28 | (a) |
| 29 | 120 |
| 30 | 329 |
| 31 | 434 |
| 32 | 223 |

TABLE 4-continued

ATR/ATRIP Enzyme IC50 values

| Example | ATR/ATRIP Enzyme IC50 (nM) |
|---|---|
| 33 | 183 |
| 34 | 429 |
| 35 | N/A |
| 36 | N/A |
| 37 | (a) |
| 38 | 929 |
| 39 | N/A |
| 40 | 899 |
| 41 | 472 |
| 42 | (a) |
| 43 | (a) |
| 44 | 1039 |
| 45 | 378 |
| 46 | 282 |
| 47 | 287 |
| 48a | 3331 |
| 48b | 435 |
| 49 | 3597 |
| 50a | 1203 |
| 50b | 4793 |
| 51a | 561 |
| 51b | 2205 |
| 52a | 30000 |
| 52b | 878 |
| 53a | no fit |
| 53b | 2416 |
| 54 | 123 |
| 55a | 24956 |
| 55b | 311 |
| 56 | 773 |
| 57a | 840 |
| 57b | 1470 |
| 58 | 966 |
| 59 | 2647 |
| 60 | 66 |
| 61 | 514 |
| 62 | 253 |
| 63 | 86 |
| 64 | 472 |
| 65 | 159 |
| 66 | 584 |
| 67 | 140 |
| 68 | 475 |
| 69 | 283 |
| 70 | 87 |
| 71 | 73 |
| 72 | 715 |
| 73 | 111 |
| 74 | 279 |
| 75 | 246 |
| 76 | 708 |
| 77 | 320 |
| 78 | 184 |
| 79 | 103 |
| 80 | 1091 |
| 81 | 246 |
| 82 | 796 |
| 83 | 364 |
| 84 | 722 |
| 85 | 113 |
| 86 | 329 |
| 87 | 237 |
| 88 | 615 |
| 89 | 138 |
| 90 | 269 |
| 91 | 269 |
| 92 | 1288 |
| 93 | 87 |
| 94 | 51 |
| 95 | 270 |
| 96 | 321 |
| 97 | 93 |
| 98 | 336 |
| 99 | 75 |

(a): IC$_{50}$ estimated at between 1000 nM and 10,000 nM.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula (I):

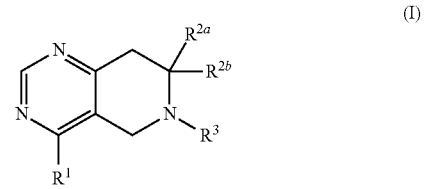

or a salt thereof, wherein:

$R^1$ is selected from aryl, heteroaryl, $C_{3-10}$cycloalkyl, $C_{6-11}$bridged cycloalkyl, $C_{6-11}$spirocycloalkyl, $C_{3-10}$heterocycloalkyl, $C_{6-11}$bridged heterocycloalkyl, and $C_{6-11}$spiroheterocycloalkyl, and is optionally substituted with one or more $R^4$ groups;

$R^{2a}$ is selected from H, $C_{1-3}$alkyl, and $C_{1-3}$haloalkyl;

$R^{2b}$ is selected from H, $C_{1-3}$alkyl, and $C_{1-3}$haloalkyl;

$R^3$ is $C_{5-10}$aryl or $C_{5-10}$heteroaryl, and is optionally substituted with one or more $R^5$ groups;

each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, =N—$R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;

each $R^5$ is independently selected from amino, halo, cyano, hydroxy, oxo, alkyl, haloalkyl, $C_{3-10}$cycloalkyl, $C_{3-10}$heterocycloalkyl, alkoxy, haloalkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$;

each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, $R^7$ and $R^8$, together with the atom to which they are both attached, can optionally form a 3-7 membered saturated or unsaturated ring optionally containing 1 or 2 heteroatoms, and $R^1$, together with $R^6$, $R^7$, or $R^8$, can optionally form a ring;

each $R^9$, $R^{10}$, and $R^{11}$ is independently selected from hydrogen, alkyl, haloalkyl, $C_{3-7}$cycloalkyl, and $C_{3-7}$heterocycloalkyl, $R^{10}$ and $R^{11}$, together with the atom to which they are both attached, can optionally form a 3-7 membered saturated or unsaturated ring optionally containing 1 or 2 heteroatoms, and $R^3$, together with $R^9$, $R^{10}$, or $R^{11}$, can optionally form a ring; and each $R^{12}$ is independently selected from halo, hydroxy, $C_{1-3}$alkyl, $C_{1-3}$haloalkyl, and alkoxy.

2. The compound as recited in claim 1, wherein:

each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups; and each $R^9$, $R^{10}$, and $R^{11}$ is independently selected from hydrogen, alkyl, haloalkyl, $C_{3-7}$cycloalkyl, and $C_{3-7}$heterocycloalkyl.

3. The compound as recited in claim 2, wherein $R^3$ is selected from thienyl, pyrrolyl, imidazolyl, pyrazolyl, oxazolyl, isoxazolyl, thiazolyl, isothiazolyl, quinolinyl, isoquinolinyl, indolyl, pyridinyl, pyrimidinyl, pyridazinyl, pyrazinyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

4. The compound as recited in claim 3, wherein $R^1$ is $C_{3-10}$heterocycloalkyl, and is optionally substituted with one, two, or three $R^4$ groups.

5. The compound as recited in claim 4, wherein $R^1$ is selected from azetidinyl, pyrrolidinyl, piperidinyl, piperazinyl, azepanyl, and diazepanyl, and is optionally substituted with one, two, or three $R^4$ groups.

6. The compound as recited in claim 2, wherein $R^1$ is selected from phenyl, pyridinyl, pyrazinyl, piperidinyl, and pyridazinyl, and is optionally substituted with one, two, or three $R^4$ groups.

7. The compound as recited in claim 1, wherein the compound has structural formula (III):

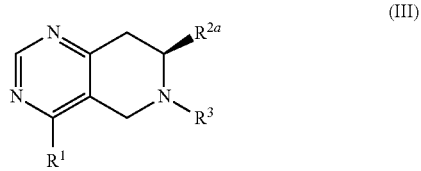

(III)

or a salt thereof, wherein:
$R^1$ is selected from aryl, heteroaryl, $C_{3-10}$cycloalkyl, $C_{6-11}$bridged cycloalkyl, $C_{6-11}$spirocycloalkyl, $C_{3-10}$heterocycloalkyl, $C_{6-11}$bridged heterocycloalkyl, and $C_{6-11}$spiroheterocycloalkyl, and is optionally substituted with one or more $R^4$ groups;
$R^{2a}$ is $C_{1-3}$alkyl;
$R^3$ is $C_{5-10}$aryl or $C_{5-10}$heteroaryl, and is optionally substituted with one or more $R^5$ groups;
each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, =N—$R^7$, $NR^6C(O)OR^7$, $OC(O)NR^7R^8$, $OC(O)R^7$, $S(O)R^7$, $S(O)_2R^7$, $S(O)_2OR^7$, $S(O)NR^7R^8$, $S(O)_2NR^7R^8$, $S(O)(NR^7)R^8$, $NR^6S(O)R^7$, $NR^6S(O)_2R^7$, $C(O)OR^7$, $C(O)R^7$, $C(O)NR^7R^8$, and $OR^7$;
each $R^5$ is independently selected from amino, halo, cyano, hydroxy, oxo, alkyl, haloakyl, $C_{3-10}$cycloalkyl, $C_{3-10}$heterocycloalkyl, alkoxy, haloalkoxy, $NR^9C(O)NR^{10}R^{11}$, $NR^9C(O)R^{10}$, $C(O)NR^{10}R^{11}$, $NR^9C(O)OR^{10}$, $OC(O)NR^{10}R^{11}$, $S(O)R^{10}$, $S(O)_2R^{10}$, $S(O)_2OR^{10}$, $S(O)NR^{10}R^{11}$, $S(O)_2NR^{10}R^{11}$, $S(O)(NR^{10})R^{11}$, and $C(O)OR^{10}$;
each $R^6$, $R^7$, and $R^8$ is independently selected from hydrogen, alkyl, haloalkyl, $C_{3-7}$cycloalkyl, and $C_{3-7}$heterocycloalkyl, any of which, excluding hydrogen, is optionally substituted with one or more $R^{12}$ groups, $R^7$ and $R^8$, together with the atom to which they are both attached, can optionally form a 3-7 membered saturated or unsaturated ring optionally containing 1 or 2 heteroatoms, and $R^1$, together with $R^6$, $R^7$, or $R^8$, can optionally form a ring;

each $R^9$, $R^{10}$, and $R^{11}$ is independently selected from hydrogen, alkyl, haloalkyl, $C_{3-7}$cycloalkyl, and $C_{3-7}$heterocycloalkyl, $R^{10}$ and $R^{11}$, together with the atom to which they are both attached, can optionally form a 3-7 membered saturated or unsaturated ring optionally containing 1 or 2 heteroatoms, and $R^3$, together with $R^9$, $R^{10}$, or $R^{11}$, can optionally form a ring; and each $R^{12}$ is independently selected from halo, hydroxy, $C_{1-3}$alkyl, $C_{1-3}$haloalkyl, and alkoxy.

8. The compound as recited in claim 7 wherein $R^3$ is selected from quinolinyl, isoquinolinyl, indolyl, benzimidazolyl, pyridinoimidazolyl, purinyl, pyrrolopyridinyl, pyrazolopyridinyl, pyrazolopyrimidinyl and pyrrolopyrimidinyl, and is optionally substituted with one or two $R^5$ groups.

9. The compound as recited in claim 8, wherein $R^3$ is selected from purinyl, pyrrolopyridinyl, pyrazolopyridinyl, pyrazolopyrimidinyl and pyrrolopyrimidinyl, and is optionally substituted with one or two $R^5$ groups.

10. The compound as recited in claim 7, wherein $R^3$ is selected from 1H-pyrrolo[2,3-b]pyridin-4-yl and 6-chloro-1H-pyrrolo[2,3-b]pyridin-4-yl.

11. The compound as recited in claim 7, wherein each $R^5$ is independently selected from amino, halo, cyano, hydroxy, oxo, and alkyl.

12. The compound as recited in claim 7, wherein $R^1$ is $C_{3-10}$heterocycloalkyl, and is optionally substituted with one, two, or three $R^4$ groups.

13. The compound as recited in claim 12, wherein $R^1$ is selected from azetidinyl, pyrrolidinyl, piperidinyl, piperazinyl, azepanyl, and diazepanyl, and is optionally substituted with one, two, or three $R^4$ groups.

14. The compound as recited in claim 7, wherein each $R^4$ is independently selected from alkyl, hydroxy, oxo, $S(O)R^6$, $S(O)_2R^6$, $C(O)NH_2$, =N—$R^7$, $C(O)NHR^7$, $C(O)NR^7R^8$, and $C(O)OR^7$.

15. The compound as recited in claim 1, wherein the compound has structural formula (IV):

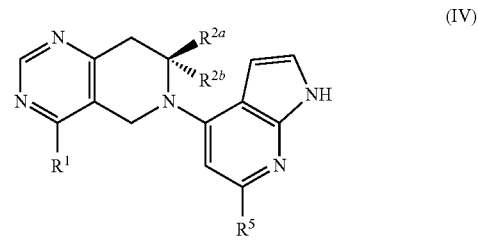

(IV)

or a salt thereof, wherein:
$R^1$ is selected from aryl, heteroaryl, $C_{3-10}$cycloalkyl, $C_{6-11}$spirocycloalkyl, $C_{6-11}$bridged cycloalkyl, $C_{3-10}$heterocycloalkyl, $C_{6-11}$bridged heterocycloalkyl, and $C_{6-11}$spiroheterocycloalkyl, and is optionally substituted with one or more $R^4$ groups;
$R^{2a}$ is selected from H, $C_{1-3}$alkyl, and $C_{1-3}$haloalkyl;
$R^{2b}$ is selected from H, $C_{1-3}$alkyl, and $C_{1-3}$haloalkyl;
each $R^4$ is independently selected from amino, halo, cyano, hydroxy, oxo, alkyl, haloakyl, $C_{3-10}$cycloalkyl, $C_{3-10}$heterocycloalkyl, hydroxyalkyl, $NR^6C(O)NR^7R^8$, $NR^6C(O)R^7$, =N—$R^7$, $NR^6C(O)OR^7$, $OC(O)NR^7R^8$, OC(O)R⁷, S(O)R⁷, S(O)₂R⁷, S(O)₂OR⁷, S(O)NR⁷R⁸, S(O)₂NR⁷R⁸, S(O)(NR⁷)R⁸, NR⁶S(O)R⁷, NR⁶S(O)₂R⁷, C(O)OR⁷, C(O)R⁷, C(O)NR⁷R⁸, and OR⁷;

R⁵ is selected from amino, halo, cyano, hydroxy, oxo, alkyl, haloalkyl, C₃₋₁₀cycloalkyl, C₃₋₁₀heterocycloalkyl, alkoxy, NR⁹C(O)NR¹⁰R¹¹ NR⁹C(O)R¹⁰, C(O)NR¹⁰R¹¹, NR⁹C(O)OR¹⁰, OC(O)NR¹⁰R¹¹, S(O)R¹⁰, S(O)₂R¹⁰, S(O)₂OR¹⁰, S(O)NR¹⁰R¹¹, S(O)₂NR¹⁰R¹¹, S(O)(NR¹⁰)R¹¹, and C(O)OR¹⁰;

each R⁶, R⁷, and R⁸ is independently selected from hydrogen, alkyl, haloalkyl, C₃₋₇cycloalkyl, and C₃₋₇heterocycloalkyl, any of which, excluding hydrogen, is optionally substituted with one or more R¹² groups, R⁷ and R⁸, together with the atom to which they are both attached, can optionally form a 3-7 membered saturated or unsaturated ring optionally containing 1 or 2 heteroatoms, and R¹, together with R⁶, R⁷, or R⁸, can optionally form a ring;

each R⁹, R¹⁰, and R¹¹ is independently selected from hydrogen, alkyl, haloalkyl, C₃₋₇cycloalkyl, and C₃₋₇heterocycloalkyl, R¹⁰ and R¹¹, together with the atom to which they are both attached, can optionally form a 3-7 membered saturated or unsaturated ring optionally containing 1 or 2 heteroatoms, and R³, together with R⁹, R¹⁰, or R¹¹, can optionally form a ring; and each R¹² is independently selected from halo, hydroxy, C₁₋₃alkyl, C₁₋₃haloalkyl, and alkoxy.

16. The compound as recited in claim 15, wherein R²ᵇ is H.

17. The compound as recited in claim 16, wherein:
each R⁶, R⁷, and R⁸ is independently selected from hydrogen, alkyl, haloalkyl, C₃₋₇cycloalkyl, and C₃₋₇heterocycloalkyl, any of which, excluding hydrogen, is optionally substituted with one or more R¹² groups; and
each R⁹, R¹⁰, and R¹¹ is independently selected from hydrogen, alkyl, haloalkyl, C₃₋₇cycloalkyl, and C₃₋₇heterocycloalkyl.

18. The compound as recited in claim 17, wherein R¹ is selected from aryl, heteroaryl, C₃₋₁₀cycloalkyl, C₆₋₁₁spirocycloalkyl, C₆₋₁₁bridged cycloalkyl, C₃₋₁₀heterocycloalkyl, C₆₋₁₁bridged heterocycloalkyl, and C6-11spiroheterocycloalkyl, and is optionally substituted with one, two, or three R⁴ groups.

19. The compound as recited in claim 18, wherein R¹ is selected from phenyl, azetidinyl, pyridinyl, pyrazinyl, piperidinyl, and pyridazinyl, and is optionally substituted with one, two, or three R⁴ groups.

20. The compound as recited in claim 18, wherein R¹ is selected from C₃₋₁₀heterocycloalkyl, C₆₋₁₁bridged heterocycloalkyl, and C₆₋₁₁spiroheterocycloalkyl, and is optionally substituted with one, two, or three R⁴ groups.

21. The compound as recited in claim 20, wherein R¹ is selected from azetidinyl, pyrrolidinyl, piperidinyl, piperazinyl, azepanyl, and diazepanyl, and is optionally substituted with one, two, or three R⁴ groups.

22. The compound as recited in claim 21, wherein R¹ is azetidinyl.

23. The compound as recited in claim 21, wherein R¹ is piperidinyl.

24. The compound as recited in claim 21, wherein each R⁴ is independently selected from hydroxy, =N—R⁷, S(O)₂R⁷, C(O)NR⁷R⁸, and NHS(O)₂R⁷.

25. The compound as recited in claim 1, wherein the structure is selected from

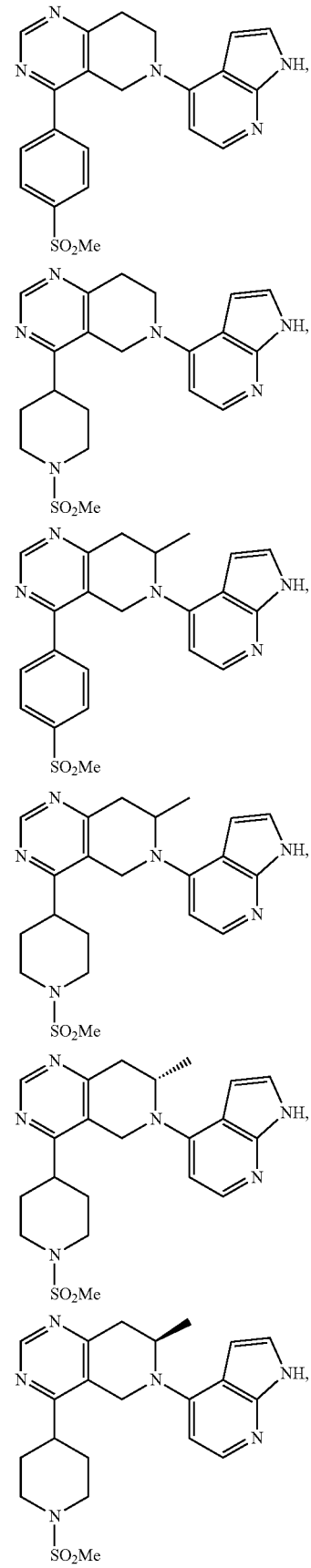

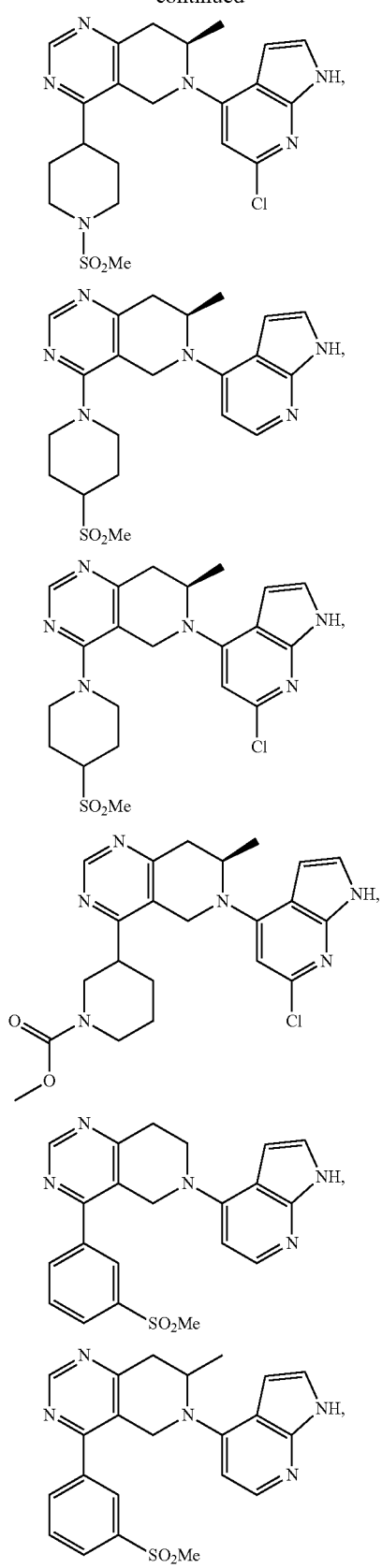
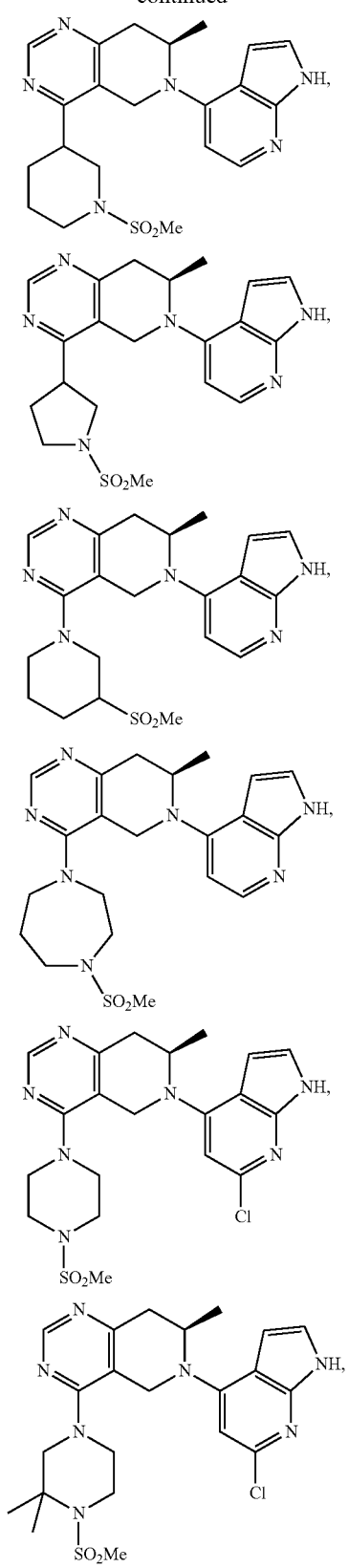

197
-continued
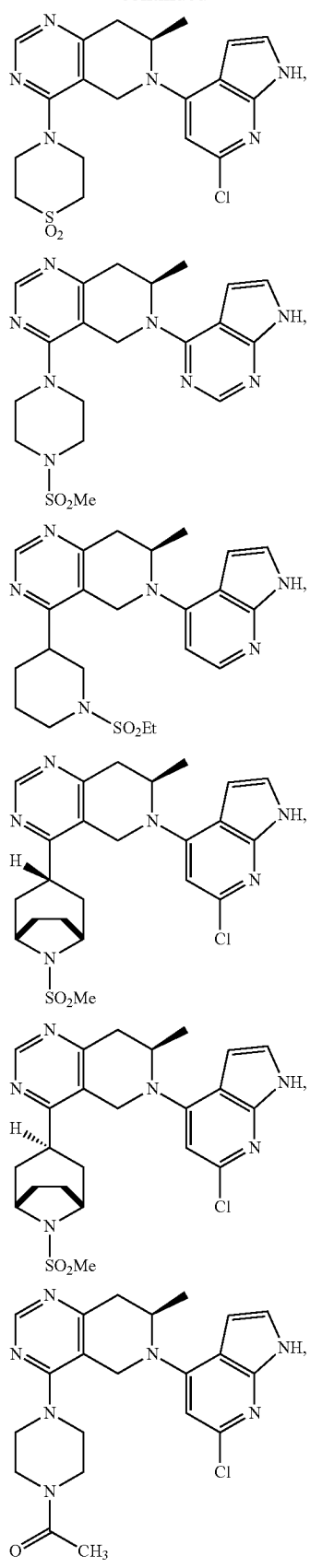
198
-continued
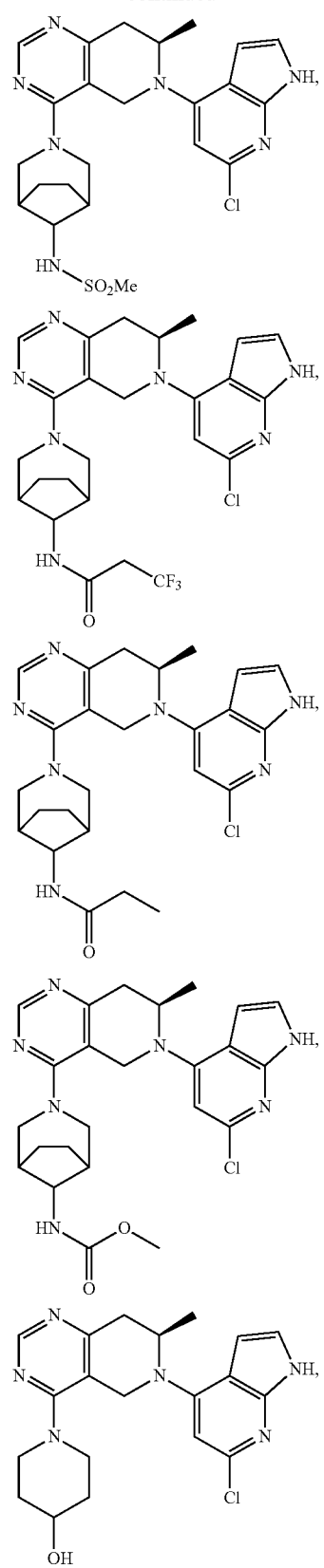

199
-continued
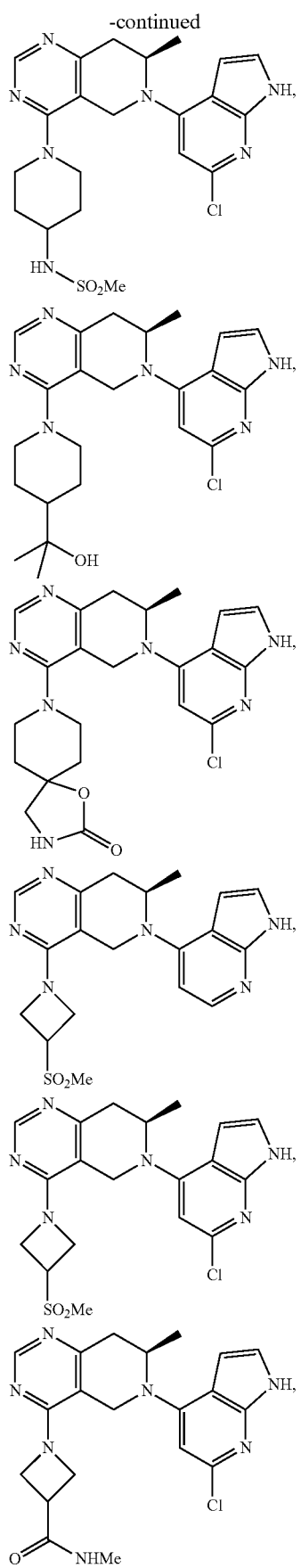
200
-continued
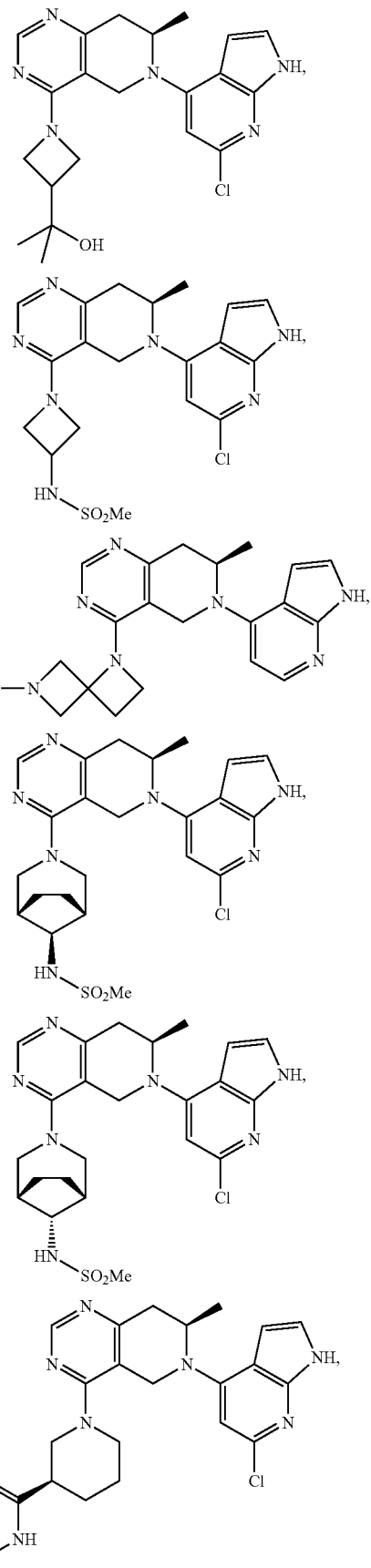

201
-continued
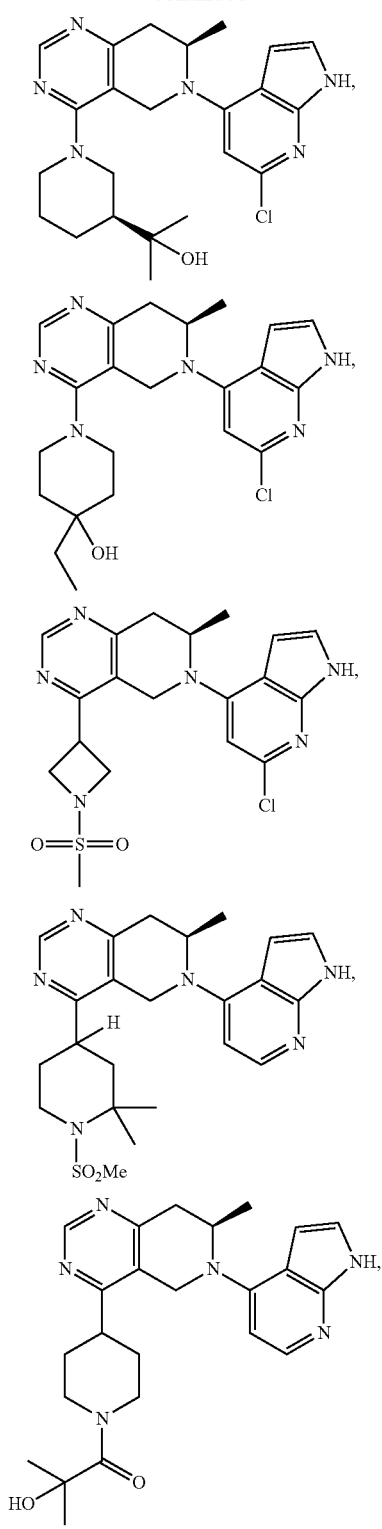
202
-continued
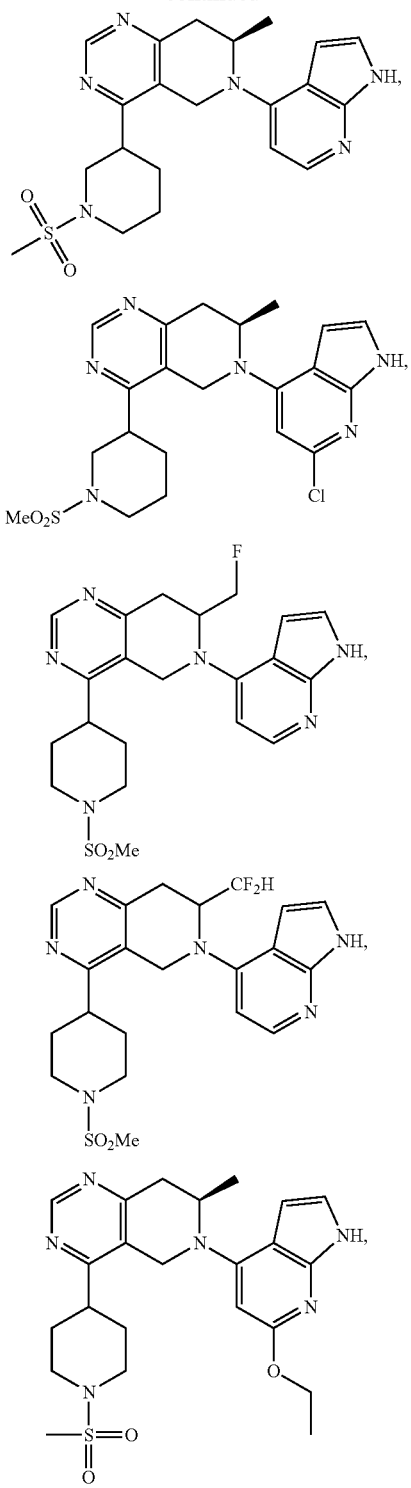

203
-continued
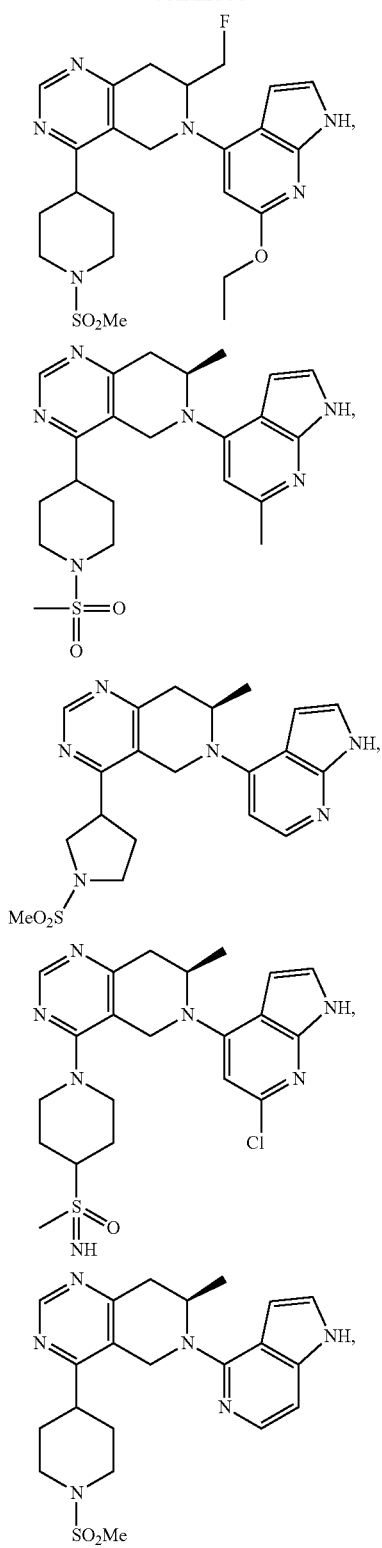
204
-continued
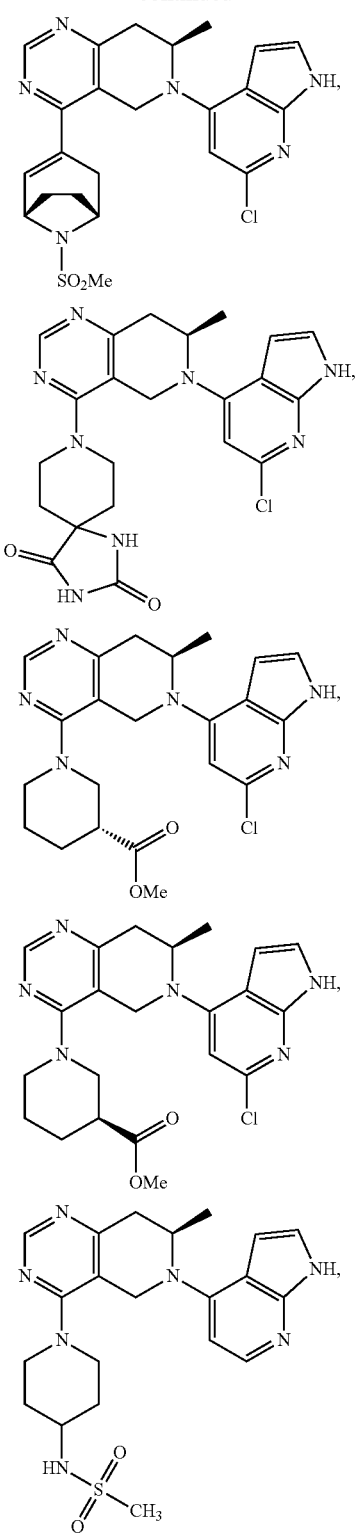

-continued
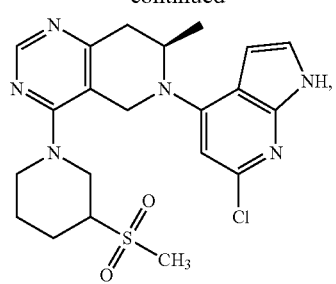
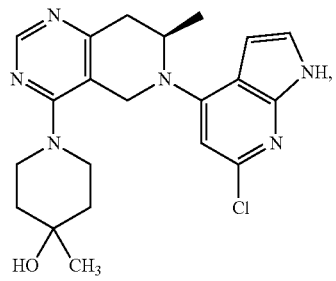
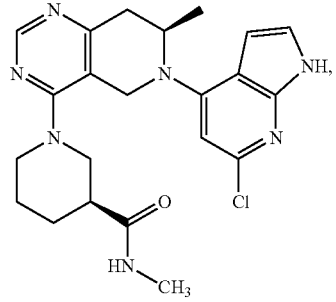
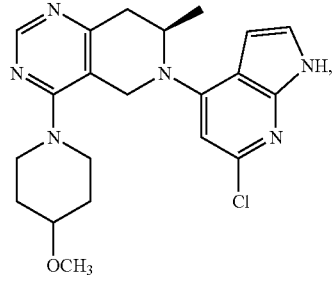
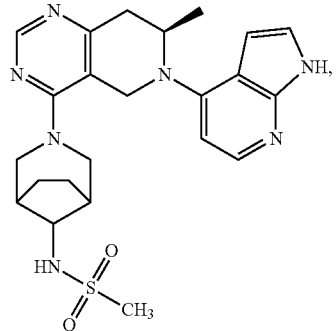
-continued
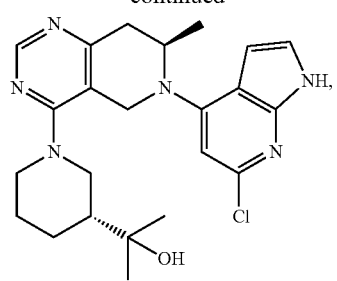
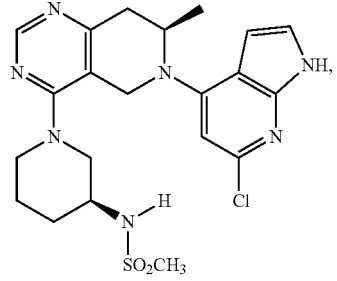
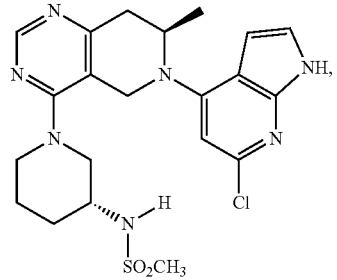
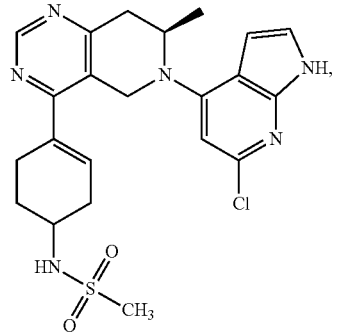
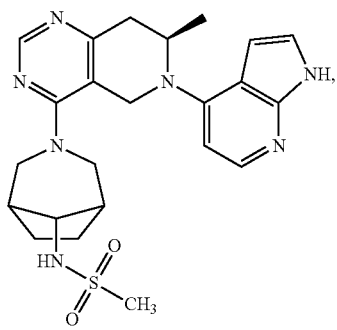

207
-continued
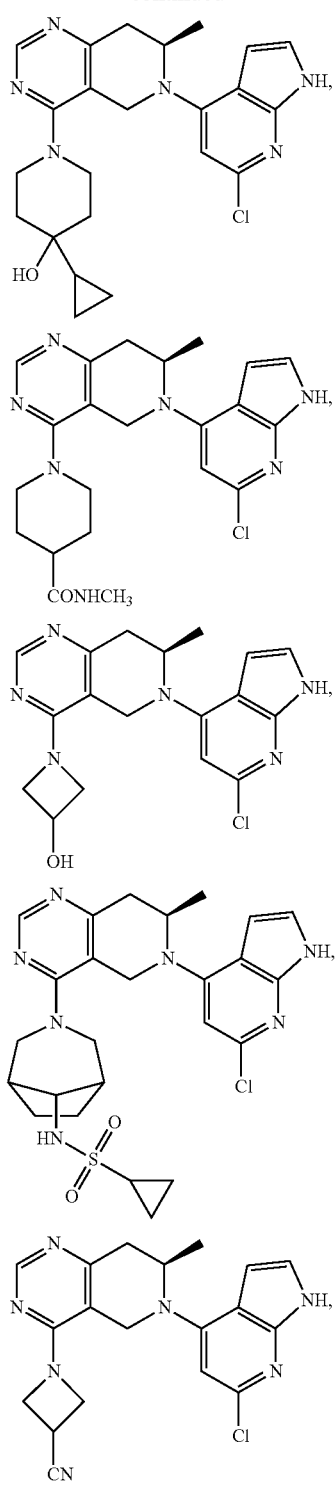
208
-continued
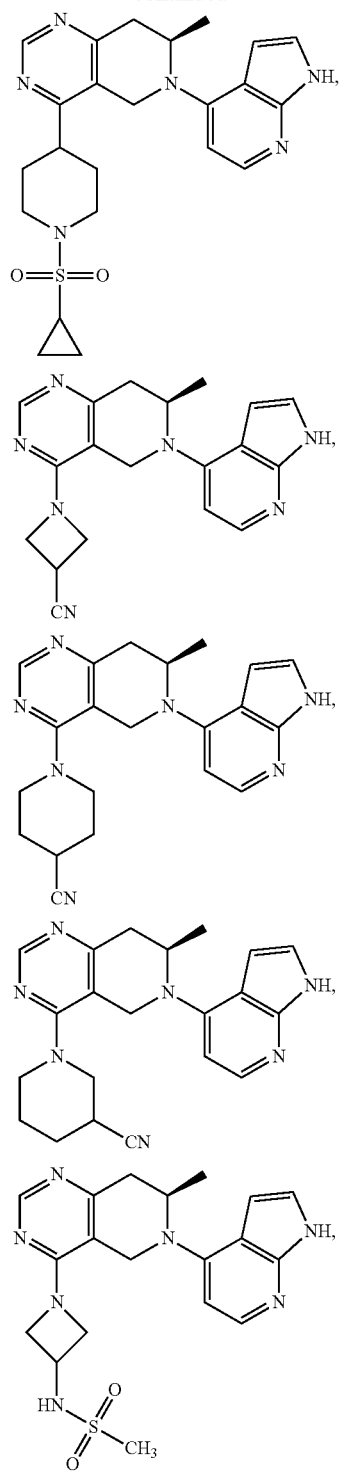

209
-continued
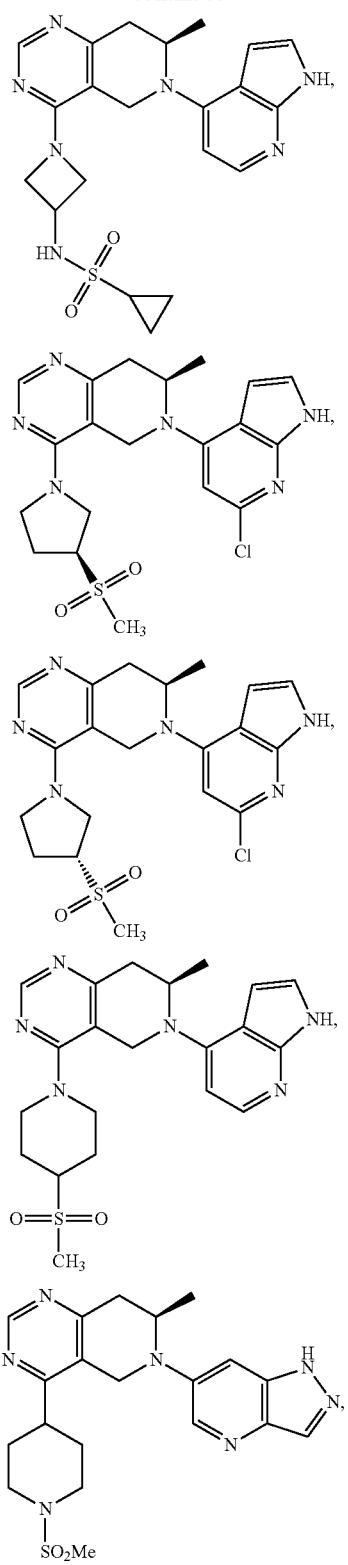
210
-continued
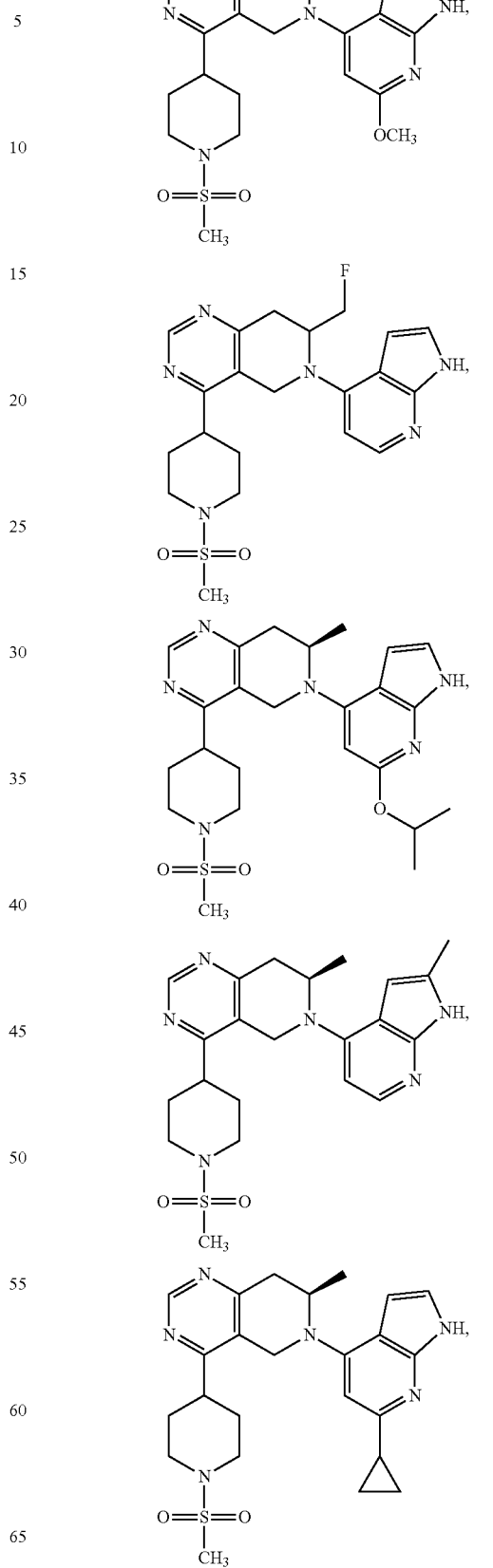

211
-continued
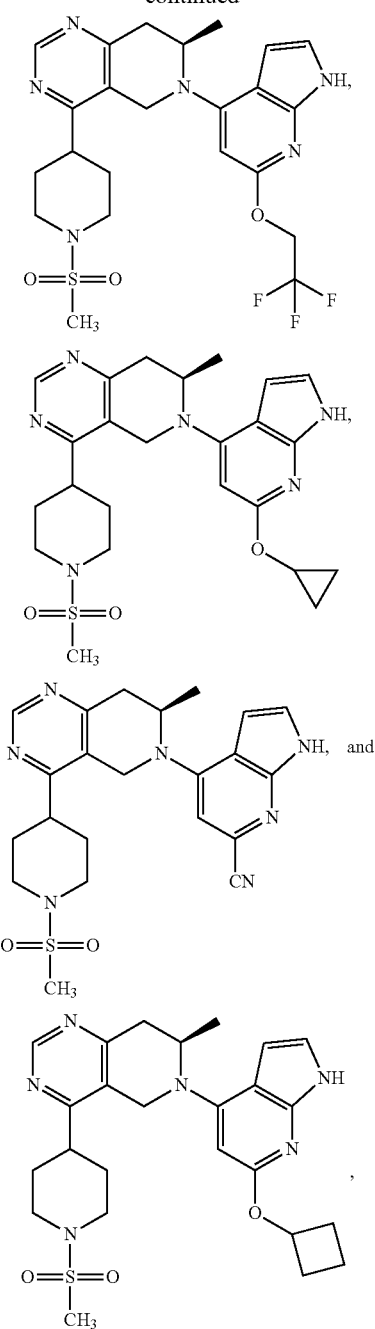
or a salt thereof.
26. The compound as recited in claim 1, wherein the structure is selected from
212
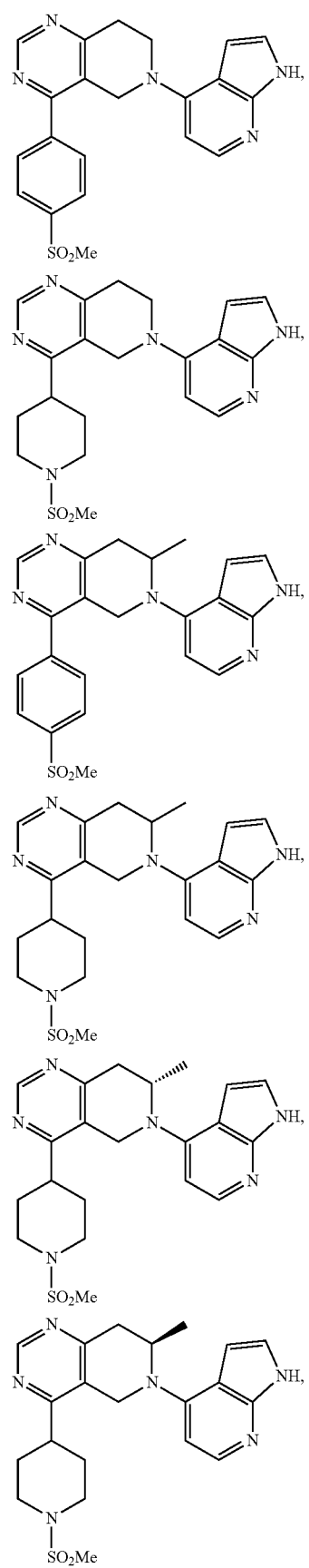

213
-continued
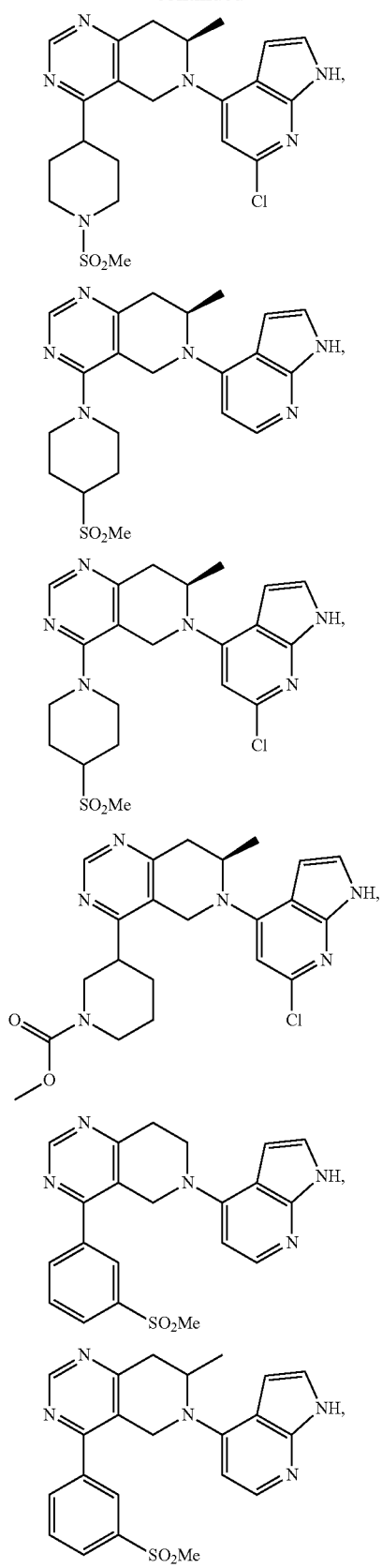
214
-continued
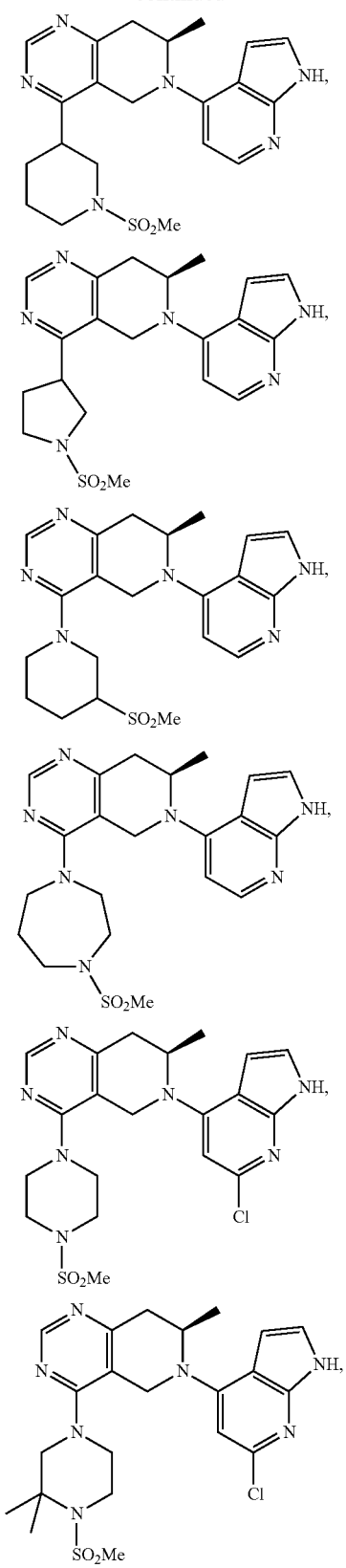

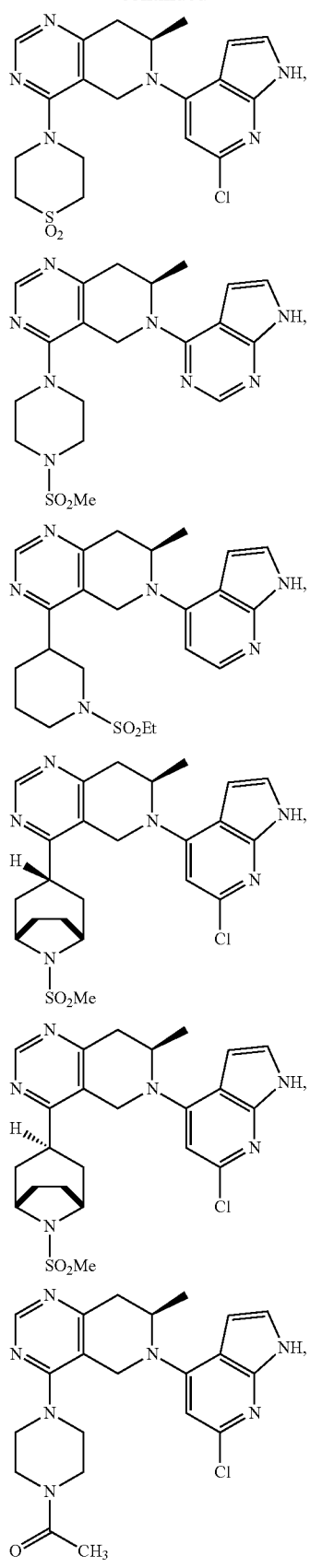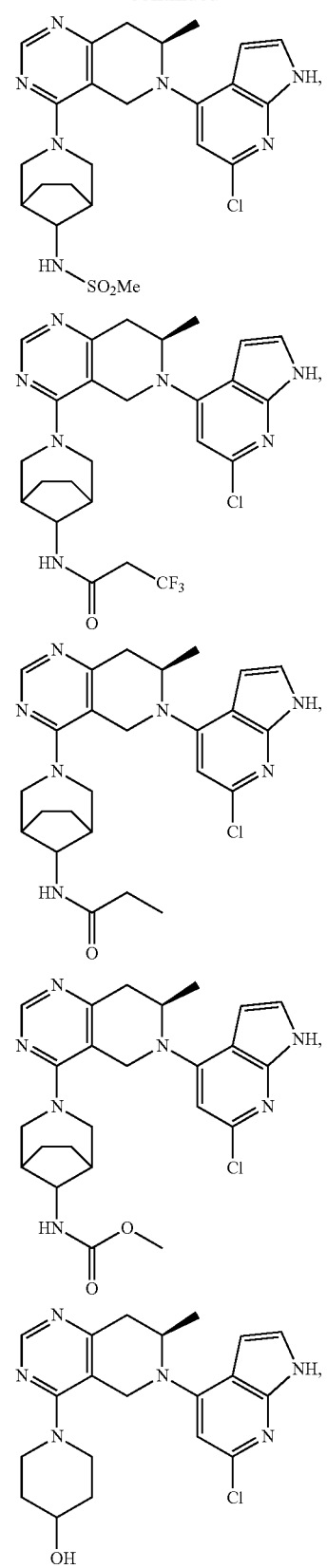

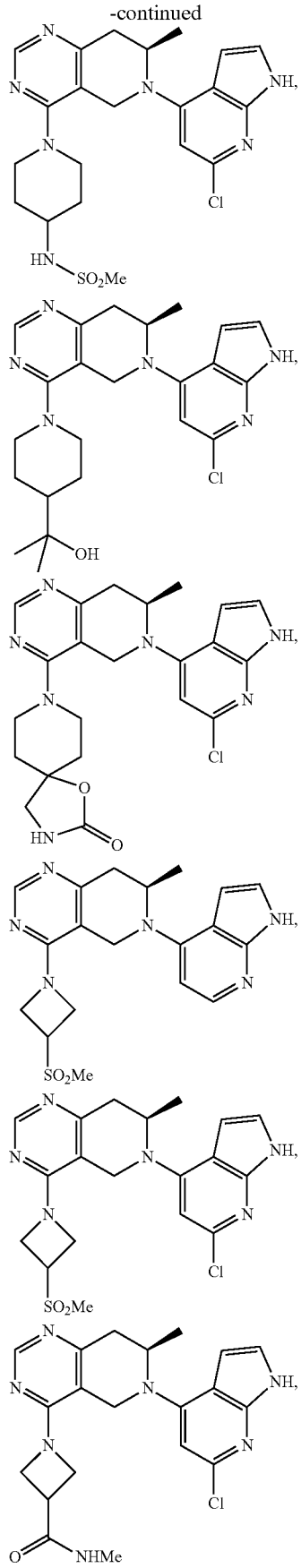
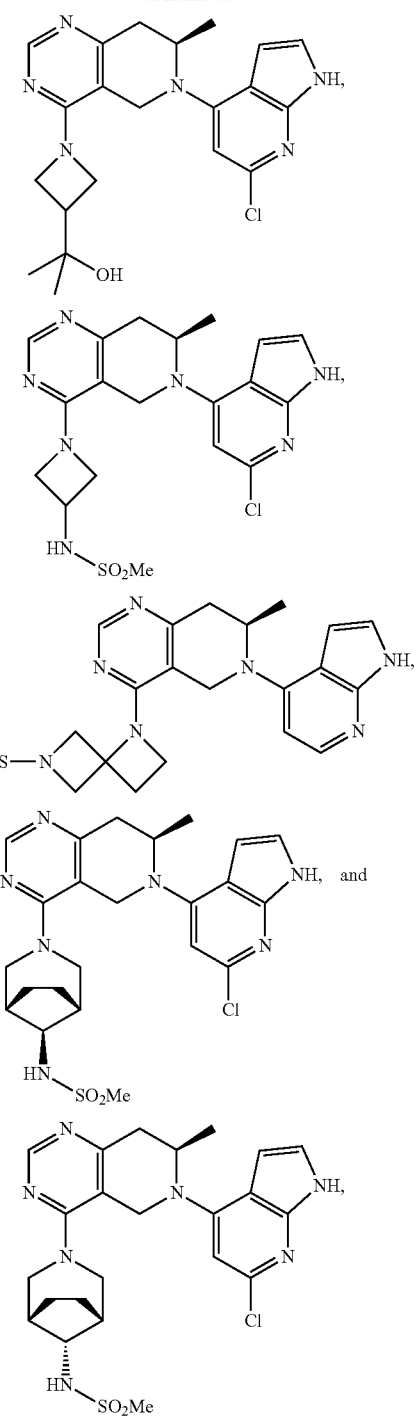
or a salt thereof.
27. The compound as recited in claim 1, wherein the structure is selected from

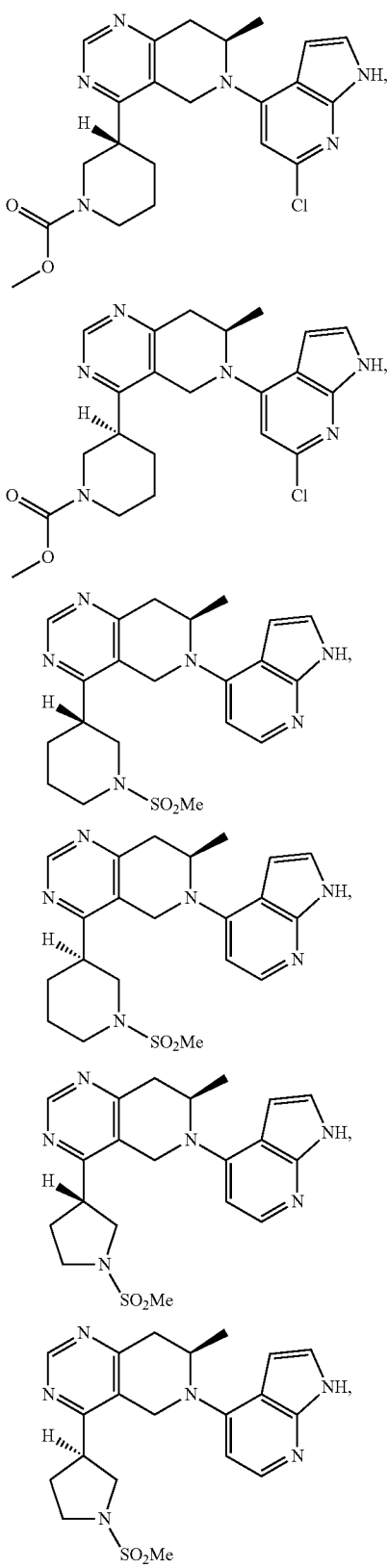

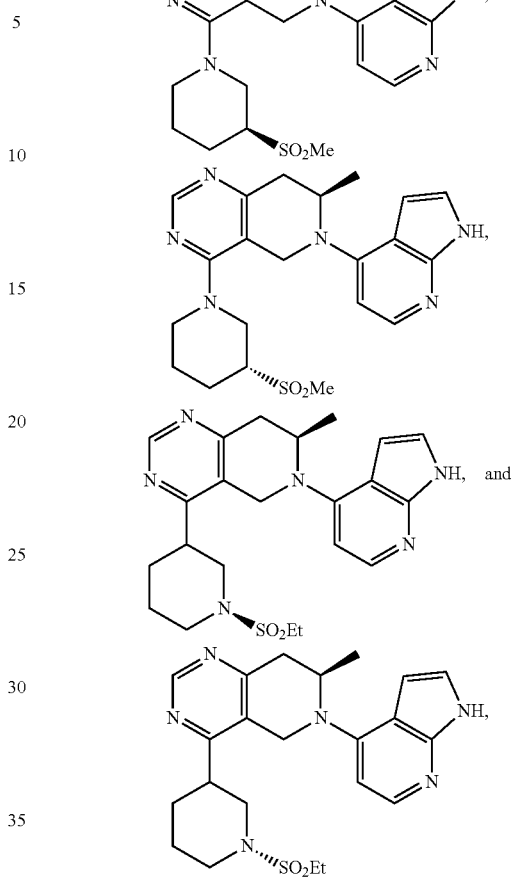

or a salt thereof.

28. A pharmaceutical composition comprising a compound as recited in claim 1 together with a pharmaceutically acceptable carrier.

29. A method of sensitizing cells to DNA-damaging agents comprising administering to a patient a compound as recited in claim 1.

30. A method of preventing cell repair from DNA damage comprising administering to a patient a compound as recited in claim 1.

31. A method of inhibition of ATR kinase comprising contacting ATR kinase with a compound as recited in claim 1.

32. A method of therapeutic treatment of an ATR kinase-mediated disease comprising the administration of a therapeutically effective amount of a compound as recited in claim 1 to a patient in need thereof.

33. The method as recited in claim 32 wherein said disease is an ATR kinase-mediated cancer.

34. The method as recited in claim 33, wherein said ATR kinase-mediated cancer is a chemotherapy-resistant cancer.

35. The method as recited in claim 33, wherein said ATR kinase-mediated cancer is a radiotherapy-resistant cancer.

36. The method as recited in claim 33, wherein said cancer is an ALT-positive cancer.

37. A method of therapeutic treatment of an ATR kinase-mediated disease comprising the administration of:
 a. a therapeutically effective amount of a compound as recited in claim 1; and b. another therapeutic agent.

38. The method of claim 33, wherein the method further comprises administering non-chemical methods of cancer treatment.

39. A method of increasing the sensitivity of cancer cells to a cancer therapy selected from chemotherapy or radiation therapy by administering to a patient a compound as recited in claim 1.

* * * * *